(12) United States Patent
Kowarik et al.

(10) Patent No.: US 10,441,647 B2
(45) Date of Patent: *Oct. 15, 2019

(54) POLYSACCHARIDE AND USES THEREOF

(71) Applicant: GLAXOSMITHKLINE BIOLOGICALS S.A., Rixensart (BE)

(72) Inventors: Michael T. Kowarik, Zurich (CH);
Michael L. Wetter, Zurich (CH);
Stefan J. Kemmler, Zurich (CH);
Micha A. Häuptle, Zurich (CH);
Veronica Gambillara, Meilen (CH);
Manuela Mally, Watt (CH)

(73) Assignee: GLAXOSMITHKLINE CIOLOGICALS S.A., Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/643,788

(22) Filed: Jul. 7, 2017

(65) Prior Publication Data
US 2017/0340718 A1 Nov. 30, 2017

Related U.S. Application Data

(63) Continuation of application No. 14/628,844, filed on Feb. 23, 2015, now Pat. No. 9,700,612.

(60) Provisional application No. 61/943,710, filed on Feb. 24, 2014.

(51) Int. Cl.

| | |
|---|---|
| *A61K 39/108* | (2006.01) |
| *C07K 14/21* | (2006.01) |
| *A61K 39/02* | (2006.01) |
| *C08B 37/00* | (2006.01) |
| *A61K 47/64* | (2017.01) |
| *A61K 39/00* | (2006.01) |
| *C07K 14/245* | (2006.01) |

(52) U.S. Cl.
CPC .......... *A61K 39/0258* (2013.01); *A61K 39/02* (2013.01); *A61K 47/646* (2017.08); *C07K 14/21* (2013.01); *C08B 37/0063* (2013.01); *C08B 37/0066* (2013.01); *A61K 2039/55583* (2013.01); *A61K 2039/6037* (2013.01); *A61K 2039/6087* (2013.01); *A61K 2039/70* (2013.01); *C07K 14/245* (2013.01); *Y02A 50/47* (2018.01)

(58) Field of Classification Search
None
See application file for complete search history.

(56) References Cited

U.S. PATENT DOCUMENTS 5,370,872 A    12/1994  Cryz et al.

FOREIGN PATENT DOCUMENTS

| WO | 2003074687 A1 | 9/2003 |
|---|---|---|
| WO | 2006119987 A2 | 11/2006 |
| WO | 2009089396 A2 | 7/2009 |
| WO | 2009104074 A2 | 8/2009 |
| WO | 201162615 A1 | 5/2011 |
| WO | 2012078482 A1 | 6/2012 |
| WO | 2013034664 A1 | 3/2013 |
| WO | 2014037585 A1 | 3/2014 |
| WO | 2014057109 A1 | 4/2014 |
| WO | 2014102265 A1 | 7/2014 |
| WO | 2014111516 A1 | 7/2014 |
| WO | 201552344 A1 | 4/2015 |
| WO | 2015117711 A1 | 8/2015 |
| WO | 2015124769 A1 | 8/2015 |

OTHER PUBLICATIONS

Stenutz et al., "The structures of *Escherichia coli* O-polysaccharide antigens," Federation of European Microbiological Society, vol. 30, pp. 382-403 (2006).
Szijarto et al., "Diagnostic Potential of Monoclonal Antibodies Specific to the Unique O-Antigen of Multidrug-Resistant Epidemic *Escherichia coli* Clone ST131-O25b:H4," Clinical and Vaccine Immunology, vol. 21, No. 7, pp. 930-939 (2014).
Rogers et al., "*Escherichia coli* O25b-ST131: a pandemic, multiresistant, community-associated strain," Journal of Antimicrobial Chemotherapy, vol. 66, pp. 1-14 (2011).
Pitout et al., "Extraintestinal Pathogenic *Escherichia coli*: An Update on Antimicrobial Resistance, Laboratory Diagnosis and Treatment," Expert Rev. Anti. Infect. Ther., vol. 10, No. 10, pp. 1165-1176 (2012).
Ihssen et al., "Production of glycoprotein vaccines in *Escherichia coli*," Microbial Cell Factories, vol. 9, No. 61, pp. 1-13 (2010).
Feldman et al., "Engineering N-linked protein glycosylation with diverse O antigen lipopolysaccharide structures in *Escherichia coli*," Proc Natl Acad Sci USA, vol. 102, No. 8, pp. 3016-3021 (2005).
Fratamico et al., "*Escherichia coil* serogroup O2 and O28ac O-antigen gene cluster sequences and detection of pathogenic *E. coli* O2 and O28ac by PCR," Canadian Journal of Microbiology, vol. 56, No. 4, pp. 308-316 (2010).
Jann et al., "Structural Comparison of the O6 Specific Polysaccharides From *E. coli* O6:K2:H1, *E. coli* O6:K13:H1, and *E. coli* O6:K54:H10," Carbohydrate Research, vol. 263, No. 2, pp. 217-225 (1994).
Jansson et al., "Structural studies of the *Escherichia coli* O-antigen 6," Carbohydrate Research, vol. 131, No. 2, pp. 277-283 (1984).
Wacker et al., "N-linked glycosylation in Campylobacter jejuni and its functional transfer into *E. coli*," Science, vol. 298, No. 5599, pp. 1790-1793 (2002).

(Continued)

*Primary Examiner* — Brian Gangle
(74) *Attorney, Agent, or Firm* — Panitch Schwarze Belisario & Nadel LLP

(57) ABSTRACT

Provided herein is a novel *E. coli* O polysaccharide, O25B. Also provided herein are prokaryotic host cells containing enzymes (e.g., glycosyltransferases) used in O25B production. The host cells provided herein produce O25B bioconjugates, wherein said bioconjugates contain O25B linked to a carrier protein. Further provided herein are compositions, e.g., pharmaceutical compositions, including O25B and/or bioconjugates containing O25B. Such compositions can be used as vaccines against infection with ExPEC, and may further include one or more additional bioconjugates.

20 Claims, 43 Drawing Sheets

Figure 1:
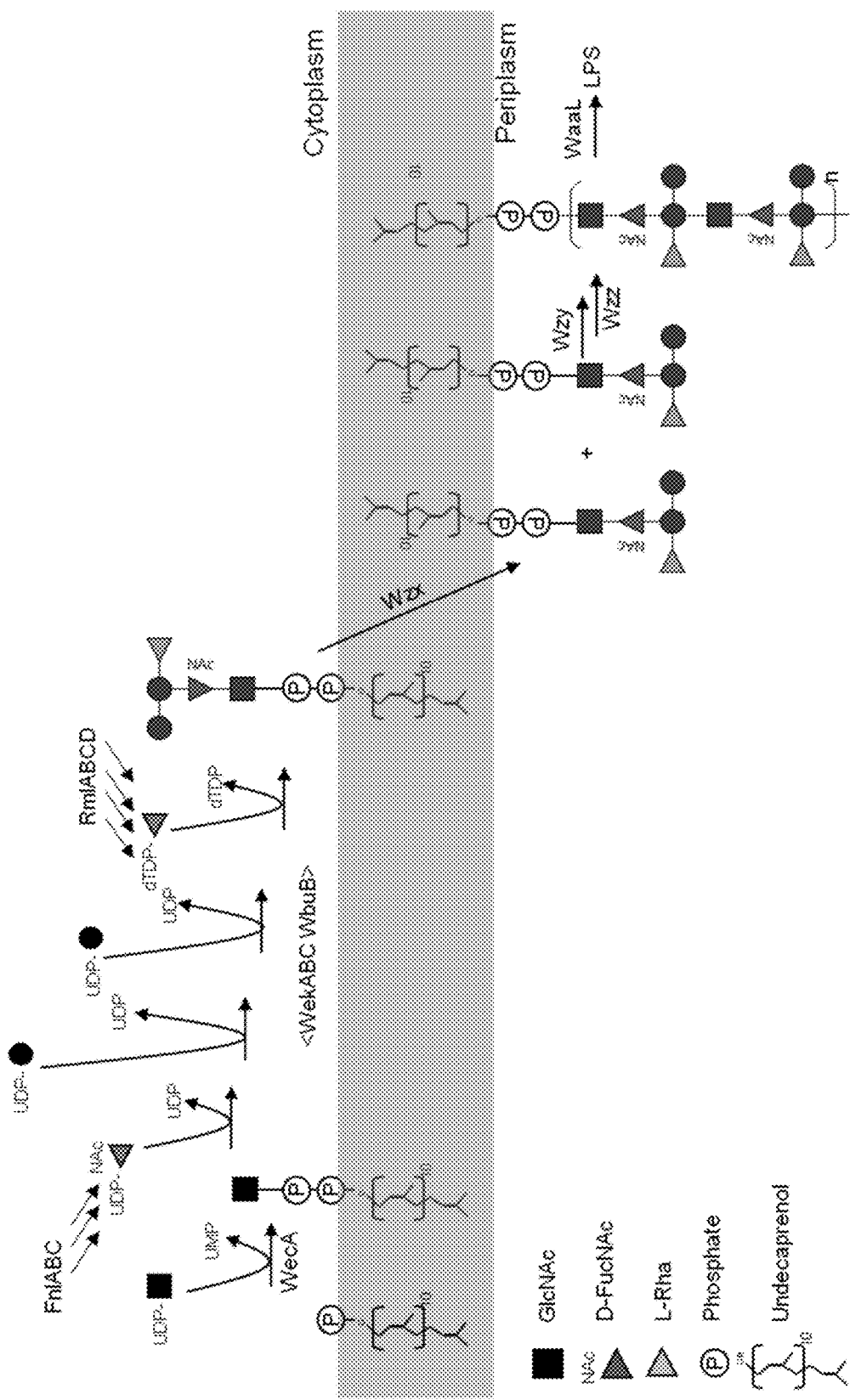

Specification includes a Sequence Listing.

(56) References Cited

OTHER PUBLICATIONS

Debroy et al., "Detection of O antigens in *Escherichia coli*," Animal Health Research Reviews, vol. 12, No. 2, pp. 169-185 (2011).
Blanco et al., "Virulence factors and O groups of *Escherichia coli* isolates from patients with acute pyelonephritis, cystitis and asymptomatic bacteriuria," Eur. J. Epidemiol., vol. 12, No. 2, pp. 191-198 (1996).
Molina-Lopez et al., "Drug resistance, serotypes, and phylogenetic groups among uropathogenic *Escherichia coli* Including O25-ST131 in Mexico City," J Infect Dev Ctries, vol. 5, No. 12, pp. 840-849 (2011).
Terai et al., "*Escherichia coli* Virulence Factors and Serotypes in Acute Bacterial Prostatitis," Int. Journal of Urology, vol. 4, No. 3, pp. 289-294 (1997).
Kenne et al., "Structural studies of the *Escherichia coli* O-antigen 25," Carbohydrate Research, vol. 122, No. 2, pp. 249-256 (1983).
Fundin et al., "NMR analysis of the O-antigen polysaccharide from *Escherichia coli* strain F171," Magnetic Resonance in Chemistry, vol. 41, No. 3, pp. 202-205 (2003).
Johnson et al., "*Escherichia coli* sequence type ST131 as an emerging fluoroquinolone-resistant uropathogen among renal transplant recipients," Antimicrob Agents Chemother. vol. 54, No. 1, pp. 546-550 (2010).
Banerjee et al., "A new clone sweeps clean: the enigmatic emergence of *Escherichia coli* sequence type 131," Antimicrob Agents Chemother. vol. 58, No. 9, pp. 4997-5004 (2014).
Lukac et al., "Toxoid of Pseudomonas aeruginosa exotoxin A generated by deletion of an active-site residue," Infect Immun, vol. 56, pp. 3095-3098 (1988).
Szijarto et al. "The rapidly emerging ESBL-producing *Escherichia coli* O25-ST131 clone carries LPS core synthesis genes of the K-12 type," FEMS Microbiol. Lett., vol. 332, pp. 131-136 (2012).
Clermont et al,"The CTX-M-15-producing *Escherichia coli* diffusing clone belongs to a highly virulent B2 phylogenetic subgroup," J. Antimicrob. Chemother., vol. 61, No. 5, pp. 1024-1028 (2008).
Blanco et al.,"Molecular epidemiology of *Escherichia coli* producing extended-spectrum {beta}-lactamases in Lugo (Spain): dissemination of clone O25b:H4-ST131 producing CTX-M-15," J. Antimicrob. Chemother., vol. 63, pp. 1135-1141 (2009).
Phan et al., "The serum resistome of a globally disseminated multidrug resistant uropathogenic *Escherichia coli* clone," PLOS Genetics, vol. 9, No. 10, pp. 1-18 (2013).
Stevenson et al., "Structure of the O antigen of *Escherichia coli* K-12 and the sequence of its rfb gene cluster," J. Bacteriol., vol. 176, No. 13, pp. 4144-4156 (1994).
Amor et al., "Distribution of core oligosaccharide types in lipopolysaccharides from *Escherichia coli*," Infect. Immun., vol. 68, pp. 1116-1124 (2000).
Jansson et al., "Structural studies of the O-specific side-chains of the *Escherichia coli* O2 lipopolysaccharide," Carbohydrate Res., vol. 161, pp. 273-279 (1987).
Cross et al., "Safety and Immunogenicity of a Polyvalent *E. coli* Vaccine in Human Volunteers," J. Infect. Diseases, vol. 170, No. 4, pp. 834-840 (1994).
Cryz et al., "Synthesis and characterization of a polyvalent *Escherichia coli* O-polysaccharide-toxin A conjugate vaccine," Vaccine, vol. 13, No. 5, pp. 449-453 (1995).
Van Den Dobbelsteen et al.,"Immunogenicity and safety of tetravalent *E. coli* O-antigen bioconjugate vaccine in animal models," Vaccine, vol. 34, No. 35, pp. 4152-4160 (2016).
Int'l Search Report and Written Opinion dated Jun. 15, 2015 in Int'l Application No. PCT/EP2015/053739.
Int'l Search Report and Written Opinion dated Oct. 27, 2016 in Int'l Application No. PCT/US2016/048278.
Jadhav et al., "Virulence characteristics and genetic affinities of multiple drug resistant uropathogenic *Escherichia coli* from a Semi Urban Locality in India," PLOS One, vol. 6, No. 3, (2011).
Mora et al, "Emergence of clonal groups O1:HNM-D-ST59, O15:H1-D-ST393, O20:H34/HNM-D-ST354, O25b:H4-B2-ST131 and ONT:H21,42-B1-ST101 among CTX-M-14-producing *Escherichia coli* clinical isolates in Galicia, northwest Spain," International J. of Antimicrob. Agents, vol. 37, No. 1, pp. 16-21 (2011).
Clermont et al., "Rapid Detection of the O25b-ST131 clone of *Escherichia coli* encompassing the CTX-M-15-producing strains," Journal of Antimicrobial Chemotherapy, vol. 64, No. 2, pp. 274-277 (2009).
Glover et al., "Chemoenzymatic synthesis of Glycopeptides with PgIB, a bacterial oligosaccharyl transferase from Campylobacter jejuni," Chemistry and Biology, Current Biology, vol. 12, No. 12, pp. 1311-1315 (2005).
Laurentin et al., "A Microtiter Modification of the anthrone-sulfuric acid colorimetric assay for glucose-based carbohydrates", Analytical Biochemistry, 315, pp. 143-145, 2003.
Russo et al., "A killed, genetically engineered derivative of a wild-type extraintestinal pathogenic *E coli* strain is a caccine candidate", Elsevier, Vaccine 25, pp. 3859-3870, 2007.
Russo et al., "Medical and Exonomic impact of extraintestinal infections due to *Escherichia coli*: focus on an Increasingly important endemic problem", Elsevier, Microbes and Infection 5, pp. 449-456, 2003.
Kohler et al., "What defines extraintestinal pathogenic *Escherichia coli*", Elsevier, International journal of Medical Microbiology 301, pp. 642-647, 2011.
Ho et al., Preclinical Laboratory Evaluation of a Bivalent *Staphylococcus aureus* Saccharide-Exotoxin A Protein Conjugate Vaccine, Human vaccines, 2:3, pp. 89-98, May/Jun. 2006.
Lipsitch, "Bacterial vaccines and Serotype Replacement: Lessons from Haemophilus Influenzae and Prospects for *Streptococcus pneumoniae*", Emerging Infectious Diseases, vol. 5, No. 3, May/Jun. 1999.
Schito et al., "The ARESC study: an international survey on the antimicrobial resistance of pathogens involved in uncomplicated urinary tract infections", Elsevier, International Journal of Antimicrobial Agents 34, pp. 407-413, 2009.
Foxman, "Epidemiology of Urinary Tract Infections: Incidence, morbidity, and Economic Costs", The American Journal of Medicine, vol. 113(1A), 5S-13S, Jul. 2002.
Johnson et al., Extraintestinal Pathogenic *Escherichia coli*: "The other bad *E coli*", J Lab Clin Med., 139(3), pp. 155-162, 2002.
Kim et al., "Efficiency of a pneumococcal Opsonophagocytic Killing Assay Improved by Multiplexing and by Colloring Colonies", Clinical and Dianostic laboratory Immunology, pp. 616-621, Jul. 2003.
Int'l Search Report and Written Opinion dated Jul. 20, 2017 in Int'l Application No. PCT/US2016/048278.
Cryz Jr. et al., "Synthesis and Characterization of *Escherichia coli* O18 O-Polysaccharide Conjugate Vaccines," Infection and Immunity, vol. 58, No. 2, pp. 373-377 (1990).

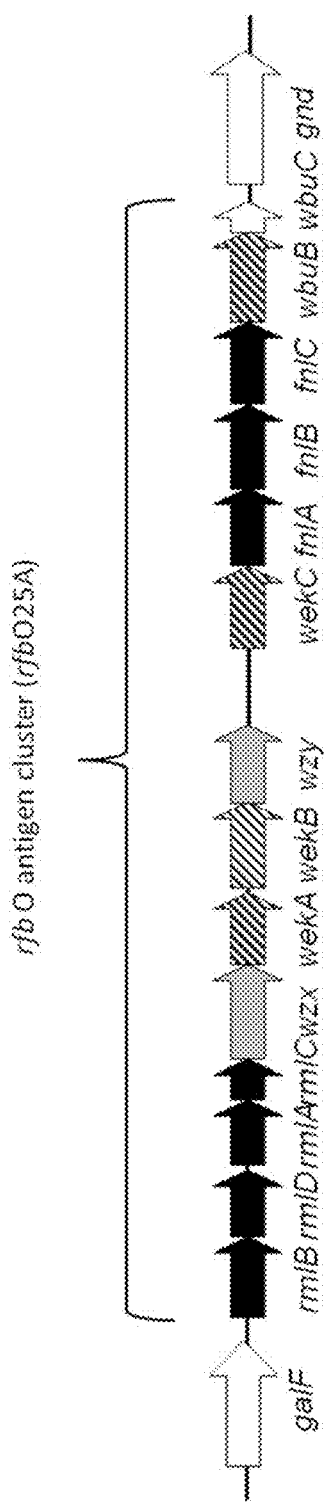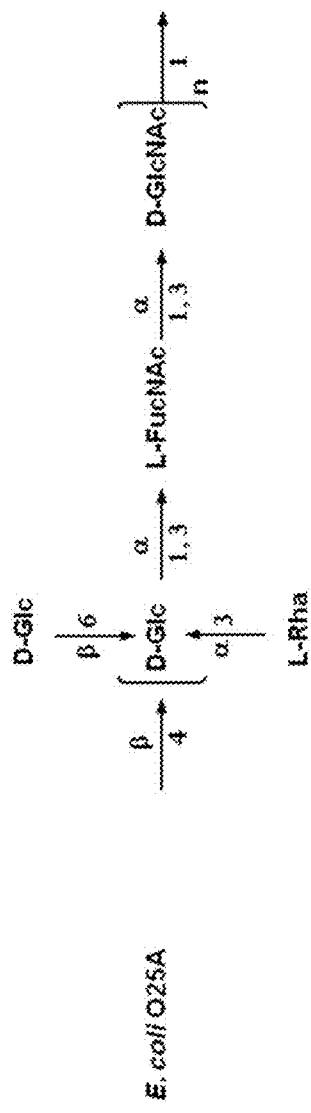
FIG. 2A
FIG. 2B

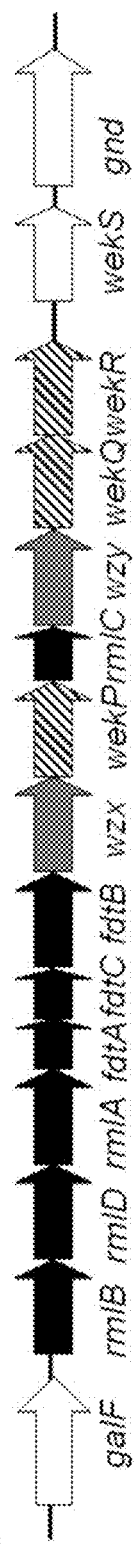
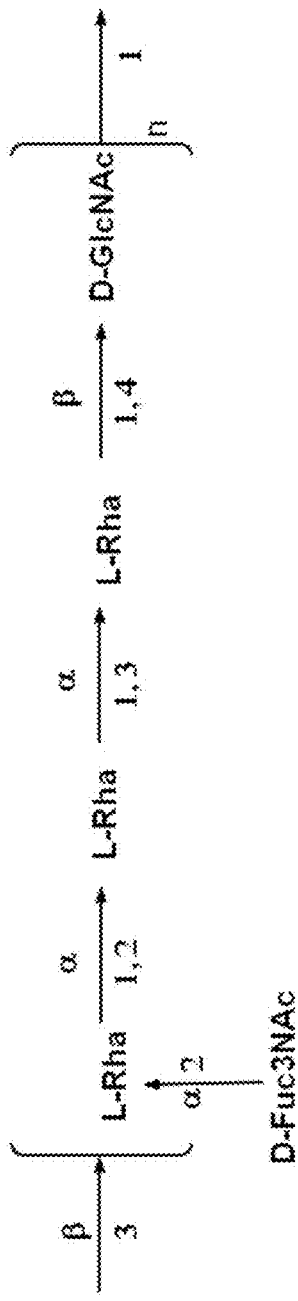
FIG. 19A
FIG. 19B

POLYSACCHARIDE AND USES THEREOF

CROSS-REFERENCE TO RELATED APPLICATIONS

This application is a continuation of U.S. application Ser. No. 14/628,844, filed on Feb. 23, 2015, allowed, which claims priority pursuant to 35 U.S.C. § 119(e) to U.S. Provisional Application No. 61/943,710, filed on Feb. 24, 2014, the disclosures of which are herein incorporated by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "689114_1U2_Sequence Listing," creation date of Jul. 6, 2017, and having a size of 35.7 kb. The sequence listing submitted via EFS-Web is part of the specification and is herein incorporated by reference in its entirety.

1. INTRODUCTION

Disclosed herein are the structure of the E. coli antigen O25B, as well as uses of O25B, methods of making of O25B, and bioconjugates comprising O25B. Applicants have identified the E. coli gene cluster responsible for production of O25B and have fully characterized the structure of the O25B antigen. Accordingly, provided herein are nucleic acids capable of producing O25B in host cells. Also provided herein are host cells, e.g., recombinantly engineered host cells, comprising nucleic acids capable of O25B production. Such host cells can be used to generate bioconjugates comprising O25B linked to a carrier protein, which can be used in, e.g., the formulation of therapeutics (e.g., vaccines). The O25B antigen described herein also is useful in the generation of antibodies, which can be used, e.g., in therapeutic methods such as passive immunization of subjects. Further provided herein are compositions comprising O25B, alone or in combination with other E. coli antigens (e.g., O1, O2, and O6 and subseotypes thereof), for use in therapeutic methods, e.g., vaccination of hosts against infection with E. coli (e.g., extra-intestinal pathogenic, such as uropathogenic, E. coli).

2. BACKGROUND

Extra-intestinal pathogenic E. coli (ExPEC) causes a wide variety of infections that are responsible for significant morbidity, mortality, and costs annually. Urinary tract infections are among the most frequent conditions caused by ExPEC in human beings. However, life-threatening conditions, such as meningitis and sepsis, also are caused by ExPEC.

Bacterial resistance to antibiotics is a major concern in the fight against bacterial infection, and multi-drug resistant (MDR) E. coli strains are becoming more and more prevalent. Schito et al., 2009, Int. J. Antimicrob. Agents 34(5): 407-413; and Pitout et al., 2012, Expert Rev. Anti. Infect. Ther. 10(10):1165-1176. Thus, the development of efficient vaccines against ExPEC is needed.

3. SUMMARY

In one aspect, provided herein is a prokaryotic host cell comprising nucleic acids encoding enzymes (e.g., glycosyl- transferases) capable of producing the novel polysaccharide disclosed herein, E. coli O25B. Also provided herein are host cells comprising nucleic acids encoding enzymes (e.g., glycosyltransferases) capable of producing other E. coli antigens, e.g., O25A, O1, O2, and O6, and subserotypes thereof. The host cells provided herein may naturally express nucleic acids specific for production of an O antigen of interest, or the host cells may be made to express such nucleic acids, i.e., in certain embodiments said nucleic acids are heterologous to the host cells. In certain embodiments, the host cells provided herein comprise nucleic acids encoding additional enzymes active in the N-glycosylation of proteins, e.g., the host cell provided herein can further comprise a nucleic acid encoding an oligosaccharyl transferase or nucleic acids encoding other glycosyltransferases. In certain embodiments, the host cells provided herein comprise a nucleic acid encoding a carrier protein, e.g., a protein to which oligosaccharides and/or polysaccharides can be attached to form a bioconjugate. In a specific embodiment, the host cell is E. coli. See Section 5.3.

In a specific embodiment, provided herein is a prokaryotic host cell comprising an E. coli rfb(upec138) gene cluster (SEQ ID NO:12), or a gene cluster that is about or at least 75%, 80%, 85%, 90%, 95%, 96%, 97%, 98%, or 99% identical to or homologous to an E. coli rfb(upec138) gene cluster (SEQ ID NO:12). In a specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is E. coli.

In another specific embodiment, provided herein is a prokaryotic host cell comprising an E. coli rfb(upec163) gene cluster, or a gene cluster that is about or at least 75%, 80%, 85%, 90%, 95%, 96%, 97%, 98%, or 99% identical to or homologous to an E. coli rfb(upec163) gene cluster. In a specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser (Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is E. coli.

In another specific embodiment, provided herein is a prokaryotic host cell comprising an E. coli rfb(upec177) gene cluster, or a gene cluster that is about or at least 75%, 80%, 85%, 90%, 95%, 96%, 97%, 98%, or 99% identical to or homologous to an E. coli rfb(upec177) gene cluster. In a specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser (Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell recombinantly engineered to comprise (e.g., by introduction of one or more vectors/plasmids into the host cell) one, two, three, four, or more of the following genes (or a nucleic acid that is about or at least 75%, 80%, 85%, 90%, 95%, 96%, 97%, 98%, or 99% identical to or homologous to one of the following genes): rmlB (SEQ ID NO:1), rmlD (SEQ ID NO:2), rmlA (SEQ ID NO:3), rmlC (SEQ ID NO:4), wzx (SEQ ID NO:5), wekA (SEQ ID NO:6), wekB (SEQ ID NO:7), wzy (SEQ ID NO:8), wbbJ (SEQ ID NO:9), wbbK (SEQ ID NO:10), and/or wbbL (SEQ ID NO:11). In another specific embodiment, the prokaryotic host cell comprises a nucleic acid sequence encoding an oligosaccharyl transferase (e.g., a heterologous oligosaccharyltransferase). In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell recombinantly engineered to comprise (e.g., by introduction of one or more vectors/plasmids into the host cell) one, two, three, four, or more of the following (i) dTDP-Glucose 4,6-dehydratase; (ii) dTDP-6-Deoxy-D-glucose 3,5-epimerase; (iii) Glucose-1-phosphate thymidylyltransferase; (iv) dTDP-4-dehydrorhamnose 3,5-epimerase; (v) O antigen flippase; (vi) dTDP-Rha:Glc-Rha (Ac)-GlcNAc-UPP α-1,3-rhamnosyltransferase; (vii) UDP-Glc:Rha-GlcNAc-UPP α-1,3-glucosyltransferase; (viii) O antigen polymerase; (ix) O-acetyl transferase; (x) UDP-Glc:Rha-GlcNAc-UPP α-1,3-glucosyltransferase; and/or (xi) dTDP-Rha: GlcNAc-UPP α-1,3-rhamnosyltransferase. In a specific embodiment, the prokaryotic host cell comprises a nucleic acid sequence encoding an oligosaccharyl transferase (e.g., a heterologous oligosaccharyltransferase). In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In certain embodiments, the prokaryotic host cells provided herein comprise a deletion or functional inactivation of one or more genes. See Section 5.3.1. In a specific embodiment, one or more of the waaL gene, gtrA gene, gtrB gene, gtrS gene, or the rfb gene cluster (or a gene or genes in the rfb cluster) is deleted or functionally inactivated from the genome of a prokaryotic host cell provided herein.

The carrier proteins expressed by the prokaryotic host cells provided herein can be selected from any carrier proteins known to those of skill in the art, e.g., detoxified Exotoxin A of *P. aeruginosa* (EPA; see, e.g., Ihssen, et al., (2010) Microbial cell factories 9, 61), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, and *C. jejuni* natural glycoproteins. In a specific embodiment, the carrier protein expressed by a prokaryotic host cell provided herein is detoxified *Pseudomonas* exotoxin (EPA). In certain embodiments, the carrier protein of a host cell provided herein comprises a signal sequence for targeting the carrier protein into the periplasmic space of the host cell. In a specific embodiment, the signal sequence is from *E. coli* DsbA, *E. coli* outer membrane porin A (OmpA), *E. coli* maltose binding protein (MalE), *Erwinia* carotovorans pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI). In certain embodiments, the nucleic acid sequence encoding the carrier protein expressed by the host cells provided herein has been engineered (e.g., via recombinant techniques) to encode one or more of the consensus sequence Asn-X-Ser(Thr), wherein X can be any amino acid except Pro (SEQ ID NO:14); and/or the consensus sequence Asp(Glu)-X-Asn-Z-Ser(Thr), wherein X and Z are independently selected from any natural amino acid except Pro (SEQ ID NO:15) (see WO 2006/119987). In certain embodiments, the carrier proteins expressed by the host cells provided herein comprise two, three, four, five or more of said consensus sequences. See Section 5.3.2.

In another aspect, provided herein is a method of producing an N-glycosylated carrier protein (also referred to herein as a bioconjugate) that comprises a carrier protein (e.g., EPA) N-linked to an *E. coli* O antigen (e.g., *E. coli* O25B), said method comprising culturing a host cell described herein under conditions suitable for the production of proteins, and purifying the N-glycosylated carrier protein. Methods for producing proteins using host cells, e.g., *E. coli*, and isolating proteins produced by host cells, are well-known in the art. See Section 5.3.

In another aspect, provided herein are bioconjugates produced by the host cells provided herein. In a specific embodiment, provided herein is a bioconjugate comprising a carrier protein (e.g., EPA) N-linked to *E. coli* O25B. See Section 5.4.

In a specific embodiment, provided herein is a bioconjugate comprising a carrier protein (e.g., EPA) linked to a compound of Formula O25B, presented below:

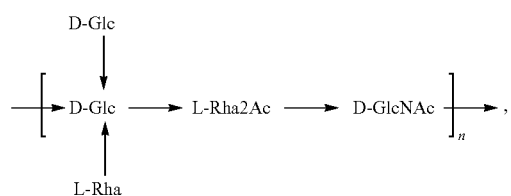

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, the carrier protein is N-linked to the O antigen of Formula O25B.

In another specific embodiment, provided herein is a bioconjugate comprising a carrier protein (e.g., EPA) linked to a compound of Formula O25B', presented below:

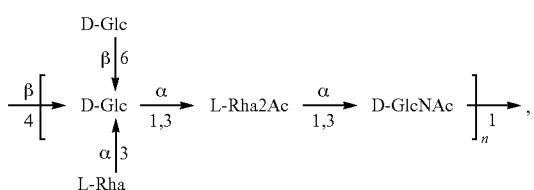

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, the carrier protein is N-linked to the O antigen of Formula O25B'.

In another aspect, provided herein is an isolated O antigen from an ExPEC *E. coli* strain, wherein said strain produces O25B. In another specific embodiment, provided herein is an isolated O antigen from *E. coli* strain upec138. In a specific embodiment, provided herein is an isolated O antigen from *E. coli* strain upec163. In another specific embodiment, provided herein is an isolated O antigen from *E. coli* strain upec177. See Section 5.2.

In another aspect, provided herein is a population of isolated macromolecules of the Formula O25B, presented below:

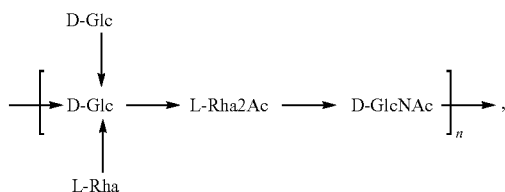

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, n of at least 80% of the macromolecules in the population is between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

In another aspect, provided herein is a population of isolated macromolecules of the Formula O25B', presented below:

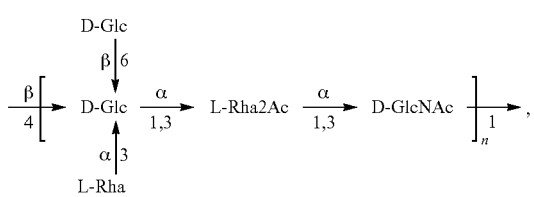

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, n of at least 80% of the macromolecules in the population is between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

In another aspect, provided herein are methods of generating anti-O25B antibodies using O25B and/or a bioconjugate comprising O25B. Further provided herein are antibodies produced according to such methods. See Section 5.5.

In another aspect, provided herein are compositions, e.g., pharmaceutical compositions, comprising the bioconjugates provided herein and/or the macromolecules (or populations thereof) provided herein. See Section 5.6.

In a specific embodiment, provided herein is a composition, e.g., a pharmaceutical composition, comprising a macromolecule comprising a structure of Formula O25B:

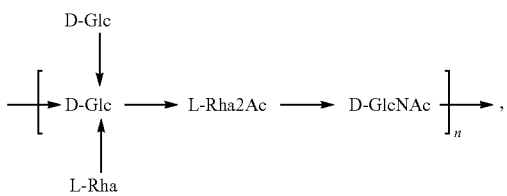

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

In another specific embodiment, provided herein is a composition, e.g., a pharmaceutical composition, comprising a macromolecule comprising a structure of Formula O25B':

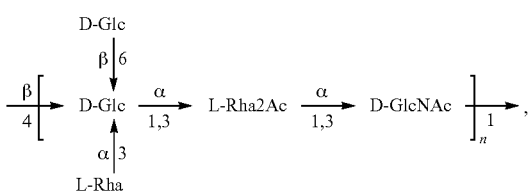

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

In another specific embodiment, provided herein is a composition, e.g., a pharmaceutical composition, comprising a bioconjugate described herein, wherein said bioconjugate comprises a carrier protein (e.g., EPA) linked to a compound of Formula O25B, presented below:

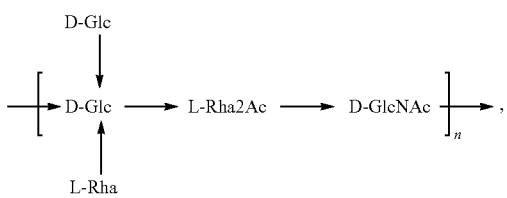

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, the carrier protein is N-linked to the O antigen of Formula O25B'.

In another specific embodiment, provided herein is a composition, e.g., a pharmaceutical composition, comprising a bioconjugate described herein, wherein said bioconjugate comprises a carrier protein (e.g., EPA) linked to a compound of Formula O25B', presented below:

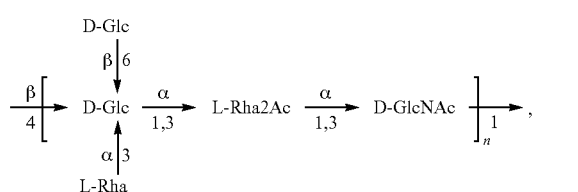

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, the carrier protein is N-linked to the O antigen of Formula O25B'.

In certain embodiments, the pharmaceutical compositions provided herein comprise one or more additional *E. coli* O antigens, wherein said antigens are not O25B (e.g., the formula O25B or the formula O25B'), e.g., O antigens from *E. coli* (e.g., ExPEC) other than those from an *E. coli* O25B serotype, and/or one or more bioconjugates comprising a carrier protein linked to an *E. coli* O antigen, wherein said antigen is not O25B (e.g., the formula O25B or the formula O25B'). Such compositions may comprise one or more additional macromolecules comprising an ExPEC O antigen and/or one or more additional bioconjugates, e.g., an O1A, O2, and/or O6 macromolecule and/or an O1A, O2, and/or O6 bioconjugate.

In a specific embodiment, provided herein is a composition, e.g., a pharmaceutical composition, comprising one or more additional macromolecules comprising an ExPEC O antigen and/or one or more additional bioconjugates, in addition to an O25B macromolecule (e.g., a macromolecule comprising the formula O25B or the formula O25B') and/or an O25B bioconjugate (e.g., a bioconjugate comprising a carrier protein linked to the formula O25B or the formula O25B'), wherein said additional macromolecules comprise a structure selected from the group consisting of:

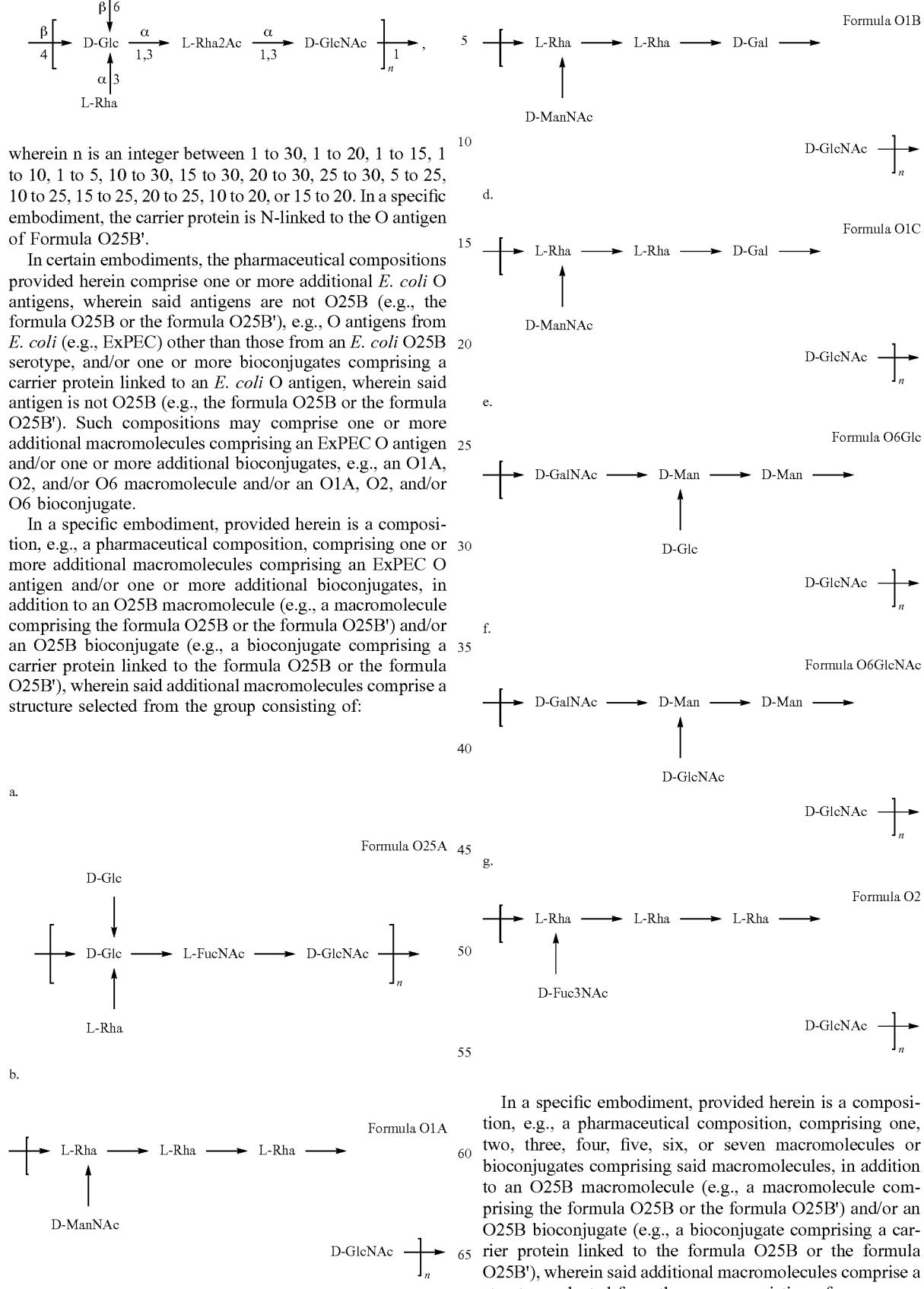

In a specific embodiment, provided herein is a composition, e.g., a pharmaceutical composition, comprising one, two, three, four, five, six, or seven macromolecules or bioconjugates comprising said macromolecules, in addition to an O25B macromolecule (e.g., a macromolecule comprising the formula O25B or the formula O25B') and/or an O25B bioconjugate (e.g., a bioconjugate comprising a carrier protein linked to the formula O25B or the formula O25B'), wherein said additional macromolecules comprise a structure selected from the group consisting of:

a.

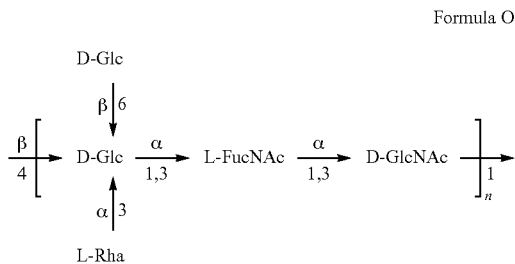

Formula O25A' b.

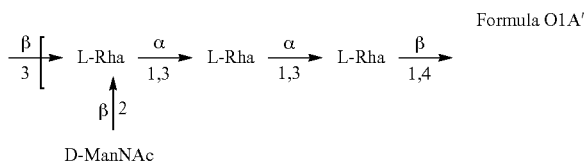

Formula O1A' c.

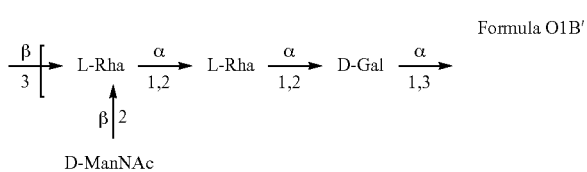

Formula O1B' d.

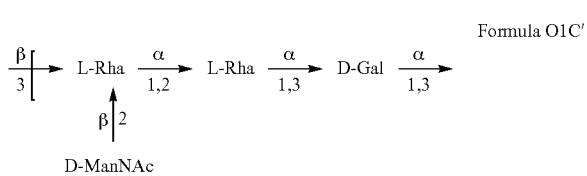

Formula O1C' e.

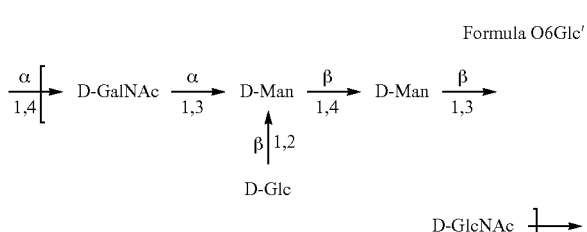

Formula O6Glc' f.

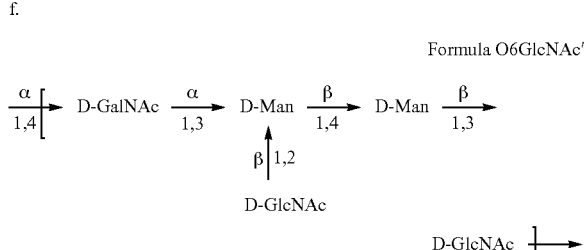

Formula O6GlcNAc' g.

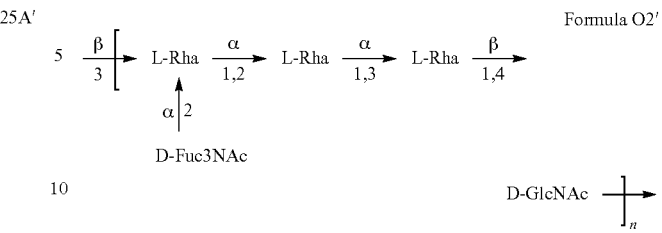

Formula O2'

In another specific embodiment, provided herein is a composition, e.g., a pharmaceutical composition, comprising (i) an O25 (e.g., O25A or O25B) macromolecule, or a bioconjugate comprising O25 (e.g., O25A or O25B) and (ii) an O1 macromolecule or a bioconjugate comprising O1. In a specific embodiment, said O25 macromolecule is an O25B macromolecule. In another specific embodiment, said O1 macromolecule is O1A. In another specific embodiment, said O1 macromolecule is O1B. In another specific embodiment, said O1 macromolecule is O1C.

In another specific embodiment, provided herein is a composition, e.g., a pharmaceutical composition, comprising (i) an O25 (e.g., O25A or O25B) macromolecule, or a bioconjugate comprising O25 (e.g., O25A or O25B) and (ii) an O2 macromolecule or a bioconjugate comprising O2. In a specific embodiment, said O25 macromolecule is an O25B macromolecule.

In another specific embodiment, provided herein is a composition, e.g., a pharmaceutical composition, comprising (i) an O25 (e.g., O25A or O25B) macromolecule, or a bioconjugate comprising O25 (e.g., O25A or O25B) and (ii) an O6 macromolecule (e.g., an O6 macromolecule comprising a branching Glc monosaccharide (O6Glc) or a branching GlcNAc monosaccharide(O6GlcNAc)) or a bioconjugate comprising O6. In a specific embodiment, said O25 macromolecule is an O25B macromolecule. In another specific embodiment, said O6 macromolecule is an O6 macromolecule comprising a branching Glc monosaccharide (O6Glc).

In another specific embodiment, provided herein is a composition, e.g., a pharmaceutical composition, comprising at least two of the following: (i) an O25 (e.g., O25A or O25B) macromolecule or a bioconjugate comprising O25 (e.g., O25A or O25B); (ii) an O1 macromolecule or a bioconjugate comprising O1; (iii) an O2 or a bioconjugate comprising O2; and/or (iv) an O6 macromolecule (e.g., a O6 macromolecule comprising a branching Glc monosaccharide or a branching GlcNAc monosaccharide) or a bioconjugate comprising O6. In a specific embodiment, said O25 macromolecule is an O25B macromolecule. In another specific embodiment, said O1 macromolecule is O1A. In another specific embodiment, said O1 macromolecule is O1B. In another specific embodiment, said O1 macromolecule is O1C. In another specific embodiment, said O6 macromolecule is an O6 macromolecule comprising a branching Glc monosaccharide (also referred to herein as O6Glc).

In another specific embodiment, provided herein is a composition, e.g., a pharmaceutical composition, comprising an O25B macromolecule, an O1A macromolecule, an O2 macromolecule, and an O6 macromolecule comprising a branching Glc monosaccharide. In certain embodiments, said macromolecules are conjugated to carrier proteins.

In another aspect, provided herein are methods of preventing infection of a subject, e.g., a human subject, by ExPEC, comprising administering to the subject a pharmaceutically effective amount of a composition (e.g., an immunogenic composition) described herein. See Section 5.7.

In another aspect, provided herein are methods of treating infection of a subject, e.g., a human subject, wherein the subject is infected with ExPEC, comprising administering to the subject a pharmaceutically effective amount of a composition (e.g., an immunogenic composition) described herein. See Section 5.7.

In another aspect, provided herein are methods of inducing an immune response against ExPEC in a subject, e.g., a human subject, comprising administering to the subject a pharmaceutically effective amount of a composition (e.g., an immunogenic composition) described herein. See Section 5.7.

In another aspect, provided herein are methods of inducing the production of opsonophagocytic antibodies against ExPEC in a subject, e.g., a human subject, comprising administering to the subject a pharmaceutically effective amount of a composition (e.g., an immunogenic composition) described herein. See Section 5.7.

Terms and Abbreviations

OPS: O polysaccharide; the O antigen of Gram-negative bacteria. OPS also are referred to herein as O antigen.

rfb cluster: a gene cluster (e.g., an $E.$ $coli$ gene cluster) that encodes enzymatic machinery capable of synthesis of an O antigen backbone structure. The term rfb cluster may apply to any O antigen biosynthetic cluster, including those from bacteria that do not belong to genus $Escherichia$.

waaL: the O antigen ligase gene encoding a membrane bound enzyme with an active site located in the periplasm. The encoded enzyme transfers undecaprenylphosphate (UPP)-bound O antigen to the lipid A core, forming lipopolysaccharide.

wecA: the first gene encoded in the wec cluster. The encoded protein catalyzes the transfer of a GlcNAc-phosphate from UDP-GlcNAc to UPP to form UPP-bound GlcNAc.

ECA: enterobacterial common antigen.

RU: repeat unit. As used herein, the RU is set equal to the Biological repeat unit, BRU. The BRU describes the RU of an O antigen as it is synthesized in vivo.

UPP: undecaprenylpyrophosphate.

LLO: lipid linked oligosaccharide.

2AB: 2 amino benzamide.

MS: mass spectroscopy.

O25B: the term O25B refers to the O25B antigen from $E.$ $coli$ identified herein (a subserotype of $E.$ $coli$ serotype O25). Reference to O25B herein encompasses the formula O25B and the formula O25B', both identified above.

O25A: the term O25A refers to the O25A antigen of $E.$ $coli$ (a subserotype of $E.$ $coli$ serotype O25). Reference to O25A herein encompasses the formula O25A and the formula O25A', both identified above.

O1A: the term O1A refers to the O1A antigen of $E.$ $coli$ (a subserotype of $E.$ $coli$ serotype O1). Reference to O1A herein encompasses the formula O1A and the formula O1A', both identified above.

O1B: the term O1B refers to the O1B antigen of $E.$ $coli$ (a subserotype of $E.$ $coli$ serotype O1). Reference to O1B herein encompasses the formula O1B and the formula O1B', both identified above.

O1C: the term O1C refers to the O1C antigen of $E.$ $coli$ (a subserotype of $E.$ $coli$ serotype O1). Reference to O1C herein encompasses the formula O1C and the formula O1C', both identified above.

O2: the term O2 refers to the O2 antigen of $E.$ $coli$ ($E.$ $coli$ serotype O2). Reference to O2 herein encompasses the formula O2 and the formula O2', both identified above.

O6: the term O6 refers to the O6 antigen of $E.$ $coli$ ($E.$ $coli$ serotype O6). Reference to O6 herein encompasses the formula O6 and the formula O6', both identified above.

Bioconjugate: the term bioconjugate refers to conjugate between a protein (e.g., a carrier protein) and an antigen, e.g., an O antigen (e.g., O25B) prepared in a host cell background, wherein host cell machinery links the antigen to the protein (e.g., N-links). Glycoconjugates include bioconjugates, as well as sugar antigen (e.g., oligo- and polysaccharides)-protein conjugates prepared by other means, e.g., by chemical linkage of the protein and sugar antigen.

The term "about," when used in conjunction with a number, refers to any number within ±1, ±5 or ±10% of the referenced number.

As used herein, the term "effective amount," in the context of administering a therapy (e.g., a composition described herein) to a subject refers to the amount of a therapy which has a prophylactic and/or therapeutic effect(s). In certain embodiments, an "effective amount" refers to the amount of a therapy which is sufficient to achieve one, two, three, four, or more of the following effects: (i) reduce or ameliorate the severity of an ExPEC infection or symptom associated therewith; (ii) reduce the duration of an ExPEC infection or symptom associated therewith; (iii) prevent the progression of an ExPEC infection or symptom associated therewith; (iv) cause regression of an ExPEC infection or symptom associated therewith; (v) prevent the development or onset of an ExPEC infection, or symptom associated therewith; (vi) prevent the recurrence of an ExPEC infection or symptom associated therewith; (vii) reduce organ failure associated with an ExPEC infection; (viii) reduce hospitalization of a subject having an ExPEC infection; (ix) reduce hospitalization length of a subject having an ExPEC infection; (x) increase the survival of a subject with an ExPEC infection; (xi) eliminate an ExPEC infection in a subject; (xii) inhibit or reduce ExPEC replication in a subject; and/or (xiii) enhance or improve the prophylactic or therapeutic effect(s) of another therapy.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "subject" refers to an animal (e.g., birds, reptiles, and mammals). In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet (e.g., a dog, cat, horse, goat, sheep, pig, donkey, or chicken). In another embodiment, a subject is a human. In another embodiment, a subject is a human infant.

In another embodiment, a subject is a human child. In another embodiment, a subject is a human adult. In another embodiment, a subject is an elderly human. In another embodiment, a subject is a premature human infant. The terms "subject" and "patient" may be used herein interchangeably.

As used herein, the term "premature human infant" refers to a human infant born at less than 37 weeks of gestational age.

As used herein, the term "human infant" refers to a newborn to 1 year old human.

As used herein, the term "human toddler" refers to a human that is 1 years to 3 years old.

As used herein, the term "human child" refers to a human that is 1 year to 18 years old.

As used herein, the term "human adult" refers to a human that is 18 years or older.

As used herein, the term "elderly human" refers to a human 65 years or older.

4. BRIEF DESCRIPTION OF THE FIGURES

FIG. 1: Pathway for O25A biosynthesis. Arrows indicate individual enzymatic conversions, enzyme names are indicated. Nucleotide activated sugars are prepared in the cytoplasm either by enzymes provided in the O antigen cluster or by housekeeping enzymes of the Gram-negative host cell. A glycosylphosphate transferase (WecA) adds D-GlcNAc phosphate to undecaprenyl phosphate (UP), forming GlcNAc-UPP. Specific glycosyltransferases then elongate the UPP-GlcNAc molecule further by adding monosaccharides forming the biological repeat unit (BRU) oligosaccharide (WekABC WbuB). The indicated order of enzymes does not refer to the sequence of events during BRU synthesis (indicated by < >). The BRU is then flipped into the periplasmic space by Wzx. Wzy linearly polymerizes periplasmic BRU's to form the O antigen polysaccharide. Polymer length is controlled by Wzz. Many bacterial oligo- and polysaccharides are assembled on UPP and then transferred to other molecules, i.e., UPP is a general building platform for oligo- and polysaccharide in bacteria. In *E. coli*, and most other gram negative bacteria, the O antigen is transferred from UPP to lipid A core by the *E. coli* enzyme WaaL to form lipopolysaccharide (LP S).

FIGS. 2A and 2B: rfb cluster, structure, and pathway for wzx/wzy-dependent O-antigen synthesis, exemplified by the *E. coli* O25A rfb cluster and O antigen. FIG. 2A. Shown is the rfb cluster structure of *E. coli* strain E47a, located between the galF and gnd genes. Genes are shown as arrows and filling is indicated according to the function of the gene products: black are genes for nucleotide-activated monosaccharide biosynthesis which are not part of the housekeeping repertoire of *E. coli* (those are encoded elsewhere in the genome), black/white diagonal stripes are glycosyltransferases responsible for adding single monosaccharide units to the BRUs, flippase wzx and polymerase wzy. FIG. 2B. Chemical structure of the BRU of the O25A O antigen as presented (see Fundin et al., 2003, Magnetic Resonance in Chemistry 41, 4).

Figure 3A:
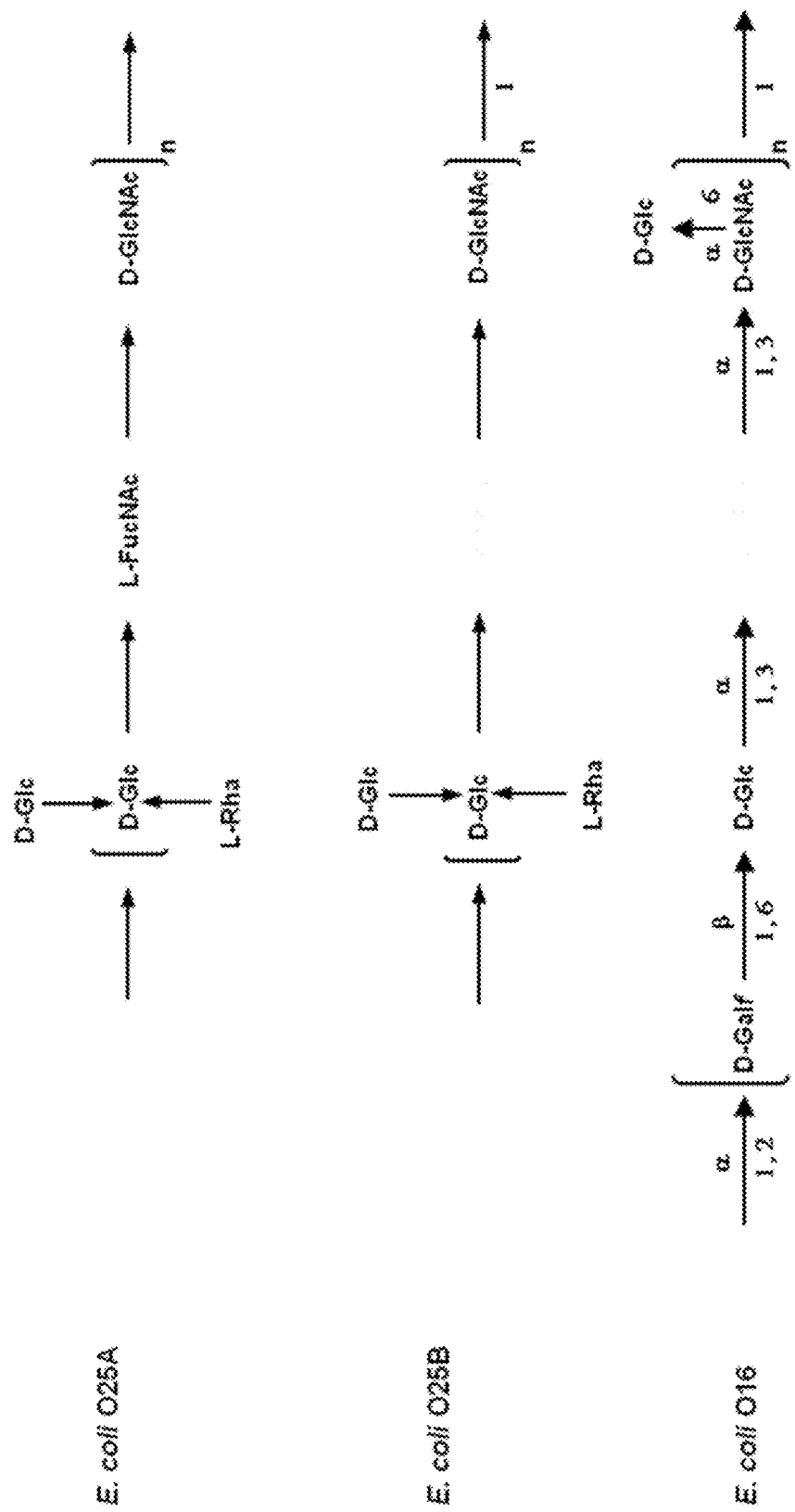
Figure 3B:
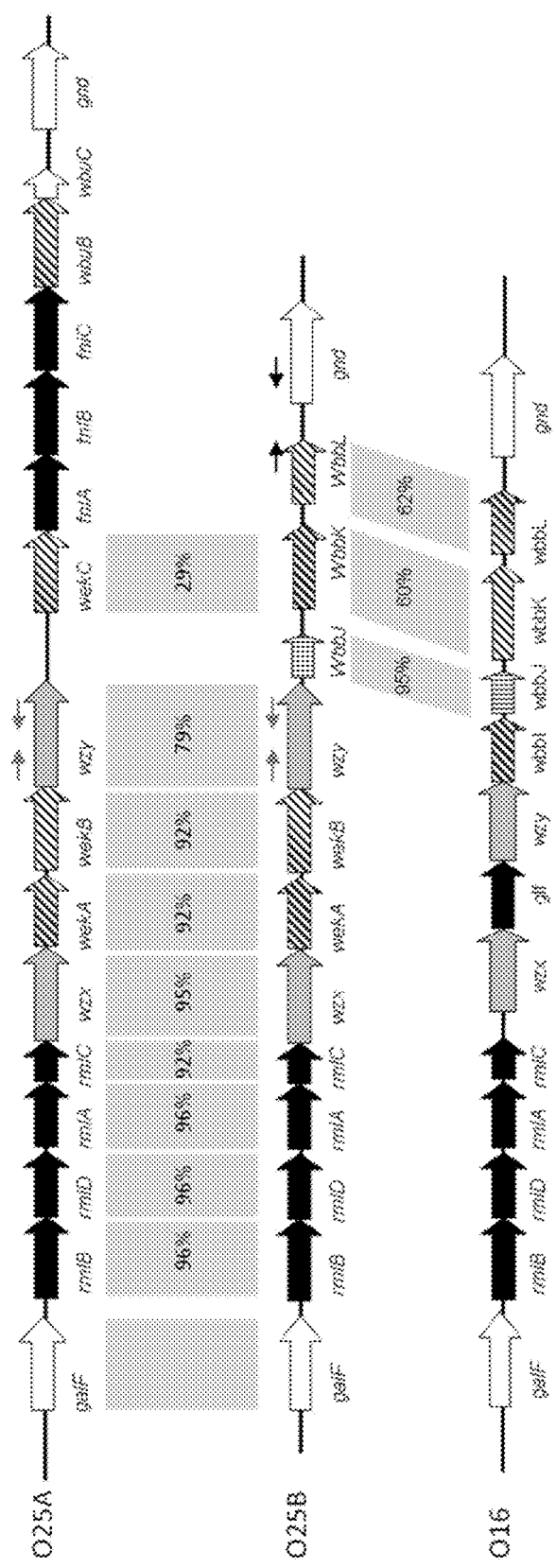

FIG. 3A: O25A, O25B, and O16 BRU structures. FIG. 3B: O antigen biosynthesis cluster (rfb cluster) comparison between O25A, O25B, and O16. Black filled genes are genes involved in nucleotide activated monosaccharide biosynthesis, diagonal stripes are predicted glycosyltransferase genes, grey filling indicates BRU processing or transportation genes, and vertical stripes show O-acetyltransferase homologies. Grey boxes indicate homology scores above 25% between the genes; detailed values are indicated. Thin black and grey arrows show annealing locations of typing PCR oligonucleotides for wzy (O25A and O25B specific) and the O25B 3' region (O25B specific).

Figure 4:
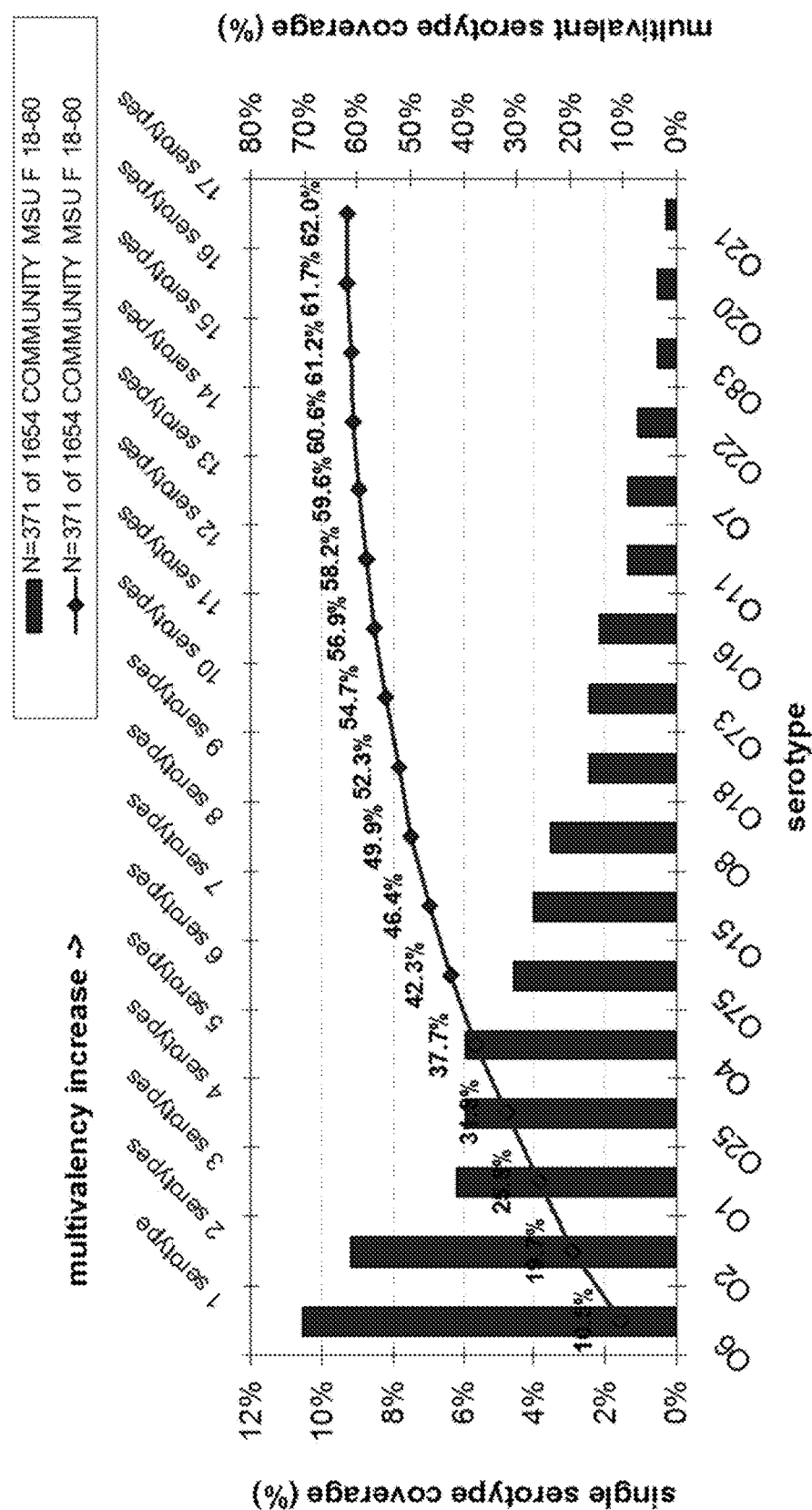
Figures 5A, 5B:
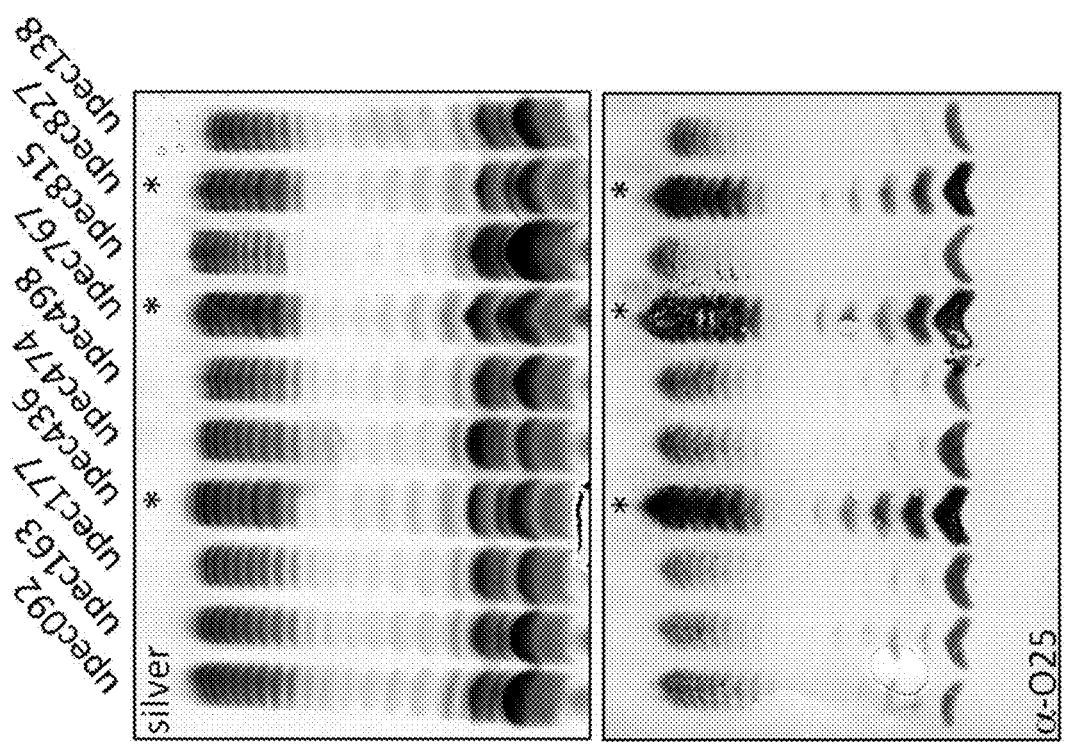

FIG. 4: Serotype distribution from the epidemiology study. *E. coli* O antigen serotypes identified in samples of community acquired UTI specimens were grouped according to occurrence FIGS. 5A and 5B: Silver and Western stain analysis of LPS from clinical isolates with an O25 positive agglutination phenotype. Strain numbers are indicated above the gel lanes. Individual clones were grown and OD normalized biomass was harvested by centrifugation. Pellets were dissolved in SDS PAGE Lämmli buffer and treated with proteinase K to hydrolyze all proteins in the sample. Standard silver staining was applied to the PAGE gel shown in FIG. 5A, and probing of nitrocellulose membranes containing electrotransferred material from identically run gels with commercial O25 agglutination antiserum is shown in FIG. 5B.

Figure 6:
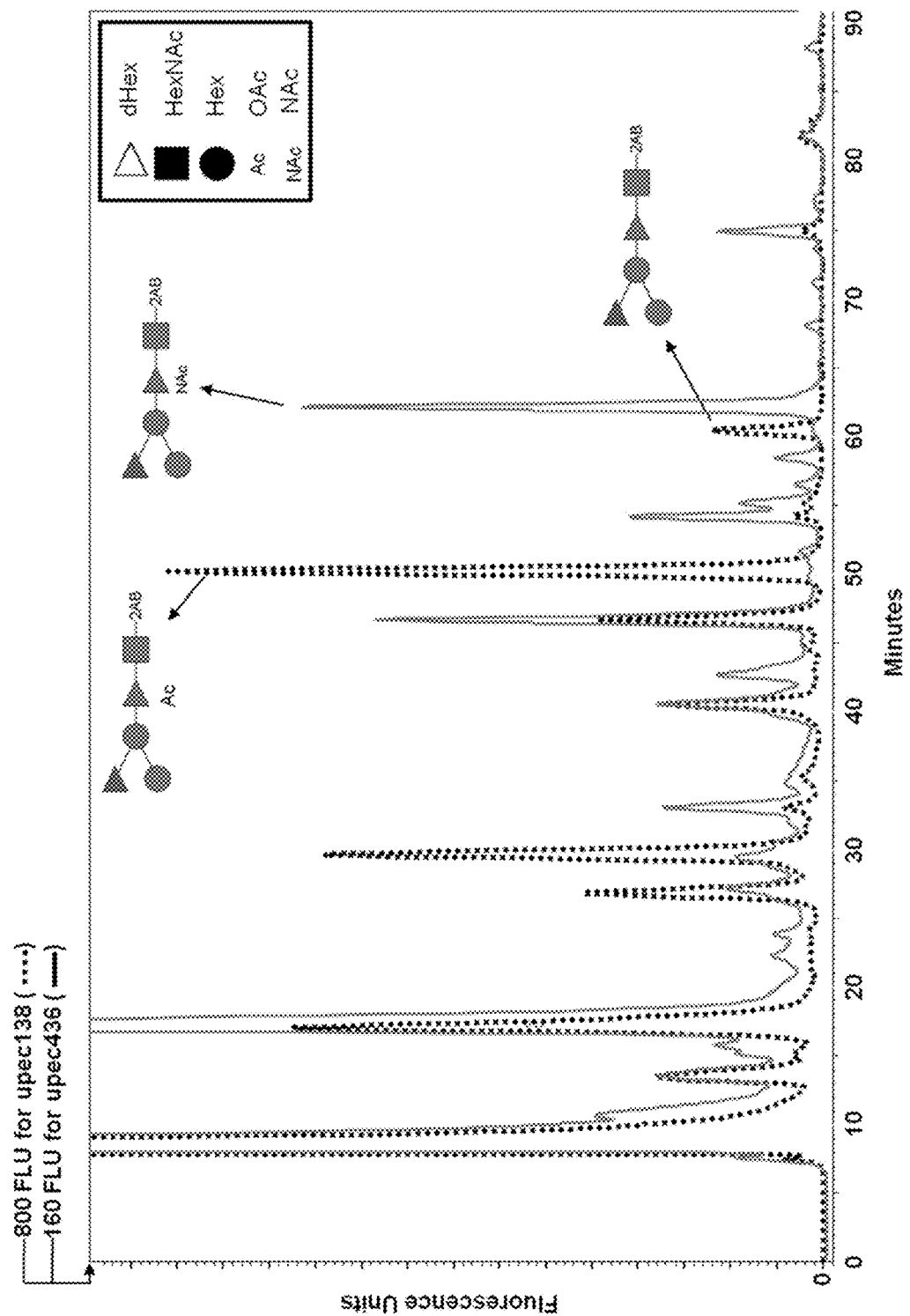

FIG. 6: 2AB HPLC traces of O25A and O25B samples. 2AB labeled LLO samples from strains upec138 (dotted line) and upec436 (solid line) were prepared. Peaks were collected and corresponding BRU structures deduced from the MS/MS fragmentation pattern detailed in FIG. 7 are indicated by arrows.

Figure 7A:
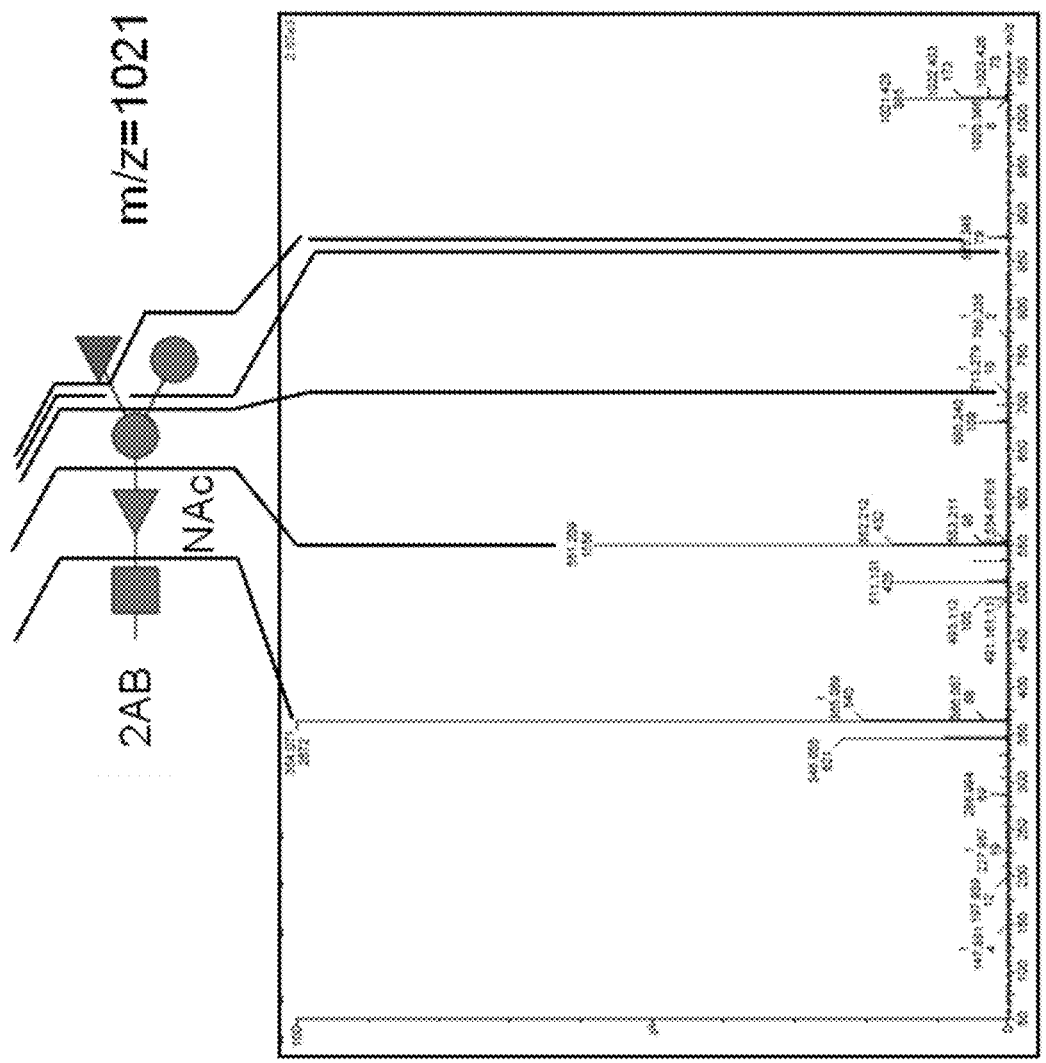
Figure 7B:
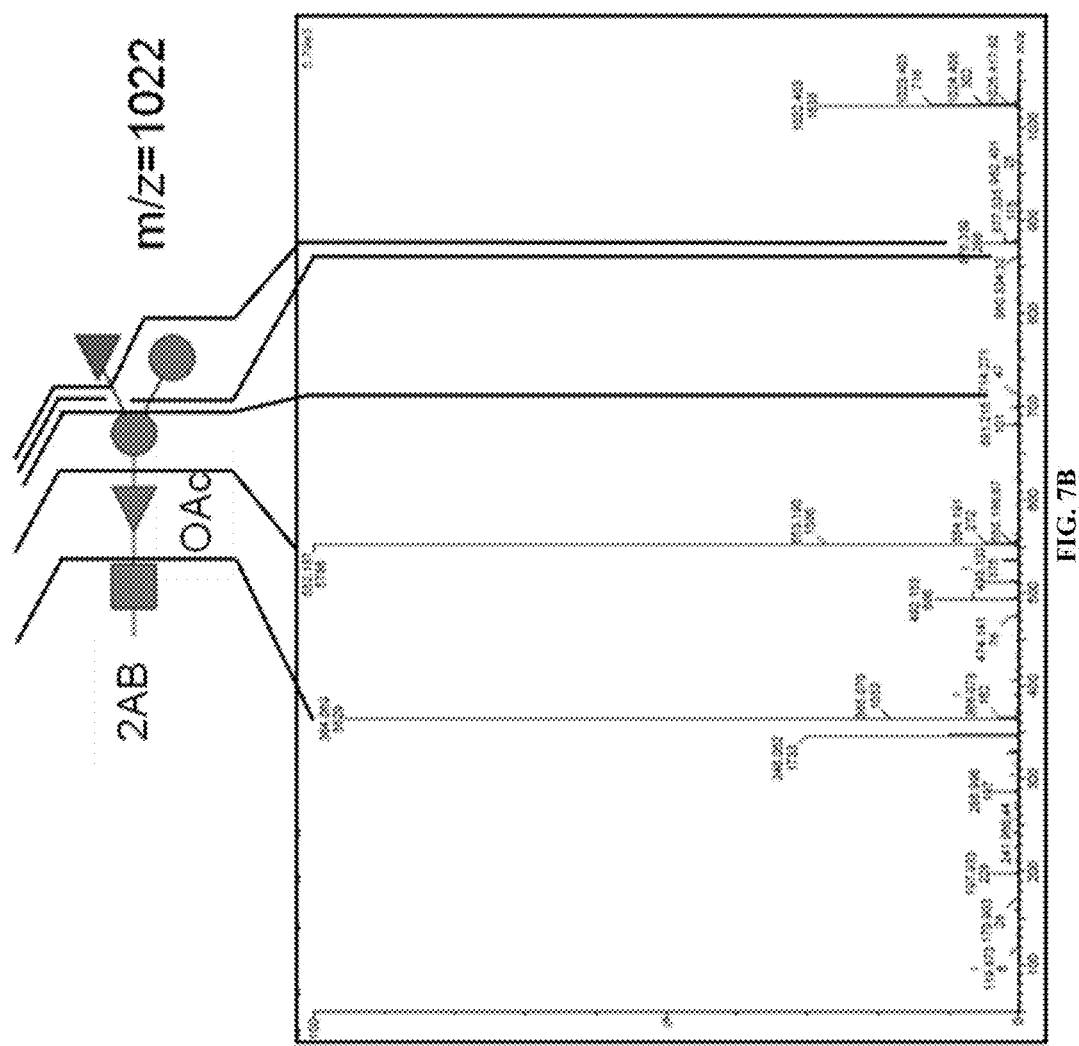

FIGS. 7A and 7B: MS/MS fragmentation ion series obtained from peaks indicated in FIG. 6 at 50' and 62' elution times of mother ions m/z=1022 (FIG. 7A; from strain upec138) or m/z=1021 (FIG. 7B; from upec_436). Ion series are shown in relation to the cartoon of the putative BRU.

Figure 8:
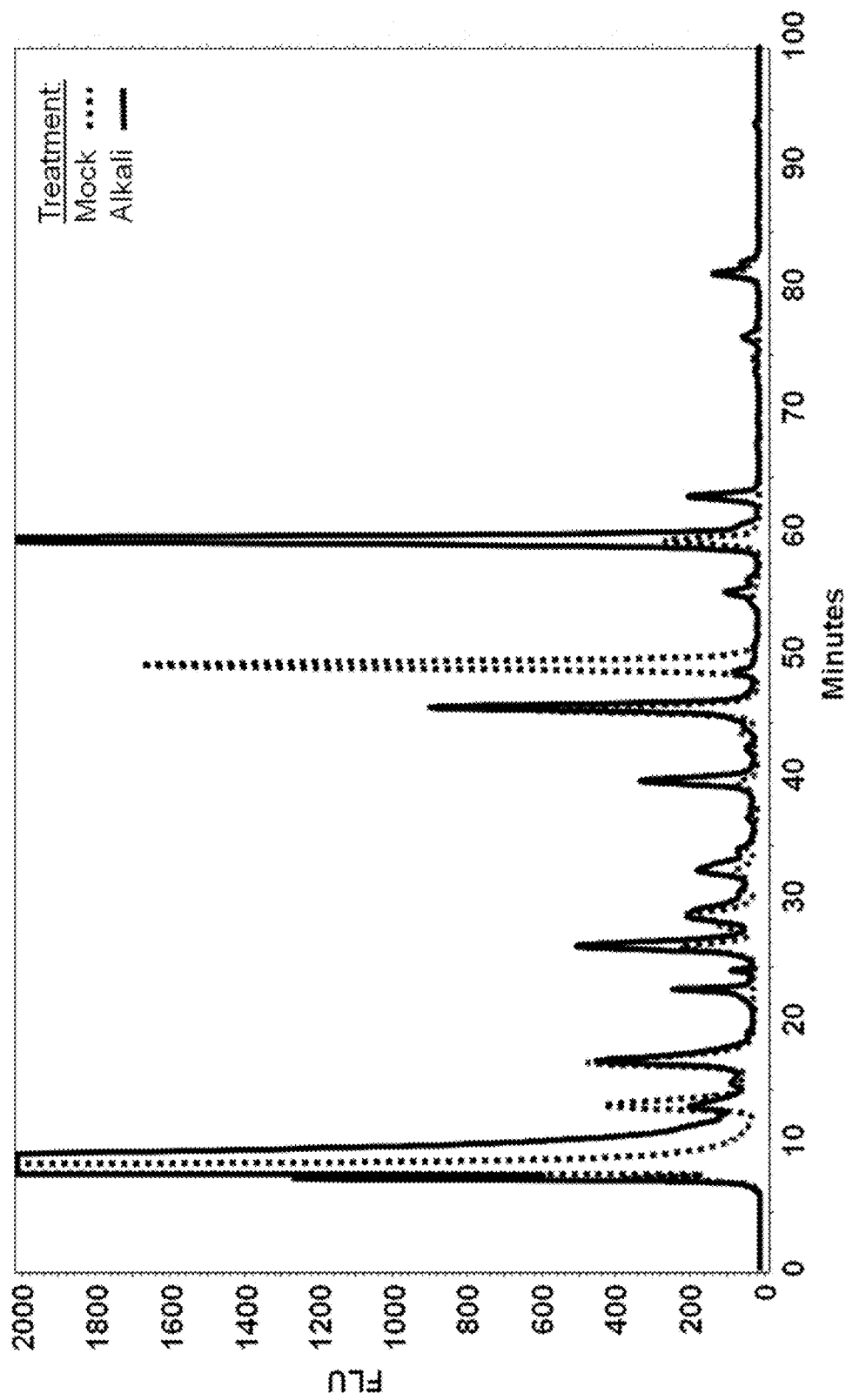

FIG. 8: Deacetylation of 2AB labeled LLO sample derived from an O25B positive clinical isolate. The O25B specific peak at 50' elution time obtained from 2AB labeled LLOs of a clinical isolate with the O25B genotype was collected, and analyzed by normal phase HPLC after treatment with (solid line) or without (dotted line) NaOH for hydrolysis of ND Cal's Special Patent Program O-acetyl groups.

Figure 9:
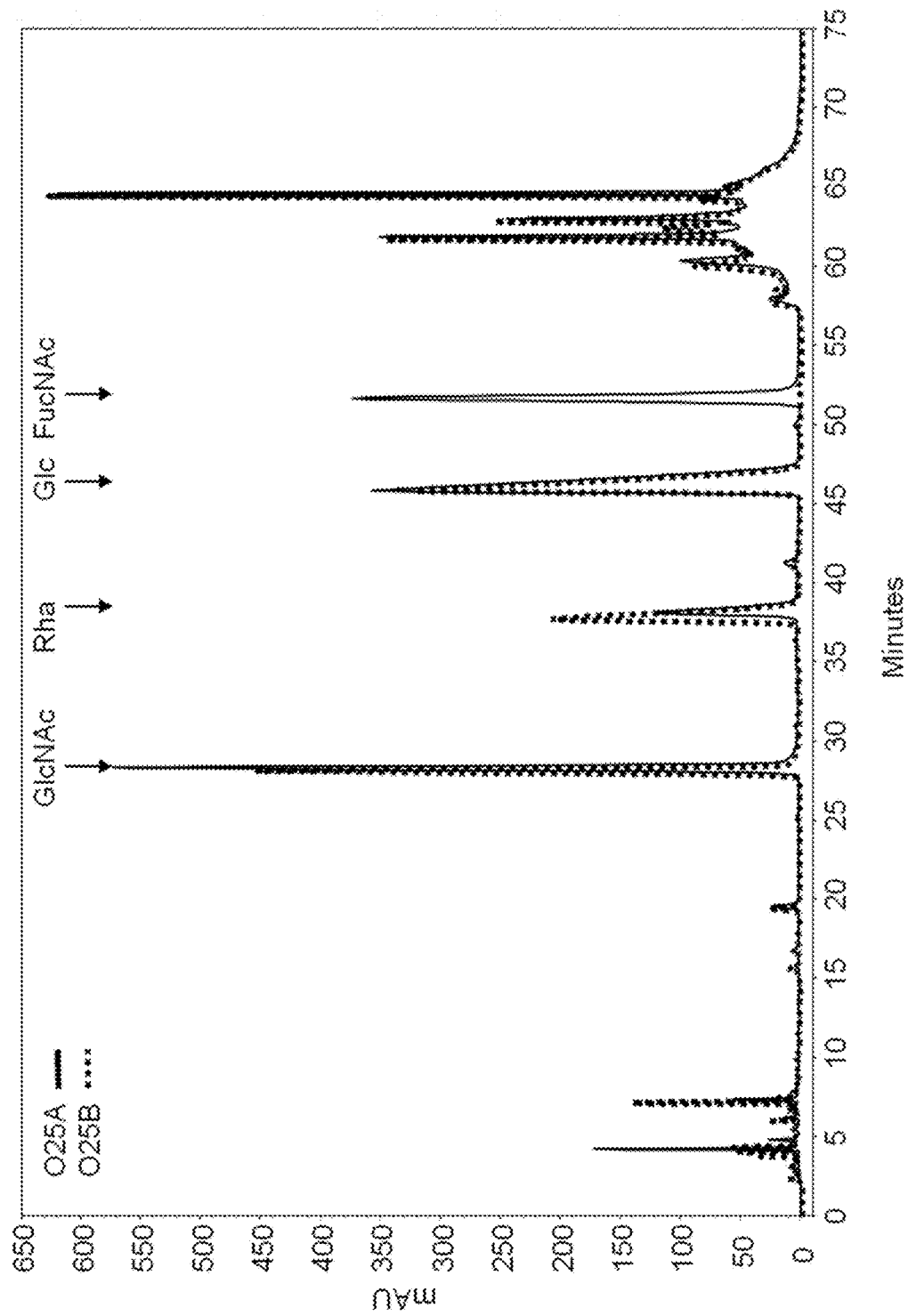

FIG. 9: Monosaccharide composition analysis of O25A and O25B bioconjugates. O25 bioconjugates were produced, purified, and processed for monosaccharide composition analysis. C18 HPLC traces of samples are shown. O25A (solid) and O25B (dotted) derived samples are compared to a mix of monosaccharides from commercial sources (Glc, GlcNAc, Rha, FucNAc). The elution times of the monosaccharides are indicated by arrows.

Figure 10:
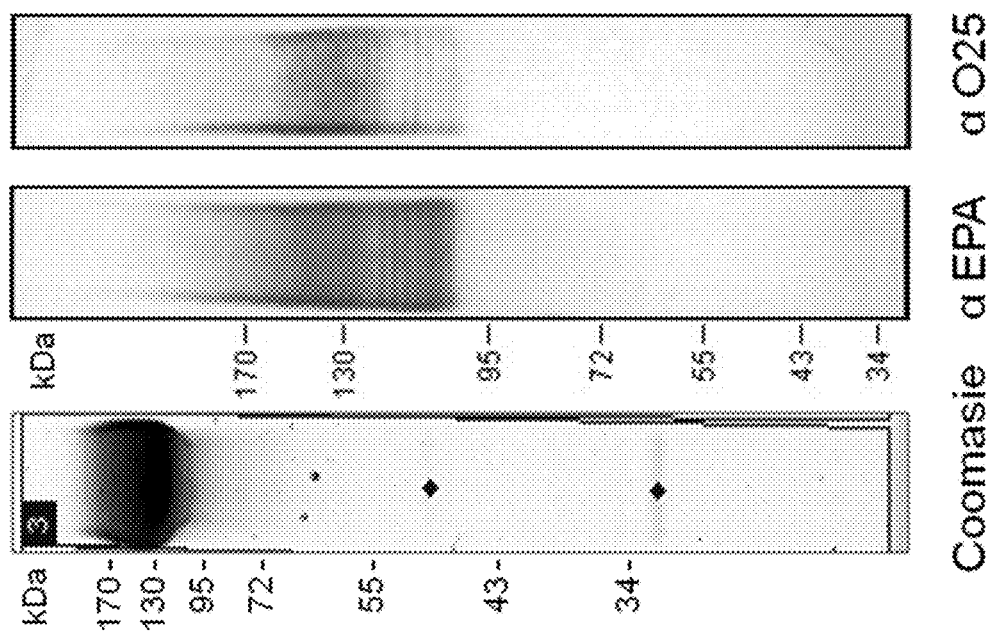

FIG. 10: Characterization of O25A bioconjugates. Purified final bulk of 4S-EPA-O25A bioconjugates was analyzed by SDS PAGE and visualized by direct Coomassie staining (C) and Western blotting using either anti-EPA antiserum or anti-O25 antiserum.

Figure 11:
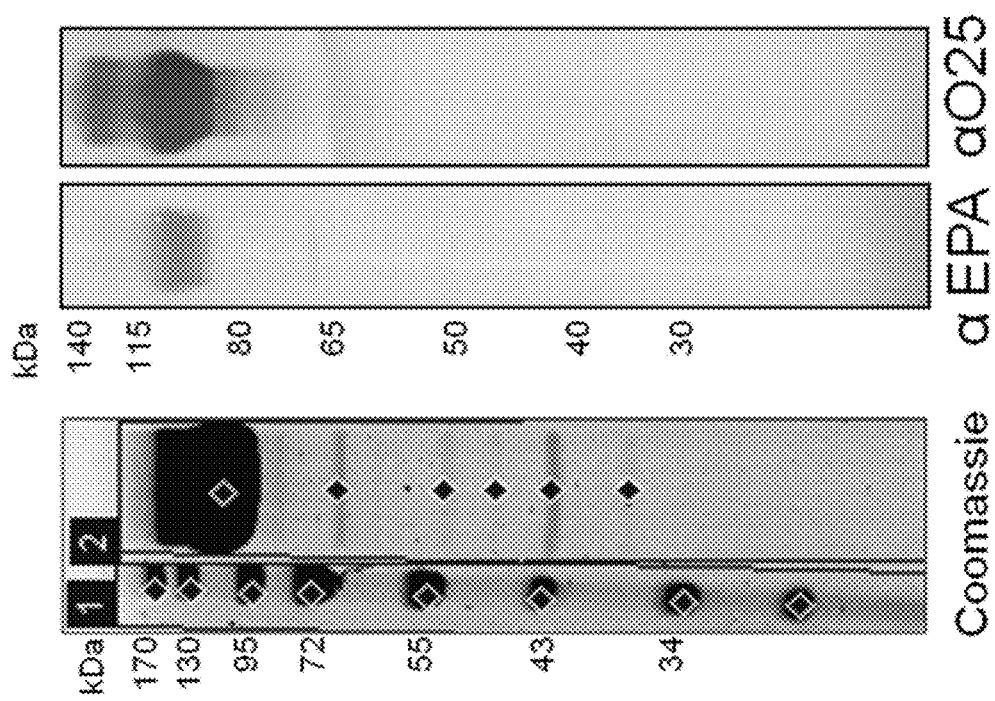

FIG. 11: Characterization of O25B bioconjugates. Purified final bulk of 4S-EPA-O25B bioconjugates was analyzed by SDS PAGE and visualized by direct Coomassie staining (C) and Western blotting using either anti-EPA antiserum or anti-O25 antiserum.

Figures 12A, 12B:
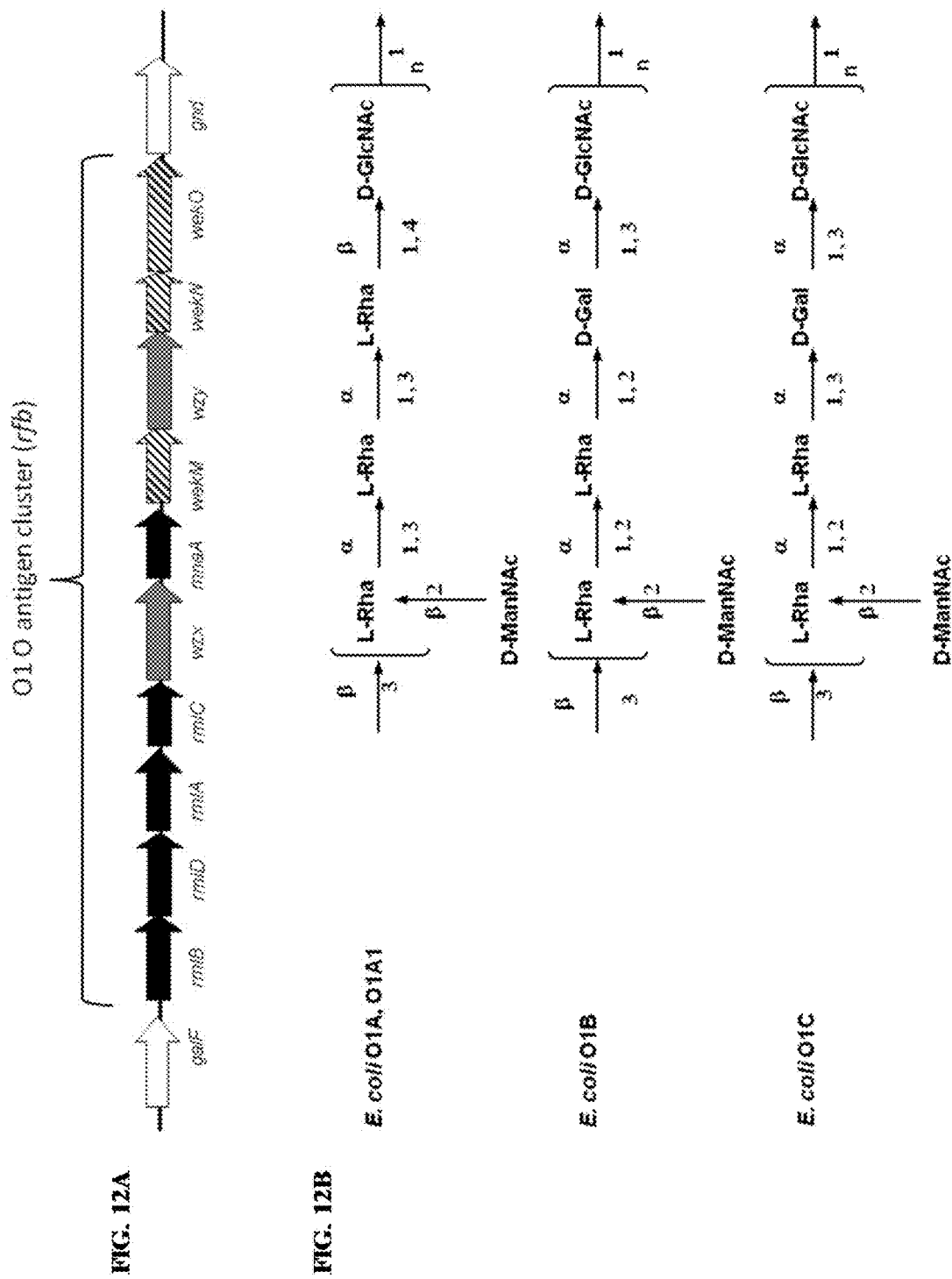

FIGS. 12A and 12B: O1 O antigen genetic biosynthesis and chemical structure. FIG. 12A. The rfb cluster and flanking genes of the O1A strain *E. coli* G1632 (ACCESSION NO. GU299791) is shown. Black, grey and striped color codes are the same as those for FIG. 2, described above. FIG. 12B. Chemical BRU structures of O1 subserotypes are shown.

Figures 13A, 13B:
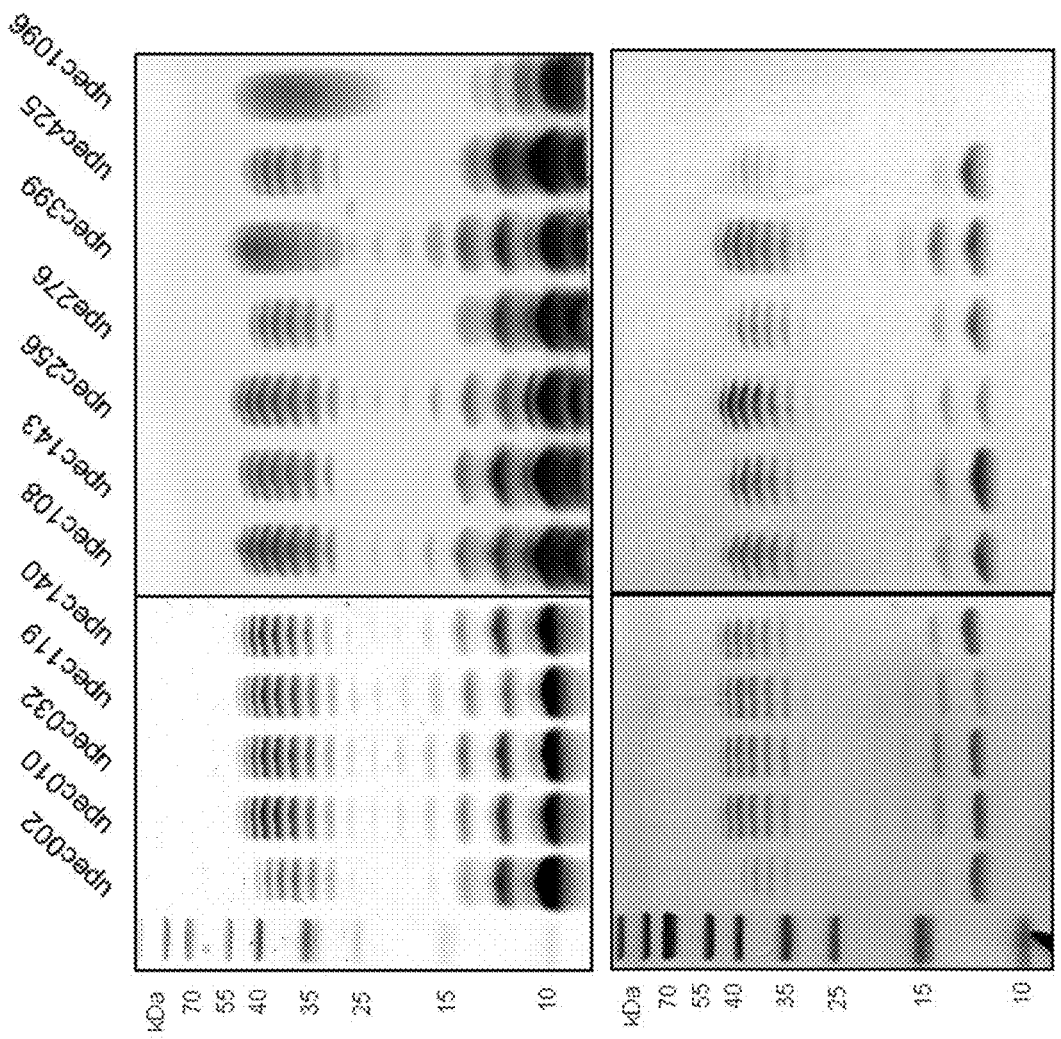

FIGS. 13A and 13B: Analysis of LPS from clinical isolates with an O1 positive agglutination phenotype. FIG. 13A. Silver staining and FIG. 13B. Western blotting using anti-O1 antiserum.

Figure 14A:
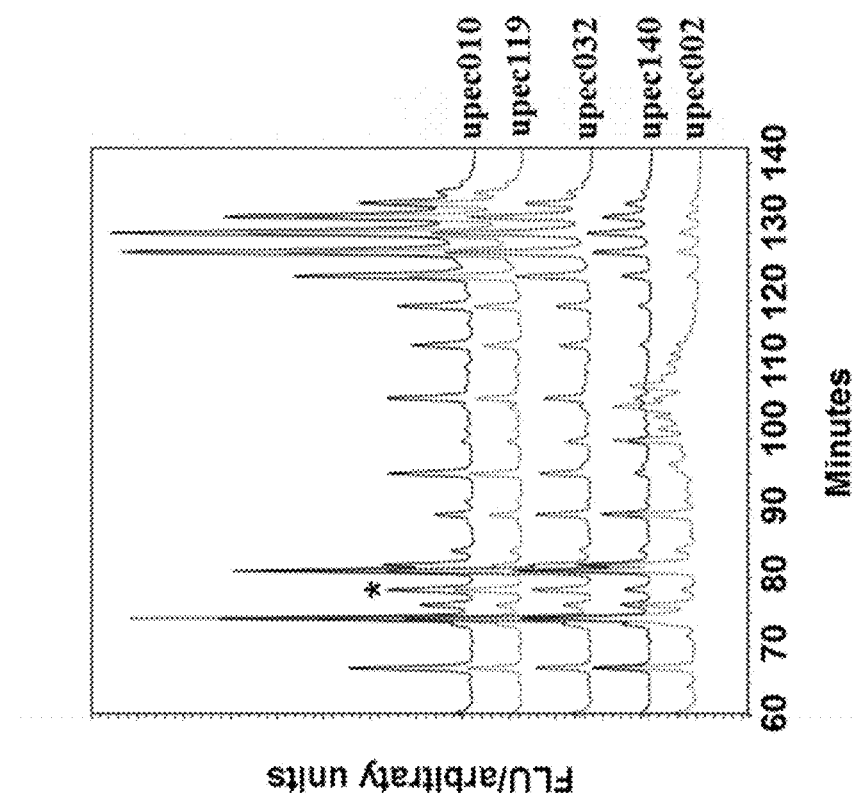
Figure 14B:
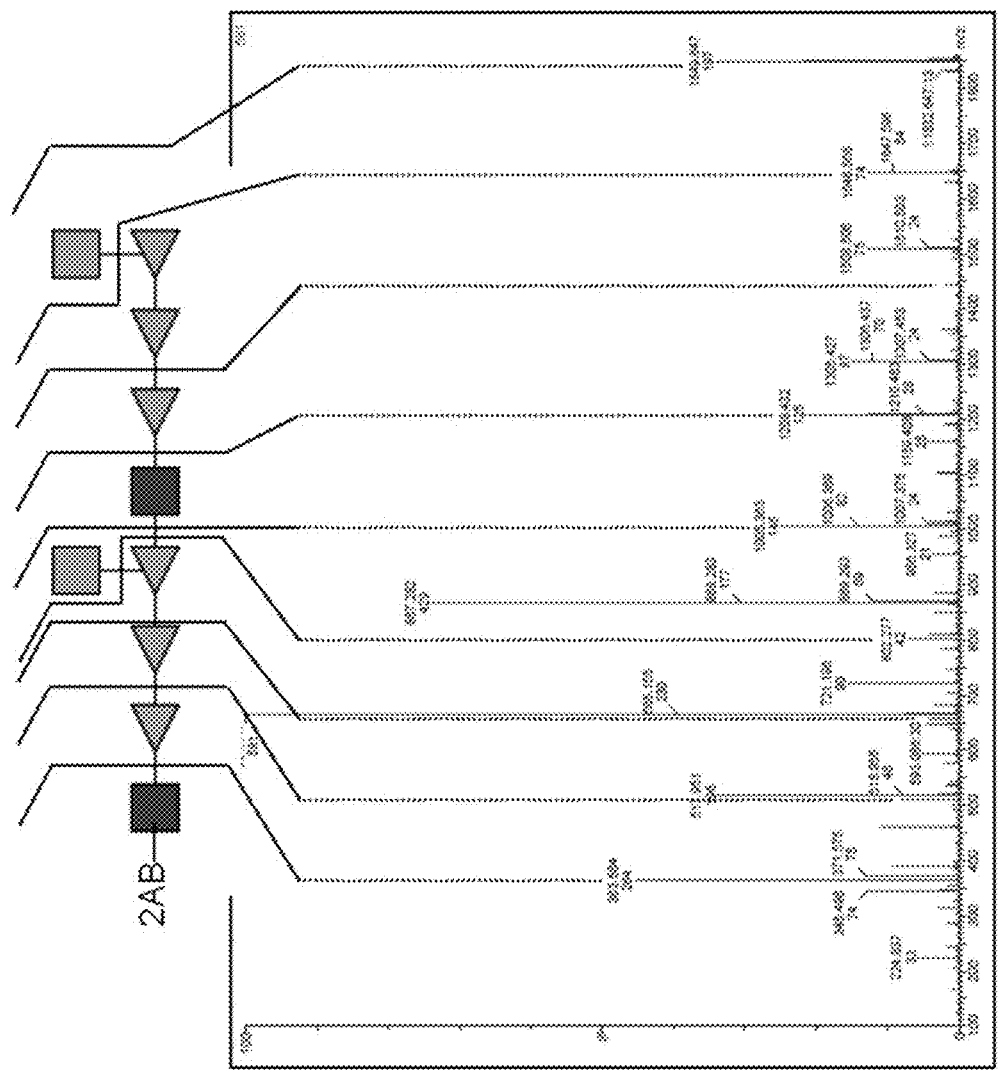

FIGS. 14A and 14B: Identification of O1A in O1 clinical isolates. 2AB labeled LLO samples from O1 clinical isolates were analyzed by LLO fingerprinting. FIG. 14A. Normal phase HPLC traces from 60' onwards are shown. The baseline for every sample was shifted to visualize co-migrating peaks. The upec number indicates the clinical strain. FIG. 14B. MS/MS fragmentation ion series of m/z=1849.6 (Na+ adduct). The cartoon assigns the fragmentation ion pattern and probable glycosidic bond breakages in an oligosaccharide of 2 BRU of O1A.

Figure 15:
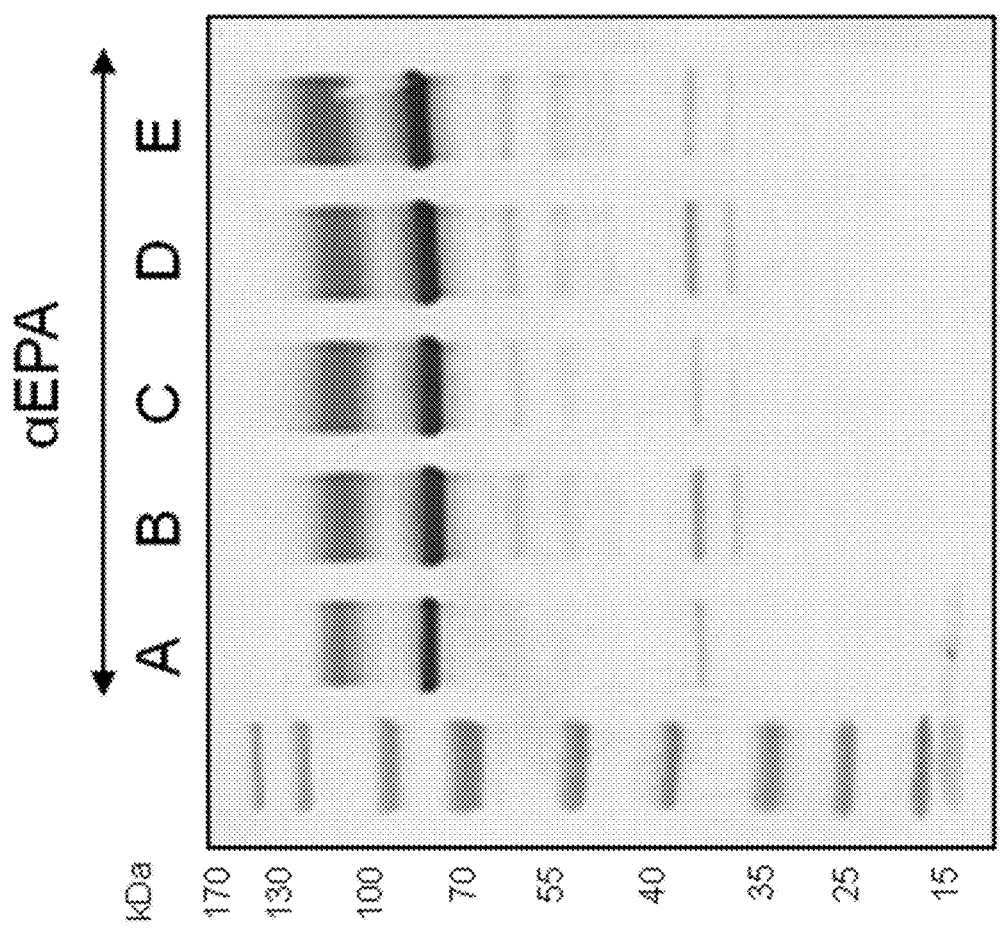

FIG. 15: O1 bioconjugates. Small scale expression test of EPA-O1 glycoprotein by $E.$ $coli$ cells (W3110 ΔrfbO16::rfbO1 ΔwaaL) transformed with an EPA expression plasmid (pGVXN659) and five different pglB expression plasmids: A, p114: expression of non-codon optimized, HA tag containing pglB; B, p939: codon optimized, HA tag containing pglB; C, p970: codon optimized, HA tag removed pglB; D, codon optimized, HA tag containing, natural glycosylation site N534Q removed pglB; and E, codon optimized, HA tag removed, natural glycosylation site N534Q removed pglB. Cells were grown and induced with arabinose and IPTG, after overnight incubation at 37° C., cells were harvested and periplasmic protein extracts were prepared. Extracts were then separated by SDS PAGE, transferred to nitrocellulose membranes by electroblotting, and immunodetected using an anti-EPA serum.

Figure 16:
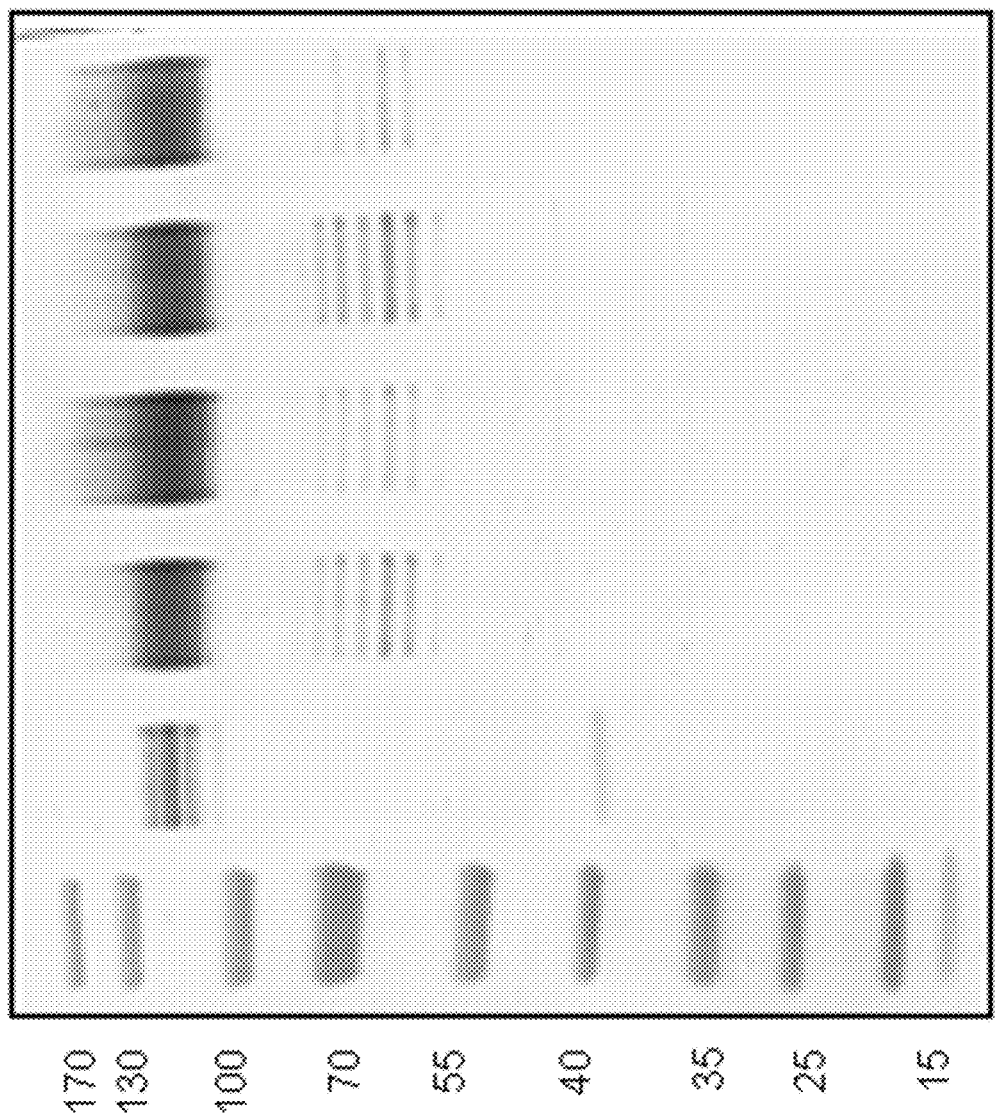

FIG. 16: The bioconjugates described in FIG. 15, detected with anti-O1 serum.

Figure 17A:
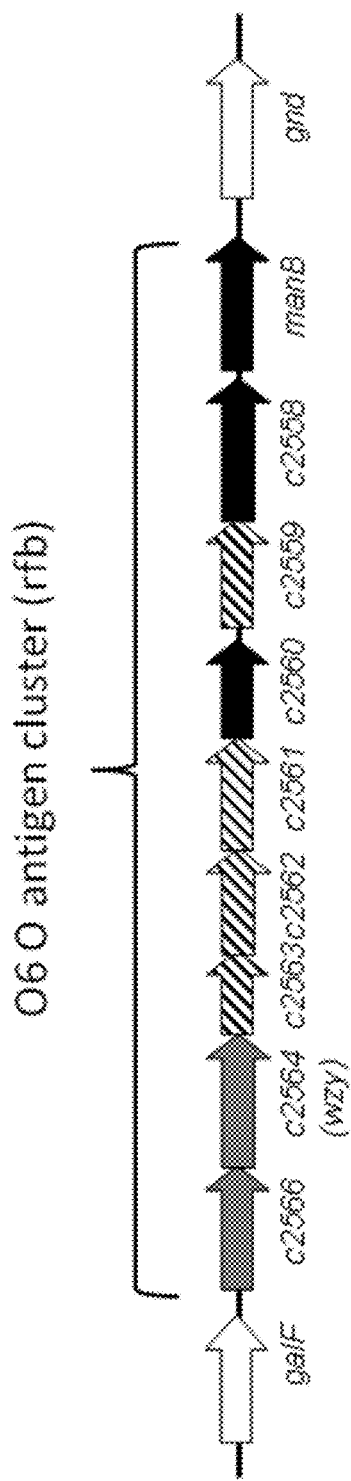
Figure 17B:
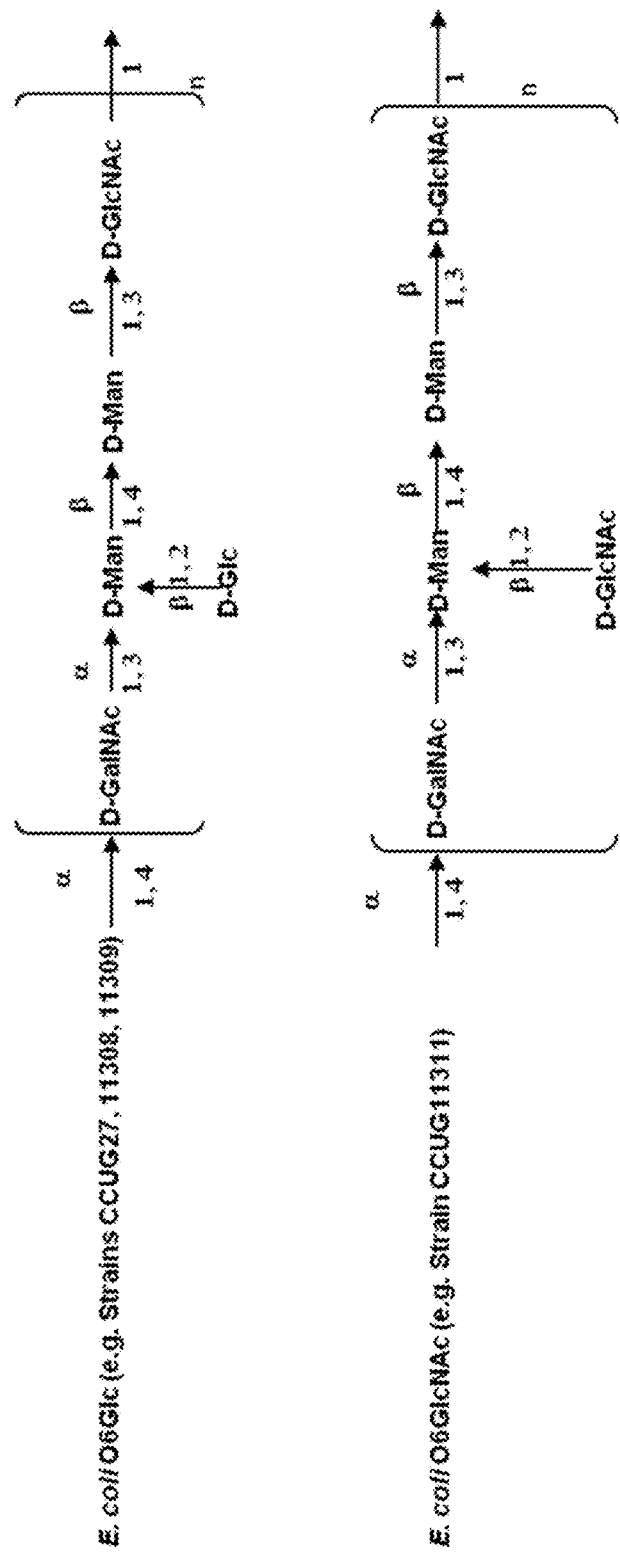

FIGS. 17A and 17B: O6 genetic and chemical structures. FIG. 17A. O antigen biosynthesis cluster (rfb cluster) and flanking genes of $E.$ $coli$ CFT073 (Genbank AE014075.1). Putative gene functions according to BLAST are indicated and genes specific for O6 O antigen biosynthesis are indicated. FIG. 17B. Chemical structures of reported O6 BRU structures (Jann et al., Carbohydr. Res. 263 (1994) 217-225).

Figure 18A:
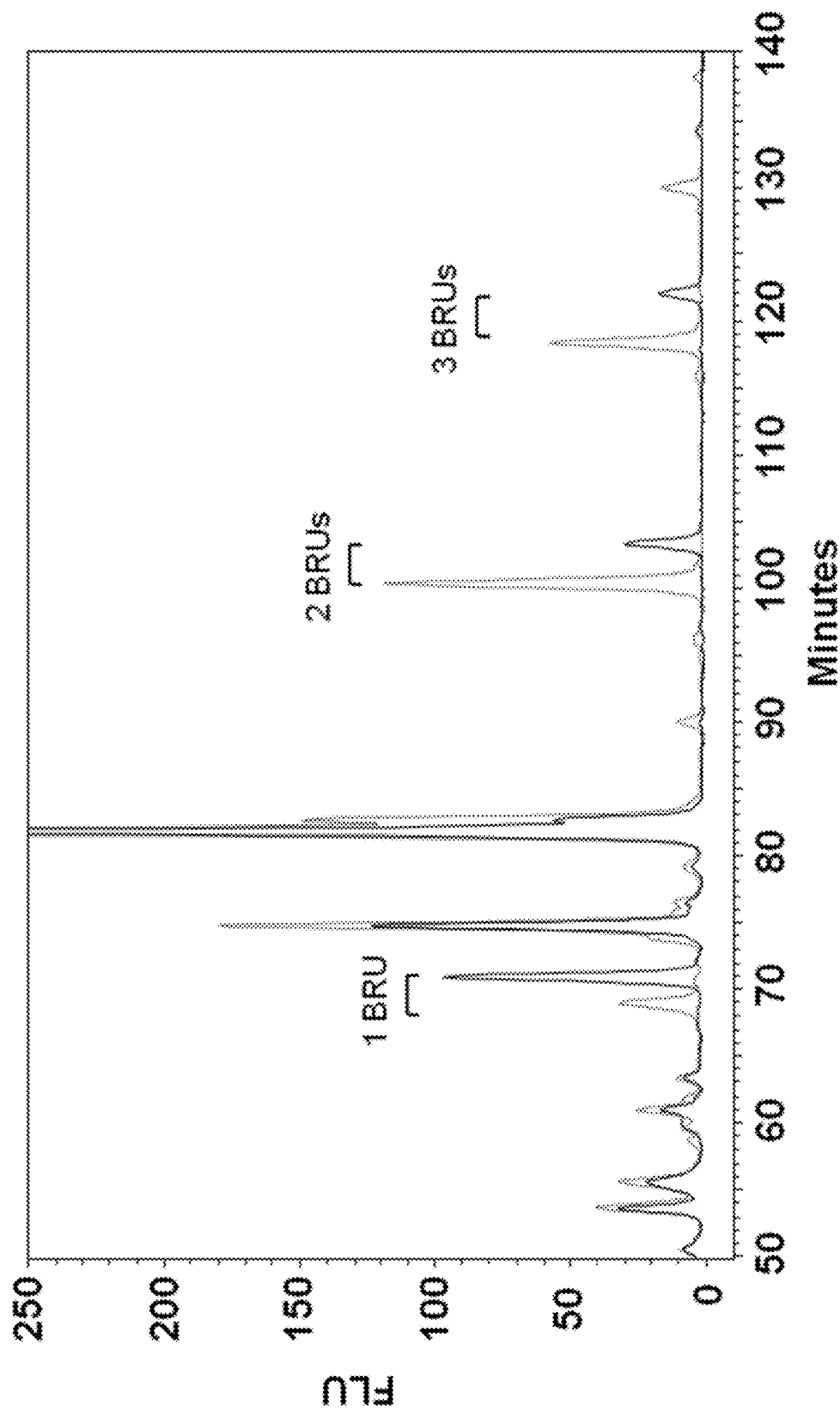
Figure 18B:
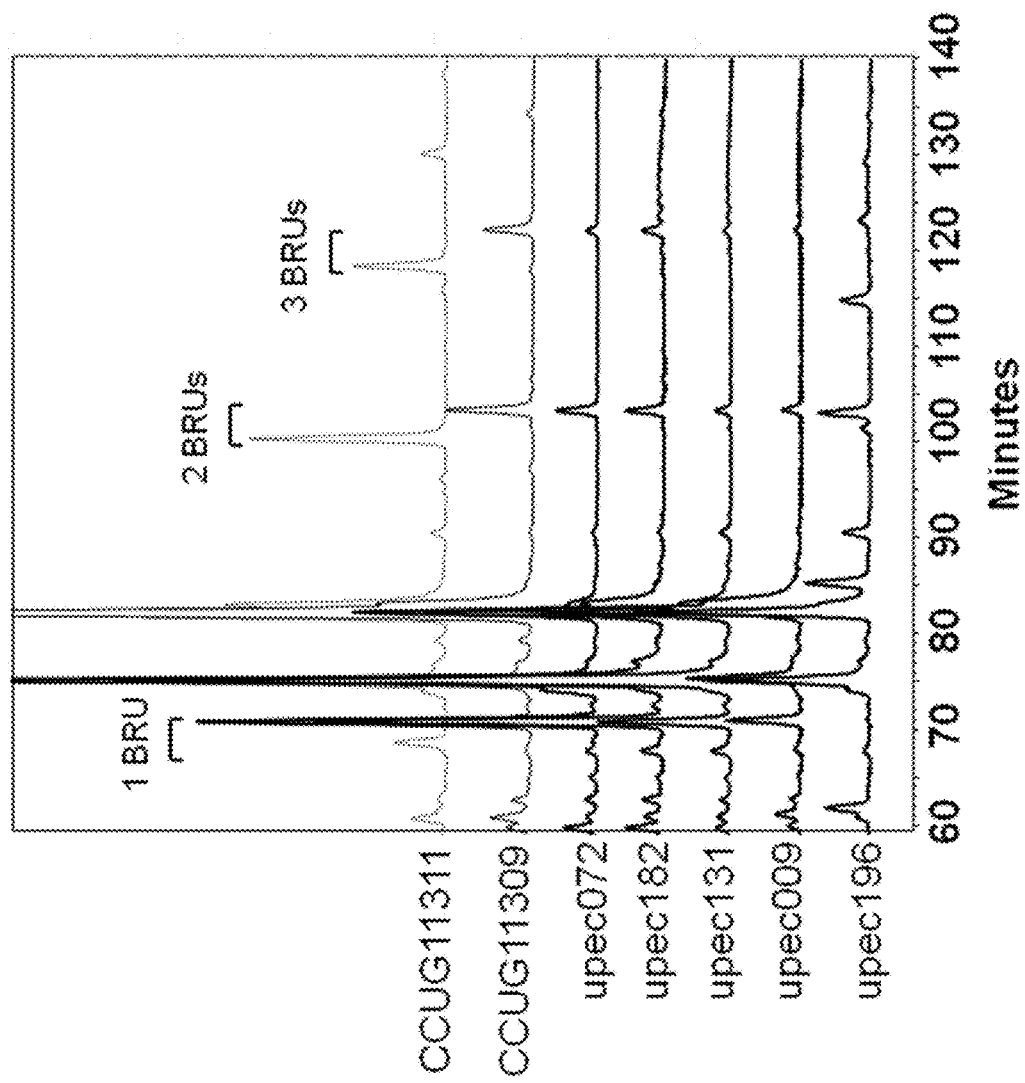

FIGS. 18A and 18B: Identification of O6 with branching Glc. 2AB labeled LLO samples from O6 clinical isolates were analyzed by LLO fingerprinting. FIG. 18A. Normal phase HPLC traces from 60' onwards are shown. Extracts were prepared from reference strains CCUG11309 (thin solid line) and 11311 (dashed) containing Glc and GlcNAC branches. The overlay shows clear differences in elution times of the indicated BRUs. FIG. 18B. Extracts from clinical isolates as indicated by upec number are compared to the reference strains from A.

FIGS. 19A and 19B: O2 O antigen genetic biosynthesis and chemical structures. FIG. 19A. O antigen biosynthesis cluster (rfb cluster) and flanking genes of strain $E.$ $coli$ G1674 (accession No. GU299792). Black, grey, and striped color codes are as described in previous figures (e.g., FIG. 2). FIG. 19B. Chemical BRU structure of O2 antigen.

Figures 20A, 20B:
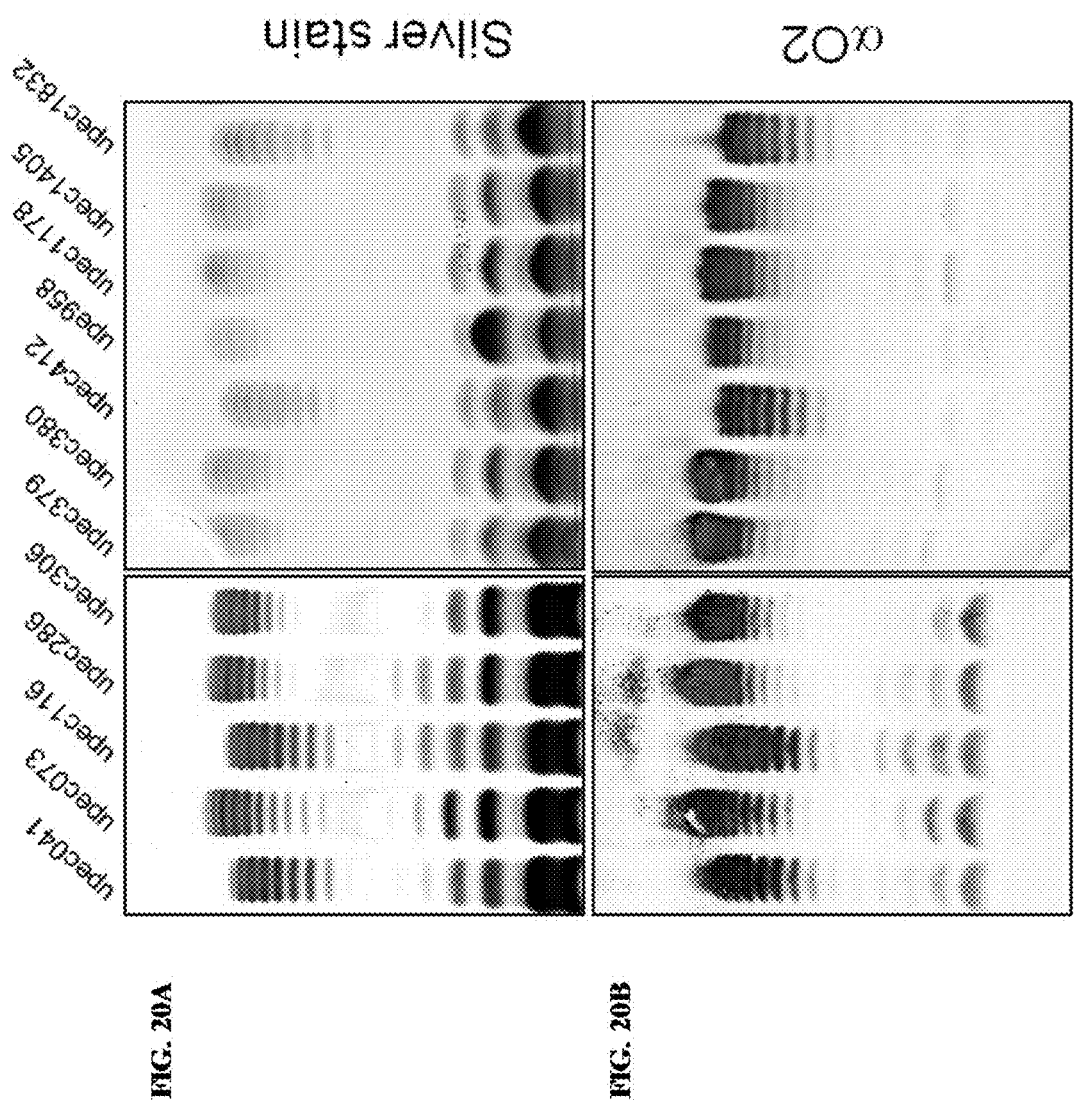

FIGS. 20A and 20B: Analysis of LPS from clinical isolates with an O2 positive agglutination phenotype. FIG. 20A. Silver staining. FIG. 20B. Western blotting using anti-O2 anti serum.

Figure 21:
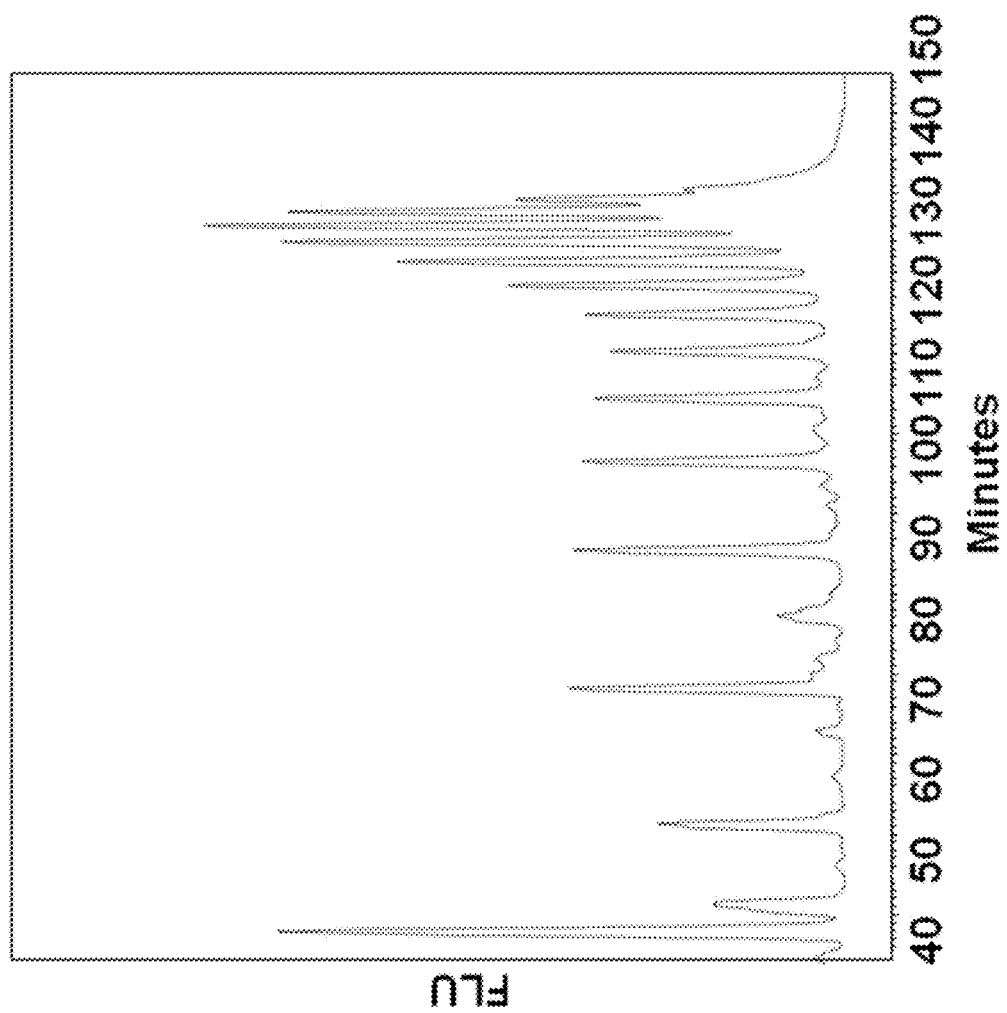

FIG. 21: OPS analysis from strain W3110 ΔwaaL ΔrfbW3110::rfbO2 ΔwekS. A chromatogram of 2AB labelled LLO analysis by normal phase HPLC is shown.

Figure 22:
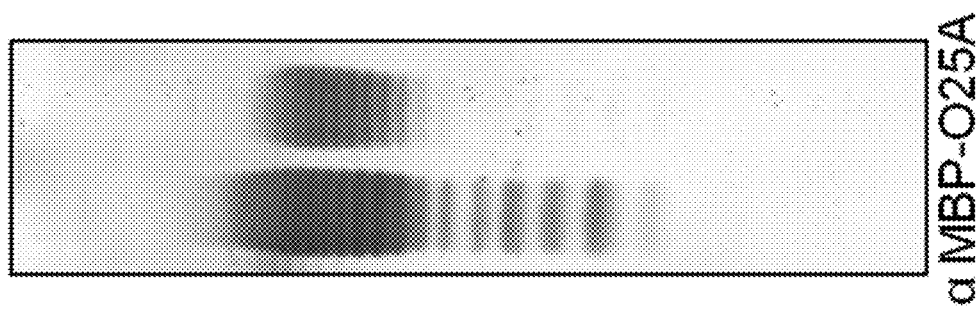
Figure 22:
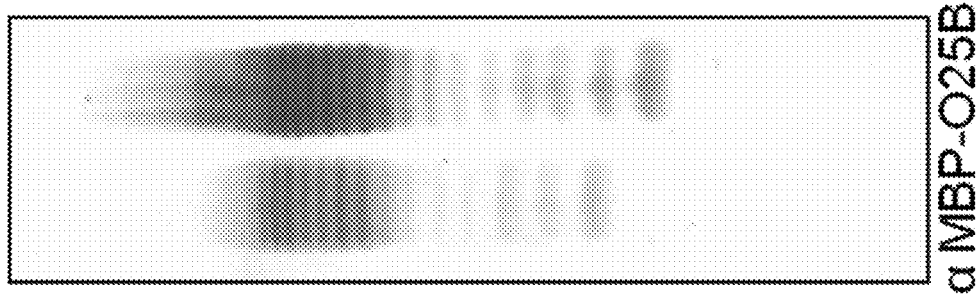

FIG. 22: Recognition of O25A and O25B LPS by anti-O25A and anti-O25B MBP antisera in a Western blotting analysis. Two nitrocellulose membranes which were obtained after electrotransfer of LPS samples prepared from upec436 (O25A) and upec138 (O25B) and separated by a SDS-PAGE. The loading pattern was identical for both membranes, left lane: O25A LPS from upec438, middle lane: O25B LPS from upec 138. MBP bioconjugates were used for immunization of rabbits. Left panel: anti O25B-MBP antiserum; right panel: anti O25A-MBP antiserum.

Figure 23:
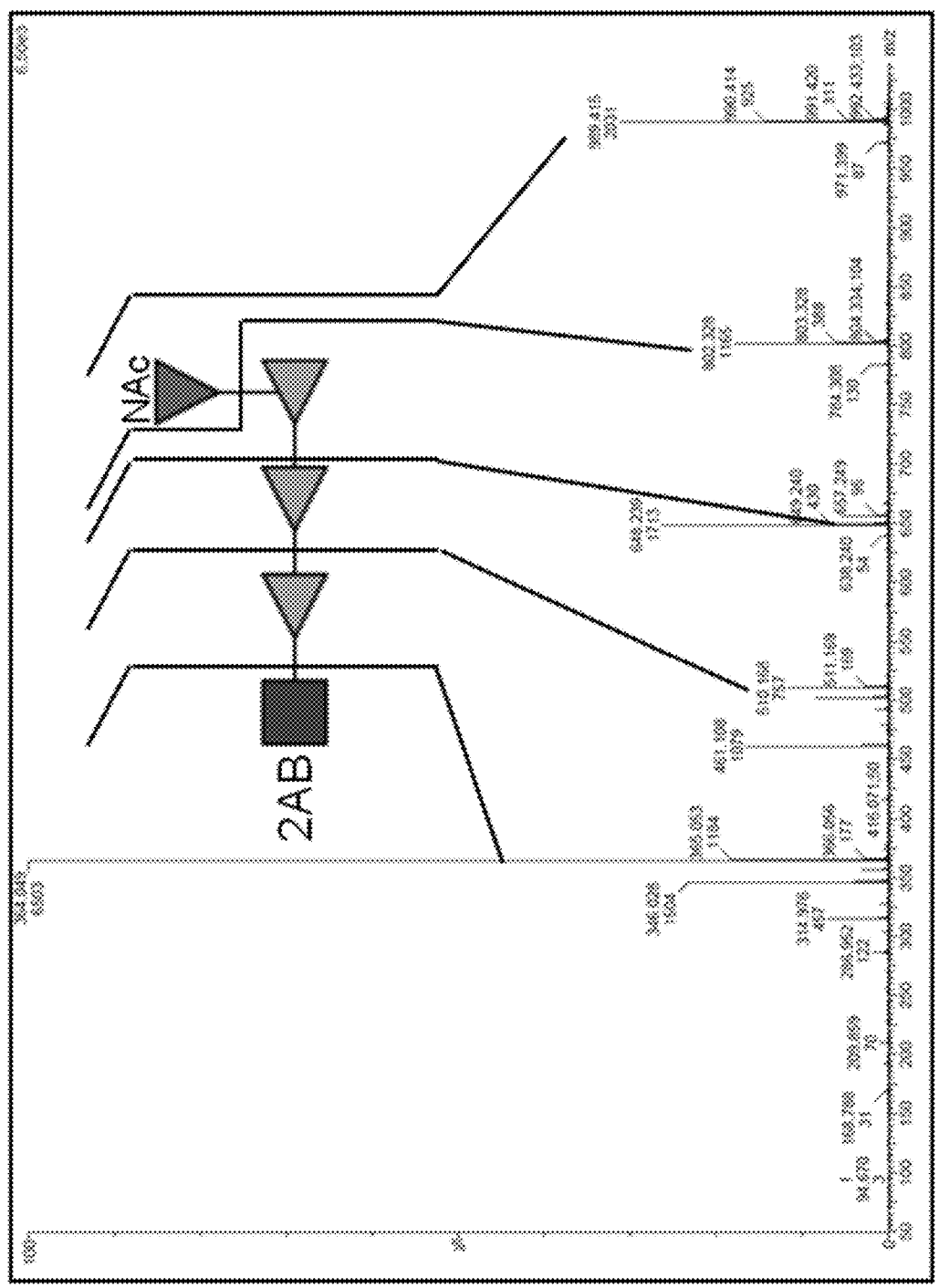

FIG. 23: MS/MS spectra of O2 OPS BRU. MS/MS spectrum of Na+ adduct with m/z=989.4 from elution peak at 43.5 min from 2AB labelled LLO extracts from strain CCUG25. The O2 BRU cartoon and the associated Y ion series is indicated confirming the expected monosaccharide sequence.

Figure 24:
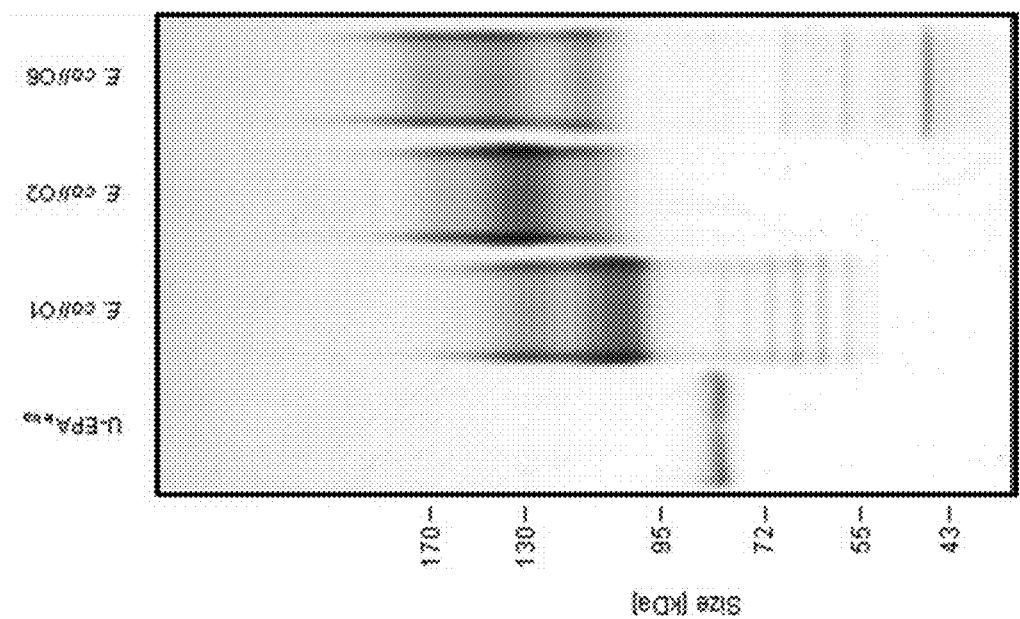

FIG. 24: EPA bioconjugates containing the O1A, O2, and O6 antigens used in the preclinical study. OPS glycans were produced and purified, and analyzed by SDS PAGE and visualized by Coomassie staining.

Figure 25:
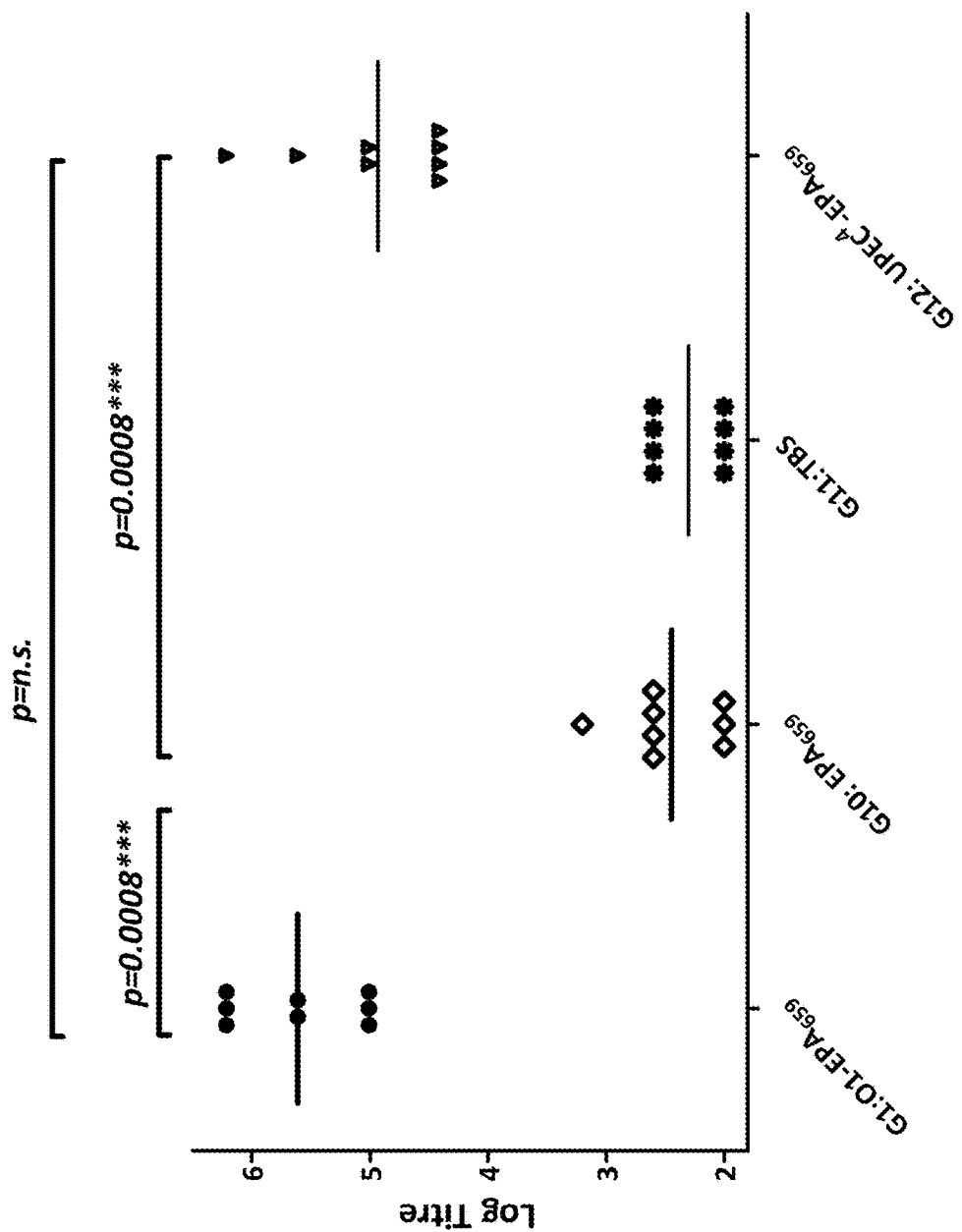

FIG. 25: shows mean ELISA titers obtained with sera from rats immunized with O1A-EPA (G1), carrier protein alone (G10), TBS (G11), or a tetravalent composition composed of EPA-O1A, O2, O6Glc, and O25B (G12), probed against an ELISA plate coated with O1A-LPS purified from strain upec032.

Figure 26:
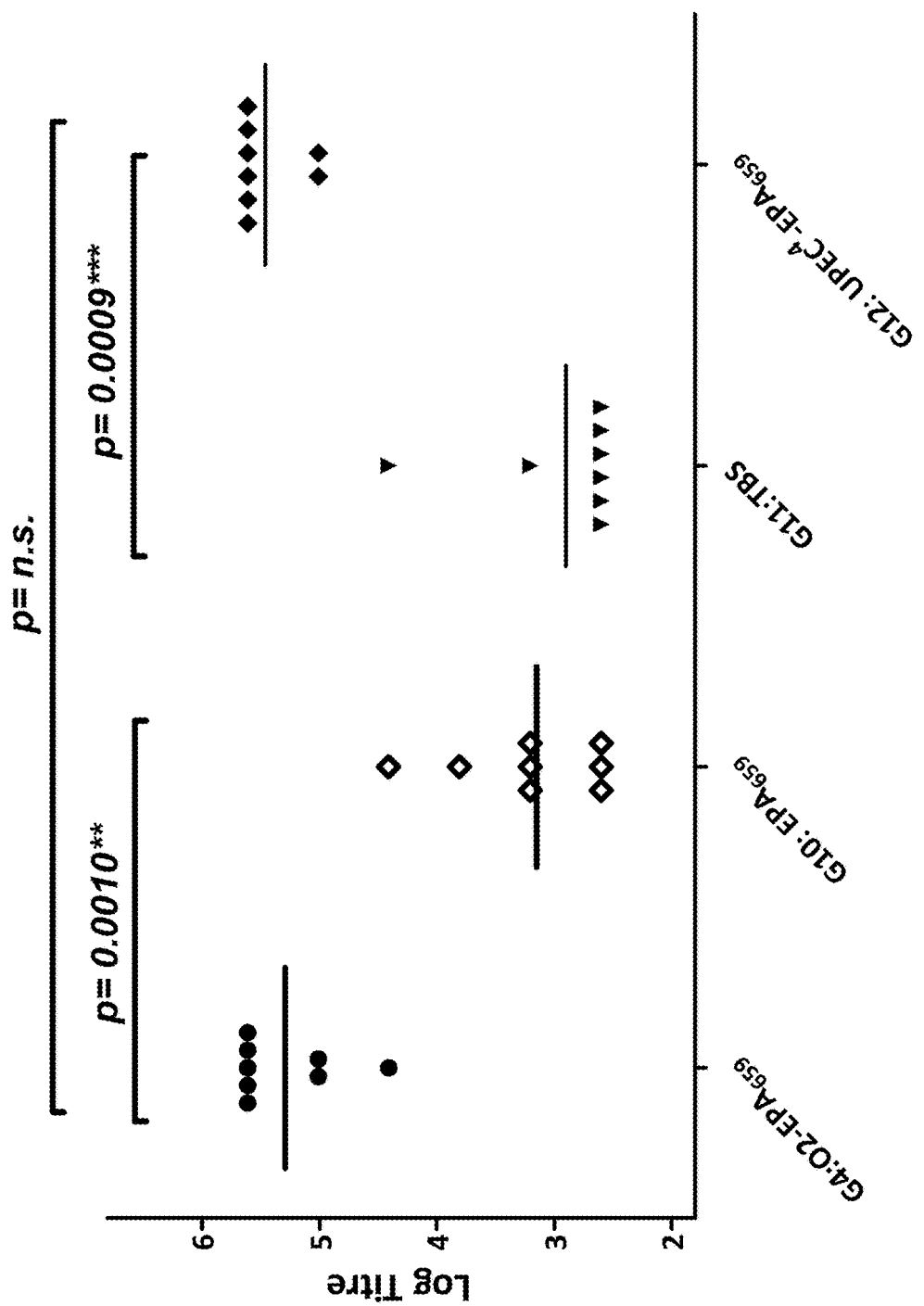

FIG. 26: shows mean ELISA titers obtained with sera from rats immunized with O2-EPA (G4), carrier protein alone (G10), TBS (G11), or a tetravalent composition composed of EPA-O1A, O2, O6Glc, and O25B (G12), probed against an ELISA plate coated with O2 LPS purified from strains CCUG25.

Figure 27:
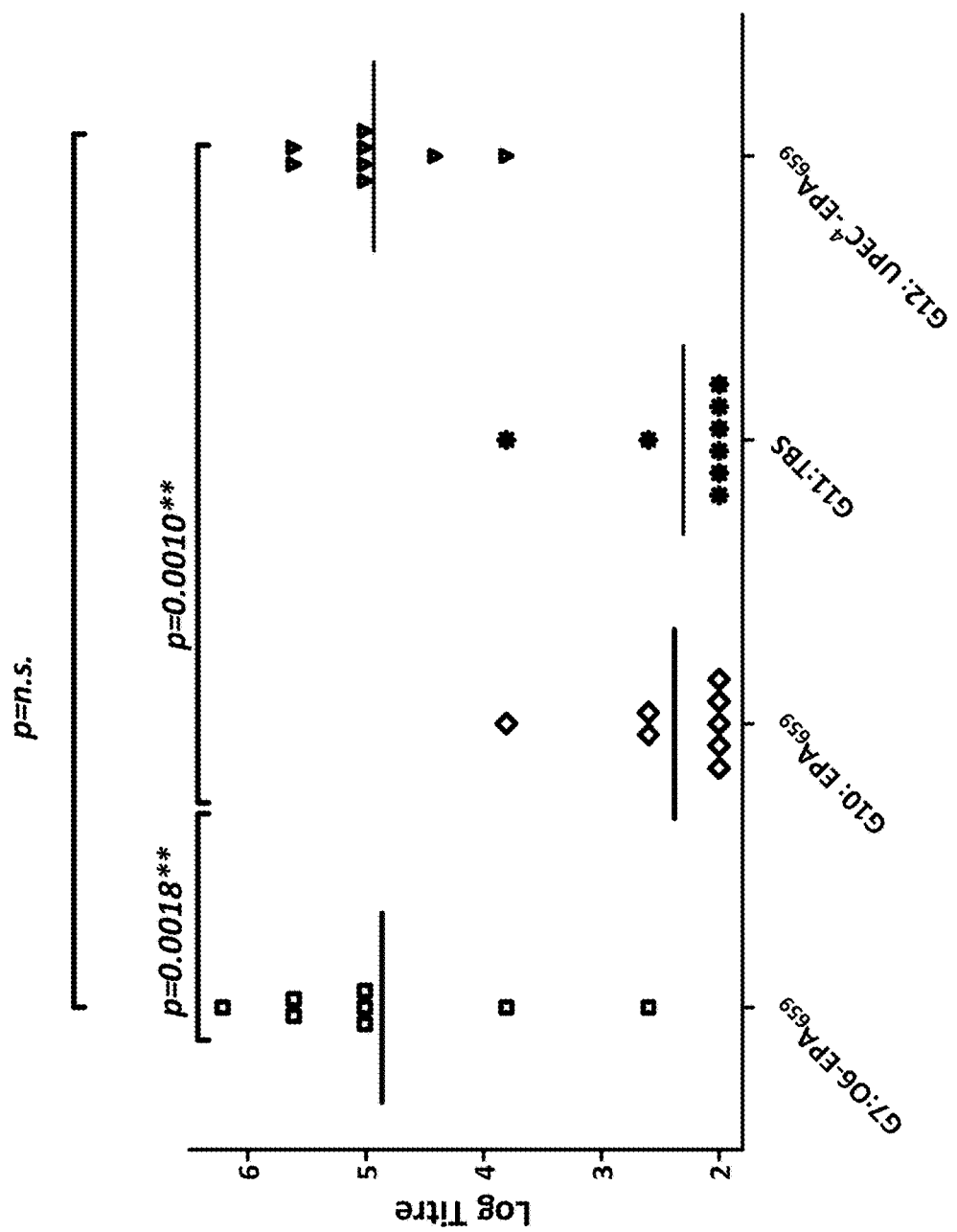

FIG. 27: shows mean ELISA titers obtained with sera from rats immunized with O6Glc-EPA (G7), carrier protein alone (G10), TBS (G11), or a tetravalent composition composed of EPA-O1A, O2, O6Glc, and O25B (G12), probed against an ELISA plate coated with O6Glc-LPS purified from strain CCUG11309.

Figure 28:
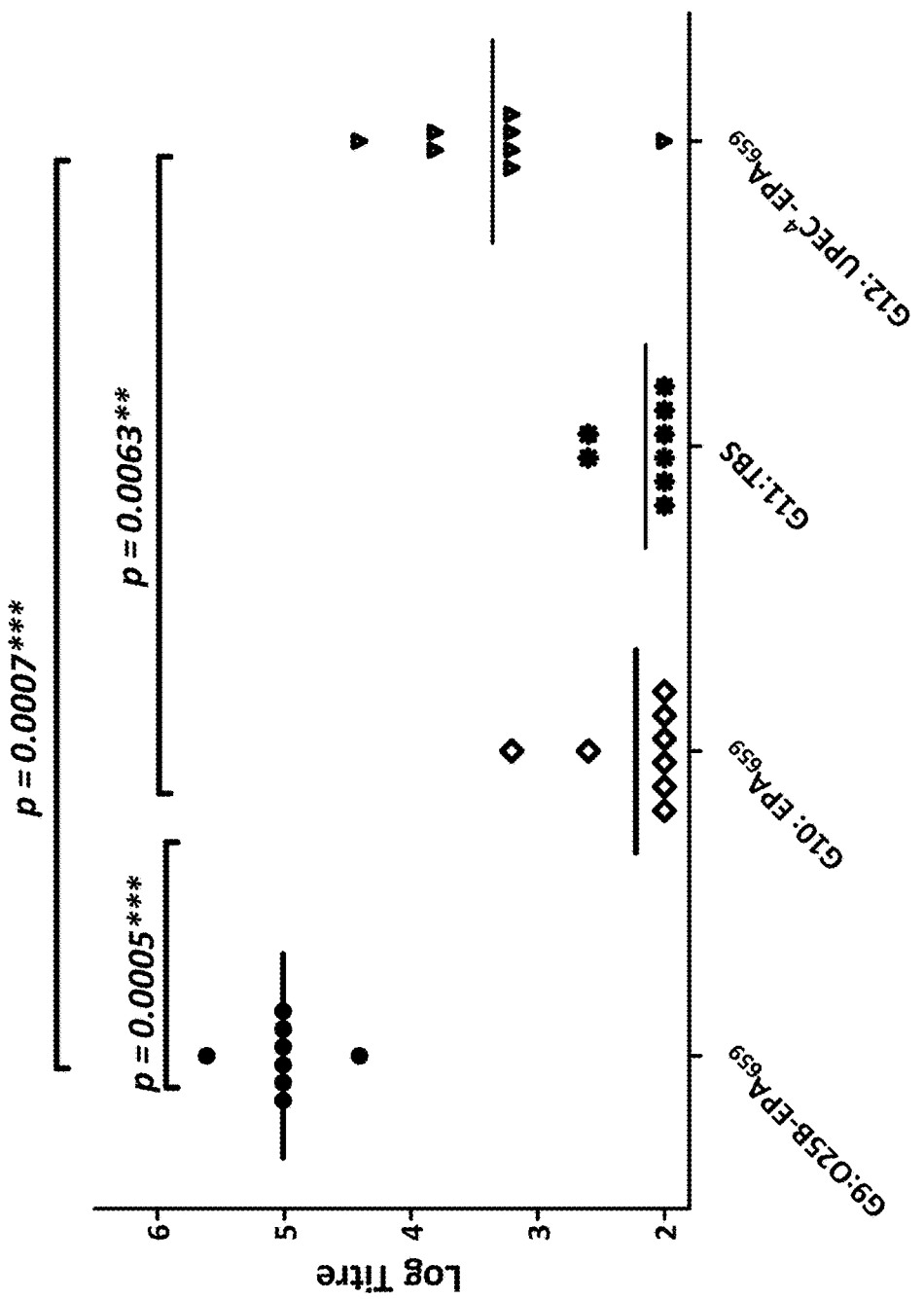

FIG. 28: shows mean ELISA titers obtained with sera from rats immunized with O25B-EPA (G9), carrier protein alone (G10), TBS (G11), or a tetravalent composition composed of O1A, O2, O6Glc, and O25B (G12), probed against an ELISA plate coated with O25B-LPS purified from strain upec177.

Figure 29A:
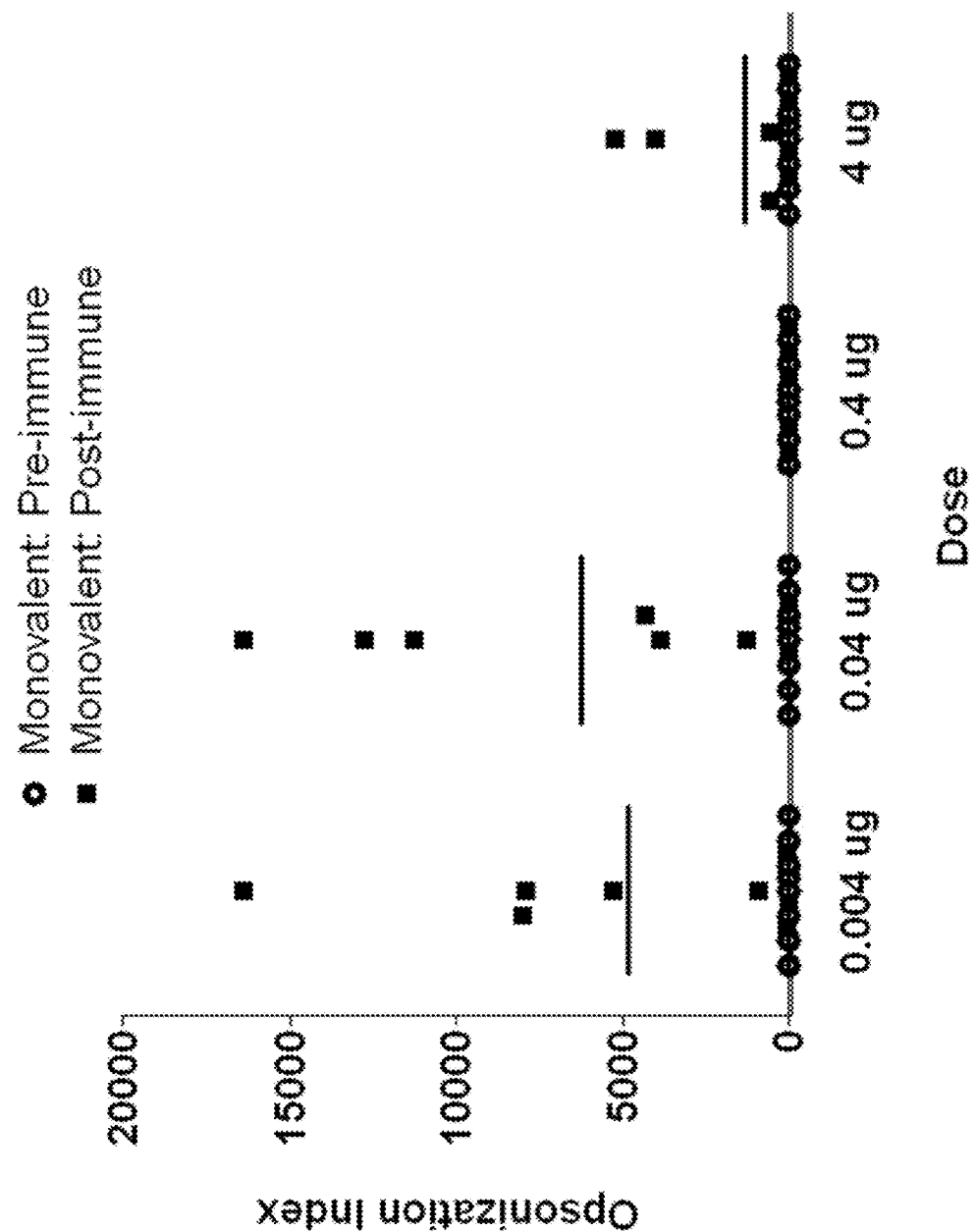
Figure 29B:
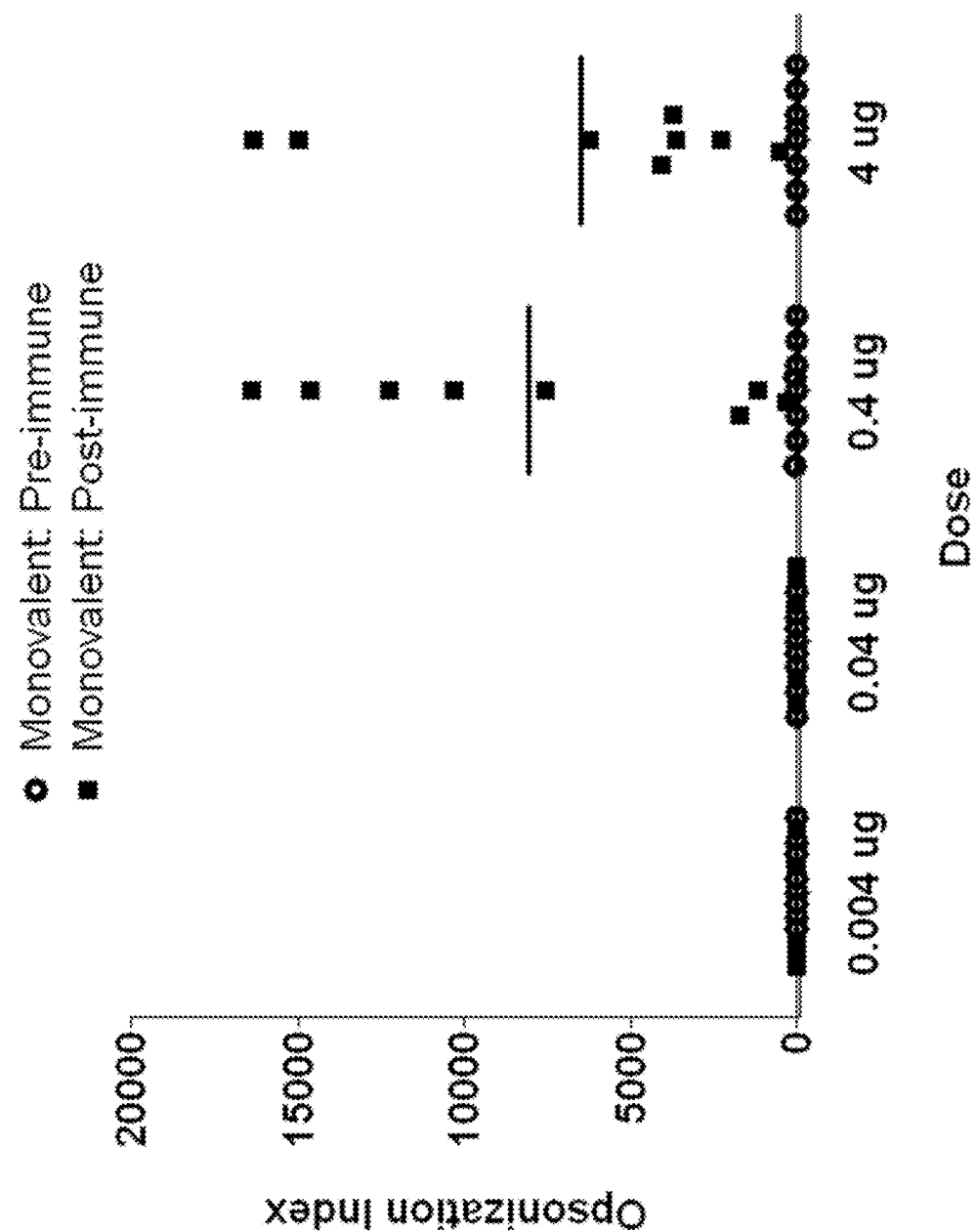
Figure 29C:
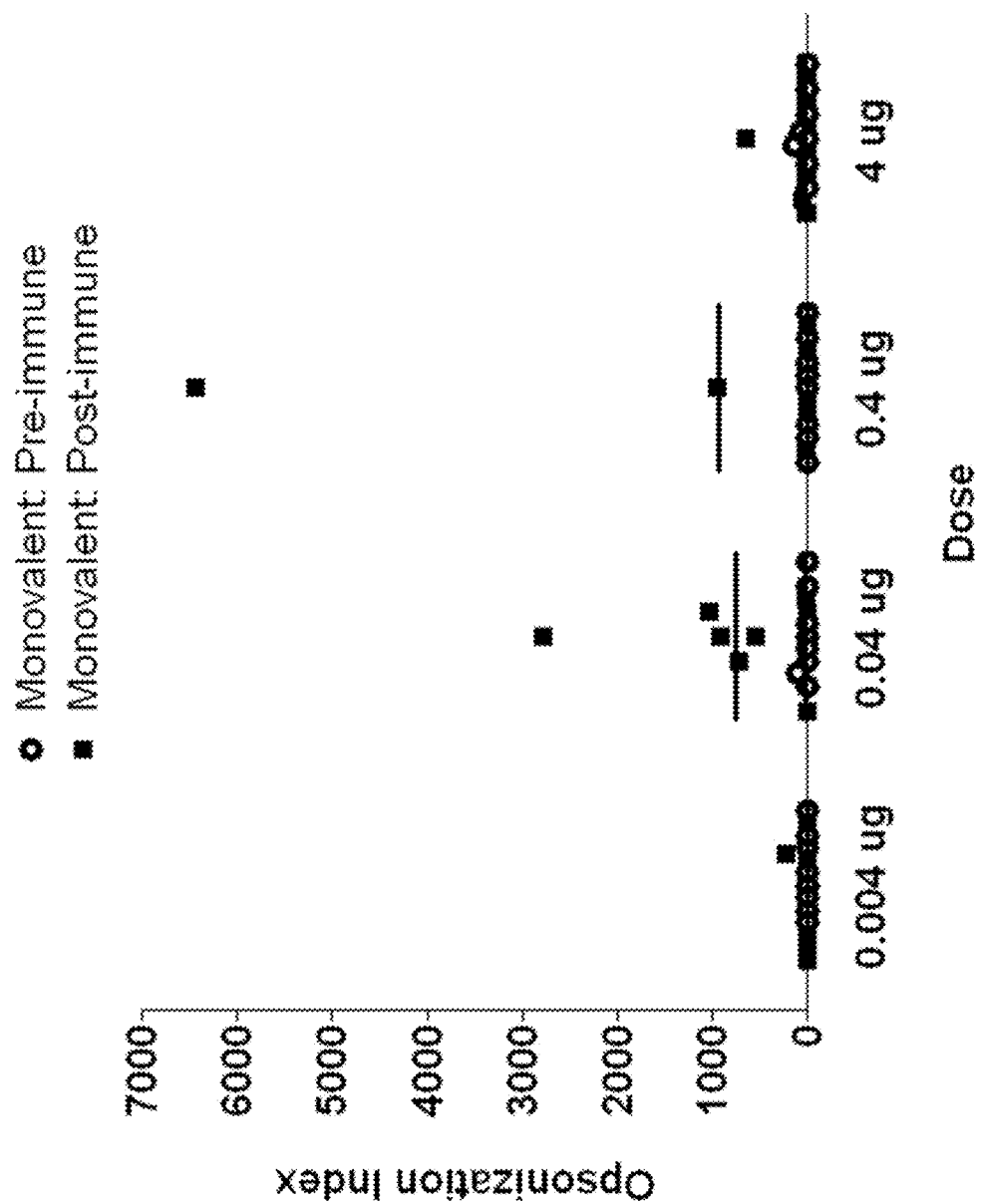

FIGS. 29A-29C: Opsonization indices of sera derived from rats pre-immunization (empty circles) compared to 42 days post-immunization (filled squares) with one priming dose and two booster doses of indicated doses of monovalent vaccine. FIG. 29A shows O2-EPA immunization; FIG. 29B shows O6-EPA immunization; FIG. 29C shows O25B-EPA immunization.

Figure 30:
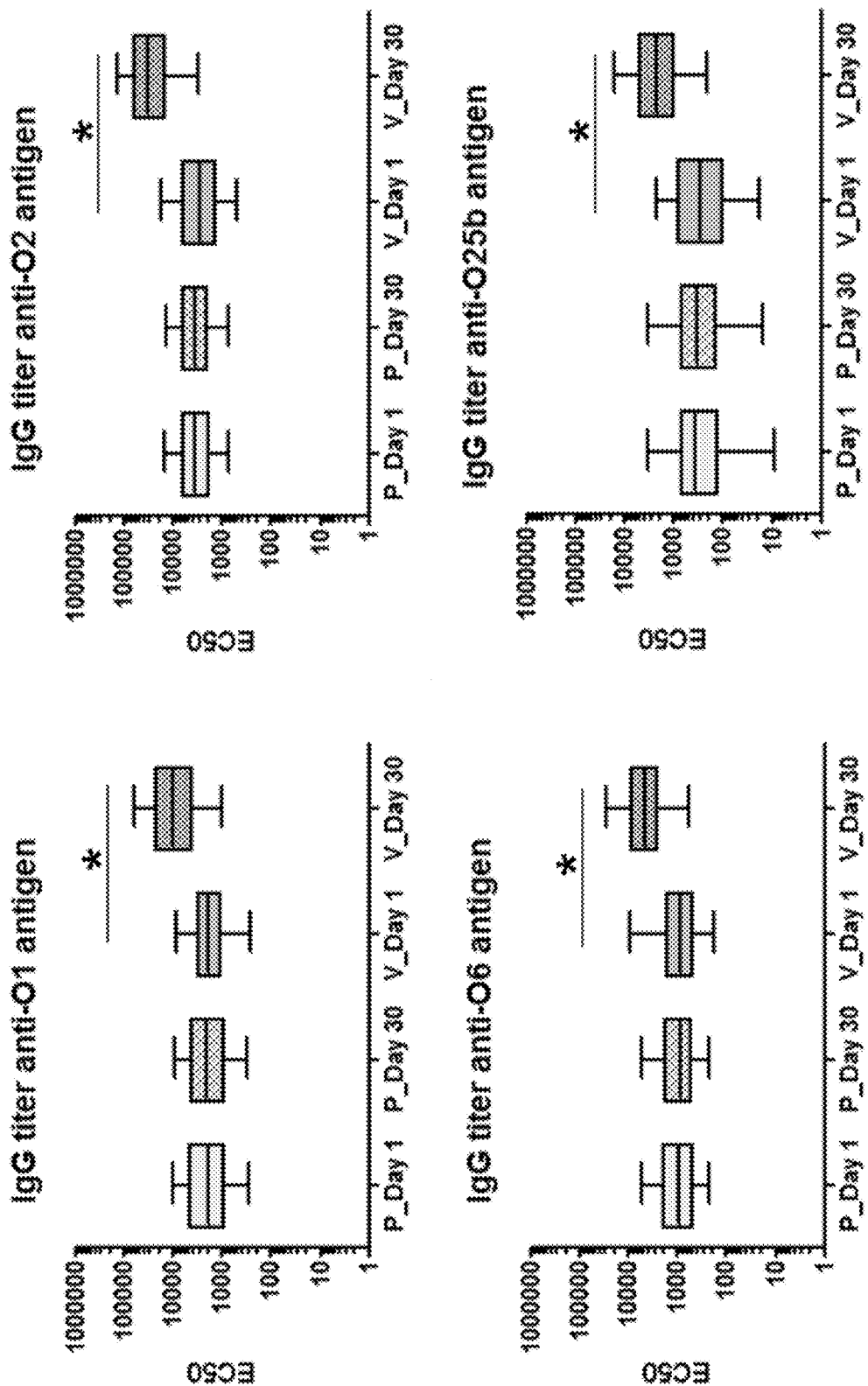
Figure 31A:
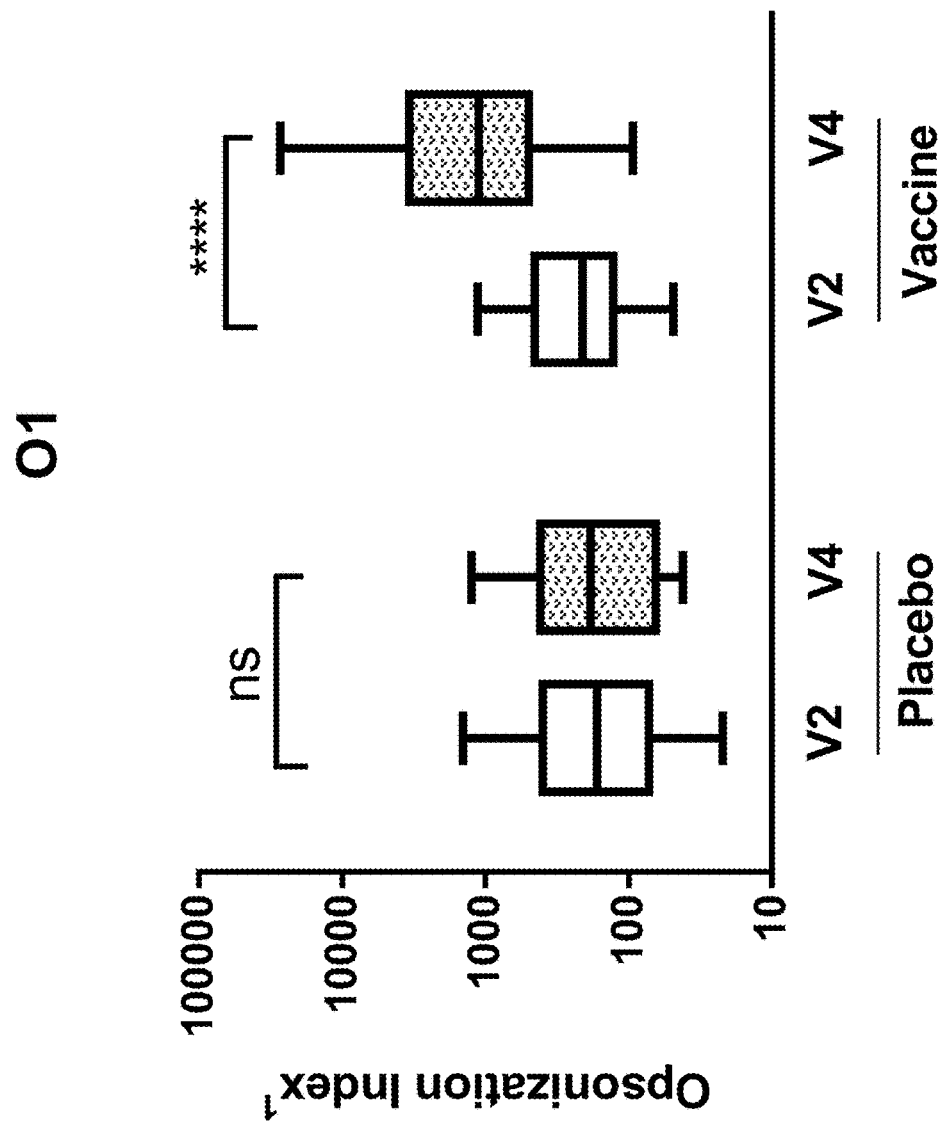
Figure 31B:
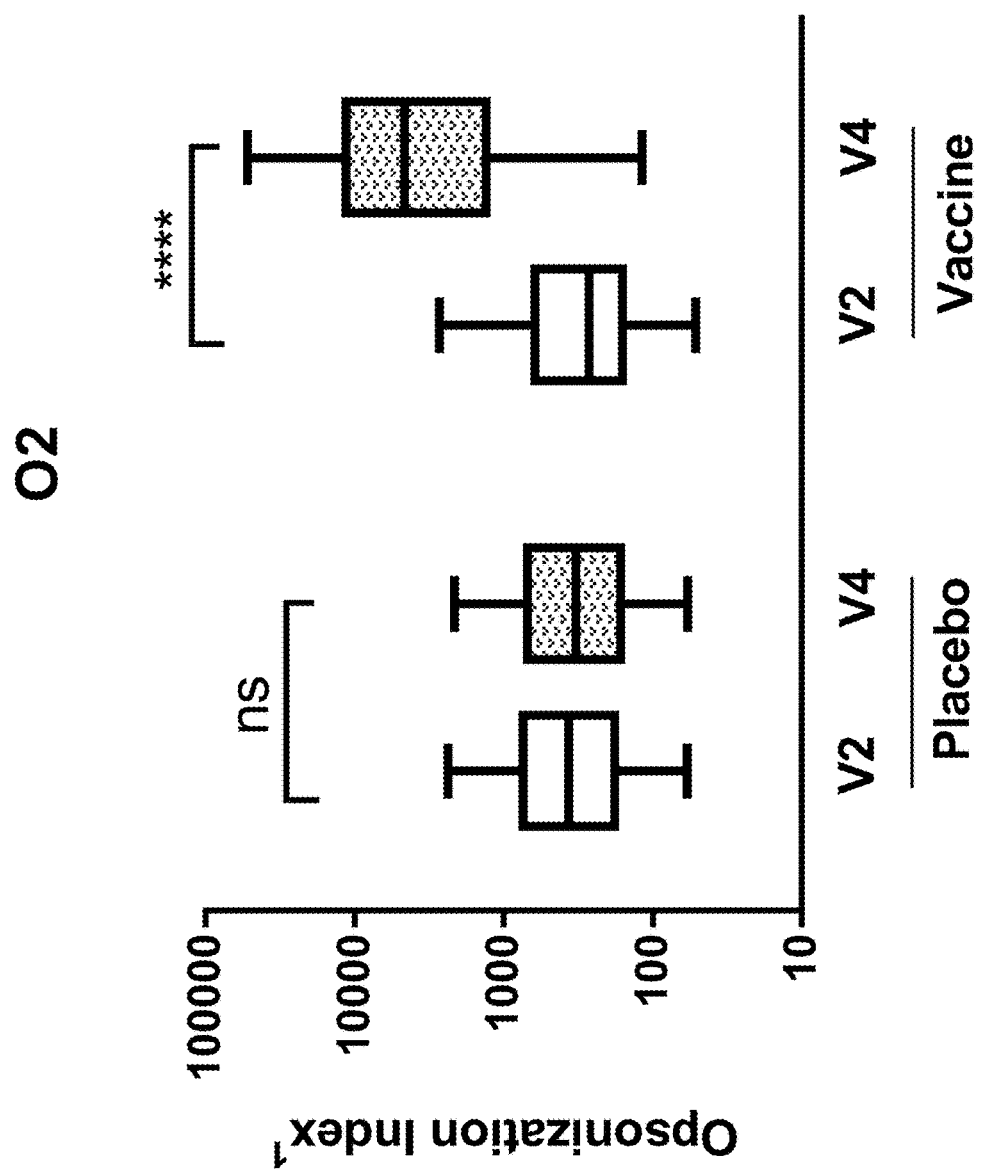
Figure 31C:
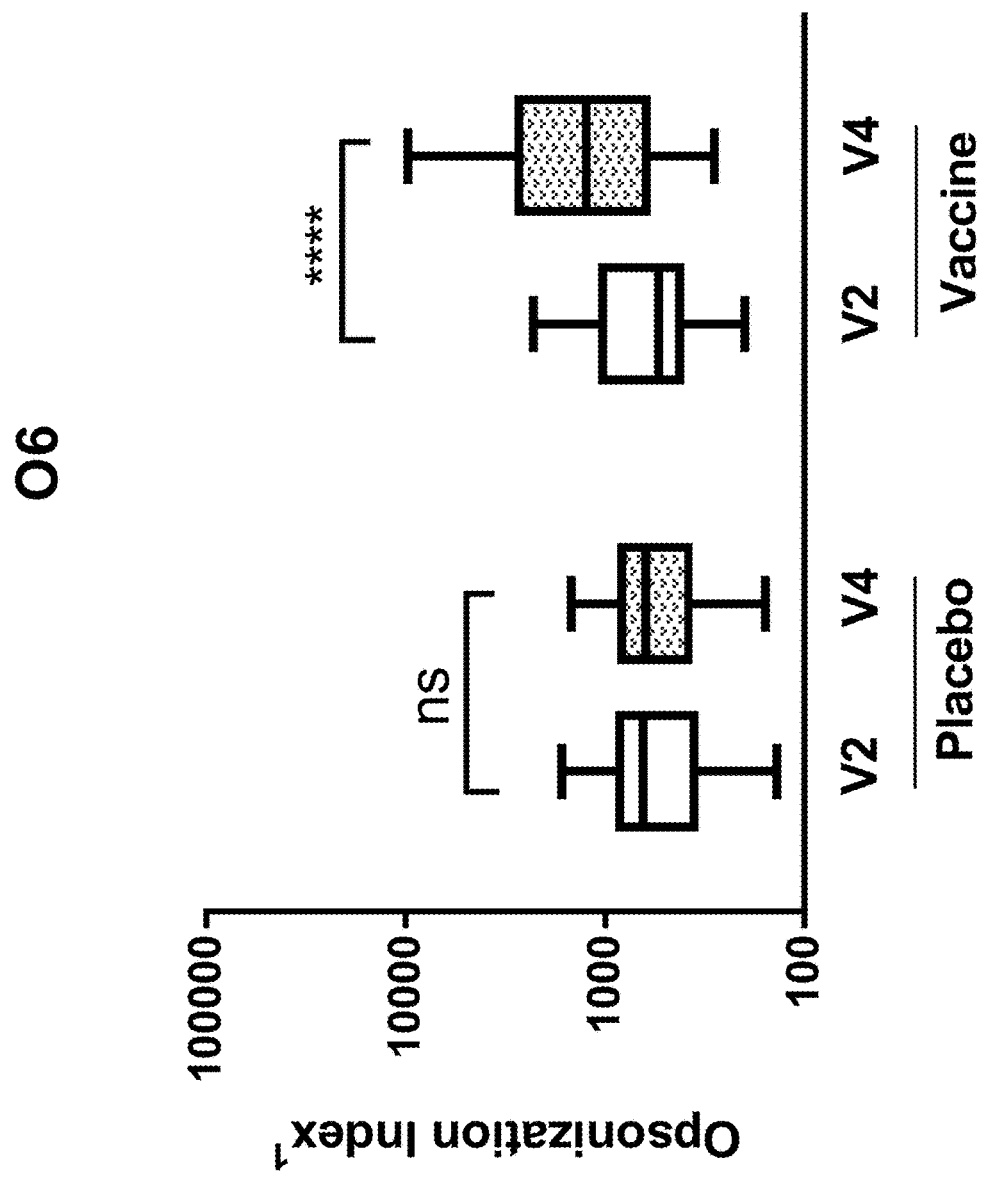
Figure 31D:
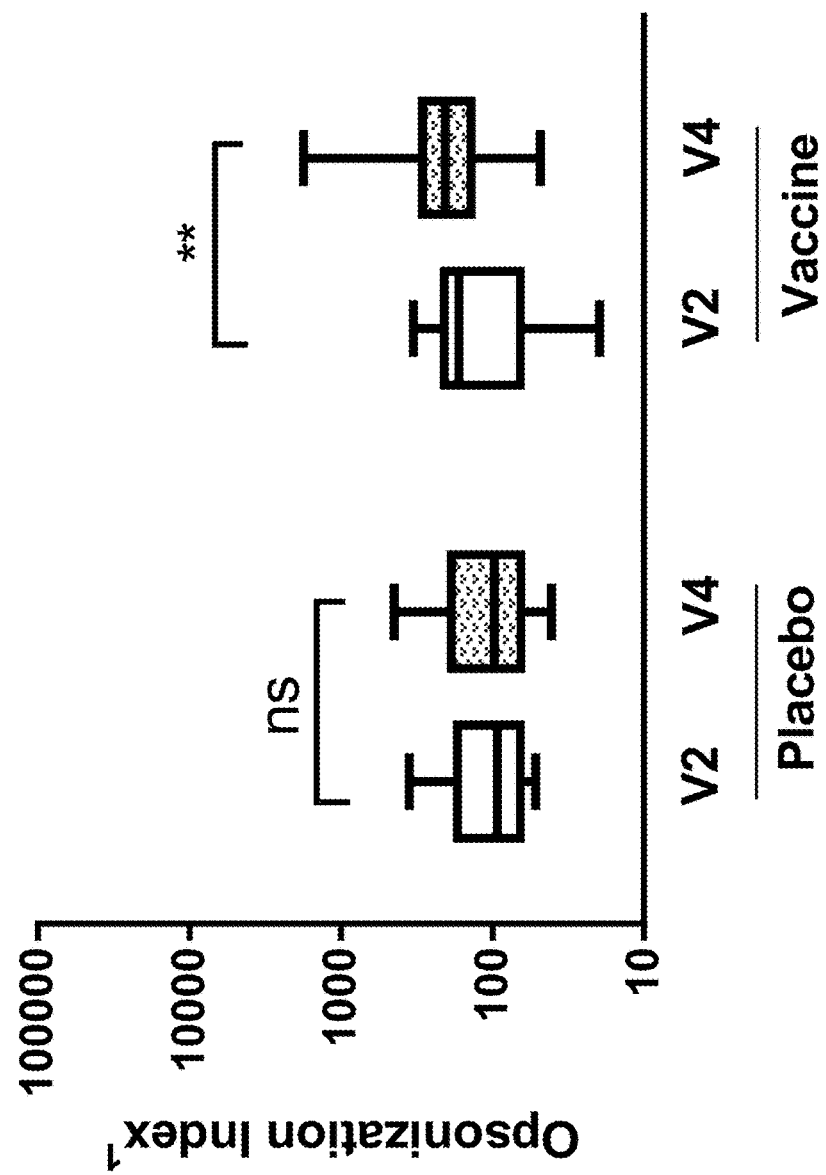

FIG. 30: ELISA titers obtained with sera from human subjects vaccinated with a tetravalent vaccine comprising $E.$ $coli$ antigens O1A, O2, O6Glc, and O25B. A significant increase in the ELISA titers between post (30 days after injection) and pre-injection (day 1) was observed only in the vaccinated groups (*, represents statistical significance).

FIGS. 31A-31D: Opsonic Index (OI) obtained with sera from human subjects vaccinated with a tetravalent vaccine comprising $E.$ $coli$ antigens O1A, O2, O6Glc, and O25B. Immune response as indicated by OI against placebo and components of the tetravalent vaccine (O1A-EPA (FIG. 31A), O2-EPA (FIG. 31B), O6Glc-EPA (FIG. 31C), and O25B-EPA (FIG. 31D)) before and after injection are depicted. Pre-injection, defined as day 1, is represented by V2 (visit 2), and post-injection, defined as day 30, is represented by V4 (visit 4). A significant increase in the OI between post- and pre-injection (indicated by *, where multiple * represent increased degree of significance) was observed only in the vaccinated groups. NS, no significant difference.

Figure 32:
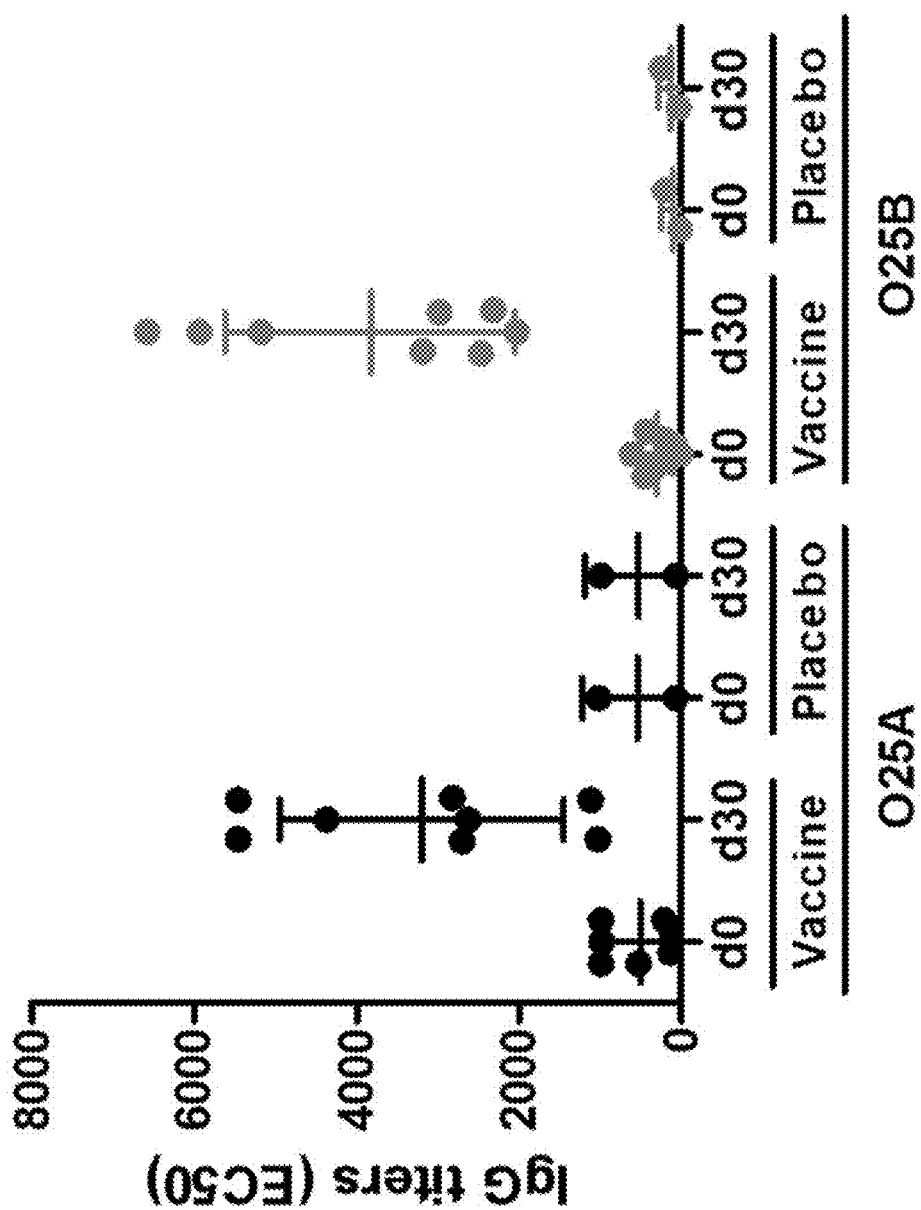

FIG. 32: ELISA titers (expressed as EC50 values) of sera from vaccinated subjects toward O25A LPS (black bars) and O25B LPS (grey bars), at day 1 (pre-vaccination) and after 30 days (post-vaccination). A statistically significant increase in the ELISA titers between post-injection (30 days after injection) and pre-injection (day 1) was observed for both serotypes: O25A LPS (black bars) and O25B LPS (grey bars).

Figure 33:
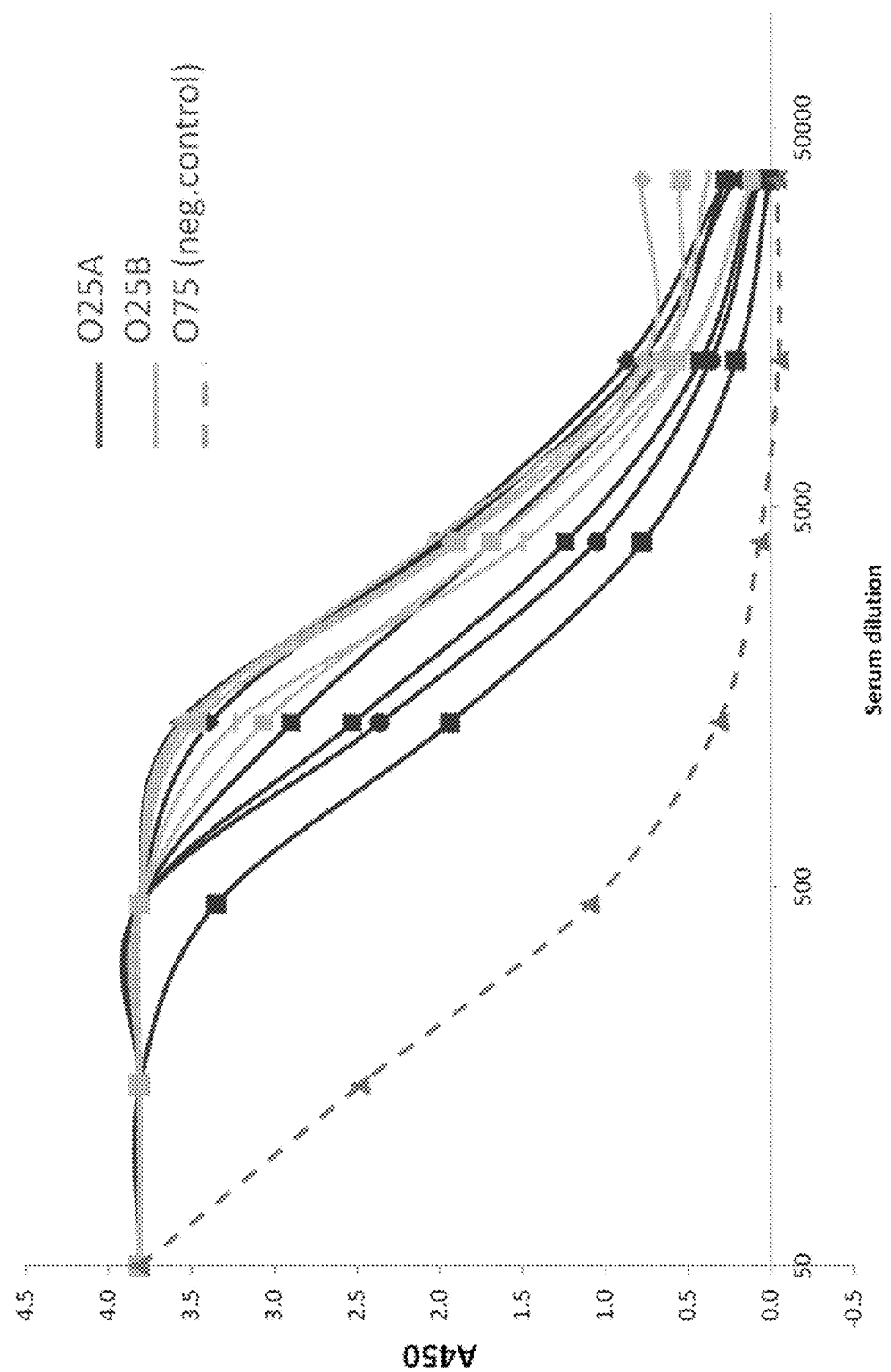

FIG. 33: Reactivity of sera from vaccinated subjects toward O25A (black lines) and O25B (grey lines) expressing *E. coli* strains. Dotted grey line: serotype O75 strain, a negative control. FIG. 33 demonstrates that vaccine-induced serum IgG antibodies from vaccinated subjects strongly respond to O25A and O25B strains.

5. DETAILED DESCRIPTION

Disclosed herein are the structure of the *E. coli* antigen O25B, as well as uses of O25B, methods of making of O25B, and bioconjugates comprising of O25B. Applicants have identified the *E. coli* gene cluster responsible for production of O25B and have fully characterized the structure of the O25B antigen. Accordingly, provided herein are nucleic acids capable of producing O25B in host cells. Also provided herein are host cells, e.g., recombinantly engineered host cells, comprising nucleic acids capable of O25B production. Such host cells can be used to generate bioconjugates comprising O25B linked to a carrier protein, which can be used in, e.g., the formulation of therapeutics (e.g., vaccines). The O25B antigen described herein also is useful in the generation of antibodies, which can be used, e.g., in therapeutic methods such as passive immunization of subjects. Further provided herein are compositions comprising O25B, alone or in combination with other *E. coli* antigens (e.g., O1, O2, and O6 and sub serotypes thereof), for use in therapeutic methods, e.g., vaccination of hosts against infection with *E. coli* (e.g., uropathogenic *E. coli*).

5.1 Nucleic Acids and Proteins

In one aspect, provided herein are isolated nucleic acids related to O25B production, e.g., nucleic acids encoding one or more proteins of an *E. coli* O25B rfb cluster. Those skilled in the art will appreciate that due to the degeneracy of the genetic code, a protein having a specific amino acid sequence can be encoded by multiple different nucleic acids. Thus, those skilled in the art will understand that a nucleic acid provided herein can be altered in such a way that its sequence differs from a sequence provided herein, without affecting the amino acid sequence of the protein encoded by the nucleic acid.

In a specific embodiment, provided herein is a nucleic acid encoding an *E. coli* O25B rfb cluster. In a specific embodiment, provided herein is a nucleic acid encoding an *E. coli* rfb(upec138) gene cluster (SEQ ID NO:12). In another specific embodiment, provided herein is a nucleic acid encoding a gene cluster that is about 75%, 80%, 85%, 90%, 95%, 96%, 97%, 98%, or 99% identical to or homologous to SEQ ID NO:12. Upec138 is an example of an *E. coli* strain of O25B serotype. The skilled person will realize that other strains from this serotype can now easily be obtained from clinical isolates according to methods described herein, and examples of such other strains are upec177 and upec163. Hence, wherever an rfb gene cluster or individual genes from such cluster of such O25B strains are mentioned herein, it is meant to include the corresponding gene clusters or genes from other O25B strains. Also the sequences provided can be found by sequencing the rfb gene clusters or if desired of individual genes from such other isolates, and will provide homologous sequences encoding homologous proteins as the gene cluster or gene. In any embodiments where a homologous gene cluster or gene is mentioned by referring to a gene cluster or gene with a certain percentage, such homologous sequence preferably encodes the protein(s) with the same function as the ones from the reference strain or sequence.

In another specific embodiment, provided herein is a nucleic acid encoding an *E. coli* O25B rfb cluster. In a specific embodiment, provided herein is a nucleic acid encoding an *E. coli* rfb(upec163) gene cluster. In another specific embodiment, provided herein is a nucleic acid encoding a gene cluster that is about 75%, 80%, 85%, 90%, 95%, 96%, 97%, 98%, or 99% identical to or homologous to an *E. coli* rfb(upec163) gene cluster.

In another specific embodiment, provided herein is a nucleic acid encoding an *E. coli* O25B rfb cluster. In a specific embodiment, provided herein is a nucleic acid encoding an *E. coli* rfb(upec177) gene cluster. In another specific embodiment, provided herein is a nucleic acid encoding a gene cluster that is about 75%, 80%, 85%, 90%, 95%, 96%, 97%, 98%, or 99% identical to or homologous to an *E. coli* rfb(upec177) gene cluster.

In another embodiment, provided herein are nucleic acid encoding proteins of an *E. coli* O25B rfb cluster.

In a specific embodiment, a nucleic acid encoding a protein of an *E. coli* O25B rfb cluster provided herein comprises or consists of SEQ ID NO:1, the rmlB gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:1.

In a specific embodiment, a nucleic acid encoding a protein of an *E. coli* O25B rfb cluster provided herein comprises or consists of SEQ ID NO:2, the rmlD gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:2.

In a specific embodiment, a nucleic acid encoding a protein of an *E. coli* O25B rfb cluster provided herein comprises or consists of SEQ ID NO:3, the rmlA gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:3.

In a specific embodiment, a nucleic acid encoding a protein of an *E. coli* O25B rfb cluster provided herein comprises or consists of SEQ ID NO:4, the rmlC gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:4.

In a specific embodiment, a nucleic acid encoding a protein of an *E. coli* O25B rfb cluster provided herein comprises or consists of SEQ ID NO:5, the wzx gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:5.

In a specific embodiment, a nucleic acid encoding a protein of an *E. coli* O25B rfb cluster provided herein comprises or consists of SEQ ID NO:6, the wekA gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:6.

In a specific embodiment, a nucleic acid encoding a protein of an *E. coli* O25B rfb cluster provided herein comprises or consists of SEQ ID NO:7, the wekB gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:7.

In a specific embodiment, a nucleic acid encoding a protein of an *E. coli* O25B rfb cluster provided herein comprises or consists of SEQ ID NO:8, the wzy gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:8.

In a specific embodiment, a nucleic acid encoding a protein of an *E. coli* O25B rfb cluster provided herein comprises or consists of SEQ ID NO:9, the wbbJ gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:9.

In a specific embodiment, a nucleic acid encoding a protein of an *E. coli* O25B rfb cluster provided herein comprises or consists of SEQ ID NO:10, the wbbK gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:10.

In a specific embodiment, a nucleic acid encoding a protein of an *E. coli* O25B rfb cluster provided herein comprises or consists of SEQ ID NO:11, the wbbL gene of the *E. coli* O25B rfb cluster. In another specific embodiment, a nucleic acid encoding a protein of an *E. coli* O25B rfb cluster provided herein is 75%, 80%, 85%, 90%, 95%, 96%, 97%, 98%, or 99% identical to or homologous to SEQ ID NO:11.

In another aspect, provided herein are proteins encoded by the nucleic acids provided herein. In a specific embodiment, provided herein is dTDP-Glucose 4,6-dehydratase, encoded by SEQ ID NO:1. In another specific embodiment, provided herein is dTDP-6-Deoxy-D-glucose 3,5-epimerase, encoded by SEQ ID NO:2. In another specific embodiment, provided herein is Glucose-1-phosphate thymidylyltransferase, encoded by SEQ ID NO:3. In another specific embodiment, provided herein is dTDP-4-dehydrorhamnose 3,5-epimerase, encoded by SEQ ID NO:4. In another specific embodiment, provided herein is O antigen flippase, encoded by SEQ ID NO:5. In another specific embodiment, provided herein is dTDP-Rha:Glc-Rha(Ac)-GlcNAc-UPP α-1,3-rhamnosyltransferase, encoded by SEQ ID NO:6. In another specific embodiment, provided herein is UDP-Glc:Glc-Rha (Ac)-GlcNAc-UPP β-1,6-glucosyltransferase, encoded by SEQ ID NO:7. In another specific embodiment, provided herein is O antigen polymerase, encoded by SEQ ID NO:8. In another specific embodiment, provided herein is O-acetyl transferase, encoded by SEQ ID NO:9. In another specific embodiment, provided herein is UDP-Glc:Rha-GlcNAc-UPP α-1,3-glucosyltransferase, encoded by SEQ ID NO:10. In another specific embodiment, provided herein is dTDP-Rha:GlcNAc-UPP α-1,3-rhamnosyltransferase, encoded by SEQ ID NO:11.

5.2 *E. coli* O Antigens

In one aspect, provided herein are isolated *E. coli* antigens of the O25, O1, O2, and O6 serotypes.

In a specific embodiment, provided herein is an isolated O antigen from *E. coli* strain upec138. In another specific embodiment, provided herein is an isolated O antigen from *E. coli* strain upec163. In another specific embodiment, provided herein is an isolated O antigen from *E. coli* strain upec177.

In another specific embodiment, provided herein is an isolated *E. coli* O25B antigen of Formula O25B:

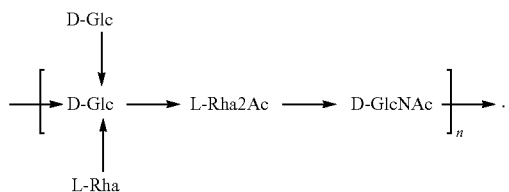

In another specific embodiment, provided herein is an isolated *E. coli* O25B antigen of Formula O25B':

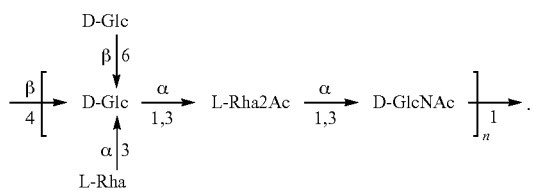

In another aspect, provided herein is a population of isolated macromolecules of the Formula O25B, presented below:

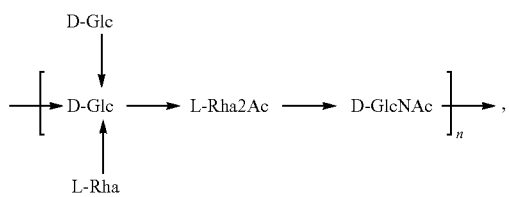

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, n of at least 80% of the macromolecules in the population is between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

In another aspect, provided herein a population of isolated macromolecules of the Formula O25B', presented below:

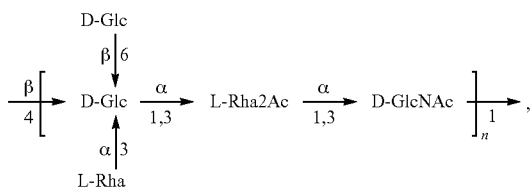

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, n of at least 80% of the macromolecules in the population is between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

Other *E. coli* antigens useful in the compositions described herein (e.g., therapeutic compositions, e.g., vaccines; see Section 5.6) include O25A, as well as O1, O2, and O6 antigens, and subserotypes thereof.

In one embodiment, an O25A antigen (e.g., in isolated form or as part of a bioconjugate) is used in a composition provided herein (e.g., in combination with an O25B antigen (or bioconjugate comprising an O25B antigen)). In a specific embodiment, the O25A antigen is Formula O25A:

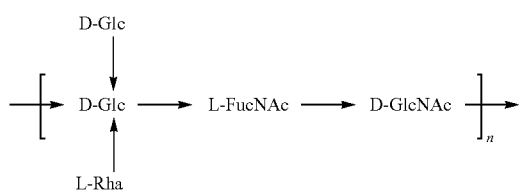

In another specific embodiment, the O25A antigen is Formula O25A':

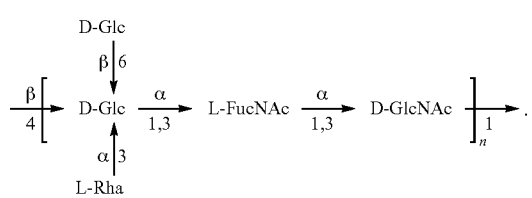

In one embodiment, an O1A antigen (e.g., in isolated form or as part of a bioconjugate) is used in a composition provided herein (e.g., in combination with an O25B antigen (or bioconjugate comprising an O25B antigen)). In a specific embodiment, the O1A antigen is Formula O1A:

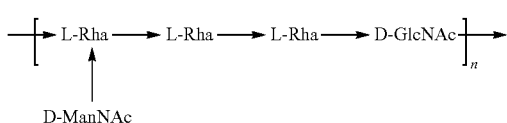

In another specific embodiment, the O1A antigen is Formula O1A':

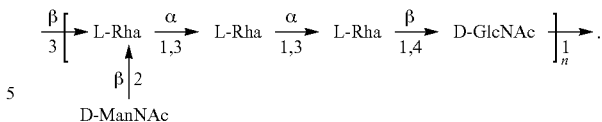

In one embodiment, an O1B antigen (e.g., in isolated form or as part of a bioconjugate) is used in a composition provided herein (e.g., in combination with an O25B antigen (or bioconjugate comprising an O25B antigen)). In a specific embodiment, the O1B antigen is Formula O1B:

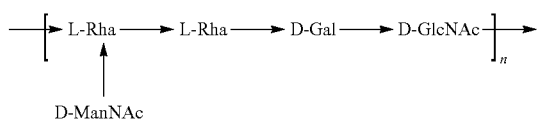

In another specific embodiment, the O1B antigen is Formula O1B':

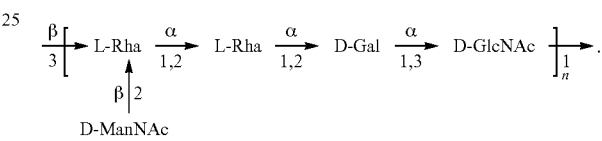

In one embodiment, an O1C antigen (e.g., in isolated form or as part of a bioconjugate) is used in a composition provided herein (e.g., in combination with an O25B antigen (or bioconjugate comprising an O25B antigen)). In a specific embodiment, the O1C antigen is Formula O1C:

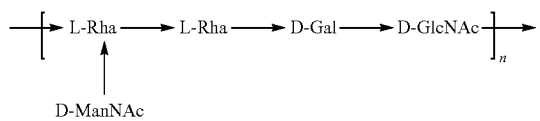

In another specific embodiment, the O1C antigen is Formula O1C':

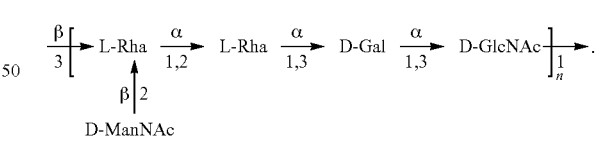

In one embodiment, an O2 antigen (e.g., in isolated form or as part of a bioconjugate) is used in a composition provided herein (e.g., in combination with an O25B antigen (or bioconjugate comprising an O25B antigen)). In a specific embodiment, the O2 antigen is Formula O2:

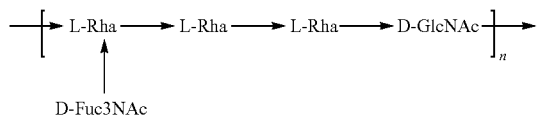

In another specific embodiment, the O2 antigen is Formula O2':

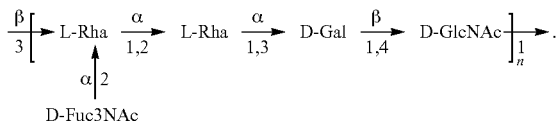

In one embodiment, an O6 antigen (e.g., in isolated form or as part of a bioconjugate) is used in a composition provided herein (e.g., in combination with an O25B antigen (or bioconjugate comprising an O25B antigen)). In a specific embodiment, the O6 antigen is Formula O6K2 (also referred to herein as O6Glc):

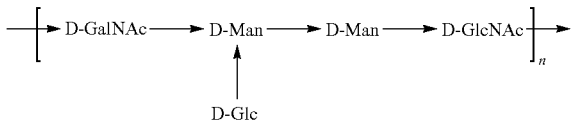

In another specific embodiment, the O6 antigen is Formula O6K2' (also referred to herein as O6Glc'):

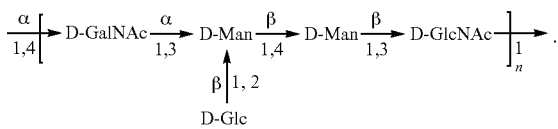

In another specific embodiment, the O6 antigen is Formula O6K54 (also referred to herein as O6GlcNAc):

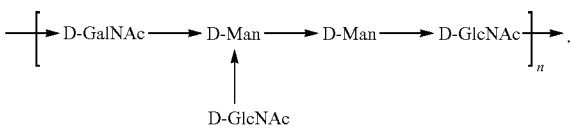

In another specific embodiment, the O6 antigen is Formula O6K54' (also referred to herein as O6GlcNAc'):

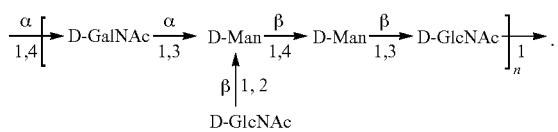

5.3 Host Cells

Provided herein are host cells, e.g., prokaryotic host cells, capable of producing *E. coli* O antigens and bioconjugates comprising such *E. coli* O antigens. In certain embodiments, the host cells provided herein comprise (e.g., naturally or through genetic engineering) one or more of the nucleic acids described herein. See Section 5.1. In certain embodiments, the host cells provided herein produce one or more of the *E. coli* O antigens described herein, and/or produce bioconjugates comprising one or more of the *E. coli* O antigens described herein. See Section 5.2.

In one aspect, provided herein is a prokaryotic host cell comprising nucleic acids encoding enzymes (e.g., glycosyltransferases) capable of producing the novel polysaccharide disclosed herein, *E. coli* O25B. Also provided herein are host cells comprising nucleic acids encoding enzymes (e.g., glycosyltransferases) capable of producing other *E. coli* antigens, e.g., O25A, O1, O2, and O6, and subserotypes thereof (see Section 5.2). The host cells provided herein may naturally express nucleic acids capable of producing of an O antigen of interest, or the host cells may be made to express such nucleic acids, i.e., in certain embodiments said nucleic acids are heterologous to the host cells and introduced into the host cells using genetic approaches known in the art. In certain embodiments, the host cells provided herein comprise nucleic acids encoding additional enzymes active in the N-glycosylation of proteins, e.g., the host cell provided herein can further comprise a nucleic acid encoding an oligosaccharyl transferase or nucleic acids encoding other glycosyltransferases. See, e.g., Section 5.3.3. In certain embodiments, the host cells provided herein comprise a nucleic acid encoding a carrier protein, e.g., a protein to which oligo- and polysaccharides can be attached to form a bioconjugate. See, e.g., Section 5.3.2 for a description of carrier proteins and Section 5.4 for a description of bioconjugates. In a specific embodiment, the host cell is *E. coli*.

Upec138 is an *E. coli* strain identified herein as belonging to the O25B serotype, and the rfb gene cluster of the strain (and strains of the O25B serotype in general) has been identified herein for the first time as comprising genes that produce a novel *E. coli* polysaccharide, O25B. In a specific embodiment, provided herein is a prokaryotic host cell comprising an *E. coli* rfb(upec138) gene cluster (SEQ ID NO:12), or a gene cluster that is about or at least 75%, 80%, 85%, 90%, 95%, 96%, 97%, 98%, or 99% identical to or homologous to SEQ ID NO:12. In a specific embodiment, the *E. coli* rfb(upec138) gene cluster (SEQ ID NO:12) is introduced into the host cell by genetic manipulation (e.g., the gene cluster is expressed on a plasmid or plasmids or integrated into the host cell genome (see, e.g., International Patent application No. PCT/EP2013/068737)). In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser (Thr), wherein X can be any amino acid except Pro (SEQ ID NO:14) or a carrier protein comprising a consensus sequence or Asp(Glu)-X-Asn-Z-Ser(Thr), wherein X and Z are independently selected from any natural amino acid except Pro (SEQ ID NO:15) (see WO 2006/119987). In another specific embodiment, some or all of the genes of the rfb cluster are heterologous to the host cell. In another specific embodiment, said oligosaccharyl transferase is heterologous to the host cell. In another specific embodiment, said carrier protein is heterologous to the host cell. In a specific embodiment, the host cell is *E. coli*.

Upec163 is an *E. coli* strain identified herein as belonging to the O25B serotype, and the rfb gene cluster of the strain (and strains of the O25B serotype in general) has been identified herein for the first time as comprising genes that produce a novel *E. coli* polysaccharide, O25B. In another specific embodiment, provided herein is a prokaryotic host cell comprising an *E. coli* rfb(upec163) gene cluster, or a gene cluster that is about or at least 75%, 80%, 85%, 90%, 95%, 96%, 97%, 98%, or 99% identical to or homologous to an *E. coli* rfb(upec163) gene cluster. In a specific embodiment, the *E. coli* rfb(upec163) gene cluster is introduced into the host cell by genetic manipulation (e.g., the gene cluster is expressed on a plasmid or plasmids or integrated into the host cell genome (see, e.g., International Patent application No. PCT/EP2013/068737)). In another embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14) or a carrier protein comprising a consensus sequence or Asp(Glu)-X-Asn-Z-Ser(Thr), wherein X and Z are independently selected from any natural amino acid except Pro (SEQ ID NO:15) (see WO 2006/119987). In another specific embodiment, some or all of the genes of the rfb cluster are heterologous to the host cell. In another specific embodiment, said oligosaccharyl transferase is heterologous to the host cell. In another specific embodiment, said carrier protein is heterologous to the host cell. In a specific embodiment, the host cell is *E. coli*.

Upec177 is an *E. coli* strain identified herein as belonging to the O25B serotype, and the rfb gene cluster of the strain (and strains of the O25B serotype in general) has been identified herein for the first time as comprising genes that produce a novel *E. coli* polysaccharide, O25B. In another specific embodiment, provided herein is a prokaryotic host cell comprising an *E. coli* rfb(upec177) gene cluster, or a gene cluster that is about or at least 75%, 80%, 85%, 90%, 95%, 96%, 97%, 98%, or 99% identical to or homologous to an *E. coli* rfb(upec177) gene cluster. In a specific embodiment, the *E. coli* rfb(upec177) gene cluster is introduced into the host cell by genetic manipulation (e.g., the gene cluster is expressed on a plasmid or plasmids or integrated into the host cell genome (see, e.g., International Patent application No. PCT/EP2013/068737)). In another embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14) or a carrier protein comprising a consensus sequence or Asp(Glu)-X-Asn-Z-Ser(Thr), wherein X and Z are independently selected from any natural amino acid except Pro (SEQ ID NO:15) (see WO 2006/119987). In another specific embodiment, some or all of the genes of the rfb cluster are heterologous to the host cell. In another specific embodiment, said oligosaccharyl transferase is heterologous to the host cell. In another specific embodiment, said carrier protein is heterologous to the host cell. In a specific embodiment, the host cell is *E. coli*.

In another specific embodiment, provided herein is a prokaryotic host cell (e.g., a recombinantly engineered prokaryotic host cell) that produces O25B, wherein said host cell comprises rmlB, rmlD, rmlA, rmlC, wzx, wekA, wekB, wzy, wbbJ, wbbK, and/or wbbL. Such host cells can be engineered using recombinant approaches to comprise one or more plasmids comprising the rmlB, rmlD, rmlA, rmlC, wzx, wekA, wekB, wzy, wbbJ, wbbK, and/or wbbL genes. In certain embodiments, said one or more plasmids is integrated into the host cell genome. In a specific embodiment, said rmlB comprises or consists of SEQ ID NO:1, or is 75%, 80%, 85%, 90%, 95%, 96%, 97%, 98%, or 99% identical to or homologous to SEQ ID NO:1. In a specific embodiment, said rmlD comprises or consists of SEQ ID NO:2, or is 75%, 80%, 85%, 90%, 95%, 96%, 97%, 98%, or 99% identical to or homologous to SEQ ID NO:2. In a specific embodiment, said rmlA comprises or consists of SEQ ID NO:3, or is 75%, 80%, 85%, 90%, 95%, 96%, 97%, 98%, or 99% identical to or homologous to SEQ ID NO:3. In a specific embodiment, said rmlC comprises or consists of SEQ ID NO:4, or is 75%, 80%, 85%, 90%, 95%, 96%, 97%, 98%, or 99% identical to or homologous to SEQ ID NO:4. In a specific embodiment, said wzx comprises or consists of SEQ ID NO:5, or is 75%, 80%, 85%, 90%, 95%, 96%, 97%, 98%, or 99% identical to or homologous to SEQ ID NO:5. In a specific embodiment, said wekA comprises or consists of SEQ ID NO:6, or is 75%, 80%, 85%, 90%, 95%, 96%, 97%, 98%, or 99% identical to or homologous to SEQ ID NO:6. In a specific embodiment, said wekB comprises or consists of SEQ ID NO:7, or is 75%, 80%, 85%, 90%, 95%, 96%, 97%, 98%, or 99% identical to or homologous to SEQ ID NO:7. In a specific embodiment, said wzy comprises or consists of SEQ ID NO:8, or is 75%, 80%, 85%, 90%, 95%, 96%, 97%, 98%, or 99% identical to or homologous to SEQ ID NO:8. In a specific embodiment, said wbbJ comprises or consists of SEQ ID NO:9, or is 75%, 80%, 85%, 90%, 95%, 96%, 97%, 98%, or 99% identical to or homologous to SEQ ID NO:9. In a specific embodiment, said wbbK comprises or consists of SEQ ID NO:10, or is 75%, 80%, 85%, 90%, 95%, 96%, 97%, 98%, or 99% identical to or homologous to SEQ ID NO:10. In a specific embodiment, said wbbL comprises or consists of SEQ ID NO:11, or is 75%, 80%, 85%, 90%, 95%, 96%, 97%, 98%, or 99% identical to or homologous to SEQ ID NO:11. In another specific embodiment, the prokaryotic host cell comprises a nucleic acid sequence encoding an oligosaccharyl transferase. In another specific embodiment, the prokaryotic host cell comprises a nucleic acid sequence encoding a carrier protein comprising a consensus sequence Asn-X-Ser(Thr), wherein X can be any amino acid except Pro (SEQ ID NO:14) or a carrier protein comprising a consensus sequence or Asp(Glu)-X-Asn-Z-Ser(Thr), wherein X and Z are independently selected from any natural amino acid except Pro (SEQ ID NO:15) (see WO 2006/119987). In another specific embodiment, some or all of the genes, rmlB, rmlD, rmlA, rmlC, wzx, wekA, wekB, wzy, wbbJ, wbbK, and wbbL, are heterologous to the host cell. In another specific embodiment, said oligosaccharyl transferase is heterologous to the host cell. In another specific embodiment, said carrier protein is heterologous to the host cell. In a specific embodiment, the host cell is *E. coli*.

In another specific embodiment, provided herein is a prokaryotic host cell (e.g., a recombinantly engineered prokaryotic host cell) that produces O25B, wherein said host cell comprises one, two, three, four, or more, e.g. all, of the following genes (or a nucleic acid that is about or at least 75%, 80%, 85%, 90%, 95%, 96%, 97%, 98%, or 99% identical to or homologous to one of the following genes, and preferably encoding protein with the same function): rmlB (SEQ ID NO:1), rmlD (SEQ ID NO:2), rmlA (SEQ ID NO:3), rmlC (SEQ ID NO:4), wzx (SEQ ID NO:5), wekA (SEQ ID NO:6), wekB (SEQ ID NO:7), wzy (SEQ ID NO:8), wbbJ (SEQ ID NO:9), wbbK (SEQ ID NO:10), and/or wbbL (SEQ ID NO:11). In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli.*

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of rmlB (SEQ ID NO:1). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes a dTDP-Glucose 4,6-dehydratase, e.g., a dTDP-Glucose 4,6-dehydratase encoded by rmlB. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic acid that is about or at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:1. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli.*

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of rmlD (SEQ ID NO:2). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes a dTDP-6-Deoxy-D-glucose 3,5-epimerase, e.g., a dTDP-6-Deoxy-D-glucose 3,5-epimerase encoded by rmlD. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic acid that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:2. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli.*

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of rmlA (SEQ ID NO:3). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes a Glucose-1-phosphate thymidylyltransferase, e.g., a Glucose-1-phosphate thymidylyltransferase encoded by rmlA. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic acid that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:3. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli.*

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of rmlC (SEQ ID NO:4). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes a dTDP-4-dehydrorhamnose 3,5-epimerase, e.g., a dTDP-4-dehydrorhamnose 3,5-epimerase encoded by rmlC. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic acid that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:4. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli.*

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of wzx (SEQ ID NO:5). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes an O antigen flippase, e.g., an O antigen flippase encoded by wzx. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic acid that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:5. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of wekA (SEQ ID NO:6). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes a rhamnosyltransferase, e.g., an dTDP-Rha:Glc-Rha(Ac)-GlcNAc-UPP α-1,3-rhamnosyltransferase encoded by wekA. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise nucleic acids that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:6. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of wekB (SEQ ID NO:7). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes a wekB glucosyltransferase, e.g., a UDP-Glc:Glc-Rha(Ac)-GlcNAc-UPP β-1,6-glucosyltransferase encoded by wekB. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise nucleic acids that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:7. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of wzy (SEQ ID NO:8). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes an O antigen polymerase, e.g., an O antigen polymerase encoded by wzy. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise nucleic acids that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:8. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of wbbJ (SEQ ID NO:9). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes an O-acetyl transferase, e.g., an O-acetyl transferase encoded by wbbJ. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise nucleic acids that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:9. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of wbbK (SEQ ID NO:10). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes a glucosyltransferase, e.g., a UDP-Glc:Rha-GlcNAc-UPP α-1,3-glucosyltransferase encoded by wbbK. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise nucleic acids that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:10. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise the nucleic acid sequence of wbbL (SEQ ID NO:11). In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise a nucleic sequence that encodes a rhamnosyl transferase, e.g., a dTDP-Rha:GlcNAc-UPP α-1,3-rhamnosyltransferase encoded by wbbL. In another specific embodiment, provided herein is a prokaryotic host cell capable of producing O25B, and/or an O25B bioconjugate (i.e., a carrier protein linked to the *E. coli* O25B antigen), wherein said host cell naturally comprises or is engineered to comprise nucleic acids that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:11. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) capable of producing O25B, and/or an O25B bioconjugate (i.e., a carrier protein linked to the *E. coli* O25B antigen), wherein said host cell naturally comprises or is engineered to comprise at least one, two, three, four or more, e.g. all, of the following: (i) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:1; (ii) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:2; (iii) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:3; (iv) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:4; (v) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:5; (vi) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:6; (vii) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:7; (viii) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:8; (ix) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:9; (x) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:10; and/or (xi) a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:11. In a specific embodiment, said host cell has been engineered to comprise each of said sequences, i.e., said sequences are heterologous to said host cell. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser (Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) that produces O25B, wherein said host cell comprises at least two of (i) wbbJ (SEQ ID NO:9) or a nucleic acid that is about or at least 75%, 80%, 85%, 90%, 95%, 96%, 97%, 98%, or 99% identical to or homologous to SEQ ID NO:9; (ii) wbbK (SEQ ID NO:10) or a nucleic acid that is about or at least 75%, 80%, 85%, 90%, 95%, 96%, 97%, 98%, or 99% identical to or homologous to SEQ ID NO:10; and/or (iii) wbbL (SEQ ID NO:11) or a nucleic acid that is about or at least 75%, 80%, 85%, 90%, 95%, 96%, 97%, 98%, or 99% identical to or homologous to SEQ ID NO:11. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) that produces O25B, wherein said host cell comprises each of (i) wbbJ (SEQ ID NO:9) or a nucleic acid that is about or at least 75%, 80%, 85%, 90%, 95%, 96%, 97%, 98%, or 99% identical to or homologous to SEQ ID NO:9; (ii) wbbK (SEQ ID NO:10) or a nucleic acid that is about or at least 75%, 80%, 85%, 90%, 95%, 96%, 97%, 98%, or 99% identical to or homologous to SEQ ID NO:10; and (iii) wbbL (SEQ ID NO:11) or a nucleic acid that is about or at least 75%, 80%, 85%, 90%, 95%, 96%, 97%, 98%, or 99% identical to or homologous to SEQ ID NO:11. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another specific embodiment, provided herein is a prokaryotic host cell (e.g., a recombinantly engineered prokaryotic host cell) that produces O25B, wherein said host cell comprises (i) dTDP-Glucose 4,6-dehydratase; (ii) dTDP-6-Deoxy-D-glucose 3,5-epimerase; (iii) Glucose-1-phosphate thymidylyltransferase; (iv) dTDP-4-dehydrorhamnose 3,5-epimerase; (v) O antigen flippase; (vi) dTDP-Rha:Glc-Rha(Ac)-GlcNAc-UPP α-1,3-rhamnosyltransferase; (vii) UDP-Glc:Glc-Rha(Ac)-GlcNAc-UPP β-1,6-glucosyltransferase (viii) O antigen polymerase; (ix) O-acetyl transferase; (x) UDP-Glc:Rha-GlcNAc-UPP α-1,3-glucosyltransferase and/or (xi) dTDP-Rha: GlcNAc-UPP α-1,3-rhamnosyltransferase. In a specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser (Thr), wherein X can be any amino acid except Pro (SEQ ID NO:14) or a carrier protein comprising a consensus sequence or Asp(Glu)-X-Asn-Z-Ser(Thr), wherein X and Z are independently selected from any natural amino acid except Pro (SEQ ID NO:15) (see WO 2006/119987). In another specific embodiment, some or all of (i) dTDP-Glucose 4,6-dehydratase; (ii) dTDP-6-Deoxy-D-glucose 3,5-epimerase; (iii) Glucose-1-phosphate thymidylyltransferase; (iv) dTDP-4-dehydrorhamnose 3,5-epimerase; (v) O antigen flippase; (vi) dTDP-Rha:Glc-Rha(Ac)-GlcNAc-UPP α-1,3-rhamnosyltransferase; (vii) UDP-Glc:Glc-Rha (Ac)-GlcNAc-UPP β-1,6-glucosyltransferase (viii) O antigen polymerase; (ix) O-acetyl transferase; (x) UDP-Glc: Rha-GlcNAc-UPP α-1,3-glucosyltransferase and/or (xi) dTDP-Rha: GlcNAc-UPP α-1,3-rhamnosyltransferase are heterologous to the host cell. In another specific embodiment, said oligosaccharyl transferase is heterologous to the host cell. In another specific embodiment, said carrier protein is heterologous to the host cell. In a specific embodiment, the host cell is *E. coli*.

In another aspect, provided herein is a prokaryotic host cell (e.g., a recombinantly engineered prokaryotic host cell) that produces *E. coli* O25A, i.e., said host cell comprises enzymes capable of synthesizing *E. coli* O25A (see, e.g., FIG. 3). In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another aspect, provided herein is a prokaryotic host cell (e.g., a recombinantly engineered prokaryotic host cell) that produces *E. coli* O1, i.e., said host cell comprises enzymes capable of synthesizing *E. coli* O1 (see, e.g., FIG. 12). In a specific embodiment, provided herein is a host cell that produces *E. coli* O1A. In a specific embodiment, provided herein is a host cell that produces *E. coli* O1B. In a specific embodiment, provided herein is a host cell that produces *E. coli* O1C. In another specific embodiment, the prokaryotic host cell comprises a nucleic acid sequence encoding an oligosaccharyl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli*.

In another aspect, provided herein is a prokaryotic host cell (e.g., a recombinantly engineered prokaryotic host cell) that produces *E. coli* O2, i.e., said host cell comprises enzymes capable of synthesizing *E. coli* O2 (see, e.g., FIG.

19). In another specific embodiment, the prokaryotic host cell comprises a nucleic acid sequence encoding an oligosacchryl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli.*

In another aspect, provided herein is a prokaryotic host cell (e.g., a recombinantly engineered prokaryotic host cell) that produces *E. coli* O6, i.e., said host cell comprises enzymes capable of synthesizing *E. coli* O6 (see, e.g., FIG. 17). In a specific embodiment, provided herein is a host cell that produces *E. coli* O6 comprising a branching Glc monosaccharide or an O6 antigen comprising a branching GlcNAc monosaccharide. In another specific embodiment, the prokaryotic host cell comprises a nucleic acid sequence encoding an oligosacchryl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli.*

Further provided herein is a prokaryotic host cell (e.g., a recombinantly engineered prokaryotic host cell) capable of producing more than one type of *E. coli* O antigen. In a specific embodiment, provided herein is a host cell capable of producing at least two of the following: O25B, O25A, O1 (e.g., O1A, O1B, O1C), O2, and O6. In another specific embodiment, provided herein is a host cell capable of producing O25B and one or more of O25A, O1 (e.g., O1A, O1B, O1C), O2, and O6. In another specific embodiment, the prokaryotic host cell comprises a nucleic acid sequence encoding an oligosacchryl transferase. In another specific embodiment, the prokaryotic host cell further comprises a nucleic acid sequence encoding a carrier protein comprising a consensus sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15) (see WO 2006/119987). In a specific embodiment, the host cell is *E. coli.*

5.3.1 Genetic Background

Any host cells known to those of skill in the art can be used to produce the *E. coli* O antigens described herein (e.g., O25B) and bioconjugates comprising the *E. coli* O antigens described herein (e.g., O25B), including archea, prokaryotic host cells, and eukaryotic host cells. Exemplary prokaryotic host cells for use in production of the *E. coli* O antigens described herein and bioconjugates comprising the *E. coli* O antigens described herein include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell used to produce the *E. coli* O antigens described herein and bioconjugates comprising the *E. coli* O antigens described herein is *E. coli.*

In certain embodiments, the host cells used to produce the *E. coli* O antigens and bioconjugates described herein are engineered to comprise heterologous nucleic acids, e.g., heterologous nucleic acids that encode one or more carrier proteins and/or heterologous nucleic acids that encode one or more proteins, e.g., genes encoding one or more proteins. In a specific embodiment, heterologous nucleic acids that encode proteins involved in glycosylation pathways (e.g., prokaryotic and/or eukaryotic glycosylation pathways) may be introduced into the host cells described herein. Such nucleic acids may encode proteins including, without limitation, oligosacchryl transferases and/or glycosyltransferases. Heterologous nucleic acids (e.g., nucleic acids that encode carrier proteins and/or nucleic acids that encode other proteins, e.g., proteins involved in glycosylation) can be introduced into the host cells described herein using any methods known to those of skill in the art, e.g., electroporation, chemical transformation by heat shock, natural transformation, phage transduction, and conjugation. In specific embodiments, heterologous nucleic acids are introduced into the host cells described herein using a plasmid, e.g., the heterologous nucleic acids are expressed in the host cells by a plasmid (e.g., an expression vector). In another specific embodiment, heterologous nucleic acids are introduced into the host cells described herein using the method of insertion described in International Patent application No. PCT/EP2013/068737.

In certain embodiments, additional modifications may be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein or do not encode a protein whatsoever). In certain embodiments, when nucleic acids are deleted from the genome of the host cells provided herein, they are replaced by a desirable sequence, e.g., a sequence that is useful for glycoprotein production.

Exemplary genes that can be deleted in host cells (and, in some cases, replaced with other desired nucleic acid sequences) include genes of host cells involved in glycolipid biosynthesis, such as waaL (see, e.g., Feldman et al., 2005, PNAS USA 102:3016-3021), the lipid A core biosynthesis cluster (waa), galactose cluster (gal), arabinose cluster (ara), colonic acid cluster (wc), capsular polysaccharide cluster, undecaprenol-p biosynthesis genes (e.g. uppS, uppP), und-P recycling genes, metabolic enzymes involved in nucleotide activated sugar biosynthesis, enterobacterial common antigen cluster, and prophage O antigen modification clusters like the gtrABS cluster. In a specific embodiment, the host cells described herein are modified such that they do not produce any O antigens other than a desired O antigen from an ExPEC, e.g., O25B. In a specific embodiment, one or more of the waaL gene, gtrA gene, gtrB gene, gtrS gene, or the rfb gene cluster is deleted or functionally inactivated from the genome of a prokaryotic host cell provided herein. In one embodiment, a host cell used herein is *E. coli* that produces O25B antigen, wherein the waaL gene, gtrA gene, gtrB gene, and gtrS gene are deleted or functionally inactivated from the genome of the host cell. In another embodiment, a host cell used herein is *E. coli* that produces O25B antigen, wherein the waaL gene and gtrS gene are deleted or functionally inactivated from the genome of the host cell.

In certain embodiments, the modified host cells provided herein can be used for protein glycosylation. Protein glycosylation may be designed to produce bioconjugates for use in vaccine formulations, e.g., vaccines that contain *E. coli* polysaccharide antigen(s), e.g., O25 (e.g., O25B), O1, O2, and O6.

5.3.2 Carrier Proteins

Any carrier protein suitable for use in the production of conjugate vaccines (e.g., bioconjugates for use in vaccines) can be used herein, e.g., nucleic acids encoding the carrier protein can be introduced into a host provided herein for the production of a bioconjugate comprising a carrier protein linked to an ExPEC antigen (e.g., O25B). Exemplary carrier proteins include, without limitation, detoxified Exotoxin A of *P. aeruginosa* (EPA; see, e.g., Ihssen, et al., (2010) Microbial cell factories 9, 61), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, and *C. jejuni* natural glycoproteins. For EPA, various detoxified protein variants have been described in literature and could be used as carrier proteins.

In certain embodiments, the carrier proteins used in the generation of the bioconjugates described herein are modified, e.g., modified in such a way that the protein is less toxic and/or more susceptible to glycosylation. In a specific embodiment, the carrier proteins used in the generation of the bioconjugates described herein are modified such that the number of glycosylation sites in the carrier proteins is maximized in a manner that allows for lower concentrations of the protein to be administered, e.g., in an immunogenic composition, in its bioconjugate form.

In certain embodiments, the carrier proteins described herein are modified to include 1, 2, 3, 4, 5, 6, 7, 8, 9, 10, or more glycosylation sites than would normally be associated with the carrier protein (e.g., relative to the number of glycosylation sites associated with the carrier protein in its native/natural, e.g., "wild-type" state). In specific embodiments, introduction of glycosylation sites is accomplished by insertion of glycosylation consensus sequences (e.g., Asn-X-Ser(Thr), wherein X can be any amino acid except Pro (SEQ ID NO:14); or Asp(Glu)-X-Asn-Z-Ser(Thr), wherein X and Z are independently selected from any natural amino acid except Pro (SEQ ID NO:15) (see WO 2006/119987)) anywhere in the primary structure of the protein. Introduction of such glycosylation sites can be accomplished by, e.g., adding new amino acids to the primary structure of the protein (i.e., the glycosylation sites are added, in full or in part), or by mutating existing amino acids in the protein in order to generate the glycosylation sites (i.e., amino acids are not added to the protein, but selected amino acids of the protein are mutated so as to form glycosylation sites). Those of skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In certain embodiments, the classical 5 amino acid glycosylation consensus sequence may be extended by lysine residues for more efficient glycosylation, and thus the inserted consensus sequence may encode 5, 6, or 7 amino acids that should be inserted or that replace acceptor protein amino acids. In one particular embodiment a carrier protein is detoxified EPA comprising 4 consensus glycosylation sequences Asp/Glu-X-Asn-Z-Ser/Thr (SEQ ID NO:15), and has an amino acid sequence as provided in SEQ ID NO: 13.

In certain embodiments, the carrier proteins used in the generation of the bioconjugates described herein comprise a "tag," i.e., a sequence of amino acids that allows for the isolation and/or identification of the carrier protein. For example, adding a tag to a carrier protein described herein can be useful in the purification of that protein and, hence, the purification of conjugate vaccines comprising the tagged carrier protein. Exemplary tags that can be used herein include, without limitation, histidine (HIS) tags (e.g., hexa histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia* carotovorans pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI).

5.3.3 Glycosylation Machinery

The host cells provided herein comprise, and/or can be modified to comprise, nucleic acids that encode genetic machinery (e.g., glycosyltransferases) capable of producing O antigens from ExPEC, e.g., the O25 (e.g., O25B), O1, O2, and/or O6 antigens. See Section 5.1.

Glycosyltransferases

The host cells provided herein comprise nucleic acids that encode glycosyltransferases capable of producing ExPEC O antigens, e.g., an O antigen from *E. coli* of serotype O25 (e.g., O25A or O25B, see FIG. 3B), O1 (see FIG. 12), O2 (see FIG. 19), and O6 (e.g., an O6 serotype producing an O6 antigen comprising a branching Glc monosaccharide or an O6 antigen comprising a branching GlcNAc monosaccharide, see FIG. 17). Exemplary nucleic acids are described in Section 5.1. In certain embodiments, some or all of the nucleic acids that encode glycosyltransferases capable of producing an ExPEC O antigen are naturally expressed by the host cells provided herein (e.g., the nucleic acids are present in the "wild-type" background of the host cell). In certain embodiments, some or all of the nucleic acids that encode glycosyltransferases capable of producing an ExPEC O antigen are not naturally expressed by the host cells provided herein, i.e., some or all of the nucleic acids are heterologous to the host cell. Host cells can be engineered to comprise specific nucleic acids, e.g., the nucleic acids described in Section 5.1, using methods known in the art, e.g., the methods described in Section 5.3.

In a specific embodiment, the host cells provided herein comprise nucleic acids that encode glycosyltransferases capable of producing an *E. coli* O antigen of the O25B serotype, i.e., an O25B antigen described herein. In a specific embodiment, said nucleic acids encode the rfb cluster from upec138 (SEQ ID NO:12), or a gene cluster that is about or at least 75%, 80%, 85%, 90%, 95%, 96%, 97%, 98% or 99% identical to or homologous to SEQ ID NO:12.

In another specific embodiment, said nucleic acids encode the rfb cluster from upec163, or a gene cluster that is about or at least 75%, 80%, 85%, 90%, 95%, 96%, 97%, 98% or 99% identical to or homologous to the rfb cluster from upec163. In another specific embodiment, said nucleic acids encode the rfb cluster from upec177, or a gene cluster that is about or at least 75%, 80%, 85%, 90%, 95%, 96%, 97%, 98% or 99% identical to or homologous to the rfb cluster from upec177.

In another specific embodiment, said nucleic acids that encode glycosyltransferases capable of producing an *E. coli* O antigen of the O25B serotype are genes of an O25B serotype, wherein said genes are rmlB (SEQ ID NO:1), rmlD (SEQ ID NO:2) rmlA (SEQ ID NO:3), rmlC (SEQ ID NO:4), wzx (SEQ ID NO:5), wekA (SEQ ID NO:6), wekB (SEQ ID NO:7), wzy (SEQ ID NO:8), wbbJ (SEQ ID NO:9), wbbK (SEQ ID NO:10), and wbbL (SEQ ID NO:11). See tables 3 and 9.

In a specific embodiment, the host cells provided herein comprise nucleic acids that encode proteins (e.g., glycosyltransferases) capable of producing an *E. coli* O antigen of the O25A serotype, i.e., an O25A antigen described herein. In another specific embodiment, said nucleic acids that encode proteins (e.g., glycosyltransferases) capable of producing an *E. coli* O antigen of the O25A serotype are genes of an O25 serotype, wherein said genes are rmlB, rmlD, rmlA, rmlC, wzx, wekA, wekB, wekC, wzy, fnlA, fnlB, fnlC, wbuB, and/or wbuC. See Wang, et al. (2010) J Clin Microbiol 48, 2066-2074; GenBank GU014554; and Table 2.

In another specific embodiment, the host cells provided herein comprise nucleic acids that encode glycosyltransferases capable of producing an O antigen *E. coli* of the O2 serotype. In another specific embodiment, said nucleic acids that encode glycosyltransferases capable of producing an *E. coli* O antigen of the O2 serotype are genes of an O2 serotype, wherein said genes are rmlB, rmlD, rmlA, rmlC, wzx, wekP, wekQ, wekR, wzy, fdtA, fdtB, and/or fdtC. See Li, et al., (2010) J Microbiol Methods 82, 71-77; Fratamico, et al., 2010, Canadian Journal of Microbiology 56, 308-316; and Table 5.

In another specific embodiment, the host cells provided herein comprise nucleic acids that encode glycosyltransferases capable of producing an O antigen *E. coli* of the O6 serotype. See Welch et al., 2002, PNAS USA 99(26):17020-17024; Jann et al., Carbohydr. Res. 263 (1994) 217-225, and Jansson et al., Carbohydr. Res. 131 (1984) 277-283. In a specific embodiment, said O6 serotype comprises a branched Glc monosaccharide.

In another specific embodiment, the host cells provided herein comprise nucleic acids that encode glycosyltransferases capable of producing an O antigen *E. coli* of the O1 serotype. In a specific embodiment, said O1 serotype is O1A. In another specific embodiment, said nucleic acids that encode glycosyltransferases capable of producing an *E. coli* O antigen of the O1 serotype are genes of an O1 serotype, wherein said genes are rmlB, rmlD, rmlA, rmlC, wzx, mnaA, wekM, wzy, wekN, and/or wekO.

Oligosaccharyl Transferases

Oligosaccharyl transferases transfer lipid-linked oligosaccharides to asparagine residues of nascent polypeptide chains that comprise an N-glycoxylation consensus motif, e.g., Asn-X-Ser(Thr), wherein X can be any amino acid except Pro (SEQ ID NO:14); or Asp(Glu)-X-Asn-Z-Ser (Thr), wherein X and Z are independently selected from any natural amino acid except Pro (SEQ ID NO:15) (see WO 2006/119987). See, e.g., WO 2003/074687 and WO 2006/119987, the disclosures of which are herein incorporated by reference in their entirety.

In certain embodiments, the host cells provided herein comprise a nucleic acid that encodes an oligosaccharyl transferase. The nucleic acid that encodes an oligosaccharyl transferase can be native to the host cell, or can be introduced into the host cell using genetic approaches, as described above. The oligosaccharyl transferase can be from any source known in the art. In a specific embodiment, the oligosaccharyl transferase is an oligosaccharyl transferase from *Campylobacter*. In another specific embodiment, the oligosaccharyl transferase is an oligosaccharyl transferase from *Campylobacter jejuni* (i.e., pglB; see, e.g., Wacker et al., 2002, Science 298:1790-1793; see also, e.g., NCBI Gene ID: 3231775, UniProt Accession No. O86154). In another specific embodiment, the oligosaccharyl transferase is an oligosaccharyl transferase from *Campylobacter lari* (see, e.g., NCBI Gene ID: 7410986).

5.4 Bioconjugates

In certain embodiments, the host cells described herein can be used to produce bioconjugates comprising an *E. coli* O antigen described herein (e.g., O25B; see Section 5.2) linked to a carrier protein. Methods of producing such bioconjugates using host cells are known in the art. See, e.g., WO 2003/074687 and WO 2006/119987.

Alternatively, glycoconjugates can be prepared by chemical synthesis, i.e., prepared outside of host cells (in vitro). For example, the *E. coli* O antigens described herein, e.g., O25B, can be conjugated to carrier proteins using methods known to those of skill in the art, including by means of using activation reactive groups in the polysaccharide/oligosaccharide as well as the protein carrier. See, e.g., Pawlowski et al., 2000, Vaccine 18:1873-1885; and Robbins, et al., 2009, Proc Natl Acad Sci USA 106:7974-7978), the disclosures of which are herein incorporated by reference. Such approaches comprise extraction of antigenic polysaccharides/oligosaccharides from host cells, purifying the polysaccharides/oligosaccharides, chemically activating the polysaccharides/oligosaccharides, and conjugating the polysaccharides/oligosaccharides to a carrier protein.

Bioconjugates, as described herein, have advantageous properties over glycoconjugates, e.g., bioconjugates require less chemicals in manufacture and are more consistent in terms of the final product generated. Thus, bioconjugates are preferred over chemically produced glycoconjugates.

In a specific embodiment, provided herein are bioconjugates comprising a carrier protein linked to an ExPEC O antigen described herein. See Section 5.2.

In a specific embodiment, provided herein is a bioconjugate comprising a carrier protein (e.g., EPA) N-linked to *E. coli* O25B.

In another specific embodiment, provided herein is a bioconjugate comprising a carrier protein (e.g., EPA) linked to a compound of Formula O25B presented below:

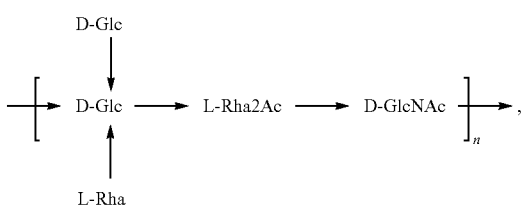

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, the carrier protein is N-linked to the O antigen of Formula O25B, i.e., O25B is linked to the Asn residue of a carrier protein comprising the sequence Asn-X-Ser(Thr), wherein X can be any amino acid except Pro (SEQ ID NO:14); or a carrier protein comprising a consensus sequence Asp(Glu)-X-Asn-Z-Ser(Thr), wherein X and Z are independently selected from any natural amino acid except Pro (SEQ ID NO:15).

In another specific embodiment, provided herein is a bioconjugate comprising a carrier protein (e.g., EPA) linked to a compound of Formula O25B', presented below:

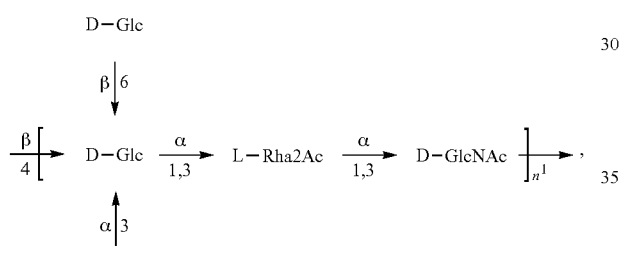

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In a specific embodiment, the carrier protein is N-linked to the O antigen of Formula O25B'.

In another specific embodiment, provided herein is a bioconjugate comprising a carrier protein (e.g., EPA) linked to an O25A antigen. In a specific embodiment, said O25A antigen comprises the formula O25A:

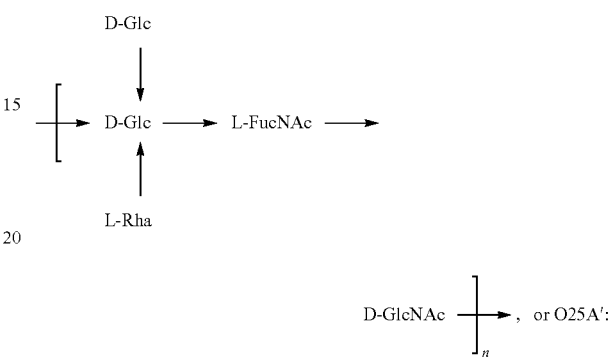

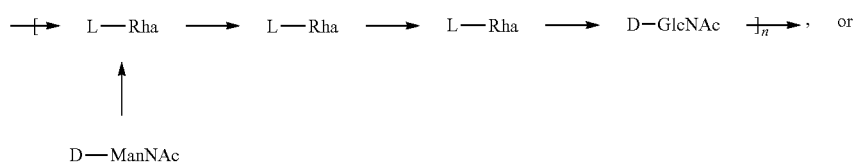

In another specific embodiment, provided herein is a bioconjugate comprising a carrier protein (e.g., EPA) linked to an O1 antigen. In a specific embodiment, said O1 antigen is O1A, e.g., said antigen comprises the formula O1A:

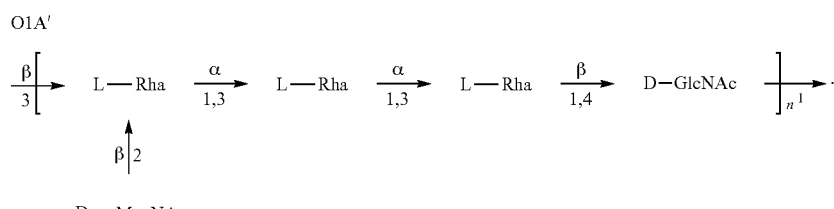

In another specific embodiment, said O1 antigen is O1B, e.g., said antigen comprises the formula O1B:

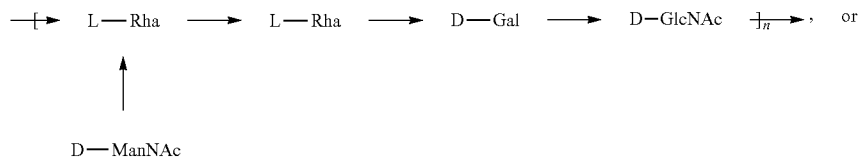

O1B'

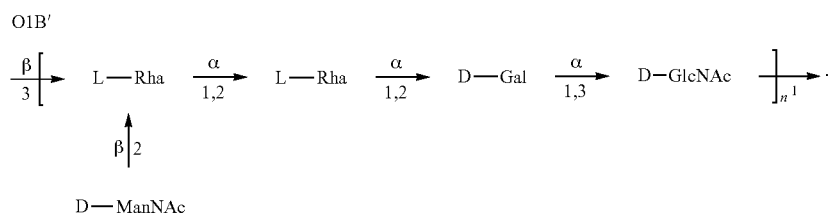

In another specific embodiment, said O1 antigen is O1C, e.g., said antigen comprises the formula O1C:

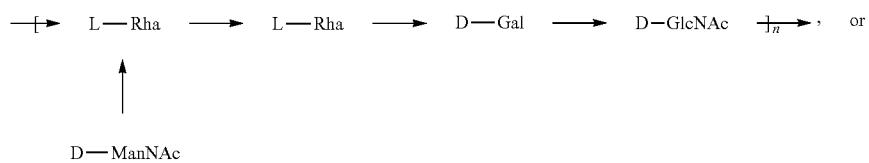

O1C'

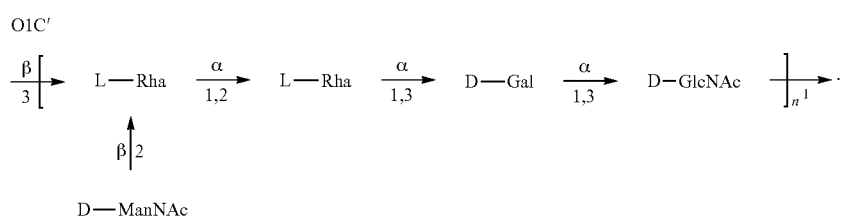

In another specific embodiment, provided herein is a bioconjugate comprising a carrier protein (e.g., EPA) linked to an O2 antigen. In a specific embodiment, said O2 antigen comprises the formula O2:

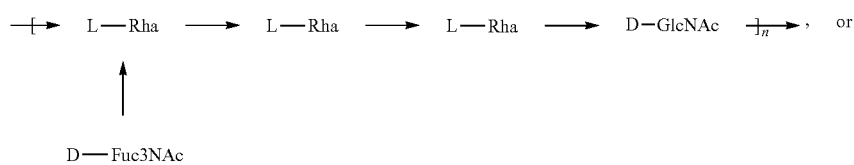

O2'

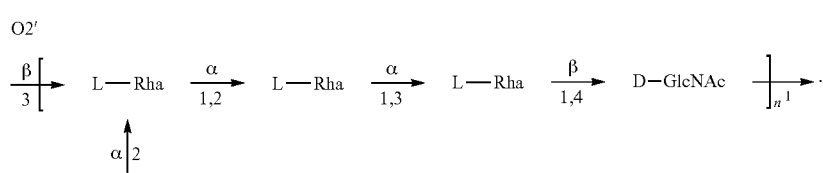

In another specific embodiment, provided herein is a bioconjugate comprising a carrier protein (e.g., EPA) linked to an O6 antigen. In a specific embodiment, said O6 antigen comprises the formula O6Glc:

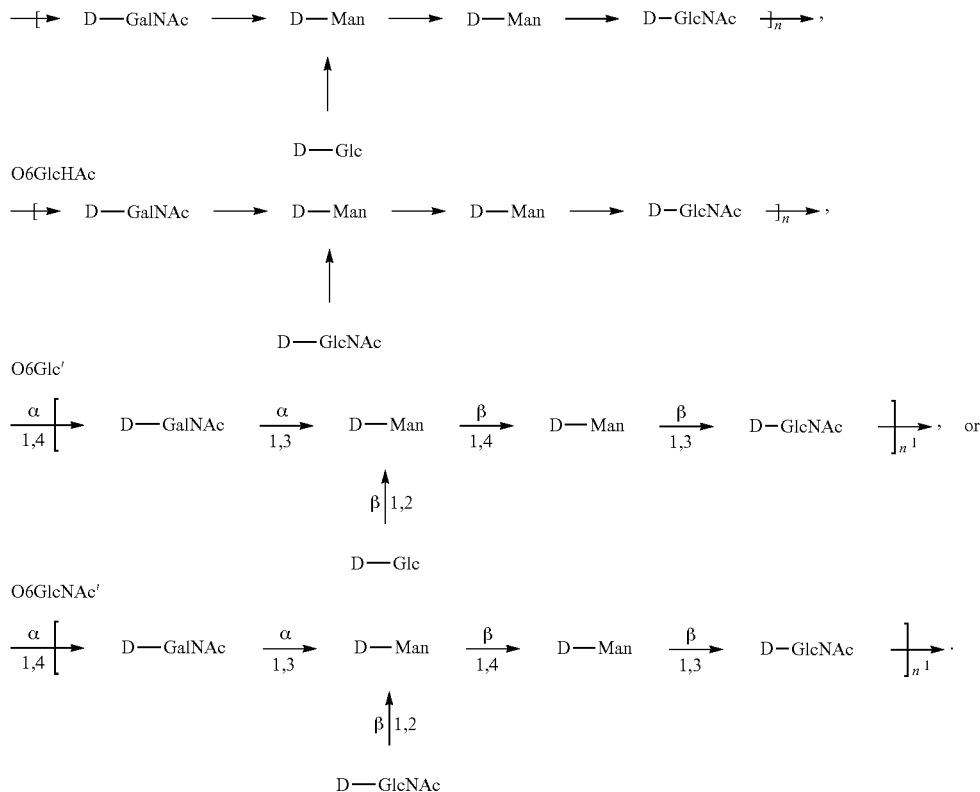

The bioconjugates described herein can be purified by any method known in the art for purification of a protein, for example, by chromatography (e.g., ion exchange, anionic exchange, affinity, and sizing column chromatography), centrifugation, differential solubility, or by any other standard technique for the purification of proteins. See, e.g., Saraswat et al., 2013, Biomed. Res. Int. ID#312709 (p. 1-18); see also the methods described in WO 2009/104074. Further, the bioconjugates may be fused to heterologous polypeptide sequences described herein or otherwise known in the art to facilitate purification. The actual conditions used to purify a particular bioconjugate will depend, in part, on the synthesis strategy (e.g., synthetic production vs. recombinant production) and on factors such as net charge, hydrophobicity, and/or hydrophilicity of the bioconjugate, and will be apparent to those having skill in the art.

5.5 Antibodies Against O25B

The O25B antigen described herein (see Section 5.2) and/or bioconjugates comprising the O25B antigen described herein (see Section 5.4) can be used to elicit neutralizing antibodies against ExPEC. In a specific embodiment, the O25B antigen described herein and/or bioconjugates comprising the O25B antigen described herein can be administered to a subject (e.g., a human, mouse, rabbit, rat, guinea pig, etc.) to induce an immune response that includes the production of antibodies. Such antibodies can be isolated using techniques known to one of skill in the art (e.g., immunoaffinity chromatography, centrifugation, precipitation, etc.).

In addition, the O25B antigen described herein can be used to screen for antibodies from antibody libraries. For example, isolated O25B can be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, antibodies to be screened may be immobilized to a solid support and screened for binding to O25B. Any screening assay, such as a panning assay, ELISA, surface plasmon resonance, or other antibody screening assay known in the art may be used to screen for antibodies that bind to O25B. The antibody library screened may be a commercially available antibody library, an in vitro generated library, or a library obtained by identifying and cloning or isolating antibodies from an individual infected with EXPEC. Antibody libraries may be generated in accordance with methods known in the art. In a particular embodiment, the antibody library is generated by cloning the antibodies and using them in phage display libraries or a phagemid display library.

Antibodies identified or elicited using O25B and/or a bioconjugate of O25B can include immunoglobulin molecules and immunologically active portions of immunoglobulin molecules, i.e., molecules that contain an antigen binding site that specifically binds to O25B. The immunoglobulin molecules may be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above. In a specific embodiment, an antibody elicited or identified using O25B and/or a bioconjugate of O25B is a human or humanized monoclonal antibody.

Antibodies elicited or identified using using O25B and/or a bioconjugate of O25B can be used to monitor the efficacy of a therapy and/or disease progression. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, immunoradiometric assays, fluorescent immunoassays, protein A immunoassays and immunoelectrophoresis assays.

Antibodies elicited or identified using using O25B and/or a bioconjugate of O25B can be used to detect *E. coli* O25B strains, for example, from a plurality of *E. coli* strains and/or to diagnose an infection by an *E. coli* O25B strain.

5.6 Compositions 5.6.1 Compositions Comprising Host Cells

In one aspect, provided herein are compositions comprising the host cells described herein. Such compositions can be used in methods for generating the bioconjugates described herein (see Section 5.4), e.g., the compositions can be cultured under conditions suitable for the production of proteins. Subsequently, bioconjugates can be isolated from said compositions using methods known in the art.

The compositions comprising the host cells provided herein can comprise additional components suitable for maintenance and survival of the host cells described herein, and can additionally comprise additional components required or beneficial to the production of proteins by the host cells, e.g., inducers for inducible promoters, such as arabinose, IPTG.

5.6.2 Compositions Comprising Antigens and/or Bioconjugates

In another aspect, provided herein are compositions (e.g., pharmaceutical compositions) comprising one or more of the *E. coli* O antigens described herein (see Section 5.2) and compositions (e.g., pharmaceutical compositions) comprising one or more of the bioconjugates described herein (see Section 5.4). In a specific embodiment, a composition provided herein comprises one or more of the *E. coli* O antigens described herein (see Section 5.2). In another specific embodiment, a composition provided herein comprises one or more of the bioconjugates described herein (see Section 5.4). In another specific embodiment, a composition provided herein comprises one or more of the *E. coli* O antigens described herein (see Section 5.2) and one or more of the bioconjugates described herein (see Section 5.4). The compositions described herein are useful in the treatment and prevention of infection of subjects (e.g., human subjects) with extra-intestinal pathogenic *E. coli* (ExPEC). See Section 5.7.

In certain embodiments, in addition to comprising an *E. coli* O antigen described herein (see Section 5.2) and/or a bioconjugate described herein (see Section 5.4), the compositions (e.g., pharmaceutical compositions) described herein comprise a pharmaceutically acceptable carrier. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier," as used herein in the context of a pharmaceutically acceptable carrier, refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E.W. Martin.

In a specific embodiment, provided herein is a composition comprising a carrier protein (e.g., a carrier protein described in Section 5.3.2) linked to an antigen described herein, e.g., an ExPEC O antigen described in Section 5.2.

In another specific embodiment, a composition provided herein comprises a carrier protein (e.g., a carrier protein described in Section 5.3.2, e.g., EPA or MBP) linked to *E. coli* O25B (see Section 5.2).

In another specific embodiment, a composition provided herein comprises a carrier protein (e.g., a carrier protein described in Section 5.3.2, e.g., EPA or MBP) linked to *E. coli* O25A (see Section 5.2).

In another specific embodiment, a composition provided herein comprises a carrier protein (e.g., a carrier protein described in Section 5.3.2, e.g., EPA or MBP) linked to *E. coli* O1 (see Section 5.2). In another specific embodiment, said O1 macromolecule is O1A. In another specific embodiment, said O1 macromolecule is O1B. In another specific embodiment, said O1 macromolecule is O1C.

In another specific embodiment, a composition provided herein comprises a carrier protein (e.g., a carrier protein described in Section 5.3.2, e.g., EPA or MBP) linked to *E. coli* O2 (see Section 5.2).

In another specific embodiment, a composition provided herein comprises a carrier protein (e.g., a carrier protein described in Section 5.3.2, e.g., EPA or MBP) linked to *E. coli* O6 (see Section 5.2). In a specific embodiment, said O6 macromolecule is an O6 macromolecule comprising a branching Glc monosaccharide.

In another specific embodiment, provided herein is a composition, e.g., a pharmaceutical composition, comprising (i) an O25 (e.g., O25A or O25B) macromolecule, or a bioconjugate comprising O25 (e.g., O25A or O25B) and (ii) an O1 macromolecule or a bioconjugate comprising O1. See Section 5.2. In a specific embodiment, said O25 macromolecule is an O25B macromolecule. In another specific embodiment, said O1 macromolecule is O1A. In another specific embodiment, said O1 macromolecule is O1B. In another specific embodiment, said O1 macromolecule is O1C.

In another specific embodiment, provided herein is a composition, e.g., a pharmaceutical composition, comprising (i) an O25 (e.g., O25A or O25B) macromolecule, or a bioconjugate comprising O25 (e.g., O25A or O25B) and (ii) an O2 macromolecule or a bioconjugate comprising O2. See Sections 5.2 and 5.4. In a specific embodiment, said O25 macromolecule is an O25B macromolecule.

In another specific embodiment, provided herein is a composition, e.g., a pharmaceutical composition, comprising (i) an O25 (e.g., O25A or O25B) macromolecule, or a bioconjugate comprising O25 (e.g., O25A or O25B) and (ii) an O6 macromolecule (e.g., a O6 macromolecule comprising a branching Glc monosaccharide or a branching GlcNAc monosaccharide) or a bioconjugate comprising O6. See Sections 5.2 and 5.4. In a specific embodiment, said O25 macromolecule is an O25B macromolecule. In another specific embodiment, said O6 macromolecule is an O6 macromolecule comprising a branching Glc monosaccharide.

In another specific embodiment, provided herein is a composition, e.g., a pharmaceutical composition, comprising *E. coli* O25B (see Section 5.2) or a or a bioconjugate comprising O25 (see Section 5.4) and at least one of the following: (i) *E. coli* O1 or a bioconjugate comprising O1 (see Sections 5.2 and 5.4); (ii) *E. coli* O2 or a bioconjugate comprising O2 (see Sections 5.2 and 5.4); and/or (iii) *E. coli* O6 or a bioconjugate comprising O6 (see Sections 5.2 and 5.4). In another specific embodiment, said O1 is O1A. In another specific embodiment, said O1 is O1B. In another specific embodiment, said O1 is O1C. In another specific embodiment, said O6 is O6 comprising a branching Glc monosaccharide.

In another specific embodiment, provided herein is a composition, e.g., a pharmaceutical composition, comprising at least two of the following: (i) an O25 (e.g., O25A or O25B) macromolecule or a bioconjugate comprising O25 (e.g., O25A or O25B); (ii) an O1 macromolecule or a bioconjugate comprising O1; (iii) an O2 macromolecule or a bioconjugate comprising O2; and/or (iv) an O6 macromolecule (e.g., a O6 macromolecule comprising a branching Glc monosaccharide or a branching GlcNAc monosaccharide) or a bioconjugate comprising O6. In a specific embodiment, said O25 macromolecule is an O25B macromolecule. In another specific embodiment, said O1 macromolecule is O1A. In another specific embodiment, said O1 macromolecule is O1B. In another specific embodiment, said O1 macromolecule is O1C. In another specific embodiment, said O6 macromolecule is an O6 macromolecule comprising a branching Glc monosaccharide.

In another specific embodiment, provided herein is a composition, e.g., a pharmaceutical composition, comprising a bioconjugate comprising *E. coli* O25B and a bioconjugate comprising *E. coli* O1A. Such bioconjugates are described in Section 5.4.

In another specific embodiment, provided herein is a composition, e.g., a pharmaceutical composition, comprising a bioconjugate comprising *E. coli* O25B and a bioconjugate comprising *E. coli* O1B. Such bioconjugates are described in Section 5.4.

In another specific embodiment, provided herein is a composition, e.g., a pharmaceutical composition, comprising a bioconjugate comprising *E. coli* O25B and a bioconjugate comprising *E. coli* O1C. Such bioconjugates are described in Section 5.4.

In another specific embodiment, provided herein is a composition, e.g., a pharmaceutical composition, comprising a bioconjugate comprising *E. coli* O25B and a bioconjugate comprising *E. coli* O2. Such bioconjugates are described in Section 5.4.

In another specific embodiment, provided herein is a composition, e.g., a pharmaceutical composition, comprising a bioconjugate comprising *E. coli* O25B and a bioconjugate comprising *E. coli* O6. Such bioconjugates are described in Section 5.4.

In another specific embodiment, a composition provided herein comprises a carrier protein (e.g., a carrier protein described in Section 5.3.2, e.g., EPA or MBP) linked to *E. coli* O25B (see Section 5.2), (ii) a carrier protein (e.g., a carrier protein described in Section 5.3.2, e.g., EPA or MBP) linked to an *E. coli* O antigen of the O1 serotype, e.g., O1A (see Section 5.2), (iii) a carrier protein (e.g., a carrier protein described in Section 5.1.2, e.g., EPA or MBP) linked to an *E. coli* O antigen of the O2 serotype (see Section 5.2), and (iv) a carrier protein (e.g., a carrier protein described in Section 5.3.2, e.g., EPA or MBP) linked to an *E. coli* O antigen of the O6 serotype (see Section 5.2).

In certain embodiments, the foregoing compositions comprise a carrier protein (e.g., a carrier protein described in Section 5.3.2, e.g., EPA or MBP) linked to an *E. coli* O antigen of an *E. coli* serotype other than O1, O2, O6, or O25. Other useful *E. coli* serotypes are described, e.g., in Example 1 and Table 1, below.

In another specific embodiment, a composition provided herein comprises an O25 (e.g., O25A or O25B) macromolecule.

In another specific embodiment, a composition provided herein comprises an O1 macromolecule (e.g., O1A, O1B, or O1C).

In another specific embodiment, a composition provided herein comprises an O2 macromolecule.

In another specific embodiment, a composition provided herein comprises an O6 macromolecule (e.g., a O6 macromolecule comprising a branching Glc monosaccharide or a branching GlcNAc monosaccharide).

In another specific embodiment, a composition provided herein comprises an O25 (e.g., O25A or O25B) macromolecule, an O1 macromolecule, an O2 macromolecule, and an O6 macromolecule (e.g., a O6 macromolecule comprising a branching Glc monosaccharide or a branching GlcNAc monosaccharide). In a specific embodiment, said O25 macromolecule is an O25B macromolecule. In another specific embodiment, said O1 macromolecule is O1A. In another specific embodiment, said O6 macromolecule is an O6 macromolecule comprising a branching Glc monosaccharide.

The compositions provided herein can be used for eliciting an immune response in a host to whom the composition is administered, i.e., are immunogenic. Thus, the compositions described herein can be used as vaccines against ExPEC infection, or can be used in the treatment of ExPEC infection, and can accordingly be formulated as pharmaceutical compositions. See Section 5.7.

The compositions comprising the bioconjugates and/or macromolecules described herein may comprise any additional components suitable for use in pharmaceutical administration. In specific embodiments, the compositions described herein are monovalent formulations. In other embodiments, the compositions described herein are multivalent formulations, e.g., bivalent, trivalent, and tetravalent formulations. For example, a multivalent formulation comprises more than one bioconjugate or *E. coli* O antigen described herein. See Sections 5.2 and 5.4 for description of *E. coli* O antigens and bioconjugates, respectively. In a specific embodiment, a composition described herein is a tetravalent formulation comprising a macromolecule or bioconjugate, wherein said valences are from *E. coli* O antigens of the O25B, O1A, O6, and O2 serotypes/subserotypes.

In certain embodiments, the compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative.

In certain embodiments, the compositions described herein (e.g., the immunogenic compositions) comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a bioconjugate, but when the compound is administered alone does not generate an immune response to the bioconjugate. In some embodiments, the adjuvant generates an immune response to the poly bioconjugate peptide and does not produce an allergy or other adverse reaction. Adjuvants can enhance an immune response by several mechanisms including, e.g., lymphocyte recruitment, stimulation of B and/or T cells, and stimulation of macrophages.

Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998).

In certain embodiments, the compositions described herein are formulated to be suitable for the intended route of administration to a subject. For example, the compositions described herein may be formulated to be suitable for subcutaneous, parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, the compositions described herein additionally comprise one or more buffers, e.g., phosphate buffer and sucrose phosphate glutamate buffer. In other embodiments, the compositions described herein do not comprise buffers.

In certain embodiments, the compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the compositions described herein do not comprise salts.

The compositions described herein can be included in a container, pack, or dispenser together with instructions for administration.

The compositions described herein can be stored before use, e.g., the compositions can be stored frozen (e.g., at about −20° C. or at about −70° C.); stored in refrigerated conditions (e.g., at about 4° C.); or stored at room temperature.

5.7 Prophylactic and Therapeutic Uses

Provided herein are methods of treating and preventing extraintestinal *E. coli* (ExPEC) infection of a subject comprising administering to the subject an *E. coli* O antigen described herein (see Section 5.2), a bioconjugate described herein (see Section 5.4), or a composition described herein (see Section 5.6.2). In a specific embodiment, the compositions described herein (see Section 5.6.2) are used in the prevention of infection of a subject (e.g., human subjects) by ExPEC, i.e., the compositions described herein are used to vaccinate a subject against ExPEC infection. In another specific embodiment, the compositions described herein (see Section 5.6.2) are used in the treatment of a subject that has been infected by ExPEC.

Also provided herein are methods of inducing an immune response in a subject against ExPEC, comprising administering to the subject an *E. coli* O antigen described herein (see Section 5.2), a bioconjugate described herein (see Section 5.4), or a composition described herein (see Section 5.6.2). In one embodiment, said subject has an ExPEC infection at the time of administration. In another embodiment, said subject does not have an ExPEC infection at the time of administration.

Also provided herein are methods of inducing the production of opsonophagocytic antibodies against ExPEC in a subject, comprising administering to the subject an *E. coli* O antigen described herein (see Section 5.2), a bioconjugate described herein (see Section 5.4), or a composition described herein (see Section 5.6.2). In one embodiment, said subject has an ExPEC infection at the time of administration. In another embodiment, said subject does not have an ExPEC infection at the time of administration.

In a specific embodiment, provided herein is a method for preventing an *E. coli* (e.g., ExPEC) infection in a subject, wherein said method comprises administering to a subject in need thereof an effective amount of a composition described in Section 5.6.2. The methods of preventing ExPEC infection in a subject provided herein result in the induction of an immune response in a subject comprising administering to the subject a of a composition described in Section 5.6.2. One of skill in the art will understand that the methods of inducing an immune response in a subject described herein result in vaccination of the subject against infection by the ExPEC strains whose O antigens are present in the composition(s).

In a specific embodiment, provided herein is a method for treating an *E. coli* (e.g., ExPEC) infection in a subject, wherein said method comprises administering to a subject in need thereof an effective amount of a composition described in Section B 5.6.2.

In certain embodiments, the immune response induced by an *E. coli* O antigen described herein (see Section 5.2), a bioconjugate described herein (see Section 5.4), or a composition described herein (see Section 5.6.2) is effective to prevent and/or treat an ExPEC infection caused by any serotype, subserotype, or strain of ExPEC. In certain embodiments, the immune response induced by an *E. coli* O antigen described herein (see Section 5.2), a bioconjugate described herein (see Section 5.4), or a composition described herein (see Section 5.6.2) is effective to prevent and/or treat an ExPEC infection more than one serotype of ExPEC.

In a specific embodiment, the immune response induced by an *E. coli* O antigen described herein (see Section 5.2), a bioconjugate described herein (see Section 5.4), or a composition described herein (see Section 5.6.2) is effective to prevent and/or treat an infection caused by *E. coli* of the O25 serotype. In a specific embodiment, said O25 serotype is O25B. In a specific embodiment, said O25 serotype is O25A.

In a specific embodiment, the immune response induced by an *E. coli* O antigen described herein (see Section 5.2), a bioconjugate described herein (see Section 5.4), or a composition described herein (see Section 5.6.2) is effective to prevent and/or treat an infection caused by *E. coli* of the O1 serotype. In a specific embodiment, said O1 serotype is O1A. In another specific embodiment, said O1 serotype is O1B. In another specific embodiment, said O1 serotype is O1C.

In a specific embodiment, the immune response induced by an *E. coli* O antigen described herein (see Section 5.2), a bioconjugate described herein (see Section 5.4), or a composition described herein (see Section 5.6.2) is effective to prevent and/or treat an infection caused by *E. coli* of the O2 serotype.

In a specific embodiment, the immune response induced by an *E. coli* O antigen described herein (see Section 5.2), a bioconjugate described herein (see Section 5.4), or a composition described herein (see Section 5.6.2) is effective to prevent and/or treat an infection caused by *E. coli* of the O6 serotype.

In a specific embodiment, the immune response induced by an *E. coli* O antigen described herein (see Section 5.2), a bioconjugate described herein (see Section 5.4), or a composition described herein (see Section 5.6.2) is effective to prevent and/or treat an infection caused by two or more of the following *E. coli* serotypes: O25 (e.g., O25B and O25A), O1 (e.g., O1A, O1B, and O1C), O2, and/or O6.

In a specific embodiment, the immune response induced by an *E. coli* O antigen described herein (see Section 5.2), a bioconjugate described herein (see Section 5.4), or a composition described herein (see Section 5.6.2) is effective to prevent and/or treat an infection caused by each of the following *E. coli* serotypes: O25 (e.g., O25B and O25A), O1 (e.g., O1A, O1B, and O1C), O2, and O6.

In order to treat a subject having an ExPEC infection or immunize a subject against an ExPEC infection, the subject may be administered a single composition described herein, wherein said composition comprises one, two, three, four, or more *E. coli* antigens described herein. See Section 5.2. Alternatively, in order to treat a subject having an ExPEC infection or immunize a subject against an ExPEC infection, the subject may be administered multiple bioconjugates described herein, e.g., a subject may be administered two, three, four, or more bioconjugates described in Section 5.4. Alternatively, in order to treat a subject having an ExPEC infection or immunize a subject against an ExPEC infection, the subject may be administered multiple compositions described herein, e.g., a subject may be administered two, three, four, or more compositions described in Section 5.6.2.

In certain embodiments, the immune response induced in a subject following administration of an *E. coli* O antigen described herein (see Section 5.2), a bioconjugate described herein (see Section 5.4), or a composition described herein (see Section 5.6.2) is effective to reduce symptoms resulting from an ExPEC infection. Symptoms of ExPEC infection may vary depending on the nature of the infection and may include, but are not limited to: dysuria, increased urinary frequency or urgency, pyuria, hematuria, back pain, pain while urinating, fever, chills, and/or nausea (e.g., in subjects having a urinary tract infection caused by ExPEC); high fever, headache, stiff neck, nausea, vomiting, seizures, sleepiness, and/or light sensitivity (e.g., in subjects having meningitis caused by ExPEC); fever, increased heart rate, increased respiratory rate, decreased urine output, decreased platelet count, abdominal pain, difficulty breathing, and/or abnormal heart function (e.g., in subjects having sepsis caused by ExPEC).

In certain embodiments, the immune response induced in a subject following administration of an *E. coli* O antigen described herein (see Section 5.2), a bioconjugate described herein (see Section 5.4), or a composition described herein (see Section 5.6.2) is effective to reduce the likelihood of hospitalization of a subject suffering from an ExPEC infection. In some embodiments, the immune response induced in a subject following administration of an *E. coli* O antigen described herein (see Section 5.2), a bioconjugate described herein (see Section 5.4), or a composition described herein (see Section 5.6.2) is effective to reduce the duration of hospitalization of a subject suffering from an ExPEC infection.

In another aspect, provided herein are methods of preventing and/or treating an ExPEC infection in a subject caused by *E. coli* of the O25B serotype by administering an antibody described herein, i.e., an anti-O25B antibody described herein. In particular embodiments, the neutralizing antibody is a monoclonal antibody.

5.7.1 Combination Therapies

In certain embodiments, an *E. coli* O antigen described herein (see Section 5.2), a bioconjugate described herein (see Section 5.4), or a composition described herein (see Section 5.6.2) is administered to a subject in combination with one or more other therapies (e.g., antibacterial or immunomodulatory therapies). The one or more other therapies may be beneficial in the treatment or prevention of an ExPEC infection or may ameliorate a symptom or condition associated with an ExPEC infection. In some embodiments, the one or more other therapies are pain relievers or anti-fever medications. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part.

Any anti-bacterial agents known to one of skill in the art may be used in combination with an *E. coli* O antigen described herein (see Section 5.2), a bioconjugate described herein (see Section 5.4), or a composition described herein (see Section 5.6.2). Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

In certain embodiments, a combination therapy comprises administration of two or more *E. coli* O antigens described herein (see Section 5.2), bioconjugates described herein (see Section 5.4), and/or compositions described herein (see Section 5.6.2).

5.7.2 Patient Populations

In certain embodiments, an *E. coli* O antigen described herein (see Section 5.2), a bioconjugate described herein (see Section 5.4), or a composition described herein (see Section 5.6.2) is administered to a naïve subject, i.e., a subject that does not have an ExPEC infection or has not previously had an ExPEC infection. In one embodiment, an *E. coli* O antigen described herein (see Section 5.2), a bioconjugate described herein (see Section 5.4), or a composition described herein (see Section 5.6.2) is administered to a naïve subject that is at risk of acquiring an ExPEC infection.

In certain embodiments, an *E. coli* O antigen described herein (see Section 5.2), a bioconjugate described herein (see Section 5.4), or a composition described herein (see Section 5.6.2) is administered to a subject who has been diagnosed with an ExPEC infection. In some embodiments, an *E. coli* O antigen described herein (see Section 5.2), a bioconjugate described herein (see Section 5.4), or a composition described herein (see Section 5.6.2) is administered to a subject infected with ExPEC before symptoms manifest or symptoms become severe (e.g., before the patient requires hospitalization).

In certain embodiments, an *E. coli* O antigen described herein (see Section 5.2), a bioconjugate described herein (see Section 5.4), or a composition described herein (see Section 5.6.2) is administered to a subject who has been diagnosed with an UPEC infection. In some embodiments, an *E. coli* O antigen described herein (see Section 5.2), a bioconjugate described herein (see Section 5.4), or a composition described herein (see Section 5.6.2) is administered to a subject suffering from reoccurring urinary tract infections. In some embodiments, an *E. coli* O antigen described herein (see Section 5.2), a bioconjugate described herein (see Section 5.4), or a composition described herein (see Section 5.6.2) is administered to a subject suffering from reoccurring urinary tract infections, but is healthy at the moment of treatment. In some embodiments, an *E. coli* O antigen described herein (see Section 5.2), a bioconjugate described herein (see Section 5.4), or a composition described herein (see Section 5.6.2) is administered to a subject having or at risk of acquiring bacteremia or sepsis.

In some embodiments, a subject to be administered an *E. coli* O antigen described herein (see Section 5.2), a bioconjugate described herein (see Section 5.4), or a composition described herein (see Section 5.6.2) is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate. In a specific embodiment, the subject is a human.

In certain embodiments, a subject to be administered an *E. coli* O antigen described herein (see Section 5.2), a bioconjugate described herein (see Section 5.4), or a composition described herein (see Section 5.6.2) is a human adult. In certain embodiments, a subject to be administered an *E. coli* O antigen described herein (see Section 5.2), a bioconjugate described herein (see Section 5.4), or a composition described herein (see Section 5.6.2) is a human adult more than 50 years old. In certain embodiments, a subject to be administered an *E. coli* O antigen described herein (see Section 5.2), a bioconjugate described herein (see Section 5.4), or a composition described herein (see Section 5.6.2) is an elderly human subject.

In certain embodiments, a subject to be administered an *E. coli* O antigen described herein (see Section 5.2), a bioconjugate described herein (see Section 5.4), or a composition described herein (see Section 5.6.2) is a human child. In certain embodiments, a subject to be administered an *E. coli* O antigen described herein (see Section 5.2), a bioconjugate described herein (see Section 5.4), or a composition described herein (see Section 5.6.2) is a human infant. In certain embodiments, a subject to be administered an *E. coli* O antigen described herein (see Section 5.2), a bioconjugate described herein (see Section 5.4), or a composition described herein (see Section 5.6.2) is a premature human infant. In some embodiments, a subject to be administered an *E. coli* O antigen described herein (see Section 5.2), a bioconjugate described herein (see Section 5.4), or a composition described herein (see Section 5.6.2) is a human toddler. In certain embodiments, a subject to be administered an *E. coli* O antigen described herein (see Section 5.2), a bioconjugate described herein (see Section 5.4), or a composition described herein (see Section 5.6.2) is administered is not an infant of less than 6 months old.

In certain embodiments, a subject to be administered an *E. coli* O antigen described herein (see Section 5.2), a bioconjugate described herein (see Section 5.4), or a composition described herein (see Section 5.6.2) is an individual who is pregnant. In certain embodiments, a subject to be administered an *E. coli* O antigen described herein (see Section 5.2), a bioconjugate described herein (see Section 5.4), or a composition described herein (see Section 5.6.2) is a woman who has given birth 1, 2, 3, 4, 5, 6, 7, or 8 weeks earlier.

In certain embodiments, a subject to be administered an *E. coli* O antigen described herein (see Section 5.2), a bioconjugate described herein (see Section 5.4), or a composition described herein (see Section 5.6.2) is an individual at increased risk of ExPEC (e.g., an immunocompromised or immunodeficient individual). In certain embodiments, a subject to be administered an *E. coli* O antigen described herein (see Section 5.2), a bioconjugate described herein (see Section 5.4), or a composition described herein (see Section 5.6.2) is an individual in close contact with an individual having or at increased risk of ExPEC infection.

In certain embodiments, a subject to be administered an *E. coli* O antigen described herein (see Section 5.2), a bioconjugate described herein (see Section 5.4), or a composition described herein (see Section 5.6.2) is a health care worker (e.g., a doctor or nurse). In certain embodiments, a subject to be administered an *E. coli* O antigen described herein (see Section 5.2), a bioconjugate described herein (see Section 5.4), or a composition described herein (see Section 5.6.2) is immunocompromised (e.g., suffers from HIV infection) or immunosuppressed.

In certain embodiments, a subject to be administered an *E. coli* O antigen described herein (see Section 5.2), a bioconjugate described herein (see Section 5.4), or a composition described herein (see Section 5.6.2) has diabetes. In certain embodiments, a subject to be administered an *E. coli* O antigen described herein (see Section 5.2), a bioconjugate described herein (see Section 5.4), or a composition described herein (see Section 5.6.2) has multiple sclerosis.

In certain embodiments, a subject to be administered an *E. coli* O antigen described herein (see Section 5.2), a bioconjugate described herein (see Section 5.4), or a composition described herein (see Section 5.6.2) has a condition that requires them to use a catheter. In certain embodiments, a subject to be administered an *E. coli* O antigen described herein (see Section 5.2), a bioconjugate described herein (see Section 5.4), or a composition described herein (see Section 5.6.2) has a spinal cord injury.

5.7.3 Dosage and Frequency of Administration

The amount of an *E. coli* O antigen described herein (see Section 5.2), a bioconjugate described herein (see Section 5.4), or a composition described herein (see Section 5.6.2) which will be effective in the treatment and/or prevention of an ExPEC infection will depend on the nature of the disease, and can be determined by standard clinical techniques. Administration of the O-antigen, bioconjugate and/or composition can be done via various routes known to the clinician, for instance subcutaneous, parenteral, intravenous, intramuscular, topical, oral, intradermal, transdermal, intranasal, etc. In one embodiment, administration is via intramuscular injection.

The precise dosage to be employed in the formulation will also depend on the route of administration, and the seriousness of the infection, and should be decided according to the judgment of the practitioner and each subject's circumstances. For example, effective dosages may also vary depending upon means of administration, target site, physiological state of the patient (including age, body weight, health), whether the patient is human or an animal, other medications administered, and whether treatment is prophylactic or therapeutic. Treatment dosages are optimally titrated to optimize safety and efficacy.

In certain embodiments, an in vitro assay is employed to help identify optimal dosage ranges. See Section 5.8. Effective doses may be extrapolated from dosage response curves derived from in vitro or animal model test systems.

In certain embodiments, exemplary dosages for glycoconjugate based vaccines (e.g., compositions comprising bioconjugates) range from about 0.1 µg to 400 µg of carbohydrate per dose. In other embodiments, exemplary dosages for glycoconjugate based vaccines (e.g., compositions comprising bioconjugates) range from about 0.1 µg to 4000 µg of protein(s) per dose. In certain embodiments, an exemplary dosage for a glycoconjugate based vaccine (e.g., a composition comprising bioconjugates) comprises 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 µg of carbohydrate(s) per dose. In certain embodiments, an exemplary dosage for a glycoconjugate based vaccine (e.g., a composition comprising bioconjugates) comprises 50, 55, 60, 65, 70, 75, 80, 85, 90, 95, or 100 µg of protein(s) per dose. In certain exemplary embodiments, a dosage for administration to a human corresponds to 0.5 ml containing about 1-10, e.g. about 2-6, e.g. about 4 µg of polysaccharide for each of the glycoconjugates included.

In certain embodiments, an *E. coli* O antigen described herein (see Section 5.2), a bioconjugate described herein (see Section 5.4), or a composition described herein (see Section 5.6.2) is administered to a subject once as a single dose. In certain embodiments, an *E. coli* O antigen described herein (see Section 5.2), a bioconjugate described herein (see Section 5.4), or a composition described herein (see Section 5.6.2) is administered to a subject as a single dose followed by a second dose 3 to 6 weeks later. In accordance with these embodiments, booster inoculations may be administered to the subject at 6 to 12 month intervals following the second inoculation. In certain embodiments, the booster inoculations may utilize a different *E. coli* O antigen, bioconjugate, or composition. In some embodiments, the administration of the same *E. coli* O antigen, bioconjugate, or composition may be repeated and the administrations may be separated by at least 1 day, 2 days, 3 days, 5 days, 7 days, 10 days, 15 days, 30 days, 45 days, 2 months, 75 days, 3 months, or at least 6 months. In certain embodiments, an *E. coli* O antigen described herein (see Section 5.2), a bioconjugate described herein (see Section 5.4), or a composition described herein (see Section 5.6.2) is administered to a subject as a single dose once per year.

In certain embodiments, an *E. coli* O antigen described herein (see Section 5.2), a bioconjugate described herein (see Section 5.4), or a composition described herein (see Section 5.6.2) is administered to a subject as 2, 3, 4, 5 or more doses 2 weeks, 3 weeks, 4 weeks, 5 weeks or 6 weeks apart. In some embodiments, 2, 3, 4, 5 or more doses of an *E. coli* O antigen described herein (see Section 5.2), a bioconjugate described herein (see Section 5.4), or a composition described herein (see Section 5.6.2) are administered to a subject 2, 3, 4, 5 or 6 weeks apart at a dosage of 0.1 µg to 0.5 mg, 0.1 µg to 0.4 mg, 0.1 µg to 0.3 mg, 0.1 µg to 0.2 mg, or 0.1 µg to 0.1 mg carbohydrate content. In certain embodiments, the *E. coli* O antigen, bioconjugate, or composition administered is the same each time. In certain embodiments, the *E. coli* O antigen, bioconjugate, or composition administered is different each time.

For passive immunization with an antibody (e.g., an anti-O25B antibody), the dosage can range from about 0.0001 to 100 mg of antibody per kg of body weight, or from 0.01 to 5 antibody per kg of body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. Intervals can be irregular and altered based on blood levels of antibody in the patient.

5.8 Assays

Assay for Assessing Ability of Bioconjugates to Induce an Immune Response

The ability of the bioconjugates/compositions described herein to generate an immune response in a subject can be assessed using any approach known to those of skill in the art or described herein. In some embodiments, the ability of a bioconjugate to generate an immune response in a subject can be assessed by immunizing a subject (e.g., a mouse) or set of subjects with a bioconjugate described herein and immunizing an additional subject (e.g., a mouse) or set of subjects with a control (PBS). The subjects or set of subjects can subsequently be challenged with ExPEC and the ability of the ExPEC to cause disease (e.g., UTI) in the subjects or set of subjects can be determined. Those skilled in the art will recognize that if the subject or set of subjects immunized with the control suffer(s) from disease subsequent to challenge with the ExPEC but the subject or set of subjects immunized with a bioconjugate(s) or composition thereof described herein suffer less from or do not suffer from disease, then the bioconjugate is able to generate an immune response in a subject. The ability of a bioconjugate(s) or composition thereof described herein to induce antiserum that cross-reacts with an O antigen from ExPEC can be tested by, e.g., an immunoassay, such as an ELISA.

In Vitro Bactericidal Assays

The ability of the bioconjugates described herein to generate an immune response in a subject can be assessed using a serum bactericidal assay (SBA) or opsonophagocytotic killing assay (OPK), which represents an established and accepted method that has been used to obtain approval of glycoconjugate-based vaccines. Such assays are well-known in the art and, briefly, comprise the steps of generating and isolating antibodies against a target of interest (e.g., an O antigen, e.g., O25B, of E. coli) by administering to a subject (e.g., a mouse) a compound that elicits such antibodies. Subsequently, the bactericidal capacity of the antibodies can be assessed by, e.g., culturing the bacteria in question (e.g., E. coli of the relevant serotype) in the presence of said antibodies and complement and—depending on the assay—neutrophilic cells and assaying the ability of the antibodies to kill and/or neutralize the bacteria, e.g., using standard microbiological approaches.

5.9 Kits

Provided herein is a pharmaceutical pack or kit comprising one or more containers filled with one or more of the ingredients of the compositions described herein (see Section 5.6.2), such as one or more E. coli antigens (see Section 5.2) and/or bioconjugates (see Section 5.4) provided herein. Optionally associated with such container(s) can be a notice in the form prescribed by a governmental agency regulating the manufacture, use or sale of pharmaceuticals or biological products, which notice reflects approval by the agency of manufacture, use or sale for human administration. The kits encompassed herein can be used in the above methods of treatment and immunization of subjects.

6. EXAMPLES

Methods

Agglutination

A process in which cells or lysed cell mass is mixed with antiserum containing antibodies specific for a polymeric structure, e.g. O antigen. Visible, insoluble aggregates form when the antiserum recognizes the cellular structures. This method is classically used to identify O, K, and H serotypes. See DebRoy, et al., (2011) Animal health research reviews/Conference of Research Workers in Animal Diseases 12, 169-185

LPS Sample Preparation for Analysis by SDS PAGE

LPS of Gram-negative cells is composed of a lipid A base, modified with a core oligosaccharide providing the attachment for the O antigen. To analyze the LPS of clinical isolates, cells were grown in standard LB medium at 37° C. for 24 h, and biomass corresponding to 1 ml of culture with an OD600 of 2 was collected and lysed in 1× Lämmli sample buffer and incubated at 95° C. for 10 minutes. Extracts were further treated for 1 hour at 65° C. to remove any protein signal using 1 g/l proteinase K. The treated extracts were separated by SDS PAGE and LPS was visualized by silver staining or Western blotting using appropriate antiserum.

LPS Preparation for Coating of ELISA Plates

LPS was prepared using a method described by Apicella, (2008) Methods Mol Biol 431, 3-13, and further purified as described by Perdomo and Montero, (2006) Biotecnologia Aplicada 23:124-129.

2AB OPS HPLC: 'LLO Fingerprinting'

This method is used to analyze the structure of UPP linked OPS.

To extract UPP-linked glycans, E. coli cells were washed with 0.9% NaCl and lyophilized. The dried cells were extracted with organic solvent (Methanol:Water (M:W=17:3 to 19:1, v/v), and/or Chloroform:Methanol:Water mixtures of optimized ratios (e.g. C:M:W=10:10:3; v/v/v)). The extracts were dried under a stream of $N_2$, and resuspended in C:M:W=3:48:47. To purify the extracted glycolipids, the 3:48:47 resuspension was passed through a $tC_{18}$ Sep-PAK cartridge. The cartridge was conditioned with 10 ml methanol, followed by equilibration with 10 ml 3:48:47 (C:M:W). After loading of the sample, the cartridge was washed with 10 ml 3:48:47 (C:M:W) and eluted with 5 ml methanol and 5 ml 10:10:3 (C:M:W). The combined elutions were dried under $N_2$. The glycolipid samples were hydrolyzed by dissolving the dried samples in 2 ml n-propanol:2 M trifluoroacetic acid (1:1), heating to 50° C. for 15 min, and then evaporating to dryness under $N_2$ (Glover, et al., Proc Natl Acad Sci USA 102(40): 14255-9). The dried samples were once more resuspended in 3:48:47 and passed through a tC18 cartridge, and the flow through was dried under N2. Labeling with 2-AB and glycan cleanup was performed using the paper disk method as described (Bigge, et al., Anal Biochem 230(2): 229-38; Merry, et al., Anal Biochem 304 (1): 91-9).

2-AB labeled glycans were separated by HPLC using a GlycoSep-N normal phase column according to Royle et al. but modified to a three solvent system (Royle, et al., Anal Biochem 304(1): 70-90). Solvent A was 10 mM ammonium formate pH 4.4 in 80% acetonitrile. Solvent B was 30 mM ammonium formate pH 4.4 in 40% acetonitrile. Solvent C was 0.5% formic acid. The column temperature was 30° C. and 2-AB labelled glycans were detected by fluorescence (excitation $\lambda ex$=330 nm, emission $\lambda em$=420 nm). Gradient conditions were a linear gradient of 100% A to 100% B over 160 min at a flow rate of 0.4 ml/min, followed by 2 min 100% B to 100% C, increasing the flow rate to 1 ml/min. The column was washed for 5 min with 100% C, returning to 100% A over 2 min and running for 15 min at 100% A at a flow rate of 1 ml/min, then returning the flow rate to 0.4 ml/min for 5 min. Samples were injected in water.

Deacetylation Assay:

An equivalent of 2-AB labeled glycan is dried in at 30° C., resuspended in 50 μl water with (sample) or without (mock) 200 mM NaOH (pH 14), and incubated for 25 hours at 37° C. The solution is then brought to room temperature and neutralized by the addition of 200 mM HCl solution (pH≈1). After drying in the speed vacuum at 30° C., the sample is relabeled with 2AB and analysis by HPLC.

Hydrazinolysis HPLC

The same normal phase HPLC technique described above was used to separate OPS released from bioconjugates after hydrazinolysis. Prior to hydrazinolysis, bioconjugates corresponding to 1 mg protein were completely dried under a stream of $N_2$. Polysaccharide release was performed using the Ludger Liberate Hydrazinolysis Glycan Release kit (Ludger #LL-HYDRAZ-A2) according to the manufacturer's instructions. Briefly, 450 μl hydrazine were added to the dried samples under a blanket of N2 and incubated for 16 hours at 85° C. The hydrazine was removed by evaporation under N2 at 45° C. Re-N-acetylation of the polysaccharides was performed by incubation in 471 μl 4.5% acetic anhydride in 1 M sodium bicarbonate for two hours on ice.

Thereafter, 600 μl of a 5% TFA solution was added and the samples were hydrolyzed for another hour on ice. Purification was performed on an EB20 column using the corresponding buffers EB20 A and B.

The released and purified polysaccharides were labeled with 2-AB and analyzed by NP-HPLC like described for the LLO samples. Peaks of interest were collected and identified by MS/MS.

MS and MS/MS of HPLC Peaks

To analyze the monosaccharide sequence of an OPS molecule of interest, mass spectroscopic analysis was performed. Dried, collected fractions corresponding to specific HPLC peaks were resuspended in 5 ul 10% acetonitrile (ACN), 0.1% trifluoro acetic acid (TFA) and mixed 1:1 with matrix solution (40 mg/ml DHB in 50% ACN, 0.1% TFA) on the target plate. MS and MS/MS data were manually acquired in the positive ion mode on an Ultraflex-II MALDI-ToF/ToF mass spectrometer (Bruker Daltonik GmbH, Bremen, Germany). MS/MS were obtained using the LIFT method. A standard peptide mixture (Bruker Daltonik GmbH) was used for external calibration. Spectra were exported using the Flex Analysis software (Bruker Daltonik GmbH) and manually analyzed.

Host Cells

Bioconjugates were produced by recombinant *E. coli* cells expressing, via plasmid(s), carrier protein(s) and the oligosaccharyl transferase from *C. jejuni* (PglB), and OPS from cosmids or chromosomal insertion mutants.

Genetically detoxified EPA (Exotoxin A from *Pseudomonas aeruginosa* containing the mutations L552V, ΔE553) was used as a carrier protein, and was modified to comprise 2 or 4 glycosylation sites (referred to herein as 2S-EPA and 4S-EPA, respectively) and a C-terminal HIS Tag, and was expressed from a pBR322 derived, arabinose inducible plasmid (see Ihssen, et al., (2010) Microbial cell factories 9, 61).

MBP (Maltose binding protein), a native periplasmic, soluble *E. coli* protein, was expressed from a pGVXN579. pGVXN579 is a modified pMAL-p2X (New England Biolabs) plasmid encoding three bacterial N glycosylation consensus sequences in a row followed by a Myc-Tag C-terminally fused to the maltose binding protein ORF encoded on the plasmid. This setup allowed affinity purification of the MBP bioconjugate independent of a HIS-tag. Induction of expression is controlled by the tac promoter and inducible using IPTG.

The PglB protein was expressed from plasmid pEXT21 (an EcoRI/BamHI fragment from pMAF10 (Feldman et al., 2005, PNAS USA 102(8):3016-3021) was cloned into pEXT21 with a C-terminally fused HA-tag. Variants of the expression plasmid are codon optimization (pGVXN939), codon optimization with a deletion of the glycosylation site (pGVXN948), and removed HA-Ttag (pGVXN970) and codon optimization and deleted HA tag (pGVXN971).

Clinical isolates were analyzed for their capability to synthetize a certain OPS using agglutination, Western blot, silver staining, LLO fingerprinting, PCR serotyping, or similar technologies that allow identification of the OPS structural characteristics, and also for their antibiotic resistance phenotype. Certain clinical isolates were further chromosomally deleted for the ligase enzyme, WaaL, for enhancing OPS availability for protein glycosylation or OPS analysis.

To further analyze clinical isolates, the rfb cluster of the laboratory strain W3110 was replaced by the rfb cluster cloned from clinical isolates, and OPS biosynthesis was analyzed. The waaL gene was deleted to enhance efficiency of bioconjugate production.

Cluster exchanges and waaL deletions were achieved by homologous recombination using an optimized method (see International Patent application No. PCT/EP2013/068737) or published procedures (Datsenko and Wanner, (2000) Proc Natl Acad Sci USA 97, 6640-6645). For OPS cluster exchange, the rfb cluster of interest of a clinical isolate was cloned into the counter selection plasmid pDOC-C, along with an antibiotic resistance cassette, for subsequent integration into the rfb locus of *E. coli* strain W3110 (Kuhlman and Cox, 2010, Nucleic acids research 38, e92; Lee et al, 2009, BMC Microbiol 9, 252). Homologous recombination of large rib clusters of interest was achieved by using DNA flanking the rfb cluster coding sequence of W3110 of 0.5 to 1.5 kilobases in length and in vivo linearization of the insert DNA from plasmid borne rib. The resulting strain contained a replaced rfb cluster (with and without antibiotic resistance cassette), i.e. the rfb cluster of W3110 was replaced for a DNA molecule between the gale and gnd genes by the analogous stretch isolated from a clinical *E. coli* isolate.

In certain experiments, W3110 strains containing a cosmid encoding the rfb cluster of a given *E. coli* serotype were used as host strains.

For the production of recombinantly expressed bioconjugates in W3110 based strains, W3110 borne genes that interfere with recombinant OPS production were deleted. For example, for the production host cell of O25B bioconjugates, the gtrABS cluster of W3110 was deleted. To achieve this, homologous recombination according to a published method (Bloor A E, Cranenburgh R M. Appl Environ Microbiol. 2006 April; 72(4):2520-5.) using homology sequences flanking upstream the gtrA gene and downstream of the gtrS gene.

To assemble production strains, the host strain was transformed with a pglB and a carrier expression plasmid by transformation. See Wacker et al., 2002, Science 298:1790-1793.

Bioconjugate Production

Bioconjugate production was performed by growing host cells and purifying bioconjugates produced in the periplasmic space. Growth was performed either in shake flasks or in an industrial scale fed batch fermentation process.

Shake flask cultivations were performed at 37° C., using a medium composed of the appropriate antibiotics in terrific broth sometimes supplemented with 5 mM MgCl2. Medium of was inoculated at an OD of 0.05 with an overnight culture from freshly transformed production cells, grown until mid-log phase, induced with 0.2% arabinose and 1 mM IPTG, further grown and harvested after 20 hs of growth.

Fed Batch Fermentations

An aliquot of a production cell line bank was used to inoculate a shake flask containing Soy LB medium with the appropriate antibiotics. The shake flask was incubated at 180 rpm, 37° C. for approximately 12 hours. The batch media without complements were sterilized directly inside the bioreactor (33 min at ≥121° C.), cooled, and complements were added. 4 M KOH or 25% phosphoric acid were attached to the fermenter for pH regulation and pH was adjusted to pH7. Inoculation of the bioreactor and batch culture from the pre-culture was done to yield an initial OD600 of 0.005. pH was stably maintained by the addition of 4 M KOH or 25% phosphoric acid. Dissolved oxygen tension (DO) is maintained. Overhead pressure was maintained at 600 mbar. Product formation was induced with L-Arabinose (0.1%) and/or IPTG (1 mM). Immediately after induction, feed was initiated by addition of feed medium containing 2.5% Arabinose and IPTG. 24±2 hours after induction, the bioreactor was cooled to 25° C., feed was stopped and harvesting was performed by tangential flow filtration or centrifugation.

The biomass was lysed in 0.5% TRITON™ X-100 by disruption during 4 cycles of high pressure homogenization at 800 bar.

Bioconjugates were purified by column chromatography. Various chromatographic techniques were used to prepare bioconjugates, mainly IMAC, Q-resin based anionic exchange chromatography (AEC), and size exclusion chromatography (SEC). See, e.g., Saraswat et al., 2013, Biomed. Res. Int. ID#312709 (p. 1-18) and WO 2009/104074 for description of such methods.

Bioconjugate Production for Preclinical Experiments

From the pre-culture, a defined amount was transferred to a bioreactor containing a rich media at 35±0.2° C. The pH and dissolved oxygen tension were maintained. Agitation rate reached 700 rpm.

When cell density reached $OD_{600}=40\pm5$, product formation was induced with L-Arabinose (0.1%) and IPTG (1 mM). Feed was initiated 24±2 hours after induction and the bioreactor was cooled. As soon as the temperature reached 25° C., feed was stopped and the cells were collected.

High Pressure Homogenization

A biomass corresponding to 50 L at harvest was thawed for 1 day at 2 to 8° C. Then 2.5 L of Lysis and Clarification Buffer was added to the container. TRITON™ X-100 was added to a final concentration of 0.5% and the completely thawed cells were disrupted by 4 cycles of high pressure homogenization at 800 bar. Cells were harvested and washed using standard techniques.

Monosaccharide Composition Analysis:

Bioconjugates containing approximately 8 ug polysaccharide were hydrolyzed for six hours in 104 μl 3 M TFA at 99° C. TFA was removed by evaporation and samples were washed once with 500 μl 2-propanol. The resulting monosaccharides were suspended in 100 μl labeling mix containing 87.1 mg/ml 1-phenyl-3-methyl-5-pyrazolone (PMP), 50% MeOH and 150 mM NaOH. Labeling was performed during 60 minutes at 70° C. The samples were neutralized by the addition of 50 μl 300 mM HCl and 20 μl 100 mM Tris/HCl pH 7.0. The PMP-labeled monosaccharides were purified by extraction, once with 1 ml di-buthyl ether and three times with 1 ml $CHCl_3$.

The PMP derivatized monosaccharides were separated by RP-HPLC (Merck-Hitachi) on a C18 Inertsil ODS-3 column (GL Sciences) equipped with a pre-column. A two-step gradient from 100% buffer A (13% acetonitrile, 87% H2O (0.045% KH2PO4, 0.05% triethylamine, pH 7.0) to 50% buffer A/50% buffer B (21% acetonitrile, 79% H2O (0.045% KH2PO4, 0.05% triethylamine, pH 7.0) over 4 minutes to 100% buffer B over 47 minutes was applied at 35° C. and a flow rate of 1 ml/min. The injection volume was 50 μl and elution was monitored by online UV-detection at 250 nm. The individual peaks were identified by overlay with chromatograms of the commercially available monosaccharide standards D-glucose (Sigma-Aldrich #G7528), L-rhamnose (Sigma-Aldrich #R3875), N-acetyl-D-glucosamine (Sigma-Aldrich #A8625) and N-acetyl-L-fucosamine (Omicron Biochemicals #FUC-006).

Example 1: Epidemiology

To determine the serotype distribution of urinary tract infection (UTI)-causing *E. coli*, an epidemiology study was performed. Over 1800 *E. coli* isolates form human urine samples were collected from subjects in Switzerland and the O antigen serotypes (OPS) from each sample was analyzed using classical agglutination techniques. See FIG. 4

Isolated human urine samples were analyzed to determine the identity of pathogens therein and their antibiotic resistance patterns. *E. coli* isolates were obtained from the samples following the analysis. *E. coli* isolates were identified by classical microbiological exclusion and inclusion strategies involving growth on chrome (CPS3) and MacConkey agar. *E. coli* isolates further were analyzed using an agglutination assay to determine their O antigen serotype. See DebRoy et al. (2011) Animal health research reviews/Conference of Research Workers in Animal Diseases 12, 169-185. Isolates from the same O antigen serogroups were further analyzed to determine the chemical structure of the O chain from each isolate. See Table 1A. Certain isolated *E. coli* strains were determined to be antibiotic resistant, including identification of fluoroquinolone-resistant strains and extended-spectrum beta-lactamase (ESBL) producing strains.

TABLE 1A

Distribution of the most common UTI-associated *E. coli* serotypes from a collection of 1841 urine samples collected in Switzerland in 2012. Shown is the serotype distribution of samples from a relevant subpopulation of 671 subjects, and the distribution from all** samples.
Most prevalent *E. coli* serotypes associated with UTI

| O-serotype | Community acquired UTI in 18-70 years old* (n = 671) | O-serotype | Community and hospital acquired UTI in all ages** (n = 1871) |
|---|---|---|---|
| 6 | 10.75% | 2 | 8.75% |
| 2 | 9.55% | 6 | 8.47% |
| 25 | 6.87% | 25 | 8.37% |
| 1 | 5.52% | 75 | 4.56% |
| 4 | 5.37% | 1 | 4.29% |
| 75 | 4.78% | 8 | 3.86% |
| 8 | 3.43% | 18 | 3.53% |
| 18 | 3.28% | 4 | 3.26% |
| 15 | 3.28% | 15 | 2.39% |
| 73 | 2.24% | 73 | 2.17% |
| 16 | 2.24% | 16 | 1.85% |
| 7 | 1.94% | 7 | 1.68% |

Serotypes O1, O2, O4, O6, O7, O8, O16, O18, O25, O73, and O75 were isolated from subjects independent of location, time of isolation, symptoms, and target population, suggesting these to be the predominant serotypes of uropathogenic *E. coli* (UPEC). Accordingly, the identification of the most prevalent O antigen serotypes indicates that O-antigen specific vaccines could be limited to a subset of serotypes, namely those most associated with disease, as identified in the study described in this example.

A retrospective analysis of UTI serotypes in 1323 isolates from the past three decades in the US obtained from the *E. coli* Reference center (ECRC) allowed a thorough comparison to literature and the current data from Switzerland. The prevalence of the top 20 serotypes was found independently on location, time of isolation, symptoms, or target population and suggests predominant serotypes associated to UPEC (see Table 1B).

TABLE 1B

Prevalence of most common UTI associated serotypes from selected literature ranging from 1987-2011 and from retrospectively analysed US data from 2000-2011 (ECRC).

| Serotype | TOTAL UTI available data from 1860 isolates | CYSTITIS available data from 1089 isolates | PYELO-NEPHRITIS available data from 373 isolates | US 2000-2010 315 (all UTI specimen except fecal, all ages, F + M) Number of non-typable were not available! |
|---|---|---|---|---|
| INDICATION | | | | |
| O1 | 4.8% | 4.1% | 5.4% | 7.0% |
| O2 | 7.1% | 4.9% | 15.3% | 14.0% |
| O4 | 7.8% | 6.0% | 3.2% | 3.2% |
| O6 | 16.9% | 16.3% | 7.8% | 18.7% |
| O7 | 3.3% | 2.4% | 2.4% | 1.9% |
| O8 | 1.7% | 3.2% | 0.8% | 3.5% |
| O15 | 0.6% | 1.5% | 0.8% | 1.3% |
| O16 | 4.3% | 3.2% | 7.2% | 1.9% |
| O18 | 7.0% | 7.1% | 6.7% | 7.0% |
| O21 | na | na | na | 1.3% |
| O22 | 0.6% | 0.6% | 0.5% | 0.0% |
| O25 | 3.0% | 4.8% | 0.5% | 8.6% |
| O75 | 7.5% | 6.0% | 8.6% | 3.8% |
| O83 | 1.9% | 0.7% | 0.5% | 1.3% |
| O20 | | | | 1.6% |
| O77 | | | | 2.2% |
| O82 | | | | 1.9% |
| others and non typable/ not available | 33.3% | 39.2% | 40.2% | |
| other O-types (NT not available) | | | | 21.0% |

Isolates from serotypes described were calculated as percentage on the total number of isolates (Andreu et al., 1997, J Infect Dis 176:464-469; Blanco et al., 1996, Eur J Epidemiol 12:191-198; Fathollahi et al., 2009, Iranian Journal of Clinical Infectious Diseases 4:77-81; Johnson et al., 2005, J Clin Microbiol 43:6064-6072; Molina-Lopez et al., 2011, Journal of infection in developing countries 5:840-849; Sandberg et al., 1988, J Clin Microbiol 26:1471-1476; K. L. 2007, The Journal of infection 55:8-18; Terai et al., 1997, Int J Urol 4:289-294.) In certain cases specific data was not available; therefore the percentage numbers can only give an indication on the overall serotype distribution from different UTI isolates in described studies and should be considered with caution. The other described serotypes identified however less prevalent (O15, O2O, O21, O22, O77 and O82) also are included.

All information from epidemiology analysis taken together, the 10 predominant serotypes could cover an estimated 60-80% of E. coli infections, assuming coverage of subportions of the non typeable strains. Furthermore, the data shows the unexpected importance of the O25 serotype in the epidemiology study from Switzerland, when compared to literature data and recent data from the USA. See Tables 1A and B.

O antigen serotypes of E. coli often are composed of subtypes, which are distinct, yet structurally and antigenically similar. To identify unknown/unreported subtypes among the collected clinical isolates, and to identify the most prevalent O antigen subtypes, the chemical structures of the O antigens from the most prevalent serotypes were analyzed in more detail.

Example 2: E. coli O25

In recent years, increased occurrence of O25-positive strains has been observed (see George and Manges (2010) Epidemiol Infect 138, 1679-1690) and is evidenced by the study described in Example 1, where the O25 serotype was found to be one of the top four E. coli serotypes in terms of prevalence.

O25A

An O antigen repeat unit structure of the E. coli O25 serotype has been published previously (see Kenne et al., 1983, Carbohydrate Research 122, 249-256; and Fundin et al., 2003, Magnetic Resonance in Chemistry 41, 4) and is presented in FIG. 2B. An rfb cluster related to the O25 O antigen from E. coli strain E47a is publicly available (GenBank GU014554), and is presented in FIG. 2A. E. coli E47a is used as a reference strain for O25 serotyping. Further rfb cluster sequence information is available from the genome sequence of a strain causing asymptomatic bacteriuria, E. coli 83972. (see Zdziarski et al., 2010, PLoS Pathog 6, e1001078). Although phenotypic O25 expression has not been confirmed, rfb cluster sequences of E. coli E47a and 83972 are 99.49% identical, strongly suggesting they encode the same O antigen.

The O antigen from E. coli strains 83972 and E47a is designated herein as "O25A," because, as described below, a novel E. coli O antigen, designated "O25B," was identified based on analysis of the clinical isolates obtained in the epidemiology study described in Example 1, above.

The functionalities for the predicted gene products of E. coli strains 83972 and E47a have been proposed. See Table 2; GenBank GU014554; and Szijarto, et al. (2012) FEMS Microbiol Lett 332, 131-136.

TABLE 2

O25A O antigen gene predictions from the rfb cluster as published by Wang, et al. (2010) J Clin Microbiol 48, 2066-2074; see also GenBank GU014554.

| Gene name | Putative Function | Most meaningful homology/Protein[organism], accession, max. identity (BLAST) |
|---|---|---|
| rmlB | dTDP-Glucose 4,6-dehydratase | dTDP-Glucose 4,6-dehydratase (E. coli IAI39), YP_002406996.1, 98% |
| rmlD | dTDP-6-Deoxy-D-glucose 3,5-epimerase | dTDP-6-Deoxy-L-mannosedehydrogenase (E. coli), ACA24825.1, 97% |
| rmlA | Glucose-1-phosphate thymidylyltransferase | Glucose-1-phosphate thymidylyltransferase (E. coli IAI39), YP_002406998.1, 99% |
| rmlC | dTDP-4-dehydrorhamnose 3,5-epimerase | RmlC (E. coli), ACA24796.1, 70% |

TABLE 2-continued

O25A O antigen gene predictions from the rfb cluster as published by Wang, et al. (2010) J Clin Microbiol 48, 2066-2074; see also GenBank GU014554.

| Gene name | Putative Function | Most meaningful homology/Protein[organism], accession, max. identity (BLAST) |
|---|---|---|
| Wzx | O antigen flippase | O-antigen transporter (E. coli), WP_000021239.1, 100% |
| wekA | Glycosyltransferase | dTDP-Rha: Glc-Rha(Ac)-GlcNAc-UPP α-1,3-rhamnosyltransferase (E. coli), WP_000639414.1, 99% |
| wekB | Glucosyltransferase | WcmS; UDP-Glc: Glc-Rha(Ac)-GlcNAc-UPP β-1,6-glucosyltransferase (E. coli O158), ADN43874.1, 40% |
| Wzy | O antigen polymerase | Wzy (E. coli), ADR74237.1, 30% |
| wekC | Glycosyltransferase | WfbF; UDP-Glc: FucNAc-GlcNAc-UPP α-1,3-glucosyltransferase (E. coli), ABG81807.1, 46% |
| fnlA | UDP-N-acetylglucosamine-4,6-dehydratase/5-epimerase | UDP-N-acetylglucosamine 4,6-dehydratase/5-epimerase (E. coli), WP_001556096.1, 95% |
| fnlB | UDP-2-acetamido-2,6-dideoxy-beta-L-talose 4-dehydrogenase | FnlB (E. coli), AAY28261.1, 97% |
| fnlC | UDP-N-acetylglucosamine 2-epimerase | UDP-N-acetylglucosamine 2-epimerase (E. coli) WP_000734424.1, 98% |
| wbuB | Glycosyltransferase | UDP-L-FucNAc: GlcNAc-UPP α-1,3-N-Acetylfucosaminyltransferase (E. coli) P12b, O26], YP_006169152.1, 73% |
| wbuC | Truncated glycosyltransferase | WbuC (E. coli), AAV74548.1, 72% |

Comparisons of structure and gene cluster imply that all functions needed for assembly of the O25A OPS are encoded within the rfb cluster located between galE and gnd. The functions of the various enzymes of the rfb gene cluster (see FIG. 2A) are as follows:

RmlBDAC encode the enzymes required for biosynthesis of dTDP-L-Rhamnose, which is the substrate for the addition of L-Rha branch to the OPS repeat unit.

FnlABC encode the enzymes required for biosynthesis of UDP-L-FucNAc, which is the donor substrate for the addition of L-FucNAc to the O25 OPS repeat.

WekABC and wbuBC are glycosyltransferases according to homology analysis. However, wbuC appears short and truncated and is unlikely functional. Thus, the most likely functional annotation indicates that there are four glycosyltransferases generating the four linkages for assembly of the repeat unit.

Wzx and Wzy are required for flipping of the BRU to the periplasmic space and their polymerization on Und-PP.

All functions required to synthetize the published O25A repeat unit structure are encoded by the E. coli E47a and 83972 rfb clusters. Thus it was concluded that the rfb cluster is responsible for encoding the O25A OPS.

O25B

In 2009, clinical E. coli isolates from a Spanish hospital setting were characterized to determine clonal groups. See Blanco, et al. (2009) J Antimicrob Chemother 63, 1135-1141. Characterization of a) the ESBL type, b) the O serotype, c) virulence genes, d) multi locus sequence typing (MLST), and e) pulsed field gel electrophoresis typing (PFGE) was done. Results indicated that about 20% of all isolates could be attributed to the same clone: Serotype and MLST O25:H4 ST131, ESBL type CTX-M15, Phylogroup B2, encoding a specific set of virulence genes. The analysis of the rfb cluster components of representative clinical isolates showed an unknown 3' sequence when compared to the typing strain sequence from the E47a strain, and also from clinical isolates identified by an allele specific PCR typing method (See Clermont et al., 2008, J Antimicrob Chemother. 61(5):1024-8; Clermont et al., Diagn. Microbiol Infect Dis. 2007, 57(2):129-36; and Li, et al., 2010, J Microbiol Methods 82, 71-77. In 2013, Phan et al. published the genome sequence of clone O25b:H4 ST131, confirming that the clone is a K-12 derivative in agreement with the structure of its waa gene cluster as reported earlier. See Phan et al., 2013, PLOS Genetics 9(10):1-18 (e1003834). Together, the data suggests that a novel O25 agglutinating clone had emerged in E. coli isolated from hospital settings, and that the clone had specific ESBL, MLST, and PFGE phenotypes and contained an altered O antigen gene cluster.

PCR Typing

To determine whether the O25B serotype was present among the isolated E. coli strains identified in the epidemiology study described in Example 1, O25 agglutination positive strains were analyzed by typing PCR for O25 and O25B. PCR was performed using colonies picked from a petri dish as template DNA source and different oligonucleotide primers. O25-specific primers, based on amplification of E47a O25 wzy, and described in Li, et al. (2010) J Microbiol Methods 82, 71-77 were used. Also used were the O25B-specific primers described in Blanco, et al. (2009) J Antimicrob Chemother 63, 1135-1141, which are specific for an undefined 3' portion of the O25b rfb cluster (LNB220). According to Phan et al., 2013, this O25B specific oligonucleotide pair anneal in a 3' portion of the O25B rfb cluster.

Of 24 tested clinical isolates with an O25 agglutination positive phenotype, 20 were assigned to the O25B serotype by PCR typing, while the remaining 4 were positively identified as belonging to the O25A serotype by PCR typing. Thus, surprisingly, strains of the O25B serotype were determined to be more frequent among the analyzed strains than strains of the O25A serotype.

Cluster Sequencing

To analyze the O25B rfb cluster genetically, the cluster of an O25B PCR-positive strain, designated "upec138" was sequenced. The genes identified and their closest relevant protein homologs along with suggested nomenclature are listed in Table 3, below. Genes specific for O25B and absent in O25A are indicated with an asterisk.

TABLE 3

O25B O antigen gene predictions from the rfb cluster.

| Gene name | Putative Function | Most meaningful homology/Protein[organism], accession, max. identity (BLAST) |
|---|---|---|
| rmlB | dTDP-Glucose 4,6-dehydratase | rffG gene product [E. coli NA114], YP_006139244, 99% |
| rmlD | dTDP-6-Deoxy-D-glucose 3,5-epimerase | dTDP-4-dehydrorhamnose reductase [E. coli NA114], YP_006139243, 100% |
| rmlA | Glucose-1-phosphate thymidylyltransferase | rffH2 gene product [E. coli NA114], YP_006139242, 100% |
| rmlC | dTDP-4-dehydrorhamnose 3,5-epimerase | dTDP-4-dehydrorhamnose 3,5-epimerase [E. coli NA114], YP_006139241, 99% |
| Wzx | Wzx, O antigen flippase | Wzx [E. coli strain E47a], ADI43260, 99% |
| wekA | Glycosyltransferase (GT) | dTDP-Rha: Glc-Rha(Ac)-GlcNAc-UPP α-1,3-rhamnosyltransferase [E. coli 83972], ZP_04004894, 93% |
| wekB | Glycosyltransferase (GT) | UDP-Glc: Glc-Rha(Ac)-GlcNAc-UPP β-1,6-glucosyltransferase [E. coli 83972], YP_006106413, 93% |
| Wzy | O antigen polymerase | membrane protein [E. coli 83972], YP_006106412, 94% |
| wbbJ* | O-acetyl transferase | O-acetyl transferase [E. coli 83972], YP_006106411, 95% |
| wbbK* | Glycosyltransferase (GT) | UDP-Glc: Rha-GlcNAc-UPP α-1,3-glucosyltransferase [E. coli K-12], AAB88407, 60% |
| wbbL* | Glucosyltransferase (GT) | lipopolysaccharide biosynthesis protein, C-ter fragment, truncated protein [E. coli DH1], YP_006129367, 62%; dTDP-Rha: GlcNAc-UPP α-1,3-rhamnosyltransferase |

The cluster composition rfb shows clear differences to the composition of the O25A cluster. The genes in the 5' portion of the cluster are close homologs of each other (rmlD to wzy; E. coli E47a and 83972). This is not surprising for the rml genes which are homologous in many E. coli strains that synthetize L-rhamnose. Homology of the gene products of O25A and B reaches into the wekC (O25A) gene, before it drops to levels below 25% identity, indicating unrelatedness of the protein sequences. See FIG. 3B. Further, it was found that the UDP-N-acetylfucosamine biosynthesis genes of O25A are absent in strain upec138 (O25B), as are two glycosyltransferases downstream of fnlABC. See FIG. 3B. Taken together this data suggests that O25B strains are unable to synthetize UDP-L-FucNAc, except that L-FucNAc biosynthesis genes could be encoded outside the rfb cluster. However, there is not a single case reported for an fnlABC locus outside the rfb cluster when L-FucNAc is present in the BRU of the O antigen. Thus it is unlikely that strain 138 is able to synthetize the published O25A basic repeat unit (BRU).

The genes identified in the O25B rfb cluster that are not present in the rfb cluster of serotype O25A encode two glycosyltransferases and an O-acetyltransferase. These three genes share the same organization and the encoded proteins have high homology with the wbbJKL genes found and characterized in K-12 strains of E. coli of the O16 rfb cluster genotype. See FIG. 3B. According to the genetic relatedness between the O25B and O16 serotypes, the nomenclature of the O16 rfb genes, wbbJKL, was applied to the homologous genes identified in the O25B rfb cluster.

The structure of the O16 BRU is known and the gene functions of wbbJKL have been determined. See Steveneson et al., (1994) J Bacteriol. 176(13):4144-56. WbbJKL are responsible for acetylation of L-Rhamnose, transfer of a D-Glc residue to L-Rha-D-Glc-UndPP, and the transfer of the L-Rha to D-GlcNAc-UPP, which is formed by wecA from the ECA cluster. Based on homology with O16 WbbJKL, and the known functions of O16 WbbJKL, it was deduced that the O25B rfb cluster synthesizes a structure containing partially O16 and partially O25A elements together. It was reasoned to be highly likely that WbbJKL$_{O25B}$ synthesize the same structure as WbbJKL$_{O16}$, i.e. α-D-Glc-1,3-α-L-Rha(2Ac)-1,3-α-D-GlcNAc. This trisaccharide structure is identical to the unbranched 'core' backbone of O25A with the only exception that the L-Rha (2Ac) replaces the L-FucNAc. The replacement would accordingly be a conservative one, as D-FucNAc and L-RhaOAc are both monosaccharides with a 6-deoxy and 2-acetyl function. The only difference is conformation, as fucose is related to galactose, and rhamnose to mannose, resulting in a different orientation of the OH group at position 3 and the methyl group at position 5. Linkages between the monosaccharides would be identical (all α-1,3), indicating that the structures would be similar in shape and chemical characteristics. In analogy, the proteins encoded in the upstream part of the O25A and B rfb clusters (rmlDCAB and wekAB) branch the BRU of O25A or B by attachment of the branching D-Glc and L-Rha to either 'core' backbone trisaccharide. This would mean they accept either backbone (with L-FucNAc OR L-Rha(2Ac)) as a substrate.

The presence of L-Rha as the second monosaccharide from the reducing end of the O25B BRU explains why the L-FucNAc biosynthesis can be absent in O25B. UDP-L-FucNAc is not needed, because it is replaced by the dTDP-L-Rha biosynthesis genes that are present in the 5' end of the cluster (rmlDBAC).

Phan et al., 2013 did a similar genetic analysis on an O25B clinical isolate, but concluded differently. They also sequenced the entire genome to search for the UDP-FucNAc biosynthesis gene cluster; however, they state that the machinery for UDP-L-FucNAc in strain O25B:H4 ST131 EC958 is missing not only in the O25B rfb cluster, but in the entire strain. However, Phan concluded that UDP-L-FucNAc must be synthetized in a different way, assuming that O25B:H4 ST131 EC958 makes the same O antigen structure as E47a, i.e., O25A. Instead, it is disclosed herein that the most likely scenario is that O25B strains cannot make L-FucNAc, but instead replace the second residue of the BRU with an O-acetylated L-rhamnose residue, and the genes required for this change are exclusively encoded in the rfb cluster.

In addition, the presence of an O-acetyl transferase homolog in the O25B cluster suggests O-acetylation in the O25B BRU, a modification absent in O25A. Accordingly, it was determined that the structures of O25 antigen from serotypes O25A and O25B must be different.

O25B Structural Analysis

To confirm the hypothesis of a different O25 antigen structure, the chemical composition and arrangement of the O antigens of the O25 clinical isolates described in Example 1 were analyzed. To characterize the O25 OPS structures in more detail, several methods were used.

First, the O antigen structure was analyzed by SDS PAGE. Lipopolysaccharide (LPS) from clinical isolates was analyzed for differences in electrophoretic mobility using different staining methods after SDS PAGE. To visualize LPS amounts, silver staining and anti-O25 specific Western blots were performed. See FIG. 5, which depicts results of the analysis of 10 isolates. The data shows that similar signal intensities are obtained by silver staining of the different LPS preparations. In contrast, probing with the specific antiserum showed stronger signal intensities in 3 out of 10 samples (isolates upec436, upec767, upec827). It was speculated that the different signal intensities arose due to differences in structure of the OPS.

To elucidate the O25B structure in detail, different analytical methods were applied. Clinical isolate upec138 was positive for the O25B by PCR, and exhibits a weaker recognition by the O25 agglutination antiserum than O25A strains. See FIG. 5. In addition, the strain is ESBL, but sensitive to FOS, IPM, and TZP, and resistant to AM, CXM, NOR, and CIP. Another clinical isolate, strain upec436, was negative for O25B by PCR, but positive for the general O25 (O25A) by PCR. upec436 also was found to be strongly reactive with the O25 agglutination antiserum when its LPS was analyzed by Western blotting. See FIG. 5. LLO from both strains was extracted, labeled with a 2AB and analyzed by normal phase HPLC. See FIG. 6; LLO of upec138 and upec436, 9.079 and 9.081). The elution patterns showed clear differences between the two extracts. MS/MS analysis of strain specific peaks detected signals compatible with the expected BRU structures.

Signals in strain upec436 (9.081): The peak at 62' elution time was analyzed by MS and found to contain as the main mass a molecule with m/z=1021 Da, i.e. a molecule corresponding to the expected mass of the complete O25A OPS BRU. MS/MS produced a fragmentation pattern compatible with the monosaccharide sequence of O25A (FIG. 7A; MS/MS of m/z=1021).

Signals in strain upec138: The main mass in the peak at 50' elution time was m/z 1022 Da, i.e. one Da more than the complete O25A repeat unit. MS/MS analysis (FIG. 7B; O25B MS/MS) showed fragmentation behavior almost identical to the O25A repeat unit, and localized a 1 Da difference to the $2^{nd}$ monosaccharide from the reducing end (identified by a fragmentation Y ion of m/z=551 in O25A MS/MS, and m/z=552 in strain upec138). An additional peak eluting at 60' showed similar fragmentation, but a 42 Da difference in the mother ion mass (m/z=980) that localized to the same monosaccharide (m/z=510), i.e. the second one from the reducing end. Interpretation of these results is given below.

The OPS extraction, hydrolysis and 2AB labeling procedure involves acid treatment to remove the Und-PP from the OPS. It was shown that the treatment conditions partially remove O-acetylation, but not N-acetylation. Thus, it is likely that the peak at 60' represents a deacetylated BRU mass that emerged from the chemical hydrolysis of the material in the 50' peak. Taken together, this data indicates that there is an O-acetylation in O25B at the same monosaccharide position as there is N-acetylation in the L-FucNAc of O25A.

To confirm chemically that the acetylation at the second residue from the reducing end is O-linked, a deacetylation assay was performed. The O25B specific peak from 2AB LLO HPLC at 50' elution time was collected from an O25B PCR positive strain and treated with alkali described under 'Methods'. Re-analysis by HPLC resulted in a peak at 60' elution time as identified in a O25B peak from FIG. 6, containing a main mass of m/z=979, with a MS/MS fragmentation ion pattern consistent with an O25B BRU that had lost its O-acetyl group. N-acetyl groups are stable towards alkali treatment as shown by the remaining N-acetyl group in the reducing end D-GlcNAc in the same molecule.

In conclusion, it was determined that the O25B representative strain upec138 is structurally and genetically related to the O25A and O16 OPS (FIG. 3A and B) from E. coli. O25B differs from O25A in having a repeat unit structure containing an O-acetyl group instead of an N-acetyl group at the second monosaccharide of the repeat unit, which is a L-Rha residue and not a D-FucNAc. These changes were most likely caused by a replacement of the UDP-FucNAc biosynthesis machinery and the D-FucNAc transferase by a DNA stretch encoding two glycosyltransferases and an O-acetyltransferase. These genes are related to the O16 gene cluster, based on homology and functionality analysis. The final structures are different, but similar, explaining the cross-reactivity observed with the O25 agglutination antiserum.

As discussed above, it was concluded and proposed based on analysis of their rfb clusters that O25A OPS contains L-FucNAc, whereas the structure is absent in O25B. To investigate if FucNAc is absent from O25B, monosaccharide composition analysis of EPA bioconjugates produced in O25A and O25B strains was performed (FIG. 9) using the PMP labeling method and HPLC analysis method described above. To produce bioconjugates, clinical E. coli isolates with the O25A and O25B phenotypes were prepared, and modified for optimal bioconjugate production. As part of the modification, the waaL genes from strains upec_436 (O25A) and uepc_138 (O25B) were deleted as previously described (see Datsenko and Wanner, (2000) Proc Natl Acad Sci USA 97, 6640-6645) informed by the method for core type determination (see Amor, et al., (2000) Infect Immun 68, 1116-1124). Resulting strains were transformed with expression plasmids for 4S-EPA (pGVXN659) and an oligosaccharyl transferase, PglB (pGVXN939), for O25A production; and with pGVXN114 and pGVXN539 (producing 2S-EPA) for production of O25B bioconjugate production. O25B bioconjugates were produced in a 2 L shake flask with subsequent affinity purification from periplasmic extracts by IMAC. O25A conjugates were produced by fed-batch fermentation, and purified by a two-step purification procedure starting from clarified whole cell homogenate generated by high pressure homogenization as described in the methods section above. Monosaccharide composition analysis was performed as described above.

The results confirmed the absence of a signal for FucNAc in the O25B-derived bioconjugates, whereas the O25A-containing bioconjugates showed a peak at the expected elution time as determined by subjecting a mix of monosaccharides to the same sample processing procedure as a control. It was thus confirmed that the putative structure of O25B is, as expected based on analysis of the rfb cluster, L-FucNAc-less.

The complete structure of the repeat unit (RU) of the O-antigen polysaccharide (O-PS) from the *Escherichia coli* O25B O-antigen was determined by nuclear magnetic resonance of the bioconjugate after partial enzymatic digestion of the EPA carrier protein moiety. The analysis confirmed that the O25B O-PS is composed of a pentasaccharide RU. The $^1$H and $^{13}$C signals were assigned by 2D NMR correlation techniques, which confirmed that the structure of the O25B O-PS RU differs from the published O25A O-PS RU structure (Kenne, L., et al. 1983. Carbohydr. Res. 122:249-256; Fundin, J., et al. 2003. Magn. Reson. Chem. 41:202-205) by the substitution of an α-3-FucpNAc residue by an α-3-Rhap residue, with more than 90% of this residue being O-acetylated at the C2 position. The complete O25B O-PS RU is shown below (O25B'):

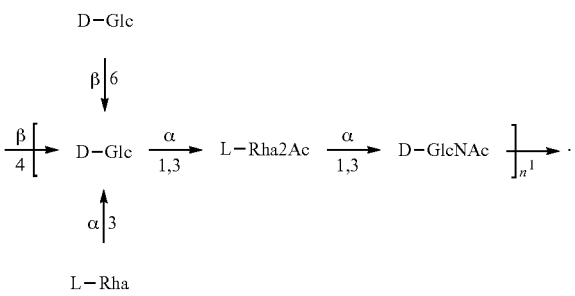

Bioconjugate Production and Characterization

To analyze the O25A and O25B polysaccharide antigens further, more bioconjugate material was produced. For O25A, the purified batch of O25A-EPA from above was used for further characterization experiments. For O25B-EPA production, a strain with a genomically integrated O25B cluster was constructed: W3110 ΔwaaL ΔgtrABS ΔrfbO16::rfb(upec138), with plasmids pGVXN1076 and pGVXN970. This strain was constructed starting from W3110 by the methods of Datsenko and Wanner and a homologous recombination technique for site directed integration of large inserts into bacterial chromosomes (see International Patent Application No. PCT/EP2013/071328).

The resulting O25B bioconjugates were characterized using standard release and characterization assays. Bioconjugates were purified using two consecutive anionic exchange and size exclusion chromatography steps, yielding 97.2 and 98.1% pure O25A and O25B bioconjugate preparations, respectively. SDS PAGE quantification was used for purity analysis. See FIG. 10 (O25A) and FIG. 11 (O25B).

Sugar to protein ratios were calculated based on sugar quantification by the anthrone assay (see Laurentin and Edwards, (2003) Anal Biochem 315, 143-145) and the BCA assay for protein concentration, resulting in 40.2 and 26.6% for O25A and O25B bioconjugates. Analytical size exclusion chromatography showed a monomeric state of the particles in agreement with the expected hydrodynamic radius of EPA with attached glycan chains.

Applications

To address the immunogenic potential of the O25B structure, several preclinical experiments using O25B and O25A bioconjugates were performed. As was shown in FIG. 5, all clinical isolates identified as O25 positive in Example 1 (i.e., both O25A and O25B isolates) were positive with O25A antisera commonly used to detect O25 serotypes (typing sera from the O25A strain E47a) in Western blots. Thus, anti O25A antiserum appears to be cross reactive to the LPS from O25B strains. To analyze the antibody response and cross reactivity in detail, O25 bioconjugates were produced. Maltose binding protein (MBP) was used as a carrier protein, and the carrier protein was linked to O25A or O25B. Table 4 depicts the strains used for protein production. The used strains were identified by PCR for their O25A or B genotype. Expression was performed in TB medium and protein product purified from periplasmic extracts.

TABLE 4

| Bioconjugate | Strain | pglB plasmid | Carrier plasmid | Purification procedure |
|---|---|---|---|---|
| MBP-O25A | upec436 ΔwaaL::kanR | pGVXN939 | pGVXN659 | Q, A |
| MBP-O25B | upec350 ΔwaaL::clmR | pGVXN939 | pGVXN659 | Q, A, S |

Q: Resource Q purification;
A: Amylose resin;
S: Size exclusion chromatography

Immunizations using the obtained bioconjugates were performed using a standard rabbit immunization protocols (the eurogentech 28-day speedy protocol). 50 μg of polysaccharide bound to MBP, were injected at days 0, 7, 8, and 18 with a proprietary Freund's free immunostimulatory compound. The resulting final bleed antisera obtained at day 28 after the first immunization were tested for their specificity towards O25A or O25B LPS. FIG. 22 shows a comparison of the antisera reactivities towards the respective LPS (O25A or O25B). LPS was prepared from upec436 and upec138 by proteinase K digestion of whole cell samples in SDS-PAGE Lämmli buffer. The same amount of LPS was loaded in two SDS-PAGE gels followed by electrotransfer to nitrocellulose membranes and detection using O25A and O25B antisera. The results show that the O25A antiserum recognizes the O25A LPS better than O25B LPS, while the O25B antiserum recognizes the O25B LPS better than O25A LPS. This result indicates that the autologous antigen makes a better antigen. Thus, inclusion of O25B antigen into a vaccine will provide better protection against the predominant O25B clinical strains of the O25 group than the O25A antigen.

Example 3: *E. coli* O1

Structural databases list different subserotype structures for *E. coli* O1. In particular, O1A, O1A1, O1B, O1C. O1A and O1A1 are structurally identical and believed to be associated with disease, although O1B and C have not been reported to be pathogenic (see Gupta, et al., (1992) J Bacteriol 174, 7963-7970), and represent a minority among O1 isolates. Structures of O1A/O1A1, O1B, and O1C are shown in FIG. 12B. To analyze the O1 subserotype distribution in the UPEC epidemiology study of Example 1, the O antigen structures of several clinical isolates from the study were analyzed in detail. First, LPS structure of 12 strains determined to be positive for O1 by agglutination assay were analyzed by SDS PAGE. See FIG. 13: O1 silver staining and Western blot.

Silver staining showed typical LPS signals in all lanes containing extracts from the O1 clinical isolates. Strong staining at an electrophoretic mobility of about 10-15 kDa depicts the lipid A core, and ladder like signals with slower mobilities represent the lipid A core modified with carbohydrate polymers composed of different numbers of O antigen repeat units. When the LPS from different isolates are compared, differences appear in the modal length distribution, the electrophoretic mobility of individual bands, and the ladder pattern. Based on these observations, three groups can be identified: (i) most isolates (upec002, upec010, upec032, upec140, upec108, upec143, upec276, upec399, and upec425) exhibited indistinguishable electrophoretic mobility of individual bands, only differing in signal intensity and average chain length (modal length distribution); (ii) two isolates (upec119 and upec256) appeared to have slightly faster mobility in every repeat unit LPS band, suggesting a different structure, e.g. a different modification of the lipid A core; and (iii) signals obtained from isolate upec1096 appeared as a smear rather than a ladder, indicating a different OPS structure. See FIG. 13A.

Analysis by Western blotting and detection using the anti O1 antiserum showed that LPS from all but upec1096 is detected by specific O1 antibodies, indicative of cross reactive LPS molecules. This means that 11 of the isolates are O1, and that upec1096 is most likely not an O1 isolate (i.e., it was a false positive by agglutination assay).

To analyze the structural similarity of the O1 antigens in detail, 2AB labeling of LLO and a high resolution normal phase HPLC technique were used as described above. FIG. 14A shows an overlay of the chromatograms obtained from 5 of the 11 clinical isolates. The fingerprinting area of the OPS appears at retention times of 110 to 150 minutes. The profiles indicate that all samples have signals appearing at the same retention times, indicating identical molecule structures. Differences observed were the intensity distribution, i.e. the elution time of the mean maximum signal, and the general signal intensities. The remaining 6 extracts resulted in peaks at the same elution times with differences in intensities. Only sample upec1096 was different with respect to the peak pattern, confirming the structural difference noted above.

MS/MS analysis of individual peak contents by MALDI-TOF/TOF analysis was used to identify the sequence of monosaccharides in the O1 samples (see FIG. 14B). MS analysis was performed from samples extracted not from clinical isolates but from a W3110 ΔwaaL strain containing a cosmid with the rfb cluster of upec032. Peaks eluting at 50, 80, 96, and 108 minutes elution time contained main masses of m/z=1021.4, 1849.6, 2693.9, 3540.4. Fragmentation ion series obtained after MS/MS were consistent with 1, 2, 3, and 4 repeat units of a HexNAc, three deoxyhexoses, and a branching HexNAc. This data can only be explained by the O1A subserotype structure. The described peak series represents the O1 OPS attached to UPP in clinical isolates, and every consecutive peak differs to the previous one by one repeat unit.

This data confirms the statements from the literature that the representative structure for the O1 O serotype of E. coli in the clinical UTI isolates from the study described in Example 1 is subtype O1A.

To produce a bioconjugate carrying the O1A polysaccharide, W3110 E. coli strains were engineered to express the O1A OPS. Resulting strains were W3110 ΔrfbO16::rfbO1 ΔwaaL, containing the rfb cluster of an O1 positive clinical isolate (GU299791*, cluster ranging from rmlB-wekO). The O1A OPS expressing host strains were constructed by homologous recombination. The rfb cluster of an O1A clinical isolate was amplified using PCR oligonucleotides annealing in the DNA flanking the rfb cluster. The amplified DNA was then used to replace the endogenous O antigen cluster of the well characterized laboratory strain W3110 by the homologous recombination described in International Patent Application No. PCT/EP2013/071328. Expression plasmids for the carrier proteins pGVXN659 and for PglB (pGVXN114, 939, 970, 971) were inserted by transformation and O1 expression was confirmed (see FIG. 15 and FIG. 16).

In a separate experiment, the clinical O1 isolate upec032 was engineered to produce bioconjugates. Engineering required that antibiotic sensitive phenotype of the clinical isolate be considered. upec032 ΔwaaL was constructed and transformed with pGVXN939 and pGVXN579 for bioconjugate production using MBP as carrier protein. The advantage of using MBP and EPA as carrier proteins is the possibility to raise antisera with both resulting in antisera that are crossreactive towards the polysaccharide component but not the carrier. Such antisera are useful tools for evaluation of preclinical experiments, e.g. as coating agents to develop polysaccharide specific ELISA assays.

Example 4: E. coli O6

The E. coli O6 serotype is the most frequent ExPEC reported to date (George, D. B., and Manges, A. R. (2010) Epidemiol Infect 138, 1679-1690). Not only the study described in Example 1, but also data taken from the literature confirms that the O6 serotype is among the top four serotypes in many ExPEC caused manifestations (see FIG. 4).

Two structures of the O6 OPS have been reported in the literature (see Jann et al., Carbohydr. Res. 263 (1994) 217-225, and Jansson et al., Carbohydr. Res. 131 (1984) 277-283). The structures of the reported O6 antigens are shown in FIG. 17B. They are identical except for the branching monosaccharide of each, which is either Glc or GlcNAc. However, the literature has not identified the predominant O6 structure in clinical isolates involved in UTI.

To choose the most representative structure of the O6 antigen for vaccine purposes, the OPS structures of O6 agglutination positive clinical E. coli isolates from the study of Example 1 was investigated using the same approach as described above for the O1 serotypes. Silver staining and Western blotting using anti O6 antiserum identified one of 12 clinical isolates not reactive to anti O6 serum, although LPS was silver stained in all samples (not shown), suggesting a false positive agglutination result. However, it is likely that Glc or GlcNAc differences would not be detected by electrophoretic mobility shift on gels.

For detailed structure analysis, LLO fingerprinting was used. As a reference for either of the two reported structures, extracts from strains with reported branching Glc (CCUG11309) and GlcNAc (CCUG11311) were included in the analysis. Comparison of the two HPLC traces show peaks series eluting at 70.8, 103.3, and 122.2' for CCUG11309 derived samples, and series of 68.8, 100.3, and 118.3 for CCUG11311 samples. See FIG. 18A. Peaks were analyzed by MS for the main masses present in the peaks and MS/MS for the monosaccharide sequence of these main masses. The data confirmed for the CCUG11311 extract derived peak series m/z=1094.4, 2027.6, and 2962 (MSO154), corresponding to GlcNAc branched 1, 2, and 3 BRU polymers as expected. m/z=1053.4, 1945.7, and 2836.9 with branching Glc were identified previously in extracts from a W3110 strain expressing the cloned rfb cluster of CFT O6 clinical isolate, having identical 2AB fingerprint peak elution times as CCUG11309 (MSO138). When chromatograms obtained from the 12 clinical isolates were compared to the reference strains, 11 signals contained the peak series indicative of the O6 OPS with a branching Glc residue. Five of these 11 chromatograms are shown in FIG. 18B. The one sample not generating signals at O6 specific elution times was not O6, i.e. most likely a false positive from the agglutination test. Thus, the O6 OPS with a Glc branch (FIG. 17B, top) is the most representative structure among the O6 serotypes isolated from the epidemiology described in Example 1.

To produce a bioconjugate carrying the O6Glc polysaccharide, W3110 *E. coli* strains were engineered to express the O6 OPS by replacing the W3110 rfb cluster with the rfb cluster from strain CCUG11309. See Table s7 and 13.

Resulting strains were W3110 ΔrfbO16::rfbCCUG11309 ΔwaaL, containing the rfb cluster of an O6 positive *E. coli* strain with reported Glc branch in the BRU (see above). The O6Glc OPS expressing host strain were constructed by homologous recombination. The rfb cluster was amplified using PCR oligonucleotides annealing in the DNA flanking the rfb cluster. The amplified DNA was then used to replace the endogenous O antigen cluster of the well characterized laboratory strain W3110 by the homologous recombination described in International Patent Application No. PCT/EP2013/071328. Expression plasmids for the carrier proteins and for PglB were inserted by transformation and expression of the expected OPS on EPA was confirmed by Western blotting.

Example 5: *E. coli* O2

The repeat unit structure of the O2 polysaccharide has been known since 1987 (Jansson, et al., (1987) Carbohydrate research 161, 273-279). It is shown in FIG. 19B. Two O2 O antigen gene cluster sequences are available from public databases (GenBank EU549863 and GU299792). Comparative analysis has been made and glycosyltransferase activities have been suggested (Table 5; Fratamico et al., 2010, Canadian journal of microbiology 56, 308-316; and Li, et al., (2010) J Microbiol Methods 82, 71-77).

TABLE 5

O2 O antigen cluster gene predictions from the rfb cluster as published by Li, et al. and Fratamico, et al. is indicated in brackets.

| Gene name | Putative Function | Most meaningful homology/Protein[organism], accession, max. identity (BLAST) |
|---|---|---|
| rmlB | dTDP-Glucose 4,6-dehydratase | dTDP-Glucose 4,6-dehydratase (*E. coli*) IAI39), YP_002406996.1, 98% |
| rmlD | dTDP-6-Deoxy-D-glucose 3,5-epimerase | dTDP-6-Deoxy-L-mannosedehydrogenase (*E. coli*, ACA24825.1, 97%) |
| rmlA | Glucose-1-phosphate thymidylyltransferase | Glucose-1-phosphate thymidylyltransferase (*E. coli* IAI39), YP_002406998.1, 99% |
| fdtA | NDP-hexose isomerase | NDP-hexose isomerase (*Yersinia intermedia* ATCC 29909), ZP_04635116.1, 67% |
| fdtC | WxcM-like protein | Hypothetical protein PROVRETT_01740 (*Providencia rettgeri* DSM 1131), ZP_03638653.1, 71% |
| fdtB | Aminotransferase | WblQ protein (*Photorhabdus luminescens* subsp. *laumondii* TTO1), NP_931971.1, 65% |
| Wzx | O antigen flippase | Polysaccharide biosynthesis protein (*Pectobacterium carotovorum* subsp. *carotovorum* PC1), YP_003016888.1, 50% |
| wekP (wegQ) | Glycosyltransferase (GT) | Hypothetical protein FIC_01940 (*Flavobacteriaceae bacterium* 3519-10), YP_003096444.1, 29% |
| rmlC | dTDP-4-dehydrorhamnose 3,5-epimerase | RmlC (*E. coli*), ACA24796.1, 70% |
| Wzy | O antigen polymerase | Hypothetical protein Gura_3055 (*Geobacter uraniireducens* Rf4), YP_001231799.1, 26% |
| wekQ (wegR) | Glycosyltransferase | Glycosyl transferase, putative, gt2D (*Cellvibrio japonicus* Ueda107), refYP_001983904.1, 31% |
| wekR | Glycosyltransferase | Glycosyl transferase, group 1 (*Shewanella frigidimarina* NCIMB 400), YP_751504.1, 57% |
| wekS (wegW) | Sulfatase | Putative transmembrane sulfatase protein (*Stenotrophomonas maltophilia* K279a), YP_001970541.1, 39% |

Comparison of structure and gene homologies indicated that all functions for biosynthesis of the polymer are present:

rmlBDAC encode the enzymes required for biosynthesis of dTDP-L-Rhamnose, which is the substrate for the addition of L-Rha to the backbone by glycosyltransferases wekPOR;

fdtABC provide dTDP-D-Fuc3NAc for the branching glycosyltransferases;

wzy and wzx homologs responsible for flipping of the Und-PP-bound repeat unit from the cytoplasm to the periplasm; and wekPOR, are predicted glycosyltransferases, and are predicted to form glycosidic linkages of the O2 BRU (three L-Rha and one L-FucNAc).

The wekS gene found in the published O2 rfb cluster sequences is a predicted membrane bound sulfatase, and thus most likely is not involved in BRU formation. This would mean that—if one assumes the one enzyme one linkage rule—that one enzyme among the group of wekPOR must be bifunctional to provide the four glycosidic linkages.

That the one enzyme—one linkage rule is not absolute was shown in multiple examples in which less glycosyltransferases than linkages are known, e.g., in *Shigella flexneri* Y, *S. flexneri* 6, *C. jejuni*, and *E. coli* O1A. In these examples, multifunctional glycosyltransferases are responsible for the formation of more than one glycosidic linkage, they are 'bi-' or 'multifunctional'. Always, it is the same monosaccharide which is added multiple times. Repeated rhamnose residues—as found in serotype O2—are often associated to such multifunctional enzymes.

Due to the presence of truncated transposon elements flanking the wekS sequence, it has been speculated that the wekS locus was inserted into the rfb cluster by a DNA recombination event (see Fratamico et al., 2010, Canadian journal of microbiology 56, 308-316). A transposon-mediated insertion of the wekS locus would suggest that the O2 OPS biosynthesis did exist without wekS presence before, and accordingly wekS would not be required for the synthesis of the O2 OPS polymer. To confirm this hypothesis, O2 OPS formation was reconstituted in a recombinant expression system a 'clean' genomic background, containing an O2 rfb cluster lacking the wekS gene. To achieve this, the O antigen cluster from strain W3110 was replaced by the rfb cluster from the O2 positive strain upec116 lacking the wekS DNA. Chromosomal replacement was done by homologous recombination as described in International Patent Application No. PCT/EP2013/071328. The resulting strain was W3110 ΔwaaL ΔrfbW3110::rfbO2 ΔwekS. OPS was prepared and analyzed by 2AB labeling and normal phase HPLC and fluorescence detection as done for O1A and O6 OPS (see above) and analyzed by normal phase HPLC (FIG. 21) and compared to the signals from wild type strain CCUG25. Analysis resulted in a series of overlapping peaks between 40 and 140 minutes elution time.

MS analysis of the rfbO2 cluster dependent peak series showed main masses with the same differences among consecutive peaks (i.e. of a single O2 RU).

MS analysis of the molecules collected in the respective peaks was performed to analyze the structure of the OPS. Peaks obtained at 43.5, 73.1, 81.4 and 90' obtained from wild type strain CCUG25 were collected and analyzed by MS and MS/MS. Masses and Y fragment ion series compatible with the expected 1, 2 and 3 repeat unit O2 OPS molecules were found (m/z=989.4 (FIG. 23), 1817.8, 2646.1, all Na$^+$ adducts).

To confirm the the O2 OPS from clinical isolates, 12 clones were analyzed for their OPS structure as described above for the O1 serotype. First, LPS was prepared to be analyzed by silver staining and Western blotting. The results are depicted in FIG. 20. All samples showed a ladder-like banding pattern with two apparent different mean ladder lengths. Anti-O2 antiserum detected all LPS samples, indicating that agglutination correctly identified all isolates as O2 serotypes.

To produce a bioconjugate carrying the O2 polysaccharide, W3110 ΔwaaL ΔrfbW3110::rfbO2 ΔwekS was used. Expression plasmids for the carrier proteins and for PglB were inserted by transformation and expression of the expected OPS on EPA was confirmed by Western blotting. See Tables 7 and 13 and above.

Example 6: Immunological Analysis of the Different O Antigens

To assess the immunological potential of bioconjugates containing the selected antigenic polysaccharides, a preclinical study was performed. O1A-EPA, O2-EPA, O6Glc-EPA and O25B-EPA bioconjugates were produced, purified, and characterized as described above and in the methods section.

TABLE 6

Overview of the preclinical rat study, including vaccine group numbers, group sizes, vaccines used, and quality indication of the vaccine preparation.

| Group | Injection route | Number of animals | Treatment [0.2 μg PS] | Purity/% | S/P ratio/% | Production strain/(Strain/plasmid/Plasmid) |
|---|---|---|---|---|---|---|
| 1 | i.m. | 8 | O1-EPA$^{tetra-pool}$ [0.2 μg PS] | 97 | 22 | upec032 ΔwaaL::kanR/ pGVXN939/ pGVXN659 |
| 4 | i.m. | 8 | O2-EPA$^{tetra-pool}$ [0.2 μg PS] | 90 | 34 | W3110 Δrfb::rfb(upec116)(ΔwekS) ΔwaaL::clmR/ pGVXN939/ pGVXN659 |
| 7 | i.m. | 8 | O6-EPA$^{tetra-pool}$ [0.2 μg PS] | 84 | 38 | W3110 ΔwzzE-wecG ΔwaaL ΔwbbIJK ΔgtrS ΔwzxO16/pGVXN348/ pGVXN114/ pGVXN659 |
| 9 | i.m. | 8 | O25B-EPA$^{tetra-pool}$ [0.2 μg PS] | 85 | 21 | upec163 ΔwaaL pGVXN112/ pGVXN659 |

TABLE 6-continued

Overview of the preclinical rat study, including vaccine group numbers,
group sizes, vaccines used, and quality indication of the vaccine preparation.

| Group | Injection route | Number of animals | Treatment [0.2 µg PS] | Purity/% | S/P ratio/% | Production strain/(Strain/plasmid/Plasmid) |
|---|---|---|---|---|---|---|
| 10 | i.m. | 8 | EPA$^{tetra}$ | | | W3110 ΔwaaL/pGVXN659 |
| 11 | i.m. | 8 | TBS | | | |
| 12 | i.m. | 8 | O1 + O2 + O25B + O6-EPA$^{tetra}$ [0.2 µg PS/each] | 89* | 29* | Blend from above batches |

*calculated values

Purified bioconjugates were used to immunize 9 week old female Sprague Dawley rats. 100 µl solutions of the same dose were injected intra muscularly (i.m.) at days 1, 22, and 43 into the rats which were terminally bled and sacrificed at day 56.

Different groups of rats received different vaccines: always unformulated, comprising bioconjugates alone or in combination as indicated in Table 6. ELISA plates coated with the cognate LPS produced in a waaL positive strain were used to measure immunogenicity in the form of ELISA titer of the rat sera at the terminal bleeding timepoint of 56 days after the first injection (FIGS. 25-28). Taken together, statistical significant immunogenicity was observed for all vaccination groups measured against controls (unglycosylated EPA or TBS buffer). Thus, the bioconjugates selected and produced represent useful vaccine candidate compounds.

For all O-antigen-EPA conjugates tested, statistically significant immunogenicity was observed for all vaccination groups measured against controls (unglycosylated EPA or TBS buffer). Thus, the bioconjugates selected and produced represent useful vaccine candidate compounds for the induction of O-antigen-specific antibodies.

Example 7: Physico-Chemical Characterization of the Bioconjugates

The four biococonjugates described in the examples above (O-antigen of O25B, O1A, O2 and O6, respectively conjugated to EPA as a carrier protein) were prepared as monovalent batches (active pharmaceutical ingredients, APIs) or combined in a single preparation as a multivalent vaccine against ExPEC. Various batches were produced: pre-clinical batches, toxicity study batches, and clinical batches. Table 7 indicates host strains used for the production of conjugates.

TABLE 7

Host strains for production of preclinical,
toxicology study and clinical batches

| Product | Strain | EPA expression plasmid | PglB expression plasmid |
|---|---|---|---|
| EPA-O1A | W3110 Δrfb::rfb(upec032) ΔwaaL | pGVXN1076 | pGVXN970 |
| EPA-O2 | W3110 Δrfb::rfb(upec116) ΔwaaL | pGVXN1076 | pGVXN971 |
| EPA-O6Glc | W3110 Δrfb::rfb(CCUG11309) ΔwaaL | pGVXN659 | pGVXN114 |
| EPA-O25B | W3110 Δrfb::rfb(upec138) ΔwaaL ΔgtrABS | pGVXN1076 | pGVXN970 |

The four monovalent pre-GMP batches and an un-glycosylated EPA reference standard were thus analyzed by size-exclusion chromatography with multi-angle light scattering (SEC-MALS), in order to quantify the degree of mono- and di-glycosylation of the individual bioconjugates, and to determine the molecular mass (MW) of the protein carrier and of the O-PS attached to it. The samples were separated on a TSKgel-G3000 SWxl column in phosphate buffer (pH 7.0; 50 mM NaCl, 150 mM sodium phosphate) and monitored by UV (214 and 280 nm), refractive index (RI) and multi angle light scattering (MALS).

For the un-glycosylated EPA carrier protein, a MW of 63-67 kDa was determined (theoretical MW of 70.5 kDa, based on amino acids sequence). In the bioconjugates, only EPA was detected at 280 nm, allowing its MW to be extracted from the total MW measured by RI and MALS: in the bioconjugates, the measured MW of the EPA moiety was 65-71 kDa.

The analysis of the pre-GMP API product standards is displayed in Table 8, indicating the presence of mono- and di-glycosylated conjugates, with a MW in the range 75-79 kDa and 87-91 kDa, respectively. The O-PS parts featured a MW of 16-24 kDa for the di-glycosylated species, and 8-14 kDa for the mono-glycosylated species, respectively. Considering the MW of the RU of each serotype, an average number of 10-16 RU per polysaccharide chain was determined, in good agreement with hydrazinolysis and MS data.

TABLE 8

SEC-MALS analysis of the monovalent
pre-GMP API product standards

| | Peak 1 | | | Peak 2 | | |
|---|---|---|---|---|---|---|
| Monovalent batch | | Total MW | O-PS MW | | Total MW | O-PS MW |
| EPA-O1A | 15% | 87 kDa | 16 kDa | 83% | 75 kDa | 8 kDa |
| EPA-O2 | 29% | 88 kDa | 19 kDa | 70% | 76 kDa | 10 kDa |
| EPA-O6 | 47% | 88 kDa | 21 kDa | 50% | 78 kDa | 12 kDa |
| EPA-O25B | 56% | 91 kDa | 24 kDa | 42% | 79 kDa | 14 kDa |

Peak 1: di-glycosylated form.
Peak 2: mono-glycosylated form.

Circular dichroism (CD) analysis of an O25B bioconjugate batch formulated in Tris buffered saline (TBS), showed that formulations at pH 6.8 to 7.4 had spectra similar to that of the un-glycosylated EPA carrier protein, with a mixture of alpha helical and beta sheet structures, as expected based on the published crystal structure of EPA. Therefore, based on these CD analyses, the glycosylation with O25B O-PS chains did not seem to affect the secondary structure of the EPA carrier protein.

Differential scanning calorimetry (DSC) analysis of an O25B bioconjugate batch formulation in TBS at pH 6.8 to 7.4, and in phosphate buffered saline (PBS) at pH 7.1 to 7.8, showed melting curves comparable to that of un-glycosylated EPA, with a melting point of approximately 52° C. This result indicated that the biophysical characteristic of the EPA carrier protein did not change upon modification with O25B O-PS chains.

Example 8: Stability of Monovalent Bulks and Tetravalent Vaccine Preparations

Prior to large scale production, consistency of the manufacturing process was assessed on a small scale. Consistency batches were evaluated in extensive stability studies that included accelerated and stress storage conditions to identify degradation pathways. Stability of the four monovalent vaccine components (APIs) was tested over a 3 month period.

Analysis of stability data of pre-clinical APIs indicated stability over at least 3 months when stored at −75±15° C. (normal storage conditions). No statistically significant trends were observed at the intended storage condition by statistical linear regression analysis. Also at the accelerated (+5±3° C.) and stress storage condition (+25±5° C.) the product was stable over at least 3 months, as evidenced by the low variability of stability-indicating parameters. The data for the O1A pre-clinical API is shown in Table 9. The three other serotypes (O2, O6, O25B) demonstrated similar stability data.

TABLE 9

Stability data of O1A pre-clinical API batch

|  | S/P t0 | S/P 3 mo. | Purity t0 | Purity 3 mo. |
| --- | --- | --- | --- | --- |
| −75 ± 15° C. | 19.3 | 19.8 | 98.1% | 97.6% |
| +5 ± 3° C. |  | 20.9 |  | 98.6% |
| +25 ± 5° C. |  | 21.3 |  | 98.3% |

S/P: sugar to protein ration as determined by anthrone and BCA assays, respectively.
Purity: as determined by reverse phase high resolution liquid chromatography (RP-HPLC).

Stability of the tetravalent vaccine composition (O25B, O1A, O2 and O6 bioconjugates) was tested during over a 3 month period. The studies included accelerated and stress storage conditions to identify degradation pathways. The resultant data are considered to be relevant for the initial justification of the GMP IMP (investigational medicinal product, the tetravalent ExPEC vaccine composition) shelf life.

Analysis of stability data of the tetravalent ExPEC vaccine pre-clinical batch indicated stability over at least 3 months when stored at +5±3° C. (normal storage conditions), as shown in Table 10. No statistically significant trends were observed at the intended storage condition by statistical linear regression analysis. Also at the accelerated storage condition (+25±5° C.) the product was stable, as evidenced by the low variability of stability-indicating parameters.

TABLE 10

Stability data of pre-clinical tetravalent vaccine batch

|  | MW t0 | MW 3 mo. | Purity t0 | Purity 3 mo. |
| --- | --- | --- | --- | --- |
| 5 ± 3° C. | 302 & 192 kDa | 294 & 188 kDa | 98.3% | 98.7% |
| 25 ± 5° C. |  | 297 & 191 kDa |  | 98.2% |

MW (molecular size distribution): two main product peaks (i.e. mono- and di-glycosylated species), as determined by size exclusion high resolution liquid chromatography (SE-HPLC).
Purity: as determined by reverse phase high resolution liquid chromatography (RP-HPLC).

Together, these studies demonstrate that the APIs and the tetravalent ExPEC vaccine composition were stable for at least three months, and thus are suitable vaccine compositions with respect to stability.

Example 9: Toxicity Study on Tetravalent Vaccine Preparation

Toxicity and local tolerance of a tetravalent vaccine preparation (O25B, O1A, O2 and O6 bioconjugates) following two intramuscular administrations (quadriceps femoris was used for treatment) in Sprague Dawley rats on days 1 and 14 was assessed. Reversibility, persistence, or delayed occurrence of any changes was assessed after a 14-day recovery period on day 28. Necropsy of the animals in the main groups (10 male and 10 female for both the vaccinated and the control group) occurred on day 17, and for the recovery groups (5 male and 5 female for both the vaccinated and the control group) on day 28 (after a 14-day recovery period). This was not associated with any effects regarded as adverse that could be ascribed to treatment. The dose administered, i.e. a full human dose equivalent of 4 μg per O-antigen (16 μg total O-antigen for the tetravalent vaccine), as administered on days 1 and 14, was considered to be the no-observed-adverse-effect-level (NOAEL) for the tetravalent ExPEC vaccine under the conditions of this study. In addition, immunogenicity of the tetravalent ExPEC vaccine was confirmed at both day 17 and day 28, following assessment of the serum samples. Higher titers of anti-O1A, anti-O2, anti-O6 and anti-O25B IgG antibodies were induced in the vaccinated group, compared to controls that received only formulation buffer (25 mM Tris, 130 mM NaCl, 2.7 mM KCl, pH 7.4).

These data confirm that the tetravalent ExPEC vaccine has a suitable toxicity profile for administration as a vaccine, and induces antibodies to at least all four *E. coli* serotypes from the O-antigens present in the vaccine (i.e., O25B, O1A, O2 and O6).

Example 10: Epidemiology of O-Serotypes Associated with Bacteremia

To determine O-serotype distribution among extraintestinal *E. coli* causing bacteremia in the elderly, an epidemiological study was conducted on a panel of *E. coli* blood isolates collected from patients older than 60 years of age. In total, 860 blood isolates from the period 2011-2013 were collected from subjects in the US, UK, Germany, Spain, and the Netherlands, and analyzed by classical O-agglutination. As shown in table 11, the O-serotype distribution of bacteremia isolates resembled the O-serotype distribution found in patients suffering from urinary tract infection (UTI, see Table 1A). Serotype O25 was most prevalent in the bacteremia population studied; subtyping of fifty-seven isolates by PCR showed that fifty-six (98%) of the O25 serotypes were typeable as O25B. In both target populations (UTI and bacteremia), serotypes O1, O2, O6, and O25 were identified as the four most prevalent serotypes. Overall, these data confirm that serotype distribution among both urinary tract infection and bacteremia isolates is highly similar and independent of geographical location, time of isolation, and indication.

TABLE 11

Distribution of the most common bacteremia-associated *E. coli* O-serotypes from a collection of 860 blood isolates collected in the US and EU in the period 2011-2013. Indicated is the relative O-serotype distribution of the samples.

| O-serotype | Bacteremia in ≥60 years old US/EU 2011-2013 (n = 860) |
|---|---|
| 25 | 19.2 |
| 2 | 8.8 |
| 6 | 8.3 |
| 1 | 7.8 |
| 75 | 3.3 |
| 4 | 2.8 |
| 16 | 2.7 |
| 18 | 2.7 |
| 15 | 2.3 |
| 8 | 2.0 |
| 153 | 1.6 |
| 73 | 1.6 |

Example 11: Induction of Functional Antibody Responses

The functionality of the antibodies raised after vaccination with monovalent and tetravalent vaccine formulations described above was investigated with an in vitro opsonophagocytic killing (OPK) assay. This type of assay has been accepted as a correlate of protection for the conjugate vaccine against *Streptococcus pneumoniae* (PREVNAR®). The OPK assay measures the ability of serum to facilitate opsonophagocytosis and killing of different *E. coli* serotypes. In 96-well plates, defined dilutions of the sample sera were incubated, in each well, with: bacteria from one of the four vaccine-specific *E. coli* serotypes, a defined amount of HL60 cells, and baby rabbit complement. After incubation, a proportion of the mixture was spotted onto tryptic soy agar (TSA) and the number of bacterial colonies was counted. The ability of the antibodies to bind the bacterial cells and activate deposition of the complement and mediate uptake and killing of the bacteria by HL60 cells was expressed as opsonic titer. The opsonic titer or opsonization index (OI) corresponds to the dilution of the sera killing 50% of the bacterial cells. Opsonic indices for pre and post-immune sera are provided. A >than 4-fold increase of OI from pre- to post-immune is considered significant. OPK assays for three serotypes O2, O6Glc and O25B were established.

Functionality of Antibody Responses Induced by Monovalent Vaccines

To assess the functional activity of vaccine-induced antibody responses of O25B, O1A, O2 and O6Glc bioconjugates, sera from vaccinated rats were analyzed using opsonophagocytic killing (OPK) assays, which measure in vitro complement- and antibody-dependent phagocytosis and killing of bacteria, e.g., *E. coli*. *E. coli* was pre-opsonized with dilutions of serum from vaccinated rats, incubated with complement and phagocytes (differentiated HL60 cells), and the colony forming units (CFUs) were determined. Subsequently, the maximum % killing and Opsonization Indices (OI: serum dilution killing of 50% of *E. coli*) were calculated. *E. coli* selected for OPK testing were OC 24453 (serotype O2), OC 24781 (serotype O6Glc) and OC 24176 (serotype O25B). As shown in FIG. 29, a robust functional immune response to O2-EPA (FIG. 29A), O6Glc-EPA (FIG. 29B) and O25B-EPA (FIG. 29C) was observed.

The data demonstrate that the vaccine components described herein induce antibody responses against *E. coli* serotypes from which O-antigens are included in the vaccine, and that such antibody responses are functional in killing *E. coli* from these serotypes.

Functionality of Antibody Responses Induced by a Tetravalent Vaccine

Table 12 shows the total OI titers for the O-antigens O2, O6Glc and O25B from animals immunized with the tetravalent vaccine with either 0.4 or 4 µg per O-antigen. The titers were determined in two separate experiments. The 0.4 µg dose induced significant OIs in all animals for the O2 and O6Glc serotypes. For O25B, ⅜ animals showed a significant increase in OI following immunization with the 0.4 µg dose. Compared to the 0.4 µg dose, the 4 µg dose induced lower OI increases for O2 in all animals. ⅜ animals showed OI increases when the sera from the 4 µg dose group were tested on O25B *E. coli*. The data confirm that a tetravalent vaccine is able to elicit O-antigen-specific opsonic antibodies against O2, O6Glc and O25B.

The data demonstrate that the vaccine components described herein induce antibody responses against *E. coli* serotypes from which O-antigens are included in the vaccine, and that such antibody responses are functional in killing *E. coli* from these serotypes.

TABLE 12

OIs against *E. coli* O2, O6 and O25. OIs for individual pre-vaccination and post 3 vaccination sera from two separate experiments are shown for all animals.

| | Tetravalent-EPA Rat Serum Opsonization Indices (OI) | | | | | | | | | | | |
|---|---|---|---|---|---|---|---|---|---|---|---|---|
| | O2 *E. coli* | | | | O6 *E. coli* | | | | O25 *E. coli* | | | |
| | 0.4 ug Dose | | 4 ug Dose | | 0.4 ug Dose | | 4 ug Dose | | 0.4 ug Dose | | 4 ug Dose | |
| Animal No. | Exp. 1 | Exp. 2 | Exp. 1 | Exp. 2 | Exp. 1 | Exp. 2 | Exp. 1 | Exp. 2 | Exp. 1 | Exp. 2 | Exp. 1 | Exp. 2 |
| 1: Pre-vacc | 6 | 7 | 5 | 0 | 17 | 6 | 6 | 16 | 2'404 | 2'082 | 0 | 0 |
| Post vacc | >16384 | 1'476 | 293 | 32 | 202 | 226 | 2'045 | 2'821 | 1'847 | 1'578 | 9 | 0 |
| 2: Pre-vacc | 21 | 11 | 11 | 20 | 11 | 90 | 0 | 0 | 0 | 0 | 0 | 0 |
| Post vacc | 11'148 | >16384 | 150 | 120 | 436 | 475 | 10'262 | 11'460 | 0 | 0 | 4 | 0 |

TABLE 12-continued

OIs against E. coli O2, O6 and O25. OIs for individual pre-vaccination and post 3
vaccination sera from two separate experiments are shown for all animals.

| | Tetravalent-EPA Rat Serum Opsonization Indices (OI) | | | | | | | | | | | |
|---|---|---|---|---|---|---|---|---|---|---|---|---|
| | O2 E. coli | | | | O6 E. coli | | | | O25 E. coli | | | |
| | 0.4 ug Dose | | 4 ug Dose | | 0.4 ug Dose | | 4 ug Dose | | 0.4 ug Dose | | 4 ug Dose | |
| Animal No. | Exp. 1 | Exp. 2 | Exp. 1 | Exp. 2 | Exp. 1 | Exp. 2 | Exp. 1 | Exp. 2 | Exp. 1 | Exp. 2 | Exp. 1 | Exp. 2 |
| 3: Pre-vacc | 6 | 6 | 0 | 0 | 0 | 5 | 0 | 0 | 0 | 0 | 0 | 0 |
| Post vacc | 11'073 | >16384 | 46 | 19 | 98 | 37 | 7'959 | 8'597 | 6 | 0 | 355 | 197 |
| 4: Pre-vacc | 5 | 5 | 5 | 6 | 23 | 17 | 0 | 0 | 0 | 0 | 0 | 0 |
| Post vacc | >16384 | 63 | 57 | 45 | 108 | 116 | 2'189 | 4'488 | 0 | 0 | 70 | 26 |
| 5: Pre-vacc | 7 | 0 | 0 | 4 | 30 | 8 | 8 | 7 | 0 | 0 | 0 | 0 |
| Post vacc | 10'413 | 7'050 | 105 | 108 | >16,384 | 12'672 | 3'107 | 7'564 | 0 | 0 | 105 | 69 |
| 6: Pre-vacc | 8 | 0 | 8 | 7 | 299 | 164 | 5 | 0 | 269 | 154 | 0 | 0 |
| Post vacc | 89 | 34 | 24 | 17 | 1'725 | 1'475 | 540 | 896 | 0 | 0 | 0 | 0 |
| 7: Pre-vacc | 9 | 9 | 6 | 6 | 18 | 21 | 22 | 5 | 0 | 0 | 0 | 0 |
| Post vacc | >16384 | >16384 | 109 | 92 | 1'249 | 1'863 | 160 | 143 | 1'130 | 630 | 9 | 8 |
| 8: Pre-vacc | 4 | 6 | 6 | 5 | 26 | 22 | 0 | 0 | 0 | 0 | 0 | 0 |
| Post vacc | 5'058 | 4'201 | 39 | 25 | 6'590 | 3'826 | 288 | 656 | 3'336 | 1'986 | 0 | 0 |
| Pre-vacc Av | 8 | 5 | 5 | 6 | 53 | 42 | 5 | 3 | 334 | 280 | 0 | 0 |
| Post-vacc Av | 10'867 | 7'747 | 103 | 57 | 3'349 | 2'586 | 3'319 | 4'578 | 790 | 624 | 69 | 37 |

The maximum % killing and Opsonization Indices (OI: serum dilution killing of 50% of E. coli) were calculated. E. coli selected for OPK testing were OC 24453 (serotype O2), OC 24781 (serotype O6Glc) and OC 24176 (serotype O25B). Robust functional immune response to O2-EPA, O6Glc-EPA and O25B-EPA was observed.

Example 12: Evaluation of a Candidate Vaccine Against Uropathogenic *Escherichia Coli* in Women with a Clinical History of Recurrent Urinary Tract Infection (RUTI)

An *E. coli* bioconjugate vaccine is used in a Phase I clinical study. The vaccine comprises four bioconjugates in a saline buffer solution. The four bioconjugates are: (i) *E. coli* O1A conjugated to EPA carrier protein, (ii) *E. coli* O2 conjugated to EPA carrier protein, (iii) *E. coli* O6Glc conjugated to EPA carrier protein, and (iv) *E. coli* O25B conjugated to EPA carrier protein.

The study population includes 194 healthy females, aged≥18 to 70 years old, with a history of recurrent urinary tract infection (RUTI), defined as ≥3 independent episodes in the previous 12 months or ≥2 episodes in the last 6 months. At least one of the urinary tract infection (UTI) episodes was caused by *E. coli* (as single pathogen or part of polymicrobial infection) and the cause was culture-confirmed and documented. For purposes of the study, UTI is defined by the presence of at least one specified UTI symptom (dysuria, urgency, frequency, flank pain, bladder tenderness, suprapubic pain, fever, nausea, vomiting) along with a bacterial count (CFU) of ≥$10^3$ CFU/ml uropathogen in mid-stream urine.

The study includes two arms: (i) candidate vaccine and (ii) placebo. The study is a staggered, randomized, single blind, placebo-controlled multi-center study in healthy women with history of RUTI.

The estimated enrollment period for the study is 4 months, with a follow-up duration period of nine months for each subject.

The objective of the study is to assess the safety, immunogenicity, and efficacy of the *E. coli* bioconjugate vaccine.

Study Design

Subjects are followed for 9 months after injection, and only injected subjects are followed throughout the study period. Subjects attend a total of 5 scheduled visits: screening (first visit), day 1 (second visit), day 7, day 30, and day 270. Subjects receive 4 follow-up phone calls, on day 2, day 90, day 150, and and day 210.

Any unscheduled visits due to occurrence of UTI include standard of care with harmonized treatment options. Urine and blood (if possible) are collected for diagnostic and serotyping purposes. Unsolicited adverse events (AE) and severe adverse events (SAEs) are recorded along the study duration whereas solicited AE are recorded for 7 days after injection.

At each visit a new diary card is given to the subject and the previous one is discussed. Dosing and Administration At first visit, eligible subjects that have provided informed consent are screened and compliance for inclusion/exclusion criteria are confirmed. Blood is drawn and urine is collected.

At visit 2 (day 1), each subject will receive one intramuscular injection of 0.5 ml of solution (vaccine candidate or placebo) in the deltoid muscle. The reduced dose of the candidate vaccine will contain 1 μg of each polysaccharide (total 4 μg polysaccharide). The target dose of the candidate vaccine will contain 4 μg of each polysaccharide (total 16 μg polysaccharide).

Objectives

The primary objective is to assess the occurrence, intensity, relationship, and duration of solicited and unsolicited adverse events (AE) and serious adverse events (SAE) post-injection of candidate vaccine compared to the placebo group throughout the study period.

The secondary objectives are (i) to compare the change in hematological and biochemical safety endpoints prior to injection (at the initial screening and day 1) and post injection (at day 7 and day 30) of candidate vaccine compared to the placebo group; (ii) evaluate the immune-response of candidate vaccine between baseline (day 1) and post injection (day 30 and day 270); (iii) compare the number of symptomatic urinary tract infection (UTI) episodes caused by the *E. coli* vaccine-serotypes between the two arms, injected with candidate-vaccine or placebo during the whole study period as most relevant efficacy endpoint; (iv) assess the rate of occurrence of vaccine-serotype specific *E. coli* UTI in vaccine group compared to the placebo group along the study duration; and (v) assess the intensity and duration of clinical symptoms of vaccine-serotype specific *E. coli* UTI in vaccine group compared to the placebo group along the study duration.

The exploratory objectives are (i) to compare the rate of UTI occurrence caused by any *E. coli* serotype in the vaccine group compared to the placebo group throughout the study period; and (ii) to compare the rate of UTI occurrence caused by any pathogens in the vaccine group compared to the placebo group throughout the study period.

Inclusion Criteria

Inclusion criteria for the study are as follows: (i) female subjects with a history of recurrent UTI, which is defined as: ≥3 UTI independent episodes in the previous 12 months or ≥2 UTI episodes in the last 6 months; at least one UTI during the last 5 years was caused by *E. coli* (as single pathogen or part of polymicrobial infection) and was culture-confirmed and documented; (ii) Age≥18 and ≤70 years; (iii) subjects in a healthy state without ongoing or suspected symptomatic UTI at the screening visit and at injection day (visit 2); (iv) general good health, without clinically significant medical history, physical examination findings or clinical laboratory abnormalities per clinical judgment of the investigator; and (v) willingness to participate in the study after all aspects of the protocol have been explained and fully understood, and written informed consent form obtained.

Exclusion Criteria

Exclusion criteria for the study are as follows: (i) history of more than 10 recurrent UTIs in the year before the screening visit; (ii) use of any short-term urinary catheter within 7 days prior to screening; (iii) use of any permanent catheter within 30 days prior to screening; (iv) history of any unresolved urinary tract diseases/abnormalities; (v) evidence of impaired immune function; (vi) significant cardiovascular, liver, renal diseases and/or insufficiency; (vii) uncontrolled diabetes mellitus; (viii) significant abnormalities in screening results for hematology, serum chemistry or urinalysis; (ix) positive test for HIV, and/or evidence of HBV or HCV; (x) BMI>34; (xi) previous immune stimulatory therapy for UTI prevention (such as Urovaxom®, Strovac® or Urovac®) in the last 3 months, or planned use during the study period; (xii) current use of any medication known to affect immune function (e.g. corticosteroids≥0.5 mg/kg BW/day); (xiii) use of UTI-related vaginal estrogen treatment newly started less than 6 months before injection and continuing during the study or planned start during the active study period; (xiv) use of any antibiotic therapy within 1 week preceding injection; (xv) planned use of post-coital antibiotics for UTI prevention during study period; (xvi) any vaccination planned within 30 days before and 30 days after injection; (xvii) participation in other clinical trials in the 60 days preceding enrolment and for the duration of the study; (xviii) previous treatment with immunoglobulins or blood products in the 3 months preceding the injection; (xix) known hypersensitivity to any component of the vaccine; (xx) presence of a significant medical or psychiatric condition that in the opinion of the investigator precludes participation in the study; (xxi) acute illness at the time of injection; (xxii) women of child bearing potential who either have a positive pregnancy test or refuse to use an effective contraception; (xxiii) women who are lactating at any time throughout the study period; (xxiv) subjects with an elective surgical intervention, planned during the study period; and (xxv) any other significant finding that in the opinion of the Investigator would increase the risk of having an adverse outcome from participating in the study.

Statistical Methods and Analysis

Descriptive statistics (n, mean, standard deviation, median and ranges for continuous variables, frequencies and percentages for categorical variables) are provided by treatment group and/or visit, where applicable. All data are listed by subject, treatment group and, where applicable, visit. All subjects from Group B receiving placebo are combined to form the placebo treatment group.

Example 13: Phase I Clinical Study Results

This Example presents certain results of the Interim Analysis of the Phase I clinical study described in Example 12.

12.1: Safety

Occurrence of adverse events and severe adverse events were comparable between the placebo and vaccinated groups. Ten severe adverse events were reported, and none were related to the study drug.

12.2: Immunogenicity

To assess the immunogenicity of the vaccine components, sera from women participating in the clinical study were obtained and analyzed by ELISA to quantify IgG against the four different O-antigens included in the tetravalent vaccine (*E. coli* O1, *E. coli* O2, *E. coli* O6, and *E. coli* O25B).

Sera from vaccinated women were incubated in plates coated with O1A, O2, O6Glc and O25B-LPS and EPA. Subsequently, plates were incubated with HRP-labeled secondary antibody (anti-human IgG). Bound antibodies were detected with TMB substrate and absorbance was measured. EC50 values were calculated by 4PL fitting.

As shown in FIG. 30, a robust immune response to O1A-EPA, O2-EPA, O6Glc-EPA and O25B-EPA occurred in the majority of the vaccinated women.

These data demonstrate immunogenicity of each component of the tetravalent vaccine.

12.3: Functional Antibody Response

OPK assays, which measure in vitro complement- and antibody-dependent phagocytosis and killing of *E. coli* bacteria, were used to assess the the functional antibody response of women participating in the clinical study.

Sera was collected from study participants. *E. coli* was pre-opsonized with dilutions of serum from the vaccinated women, incubated with complement and phagocytes (differentiated HL60 cells), and the remaining colony forming units (CFUs) was determined. Subsequently, the maximum percent killing and Opsonization Indices (OI: serum dilution killing of 50% of *E. coli*) were calculated. *E. coli* selected for OPK testing were OC 24452 (serotype O1A), OC 24453 (serotype O2), OC 24454 (serotype O6Glc), and OC 24176 (serotype O25B).

As shown in FIG. 31, a robust functional immune response to O1A-EPA (FIG. 31A), O2-EPA (FIG. 31B), O6Glc-EPA (FIG. 31C), and O25B-EPA (FIG. 31D) was observed.

These data demonstrate that each component of the tetravalent vaccine induces a serotype-specific antibody response, and that such antibody responses are functional in killing *E. coli* from these serotypes. Thus, the vaccine compositions described herein are functional in humans.

12.4: Immunization with a Tetravalent O-Antigen Conjugate Comprising O25B-EPA Elicits O25A/O25B Cross-Reactive IgG Antibodies in Humans To determine the level of cross-reactivity of vaccine-induced serum IgG antibodies toward the two known *E. coli* O25 serosubtypes, O25A and O25B, serial dilutions of serum derived from vaccinated subjects were incubated with

*purified O25A LPS, O25B LPS, or intact bacterial cells, and tested by ELISA.*

As shown in FIG. 32, similar $EC_{50}$ values were observed when reactivity towards O25A LPS (black bars) and O25B LPS (grey bars) thirty days post vaccination was tested. Overall the data suggest that the O25B bioconjugate works well for O25B and for O25A, but in most cases/tested subjects O25B works slightly better in terms of antibody response for O25B compared to O25A. This result demonstrates that with the occurrence of some natural variation, the tetravalent vaccine induces antibodies that recognize both O25A and O25B LPS. To test whether the same was true for whole bacterial cells and multiple O25A/O25B strains, reactivity towards a set of clinical O25A or O25B isolates derived from either blood or urine was also tested. In this case a serotype O75 strain, a serotype not represented in the tetravalent vaccine, was used as a negative control (dotted grey line in FIG. 33). As demonstrated in FIG. 33, vaccine-induced serum IgG antibodies showed a strong response toward each of the individual O25 strains. Although strain-to-strain variation was apparent, reactivity toward the O25A (black lines) and O25B strains (grey lines) was observed. These data demonstrate that the O25B vaccine component of the tetravalent vaccine elicits antibodies that recognize both O25A and O25B purified LPS and *E. coli* O25A and O25B strains.

Tables 13 and 14, below, provide details of certain strains and plasmids, respectively, used in the foregoing examples.

TABLE 13

Strains

| Name | Genotype | Description |
|---|---|---|
| upec032 | wt | O1A clinical isolate from GVXN epidemiology study |
| upec436 | wt | O25A clinical isolate from GVXN epidemiology study |
| upec138 | wt | O25B clinical isolate from GVXN epidemiology study |
| upec116 | wt | O2 clinical isolate from GVXN epidemiology study |
| upec163 | wt | O25B clinical isolate from GVXN epidemiology study |
| upec177 | wt | O25B clinical isolate from GVXN epidemiology study |
| W3110 | F-, λ-, IN(rrnD-rrnE)1, rph-1 | K-12 laboratory strain used for production strain synthesis, CGSC#: 4474 |
| CCUG25 | wt | O2 isolate obtained from the culture collection, University of Göteborg (CCUG), Sweden (see Jansson, et al., (1987) Carbohydrate research 161, 273-27) |
| CCUG11309 | wt | O6 isolate from the CCUG, OPS with branching Glc (see Jann, et al., (1994) Carbohydrate research 263, 217-225) |
| CCUG11311 | wt | O6 isolate from the CCUG, OPS with branching GlcNAc (see Jann, et al., (1994) Carbohydrate research 263, 217-225) |

TABLE 14

Plasmids

| Name | Description | Remarks |
|---|---|---|
| pGVXN150 | pBR322 based expression plasmid of genetically detoxified EPA-his6 encoding 2 glycosylatiion sites | See Ihssen, et al., (2010) Microbial cell factories 9, 61 |
| pGVXN659 | pBR322 based expression plasmid of genetically detoxified EPA encoding 4 glycosylatiion sites | pGVXN150 was modified to encode additional N and C terminal glycosylation sites |
| pGVXN1076 | pGVXN659 ΔampR::kanR | |
| pGVXN579 | pMAL-p2X based vector for expression of MBP with a C terminal flexible linker, followed by 3 glycosylation site sequences and a myc epitope | Allows quick bioconjugates purification avoiding a histag |
| pGVXN114 | pEXT21 based expression plasmid for PglB with an HA tag | See Ihssen, et al., (2010) Microbial cell factories 9, 61 |
| pGVXN939 | pEXT21 based expression plasmid for PglB with an HA tag, codon optimized | |
| pGVXN970 | pEXT21 based expression plasmid for PglB without tag, codon optimized | |
| pGVXN539 | pACT3 based expression plasmid for genetically detoxified, codon usage optimized, histagged EPA encoding 2 glycosylation sites as pGVXN150 | replaced chloramphenicol resistance by kanamycin from pGVXN161 (oligos: #1399/#1400) |
| pGVXN161 | pKD4 | See Datsenko and Wanner, (2000) Proc Natl Acad Sci USA 97, 6640-6645 |
| pGVXN112 | pACT3 based expression plasmid for PglB with an HA tag | |

TABLE 15

Sequences

| Description | SEQUENCE | SEQ ID NO. |
|---|---|---|
| rmlB (upec138) | GTGAAGATACTTGTTACTGGTGGCGCAGGATTTATTG GTTCTGCTGTTGTTCGTCACATAATAAATAATACGCAA GATAGTGTTGTTAATGTCGATAAATTAACATACGCCG GAAACCTGGAATCACTTGCAGATGTTTCTGATTCTGA ACGCTATTTCTTTGAACATGCGGATATTTGTGATGCA GCTGCAATGGCACGGATTTTTGCTCAGCATCAGCCG GATGCAGTGATGCACCTGGCAGCTGAAAGCCATGTT GACCGTTCAATTACAGGCCCTGCGGCATTTATTGAAA CCAATATTGTGGGTACTTATGTCCTTTTAGAAGCGGC | 1 |

TABLE 15-continued

Sequences

| Description | SEQUENCE | SEQ ID NO. |
|---|---|---|
| | TCGGAATTATTGGTCTGGTCTGGATGATGAAAAGAAA<br>AAAAACTTCCGTTTTCATCATATTTCTACTGATGAGGT<br>GTATGGTGACTTACCCCATCCGGATGAAGTAAATAGC<br>AATGAAACGTTGCCGCTATTTACGGAAACGACAGCAT<br>ACGCGCCAAGTAGTCCATATTCTGCTTCTAAAGCTTCC<br>AGCGATCATTTGGTTCGCGCATGGAAACGTACTTATG<br>GTTTACCGACCATTGTGACTAATTGCTCGAACAACTAT<br>GGTCCTTATCATTTCCCGGAAAAGCTTATTCCACTGG<br>TTATTCTTAATTCACTGGAAGGTAAGGCATTACCTATT<br>TATGGCAAAGGAGATCAGATCCGCGACTGGTTGTAT<br>GTAGAGGATCATGCTCGAGCGTTATATACCGTCGTA<br>ACCGAAGGTAAAGCGGGCGAAACTTATAACATTGGT<br>GGACACAACGAAAAGAAAAACATCGACGTAGTGTTC<br>ACTATTTGTGATTTGTTGGATGAGATAGTCCCGAAAG<br>AGAAATCTTACCGCGAGCAAATTACTTATGTTACCGA<br>TCGTCCGGGACACGATCGCCGTTATGCGATTGATGCT<br>GAGAAGATTGGTCGCGAATTGGGATGGAAACCACAG<br>GAAACGTTTGAGAGTGGGATTCGTAAAACGGTGGA<br>ATGGTACCTGTCCAATACAAAATGGGTTGATAATG<br>TGAAAAGTGGTGCCTATCAATCGTGGATTGAACAG<br>AACTATGAGGGCCGCCAGTAA | |
| rmlD<br>(upec138) | ATGAATATCCTCCTTTTTGGCAAAACAGGGCAGGTA<br>GGTTGGGAACTACAGCGTGCTCTGGCACCTCTGGGT<br>AATTTGATTGCTCTTGATGTTCACTCCACTGATTACTG<br>TGGTGATTTTAGTAATCCTGAAGGTGTAGCTGAAACC<br>GTAAGAAGCATTCGGCCTGATATTATTGTCAACGCA<br>GCCGCTCACACCGCAGTAGACAAAGCAGAATCAGA<br>ACCGAAGTTTGCACAATTACTGAACGCGACGAGTGT<br>CGAAGCGATCGCGAAAGCAGCCAATGAAGTCGGCG<br>CCTGGGTTATTCACTACTCTACTGACTACGTATTTCC<br>GGGGACCGGTGAAATACCATGGCAGGAGGAGGATG<br>CAACCGCACCGCTAAATGTTTACGGTGAAACCAAGT<br>TAGCGGGAGAAAAAGCATTACAAGAGCATTGTGCG<br>AAGCACCTTATTTTCCGGACCAGCTGGGTCTATGCA<br>GGTAAAGGAAATAACTTCGCCAAAACAATGTTGCG<br>TCTGGCAAAAGAGCGTGAAGAATTAGCCGTTATTAA<br>TGATCAGTTTGGTGCGCCAACTGGCGCAGAGTTACT<br>GGCTGATTGTACGGCACATGCTATTCGTGTGGCACT<br>GAATAAACCGGAAGTCGCAGGCTTGTACCATCTGGT<br>AGCTAGTGGTACCACAACGTGGCACGATTATGCTG<br>CGCTGGTTTTTGAAGAGGCGCGCAAAGCAGGCATT<br>CCCCTTGCACTCAACAAGCTCAACGCAGTACCAAC<br>AACAGCCTATCCTACACCAGCTCGTCGTCCACATA<br>ACTCTCGCCTTAATACAGAAAAATTTCAGCAGAA<br>CTTTGCGCTTGTCTTGCCTGACTGGCAGGTTGGCG<br>TGAAACGAATGCTTAACGAATTATTTACGACTACA<br>GCAATTTAA | 2 |
| rmlA<br>(upec138) | ATGAAAACGCGTAAAGGTATTATTTTGGCGGGTGG<br>TTCTGGTACTCGTCTTTATCCTGTGACGATGGCCGTC<br>AGTAAACAGCTGTTACCGATTTATGATAAACCGAT<br>GATCTATTACCCGCTCTCTACACTGATGTTAGCGGG<br>TATTCGCGATATTCTGATTATCAGTACACCACAGGA<br>TACTCCTCGTTTTCAACAACTGCTGGGTGACGGGAG<br>CCAGTGGGGCCTGAATCTTCAGTACAAAGTGCAAC<br>CGAGTCCGGATGGTCTTGCGCAGGCGTTTATTATCG<br>GTGAAGAGTTTATTGGTGGTGATGATTGTGCTTTGG<br>TACTTGGTGATAATATCTTCTACGGCCACGACCTGC<br>CGAAGTTAATGGACGTAGCTGTTAACAAAGAAAGT<br>GGTGCAACGGTATTTGCCTATCACGTTAATGATCCT<br>GAACGTTATGGTGTCGTGGAGTTTGATAATAACGG<br>TACTGCAATTAGCCTGGAAGAAAAACCGCTGGAAC<br>CAAAAAGTAACTATGCGGTTACTGGGCTTTATTTCTA<br>TGACAATGACGTTGTGGAAATGGCGAAAAACCTTA<br>AGCCTTCTGCCCGAGGTGAACTGGAAATTACCGATA<br>TTAACCGTATTTATATGGAACAAGGACGTTTGTCTG<br>TCGCTATGATGGGCGTGGCTATGCATGGCTGGATA<br>CAGGGACGCATCAAAGTCTTATTGAAGCAAGCAAC<br>TTCATTGCCACCATTGAAGAGCGCCAGGGACTAAAG<br>GTTTCCTGTCCGGAAGAAATTGCTTATCGTAAAGGG<br>TTTATTGATGCTGAGCAGGTAAAAGTATTAGCCGAA<br>CCGTTGAAGAAAAATGCTTATGGTCAGTATCTGCTC<br>AAAATGATTAAAGGTTATTAA | 3 |

TABLE 15-continued

Sequences

| Description | SEQUENCE | SEQ ID NO. |
|---|---|---|
| rmlC (upec138) | ATGAACGTAATTAAAACTGAAATTCCTGATGTGCTG ATTTTTGAACCAAAAGTTTTTGGGGATGAACGTGGCT TCTTTTTTGAGAGTTTTAATCAGAGGATTTTTGAAGA AGCAGTAGGTCGTAAGGTTGAGTTTGTTCAGGATAA CCATTCTAAGTCCAGTAAAGGTGTTTTACGTGGTCTT CATTATCAGTTAGAACCTTATGCTCAAGGAAAACTGG TGCGCTGTGTTGTTGGCGAGGTTTTTGATGTTGCGGTT GATATTCGTAAATCGTCACCTACATTTGGGAAATGG GTTGGGGTGAATTTGTCTGCTGAGAATAAGCGTCAG TTGTGGATTCCTGAGGGATTTGCACATGGTTTTTTGG TGCTGAGTGATTTAGCAGAAGTTTTATATAAAACGA ATCAATATTATGCTCCATCACATGAAAAAAATATTAT ATGGAATGACCTCTTGCTTAATATTAAATGGCCGAGC ACAGCACTGATCACTCTGTCTGATAAGGATGCAAA TGGGGAAAGATTTGAACTAAGTGAGTTTTGA | 4 |
| wzx (upec138) | ATGTCTCTCTTAAAACATAGTATATGGAATGTTGCGG GCTACTTTATACCAACATTAATTGCAATTCCCGCCTTT GGATTAATTGCGAGGAAAATTGGTGTAGAACTATTTG GTTTGTATACGTTAGCAATGATTTTTATAGGGTATGCA AGTATATTTGATGCTGGGTTAACAAGAGCTGTTGTGCG TGAAATAGCATTACTAAAAAACAGAGTGGACGATTGT AATACGATAATAGTAACTTCTATTATCGCTGTGATATT TTTAGGGTTTATCGGAGGCGGGGGAGTGTTTCTGCTTA AAGGCGATATTATTGAACTGTTAAATATCTCACCAATA TATTACGCCGATTCGATAAAGTCTCTAGTATTATTATCA TCTCTGATACCTGTATTCTTAGTCACGCAAATACTATTA GCAGAGCTTGAGGGTCGGGAATATTTTGGGATTCTAAA TATACAAAAAAGTGTAGGGAATTCTTTAATTGCAGGGT TACCTGCATTATTTGTTTTAATTAATCAAACGCTTTTTC TGCAATTATTGGTGTAGCGATTGCAAGAGTTATATGCTT GTGGTTAAGCTACATTATGAGCAGGGAAAGAATAACTA TCGATATCTCATTTTTTTCAATAACTGTTTTAAAGCGGTT ATTTAGATATGGCGGGTGGGTAACTATAAGTAACATAA TATCTCCTATATTAGCGAGTATGGATAGATTTATTCTATC CCATATCCAGGGAGCATCAAAAATATCATTCTATACAGT CCCTAATGAGCTGGTAACTAGGCTTGGAATAGTTCCAGG CTCTCTTGGGAAAGCTGTTTTTCCAAAATTAAGT CATGCAAGGAATTTTACAGCGTCATATGCAGAGCAAA AAAAGCTTATATATTAATGACTGTCATTGTAATGCCTTT GGTTTTATTTGTATATTATTACGCAAAGTTTATTTTAACA TTGTGGATGGGGCTGAGTATGCAGGGATTTCGGTCGA AATATTACGGATTATGCTTATAGGGTATATTTTTAACTGT TATTCACAAATCTCTTTTGCCAACATACAGGCCTTTGGA AAAGCAAAATACACTGCATACATCCATATGATGGAATT TATTCCTTATTTGATAATGTTATATATAATTTCAAAGGAA TATGGGGTTATTGGTGTTGCGTGGTTATGGACAATTCGA GTAATAATTGATTTTTTGATGCTTTTATATATGAGTTATC GTTGTAATAATCTTATGAAAAAAGGGTAG | 5 |
| wekA (upec138) | ATGATATATATTGTGGTATTAAATTGGAATGGGGCTA TAGATACCATTAATTGTGTTAAAAGTTTAATGGATTT AAATGTTAGCGATTATAAAATTATCATTGTTGATAAC TGTTCTATGGATAACTCATATGATACTATAAAAGAAA ATCTTAATTCATTATATATTGCTGATAAAAGTATCATT GAGGTGAAGTATGAGGATAGAAATAAATATAAAACC TTAGAAAACGATAAAATCATATTAATACAATCTCCGC AAAATAATGGGTACGCAAGTGGTAATAATATTGGCAT AGAGTTCGCTCTTAATCAGGAGAATATGAAATACGTC TGGGTTCTGAATAATGATACTGAAGTGGATAAAGAGG CTTTAACTCATTTAATTAGTAAATGTGATTCAGATAAA AGTATAGGGATTTGCGGTTCTCGTTTAGTCTATTTTGCC GACAGAGAGATGCAGCAAGGACTAGGTGGGGTGCATA ACAAATGGTTATGCACTACAAAAAATTATGAAATGGG AAGATTAGTTTCCAAAAAATATGATGATGAAGTCATTA GTAATGATATAGATTATATAATTGGCGCATCGATGTTTT TCTCTAGAGAATGTTTGGAAACAGTTGGATTGATGAAT GAAGAATATTTTTTATACTATGAAGAGTTAGATATTTGC CTCAGAGCAAAAGCAAAGAACTTTAAATTAGGTATTTG CTCAGAAAGTTTGGTTTATCATAAAATAGGTGCAAGTA CTGATGGGGGAAAGAGCATGATGGCTGATCTTTGCTCA ATAAAAAAATAGGCTGGTCATTACAGAAAGGTTTTATCC CCAATATTATTGGACGGTATGGTTGTCACTTTTTGTTGTA GCATTTAACCGTGCTAGAAGAGGTGAGTTTAATAAGAT GAAAAGATGTTTGAATGTTATGTTTAACTTCAAACGAAA | 6 |

TABLE 15-continued

Sequences

| Description | SEQUENCE | SEQ ID NO. |
|---|---|---|
| | CAAAGGTAGCAAATGCCATTAG | |
| wekB (upec138) | ATGAAAGTGGCTTTTTTATCTGCTTATGATCCACTATCTA<br>CATCCAGTTGGTCTGGCACACCTTATTATATGCTAAAGG<br>CATTATCGAAGAGAAATATTTCCATTGAAATATTAGGAC<br>CGGTAAATAGCTATATGATATACATGTTAAAAGTATATA<br>AATTAATATTAAGGTGTTTCGGAAAAGAATATGATTATA<br>GTCATTCGAAGTTGCTTTCCAGGTATTACGGTAGAATATT<br>CGGTAGGAAATTAAAAAAAATTGATGGTTTGGATTTTATT<br>ATCGCACCTGCAGGTTCCTCACAAATTGCTTTTTTAAAAA<br>CAACCATACCAATAATATATCTATCGGATACAACATATGA<br>TCAATTAAAAAGCTATTATCCGAATTTAAATAAAAAAAC<br>AATTATAAATGATGAGGATGCAAGTTTAATCGAACGCAA<br>GGCTATTGAAAAAGCAACAGTAGTATCTTTCCCATCTAAA<br>TGGGCAATGGATTTTTGCAGGAATTATTACAGATTAGATT<br>TTGATAAATTAGTTGAAATACCATGGGGGGCTAATTT<br>ATTTGATGATATTCACTTTGCTAATAAAAATATAATTC<br>AAAAGAATAGTTATACTTGTCTTTTCTTGGGAGTTGAT<br>TGGGAAAGAAAAGGTGGGAAAACAGCCTTGAAAGCA<br>ATTGAATATGTAAGGCAGTTATATGGGATCGATGTTAG<br>ACTAAAAATTTGTGGATGTACTCCGAATCAAAAGATTT<br>TACCTACTTGGGTTGAATTAATTGATAAAGTAGATAAA<br>AATAACGTTGACGAATATCAGAAATTCATCGATGTGTT<br>ATCTAACGCTGATATACTTCTTTTACCAACCATTGCTGA<br>ATGTTATGGAATGGTATTTTGTGAAGCTGCTGCTTTTGG<br>ATTGCCTGTTGTCGCTACAGATACAGGTGGAGTCAGTT<br>CTATAGTTATCAACGAAAGGACGGGGATATTAATTAAA<br>GACCCGTTAGACTATAAGCACTTTGGAAATGCAATTCA<br>TAAAATAATTAGTTCCGTAGAGACTTATCAAAACTACTC<br>CCAAAACGCAAGAATTAGATATAATAATATATTGCATTG<br>GGACAATTGGGCTAAAAAGATAATTGAGATTATGTATG<br>AGCATAAGAATAGAAGAATCAAATAG | 7 |
| wzy (upec138) | ATGAGCATAAGAATAGAAGAATCAAATAGCACAAAAAG<br>AATTATATGTTTATTTATACTTTTTCTTGTTTTCCCTGATTT<br>TTTGTTTTATACATTAGGGGTTGATAATTTTAGCATTTCAA<br>CGATAATCTCAATTACATTGCTTTTTGTTTTTTAAGAGCT<br>AAAAATATTTGCAAAGATAATTTTCTAATAATAGTAGCG<br>TTATTCATATTGTTGTGTTTTAACTGTTTGTTAAGTATGCTA<br>TTTAATATTGAACAGGCTTTAACATTTAAAGTTGTACTTTC<br>AATATATAGCATCTTAATAATGGCATACGTCTCCTCTTGTT<br>ATGCACAGACGTTGTGGTTATGTTCTGAAGAAATACTTAA<br>GAGATCCGTCTTTTATTTGTTCGCATTTCTTTGCCTTATTGG<br>CATTATAAGTATTCTTTTACAGAAGACTGAGATTATACATG<br>ATAAAAGTATGATTCTTTTTCCTGAACCATCAGCATTTGCA<br>TTGGTTTTTATACCTATCTTTTCATTTTGTTTATACTATACAA<br>GAGGGGGGGGCTACTATTGCTCTATATATTATCTTTGGGT<br>ATTGCGTTAGGTATCCAGAATTTAACAATGTTGGTAGGCAT<br>TGTGATTAGTGTTTTTGTGATGAAAAAAATAACTATAAGGC<br>AAACTATTGTTATACTTTTGGGGGCATGGATTTTTTCCATGA<br>TATTAAGTGATTTAGACATTTCTTACTATACATCGCGGCTTG<br>ATTTTAAAAATACTACGAACCTATCAGTGCTTGTATATCTTT<br>CAGGAATTGAAAGAGCTTTCTTGAATTTTATTACAAGTTATG<br>GTCTTGGTATTGGTTTTCAACAAATTGGGAGTGAATGGGGAG<br>ATAGGAATATATCAACAATTTTAGCTGAACTTGATGCCCC<br>TATGTTAAATATATACGATGGCTCATTTATTTCTTCTAAGTT<br>AATATCTGAGTTTGGGGTTATTGGTGCATTAATGTGTATT<br>TTCTATTTTTTTTATTTTTCCCGATTTTATCTGCGTTTCAA<br>AAAAAGTAAGAGATATTCACCGCAGTATATTTAGCAT<br>ATAGCTTCTACATGTGTTTCTTCATCCCTCTTTTTATACG<br>TGGTGCTGGTTATATAAACCCCTATGTGTTTATGTTATTT<br>TCATCAATATTTTTGTGCAAATATCACGCTAAAAATATCT<br>TGATGAAATCTAATGTCCAGATAGCTATATAA | 8 |
| wbbJ (upec138) | ATGTGCATTAAAAAAAAACTTAAGTTAATTAAACGATA<br>TGGCCTTTATGGTGGTCTTAGGCTTCTTAAAGATATATTC<br>TTAACAAAATTTTATTTTGTTCAAATGTTAGGATTATTA<br>GATTTCCATGTTATATTAGAAAAGATGGAAGTGTTAGTTT<br>TGGAAAAGGTTTTACATCAGGTGTAGGATTACGAGTTGA<br>TGCATTTATGGATGCCGTAGTTTCCATTGGAGAAAATGTT<br>CAAATTAATGACTATGTTCACATCGCGGCTATTAATAATG<br>TCATTATTGGTAGAGATACATTAATAGCAAGTAAAGTATT<br>TATTAGTGATCATAATCATGGTATTTTTTCTAAATCCGATA<br>TCCATAGTTCACCAACTATTATTCCTTCGTCTAGGCCCCTT<br>GAATCTGCACCTGTGTATATTGGAGAGCGTGTGTGGATTG | 9 |

TABLE 15-continued

Sequences

| Description | SEQUENCE | SEQ ID NO. |
|---|---|---|
| | GCGAAAATGTGACAATATTACCAGGTGCGTGTATAGGTAA TGGTGTAGTTATTGGCGCAAACAGTGTTGTTCGTGGTGAG ATTCCTAATAATGTGATCATTGCTGGTGTTCCAGCTAAAA TTGTTAAAAAATATAACTATGAGCGTATGCAATGGGAAA GAATATAG | |
| wbbK (upec138) | ATGGGAAAGAATATAGTTGTAATATCGGCTGTTAATTTT ACAACCGGAGGCCCCTTTACCGTACTAAAAAATGTGCT TACAGCAACTAAAGATAGAGCCGAATGTAAATTTATTG CACTGGTTCATAGCTCTGCTGAACTAATGGAATTATTTC CGTGGGTTGAATTTATAGAGTATCCAGAAGTCAAGTCTT CGTGGGTTAAAAGATTATATTTCGAATATATAACTTGCAA TAGATTATCTAAGGTGATTAAGGCAACTCATTGGGTATG CTTACATGATATTACAGCAAATGTTAGTGTACCCTATAG ATTTGTTTATTGCCACAATCCTGCACCGTTCTATAAATAT TTAAGCTATCGAGATATTATAGGAGAACCTAAATTTTAT CTTTTTTATCTTTTTTATGGGCTTTTATACAATATCAATAT AAAAAAGAACACAGCAGTTTTTGTTCAGCAGCAGTGGCT AAAAAAAGAATTCGAAAAAAATATAAGTTAAAGAATG TTGTTGTTAGTCGCCCTGAAGATATTTGCCCTTTTGAAAG TGATGGTTTGGTAAGAAATAATAATAAAAAGGATGTGAG GATATTTTACCCAGCAGTGCCCCGTATATTTAAAAACTTT GAAGTTATCATACGTGCTGCACAAATATTACAAGATAAA AATATTCATTTTTATCTTACTTTTGATGGTACTGAAAA TAAGTATGCAAAAAGAATATATAAATTAGCTTCCGA ACTGAAAAATGTACATTTCCTCGGTTACCTTAATGCA ACCGAGATGGTTAACTTTTATCAAGATTCAGATATTA TTTGTTTCCCATCGAAACTAGAAACGTGGGGATTACC ATTATCAGAAGCTAAAACATACAAAAAATGGATATTT GCGGCAGACTTACCTTATGCTCATGAAGTTTTATATAA CTATTCAAAAACTAGATATTTTCCATTTGACGATGAG AAAAATACTTGTTCGCTACATATTAGAGTACACAAGTA AAAATATGCATGAAGATATAAAAAATAGTAGGGTGA ATTTTAATAATGATGCATTGACTGGTTTTGAACAGTTTA TTGAATATATCCTCAAGGGGAACTGA | 10 |
| wbbL (upec138) | ATGATTATGAATAATGATTATTTTCTCTTTCTTAACCCC GATGTATTCATAACCAGTGAAAGTTTGATTAATTATGT TGATTATATAATTAGTAATGATTATAAGTTTAGCACAT TATGTCTTTATCGAGATTTTACTAAAAGCAAACATGAT TATTCAATACGGAGTTTTCCAACTTTATATGATTTTCTTT GTTCTTTTTTATTGGGGGTGAATAAAAGTAAAATTAAG AAGGAAAATATACTTTCTGATACTGTAGTTGATTGGTG TGCTGGCTCATTTATGCTTATTCATGCTTTAAGTTTCTTA AATGTGAATGGTTTTGATCAAAAATATTTTATGTATTGT GAAGATATTGACCTTTGTATGCGTTTAAAATTAAGTGG AGTAGATCTTTACTATACTCCCCATTTTGATGCTATTCA TTATGCGCAGCATGAAAATAGAAGAATATTTACTAAAG CATTTCGATGGCATATAAGGAGTATTACGCGCTACATA TTACGGAAACCAATTCTTTCTTATAAAAACTATAGAAA AATTACATCCGAACTGGTAAAGTGA | 11 |
| E. coli rfb (upec138) gene cluster | GTGAAGATACTTGTTACTGGTGGCGCAGGATTATTGGTTCT GCTGTTGTTCGTCACATAATAAATAATACGCAAGATAGTGT TGTTAATGTCGATAAATTAACATACGCCGGAAACCTGGAAT CACTTGCAGATGTTTCTGATTCTGAACGCTATTTCTTTGAAC ATGCGGATATTTGTGATGCAGCTGCAATGGCACGGATTTTT GCTCAGCATCAGCCGGATGCAGTGATGCACCTGGCAGCTGA AGCCATGTTGACCGTTCAATTACAGGCCCTGCGGCATTTA TTGAAACCAATATTGTGGGTACTTATGTCCTTTTAGAAGCGG CTCGGAATTATTGGTCTGGTCTGGATGATGAAAAGAAAAAA AACTTCCGTTTTCATCATATTTCTACTGATGAGGTGTATGGT GACTTACCCCATCCGGATGAAGTAAATAGCAATGAAACGTT GCCGCTATTTACGGAAACGACAGCATACGCGCCAAGTAGTC CATATTCTGCTTCTAAAGCTTCCAGCGATCATTTGGTTCGCG CATGGAAACGTACTTATGGTTTACCGACCATTGTGACTAATT GCTCGAACAACTATGGTCCTTATCATTTCCCGGAAAAGCTT ATTCCACTGGTTATTCTTAATTCACTGGAAGGTAAGGCATTA CCTATTTATGGCAAAGGAGATCAGATCCGCGACTGGTTGTA TGTAGAGGATCATGCTCGAGCGTTATATACCGTCGTAACCGA AAGGTAAAGCGGGCGAAACTTATAACATTGGTGGACACAA CGAAAAGAAAACATCGACGTAGTGTTCACTATTTGTGATT TGTTGGATGAGATAGTCCCGAAAGAGAAATCTTACCGCGAG CAAATTACTTATGTTACCGATCGTCCGGGACACGATCGCCG TTATGCGATTGATGCTGAGAAGATTGGTCGCGAATTGGGAT | 12 |

TABLE 15-continued

Sequences

| Description | SEQUENCE | SEQ ID NO. |
|---|---|---|
| | GGAAACCACAGGAAACGTTTGAGAGTGGGATTCGTAAAAC | |
| | GGTGGAATGGTACCTGTCCAATACAAAATGGGTTGATAATG | |
| | TGAAAAGTGGTGCCTATCAATCGTGGATTGAACAGAACTAT | |
| | GAGGGCCGCCAGTAATGAATATCCTCCTTTTTGGCAAAACA | |
| | GGGCAGGTAGGTTGGGAACTACAGCGTGCTCTGGCACCTCT | |
| | GGGTAATTTGATTGCTCTTGATGTTCACTCCACTGATTACTG | |
| | TGGTGATTTTAGTAATCCTGAAGGTGTAGCTGAAACCGTAA | |
| | GAAGCATTCGGCCTGATATTATTGTCAACGCAGCCGCTCAC | |
| | ACCGCAGTAGACAAAGCAGAATCAGAACCGAAGTTTGCAC | |
| | AATTACTGAACGCGACGAGTGTCGAAGCGATCGCGAAAGC | |
| | AGCCAATGAAGTCGGCGCCTGGGTTATTCACTACTCTACTG | |
| | ACTACGTATTTCCGGGGACCGGTGAAATACCATGGCAGGAG | |
| | GAGGATGCAACCGCACCGCTAAATGTTTACGGTGAAACCAA | |
| | GTTAGCGGGAGAAAAGCATTACAAGAGCATTGTGCGAAG | |
| | CACCTTATTTTCCGGACCAGCTGGGTCTATGCAGGTAAAGG | |
| | AAATAACTTCGCCAAAACAATGTTGCGTCTGGCAAAAGAGC | |
| | GTGAAGAATTAGCCGTTATTAATGATCAGTTTGGTGCGCCA | |
| | ACTGGCGCAGAGTTACTGGCTGATTGTACGGCACATGCTAT | |
| | TCGTGTGGCACTGAATAAACCGGAAGTCGCAGGCTTGTACC | |
| | ATCTGGTAGCTAGTGGTACCACAACGTGGCACGATTATGCT | |
| | GCGCTGGTTTTTGAAGAGGCGCGCAAAGCAGGCATTCCCCT | |
| | TGCACTCAACAAGCTCAACGCAGTACCAACAACAGCCTATC | |
| | CTACACCAGCTCGTCGTCCACATAACTCTCGCCTTAATACAG | |
| | AAAAATTTCAGCAGAACTTTGCGCTTGTCTTGCCTGACTGGC | |
| | AGGTTGGCGTGAAACGAATGCTTAACGAATTATTTACGACT | |
| | ACAGCAATTTAATAGTTTTTGCATCTTGTTCGTAATGGTGGA | |
| | GCAAGATGTATTAAAAGGAATGATGAAATGAAAACGCGTA | |
| | AAGGTATTATTTTGGCGGGTGGTTCTGGTACTCGTCTTTATC | |
| | CTGTGACGATGGCCGTCAGTAAACAGCTGTTACCGATTTAT | |
| | GATAAACCGATGATCTATTACCCGCTCTCTACACTGATGTTA | |
| | GCGGGTATTCGCGATATTCTGATTATCAGTACACCACAGGA | |
| | TACTCCTCGTTTTCAACAACTGCTGGGTGACGGGAGCCAGT | |
| | GGGGCCTGAATCTTCAGTACAAAGTGCAACCGAGTCCGGAT | |
| | GGTCTTGCGCAGGCGTTTATTATCGGTGAAGAGTTTATTGGT | |
| | GGTGATGATTGTGCTTTGGTACTTGGTGATAATATCTTCTAC | |
| | GGCCACGACCTGCCGAAGTTAATGGACGTAGCTGTTAACAA | |
| | AGAAAGTGGTGCAACGGTATTTGCCTATCACGTTAATGATC | |
| | CTGAACGTTATGGTGTCGTGGAGTTTGATAATAACGGTACT | |
| | GCAATTAGCCTGGAAGAAAAACCGCTGGAACCAAAAAGTA | |
| | ACTATGCGGTTACTGGGCTTTATTTCTATGACAATGACGTTG | |
| | TGGAAATGGCGAAAAACCTTAAGCCTTCTGCCCGAGGTGAA | |
| | CTGGAAATTACCGATATTAACCGTATTTATATGGAACAAGG | |
| | ACGTTTGTCTGTCGCTATGATGGGGCGTGGCTATGCATGGCT | |
| | GGATACAGGGACGCATCAAAGTCTTATTGAAGCAAGCAACT | |
| | TCATTGCCACCATTGAAGAGCGCCAGGGACTAAAGGTTTCC | |
| | TGTCCGGAAGAAATTGCTTATCGTAAAGGGTTTATTGATGC | |
| | TGAGCAGGTAAAAGTATTAGCCGAACCGTTGAAGAAAAAT | |
| | GCTTATGGTCAGTATCTGCTCAAAATGATTAAAGGTTATTA | |
| | ATAAGATGAACGTAATTAAAACTGAAATTCCTGATGTGCTG | |
| | ATTTTTGAACCAAAAGTTTTTGGGGATGAACGTGGCTTCTTT | |
| | TTTGAGAGTTTTAATCAGAGGATTTTTGAAGAAGCAGTAGG | |
| | TCGTAAGGTTGAGTTTGTTCAGGATAACCATTCTAAGTCCA | |
| | GTAAAGGTGTTTTACGTGGTCTTCATTATCAGTTAGAACCTT | |
| | ATGCTCAAGGAAAACTGGTGCGCTGTGTTGTTGGCGAGGTT | |
| | TTTGATGTTGCGGTTGATATTCGTAAATCGTCACCTACATTT | |
| | GGGAAATGGGTTGGGGTGAATTTGTCTGCTGAGAATAAGCG | |
| | TCAGTTGTGGATTCCTGAGGGATTTGCACATGGTTTTTTGGT | |
| | GCTGAGTGATTTAGCAGAAGTTTTATATAAAACGAATCAAT | |
| | ATTATGCTCCATCACATGAAAAAAATATTATATGGAATGAC | |
| | CTCTTGCTTAATATTAAATGGCCGAGCACAGCACTGATCAC | |
| | TCTGTCTGATAAGGATGCAAATGGGAAAGATTTGAACTAA | |
| | GTGAGTTTTGAAATGTCTCTCTTAAAACATAGTATATGGAAT | |
| | GTTGCGGGCTACTTTATACCAACATTAATTGCAATTCCCGCC | |
| | TTTGGATTAATTGCGAGGAAATTGGTGTAGAACTATTTGG | |
| | TTTGTATACGTTAGCAATGATTTTTATAGGGTATGCAAGTAT | |
| | ATTTGATGCTGGGTTAACAAGAGCTGTTGTGCGTGAAATAG | |
| | CATTACTAAAAAACAGAGTGGACGATTGTAATACGATAATA | |
| | GTAACTTCTATTATCGCTGTGATATTTTAGGGTTTATCGGA | |
| | GGCGGGGAGTGTTTCTGCTTAAAGGCGATATTATTGAACT | |
| | GTTAAATATCTCACCAATATATTACGCCGATTCGATAAAGT | |
| | CTCTAGTATTATTATCATCTCTGATACCTGTATTCTTAGTCA | |
| | CGCAAATACTATTAGCAGAGCTTGAGGGTCGGGAATATTTT | |
| | GGGATTCTAAATATACAAAAAAGTGTAGGGAATTCTTTAAT | |
| | TGCAGGGTTACCTGCATTATTTGTTTTAATTAATCAAACGCT | |
| | TTTTTCTGCAATTATTGGTGTAGCGATTGCAAGAGTTATATG | |

TABLE 15-continued

Sequences

| Description | SEQUENCE | SEQ ID NO. |
|---|---|---|
| | CTTGTGGTTAAGCTACATTATGAGCAGGGAAAGAATAACTA | |
| | TCGATATCTCATTTTTTTCAATAACTGTTTTAAAGCGGTTAT | |
| | TTAGATATGGCGGGTGGGTAACTATAAGTAACATAATATCT | |
| | CCTATATTAGCGAGTATGGATAGATTTATTCTATCCCATATC | |
| | CAGGGAGCATCAAAAATATCATTCTATACAGTCCCTAATGA | |
| | GCTGGTAACTAGGCTTGGAATAGTTCCAGGCTCTCTTGGGA | |
| | AAGCTGTTTTTCCAAAATTAAGTCATGCAAGGAATTTTACA | |
| | GCGTCATATGCAGAGCAAAAAAAAGCTTATATATTAATGAC | |
| | TGTCATTGTAATGCCTTTGGTTTTATTTGTATATTATTACGCA | |
| | AAGTTTATTTTAACATTGTGGATGGGGGCTGAGTATGCAGG | |
| | GATTTCGGTCGAAATATTACGGATTATGCTTATAGGGTATAT | |
| | TTTTAACTGTTATTCACAAATCTCTTTTGCCAACATACAGGC | |
| | CTTTGGAAAAGCAAAATACACTGCATACATCCATATGATGG | |
| | AATTTATTCCTTATTTGATAATGTTATATATAATTTCAAAGG | |
| | AATATGGGGTTATTGGTGTTGCGTGGTTATGGACAATTCGA | |
| | GTAATAATTGATTTTTTGATGCTTTTATATATATGAGTTATCGT | |
| | TGTAATAATCTTATGAAAAAGGGTAGCCTGATGATATATA | |
| | TTGTGGTATTAAATTGGAATGGGGCTATAGATACCATTAAT | |
| | TGTGTTAAAAGTTTAATGGATTTAAATGTTAGCGATTATAA | |
| | AATTATCATTGTTGATAACTGTTCTATGGATAACTCATATGA | |
| | TACTATAAAAGAAAATCTTAATTCATTATATATTGCTGATAA | |
| | AAGTATCATTGAGGTGAAGTATGAGGATAGAAATAAATATA | |
| | AAACCTTAGAAAACGATAAAATCATATTAATACAATCTCCG | |
| | CAAAATAATGGGTACGCAAGTGGTAATAATATTGGCATAGA | |
| | GTTCGCTCTTAATCAGGAGAATATGAAATACGTCTGGGTTC | |
| | TGAATAATGATACTGAAGTGGATAAAGAGGCTTTAACTCAT | |
| | TTAATTAGTAAATGTGATTCAGATAAAAGTATAGGGATTTG | |
| | CGGTTCTCGTTTAGTCTATTTTGCCGACAGAGAGATGCAGC | |
| | AAGGACTAGGTGGGGTGCATAACAAATGGTTATGCACTACA | |
| | AAAAATTATGAAATGGGAAGATTAGTTTCCAAAAAATATGA | |
| | TGATGAAGTCATTAGTAATGATATAGATTATATAATTGGCG | |
| | CATCGATGTTTTCTCTAGAGAATGTTTGGAAACAGTTGGAT | |
| | TGATGAATGAAGAATATTTTTATCTATGAAGAGTTAGAT | |
| | ATTTGCCTCAGAGCAAAAGCAAAGAACTTTAAATTAGGTAT | |
| | TTGCTCAGAAAGTTTGGTTTATCATAAAATAGGTGCAAGTA | |
| | CTGATGGGGGAAAGAGCATGATGGCTGATCTTTGCTCAATA | |
| | AAAAATAGGCTGGTCATTACAGAAAGGTTTTATCCCCAATA | |
| | TTATTGGACGGTATGGTTGTCACTTTTTGTTGTAGCATTTAA | |
| | CCGTGCTAGAAGAGGTGAGTTTAATAAGATGAAAAGATGTT | |
| | TGAATGTTATGTTTAACTTCAAACGAAACAAAGGTAGCAAA | |
| | TGCCATTAGAATATGCACTTAATCATGGTGTTAATAAATCTA | |
| | TAGTTTGATATGTTATTAAAGGGTATTTAATGAAAGTGGCTT | |
| | TTTTATCTGCTTATGATCCACTATCTACATCCAGTTGGTCTG | |
| | GCACACCTTATTATATGCTAAAGGCATTATCGAAGAGAAAT | |
| | ATTTCCATTGAAATATTAGGACCGGTAAATAGCTATATGAT | |
| | ATACATGTTAAAAGTATATAAATTAATATTAAGGTGTTTCG | |
| | GAAAAGAATATGATTATAGTCATTCGAAGTTGCTTTCCAGG | |
| | TATTACGGTAGAATATTCGGTAGGAAATTAAAAAAAATTGA | |
| | TGGTTTGGATTTTATTATCGCACCTGCAGGTTCCTCACAAAT | |
| | TGCTTTTTTAAAAACAACCATACCAATAATATATCTATCGGA | |
| | TACAACATATGATCAATTAAAAAGCTATTATCCGAATTTAA | |
| | ATAAAAAAACAATTATAAATGATGAGGATGCAAGTTTAATC | |
| | GAACGCAAGGCTATTGAAAAAGCAACAGTAGTATCTTTCCC | |
| | ATCTAAATGGGCAATGGATTTTTGCAGGAATTATTACAGAT | |
| | TAGATTTTGATAAATTAGTTGAAATACCATGGGGGCTAAT | |
| | TTATTTGATGATATTCACTTTGCTAATAAAAATATAATTCAA | |
| | AAGAATAGTTATACTTGTCTTTTCTTGGGAGTTGATTGGGAA | |
| | AGAAAAGGTGGGAAAACAGCCTTGAAAGCAATTGAATATG | |
| | TAAGGCAGTTATATGGGATCGATGTTAGACTAAAAATTTGT | |
| | GGATGTACTCCGAATCAAAAGATTTTACCTACTTGGGTTGA | |
| | ATTAATTGATAAAGTAGATAAAAATAACGTTGACGAATATC | |
| | AGAAATTCATCGATGTGTTATCTAACGCTGATATACTTCTTT | |
| | TACCAACCATTGCTGAATGTTATGGAATGGTATTTTGTGAA | |
| | GCTGCTGCTTTTGGATTGCCTGTTGTCGCTACAGATACAGGT | |
| | GGAGTCAGTTCTATAGTTATCAACGAAAGGACGGGGATATT | |
| | AATTAAAGACCCGTTAGACTATAAGCACTTTGGAAATGCAA | |
| | TTCATAAAATAATTAGTTCCGTAGAGACTTATCAAAACTAC | |
| | TCCCAAAACGCAAGAATTAGATATAATAATATATTGCATTG | |
| | GGACAATTGGGCTAAAAAGATAATTGAGATTATGTATGAGC | |
| | ATAAGAATAGAAGAATCAAATAGCACAAAAAGAATTATAT | |
| | GTTTATTTATACTTTTTCTTGTTTTCCCTGATTTTTTGTTTTAT | |
| | ACATTAGGGGTTGATAATTTTAGCATTTCAACGATAATCTCA | |
| | ATTACATTGCTTTTTGTTTTTTAAGAGCTAAAAATATTTGC | |
| | AAAGATAATTTTCTAATAATAGTAGCGTTATTCATATTGTTG | |
| | TGTTTTAACTGTTTGTTAAGTATGCTATTTAATATTGAACAG | |

TABLE 15-continued

Sequences

| Description | SEQUENCE | SEQ ID NO. |
|---|---|---|
| | GCTTTAACATTTAAAGTTGTACTTTCAATATATAGCATCTTA | |
| | ATAATGGCATACGTCTCCTCTTGTTATGCACAGACGTTGTGG | |
| | TTATGTTCTGAAGAAATACTTAAGAGATCCGTCTTTTATTTG | |
| | TTCGCATTTCTTTGCCTTATTGGCATTATAAGTATTCTTTTAC | |
| | AGAAGACTGAGATTATACATGATAAAAGTATGATTCTTTTT | |
| | CCTGAACCATCAGCATTTGCATTGGTTTTTATACCTATCTTT | |
| | TCATTTTGTTTATACTATACAAGAGGGGGGGGGCTACTATT | |
| | GCTCTATATATTATCTTTGGGTATTGCGTTAGGTATCCAGAA | |
| | TTTAACAATGTTGGTAGGCATTGTGATTAGTGTTTTTGTGAT | |
| | GAAAAAAATAACTATAAGGCAAACTATTGTTATACTTTTGG | |
| | GGGCATGGATTTTTTCCATGATATTAAGTGATTTAGACATTT | |
| | CTTACTATACATCGCGGCTTGATTTTAAAAATACTACGAACC | |
| | TATCAGTGCTTGTATATCTTTCAGGAATTGAAAGAGCTTTCT | |
| | TGAATTTTATTACAAGTTATGGTCTTGGTATTGGTTTTCAAC | |
| | AAATGGGAGTGAATGGGGAGATAGGAATATATCAACAAAT | |
| | TTTAGCTGAACTTGATGCCCCTATGTTAAATATATACGATGG | |
| | CTCATTTATTTCTTCTAAGTTAATATCTGAGTTTGGGGTTATT | |
| | GGTGCATTAATGTGTATTTTCTATTTTTTTATTTTTCCCGAT | |
| | TTTATCTGCGTTTCAAAAAAAGTAAGAGATATTCACCGCAG | |
| | TATATTTTAGCATATAGCTTCTACATGTGTTTCTTCATCCCTC | |
| | TTTTTATACGTGGTGCTGGTTATATAAACCCCTATGTGTTTA | |
| | TGTTATTTTCATCAATATTTTTGTGCAAATATCACGCTAAAA | |
| | ATATCTTGATGAAATCTAATGTCCAGATAGCTATATAATAG | |
| | TAGATTATATTATCATTATCACGTAAATTACATATTAATAGC | |
| | ATATATGATAACTAGGACATAAATAATGTGCATTAAAAAAA | |
| | AACTTAAGTTAATTAAACGATATGGCCTTTATGGTGGTCTTA | |
| | GGCTTCTTAAAGATATATTCTTAACAAAATTTTTATTTTGTT | |
| | CAAATGTTAGGATTATTAGATTTCCATGTTATATTAGAAAA | |
| | GATGAAGTGTTAGTTTTGGAAAAGGTTTTACATCAGGTGT | |
| | AGGATTACGAGTTGATGCATTTATGGATGCCGTAGTTTCCAT | |
| | TGGAGAAAATGTTCAAATTAATGACTATGTTCACATCGCGG | |
| | CTATTAATAATGTCATTATTGGTAGAGATACATTAATAGCA | |
| | AGTAAAGTATTTATTAGTGATCATAATCATGGTATTTTTTCT | |
| | AAATCCGATATCCATAGTTCACCAACTATTATTCCTTCGTCT | |
| | AGGCCCCTTGAATCTGCACCTGTGTATATTGGAGAGCGTGT | |
| | GTGGATTGGCGAAAATGTGACAATATTACCAGGTGCGTGTA | |
| | TAGGTAATGGTGTAGTTATTGGCGCAAACAGTGTTGTTCGT | |
| | GGTGAGATTCCTAATAATGTGATCATTGCTGGTGTTCCAGCT | |
| | AAAATTGTTAAAAAATATAACTATGAGCGTATGCAATGGGA | |
| | AAGAATATAGTTGTAATATCGGCTGTTAATTTTACAACCGG | |
| | AGGCCCCTTTACCGTACTAAAAAATGTGCTTACAGCAACTA | |
| | AAGATAGAGCCGAATGTAAATTTATTGCACTGGTTCATAGC | |
| | TCTGCTGAACTAATGGAATTATTTCCGTGGGTTGAATTTATA | |
| | GAGTATCCAGAAGTCAAGTCTTCGTGGGTTAAAAGATTATA | |
| | TTTCGAATATATAACTTGCAATAGATTATCTAAGGTGATTAA | |
| | GGCAACTCATTGGGTATGCTTACATGATATTACAGCAAATG | |
| | TTAGTGTACCCTATAGATTTGTTTATTGCCACAATCCTGCAC | |
| | CGTTCTATAAATATTTAAGCTATCGAGATATTATAGGAGAA | |
| | CCTAAATTTTATCTTTTTTATCTTTTTTATGGGCTTTTATACA | |
| | ATATCAATATAAAAAGAACACAGCAGTTTTTGTTCAGCAG | |
| | CAGTGGCTAAAAAAGAATTCGAAAAAAAATATAAGTTAA | |
| | AGAATGTTGTTGTTAGTCGCCCTGAAGATATTTGCCCTTTTG | |
| | AAAGTGATGGTTTGGTAAGAAATAATAATAAAAAGGATGT | |
| | GAGGATATTTTACCCAGCAGTGCCCCGTATATTTAAAAACT | |
| | TTGAAGTTATCATACGTGCTGCACAAATATTACAAGATAAA | |
| | AATATTCATTTTTATCTTACTTTTGATGGTACTGAAAATAAG | |
| | TATGCAAAAAGAATATATAAATTAGCTTCCGAACTGAAAAA | |
| | TGTACATTTCCTCGGTTACCTTAATGCAACCGAGATGGTTAA | |
| | CTTTTATCAAGATTCAGATATTATTTGTTTCCCATCGAAACT | |
| | AGAAACGTGGGATTACCATTATCAGAAGCTAAAACATACA | |
| | AAAAATGGATATTTGCGGCAGACTTACCTTATGCTCATGAA | |
| | GTTTTATATAACTATTCAAAAACTAGATATTTTCCATTTGAC | |
| | GATGAGAAAATACTTGTTCGCTACATATTAGAGTACACAAG | |
| | TAAAAATATGCATGAAGATATAAAAAATAGTAGGGTGAATT | |
| | TTAATAATGATGCATTGACTGGTTTTGAACAGTTTATTGAAT | |
| | ATATCCTCAAGGGGAACTGACGTGGTTTATATTATAATCGTT | |
| | TCACATGGCCATGATGACTATATAGAAAATCTTTTATTAAAT | |
| | TTAAAGTTGCCCTCTGGAAGATTTAAAATAATAGTTCGTGA | |
| | TAACAAAAGTTCAATGGTTTTAAAAAAAACATGCGAAAAA | |
| | AATTGCGTAACCTATTTGCATGGAGGGCAATATGGATTTGG | |
| | ACATAATAATAACATAGCAGTGTCATATATAATTAATAACT | |
| | TCATGATTATGAATAATGATTATTTTCTCTTTCTTAACCCCG | |
| | ATGTATTCATAACCAGTGAAAGTTTGATTAATTATGTTGATT | |
| | ATATAATTAGTAATGATTATAAGTTTAGCACATTATGTCTTT | |
| | ATCGAGATTTTACTAAAAGCAAACATGATTATTCAATACGG | |

TABLE 15-continued

Sequences

| Description | SEQUENCE | SEQ ID NO. |
|---|---|---|
| | AGTTTTCCAACTTTATATGATTTTCTTTGTTCTTTTTTATTGG GGGTGAATAAAAGTAAAATTAAGAAGGAAAATATACTTTCT GATACTGTAGTTGATTGGTGTGCTGGCTCATTTATGCTTATT CATGCTTTAAGTTTCTTAAATGTGAATGGTTTTGATCAAAAA TATTTTATGTATTGTGAAGATATTGACCTTTGTATGCGTTTA AAATTAAGTGGAGTAGATCTTTACTATACTCCCCATTTTGAT GCTATTCATTATGCGCAGCATGAAAATAGAAGAATATTTAC TAAAGCATTTCGATGGCATATAAGGAGTATTACGCGCTACA TATTACGGAAACCAATTCTTTCTTATAAAAACTATAGAAAA ATTACATCCGAACTGGTAAAGTGA | |
| Detoxified EPA protein comprising 4 optimized N-glycosylation sequences | GSGGGDQNATGSGGGKLAEEAFDLWNECAKACVLDLKDGVR SSRMSVDPAIADTNGQGVLHYSMVLEGGNDALKLAIDNALSIT SDGLTIRLEGGVEPNKPVRYSYTRQARGSWSLNWLVPIGHEKP SNIKVFIHELNAGNQLSHMSPIYTIEMGDELLAKLARDATFFVR AHESNEMQPTLAISHAGVSVVMAQAQPRREKRWSEWASGKV LCLLDPLDGVYNYLAQQRCNLDDTWEGKIYRVLAGNPAKHD LDIKDNNNSTPTVISHRLHFPEGGSLAALTAHQACHLPLEAFTR HRQPRGWEQLEQCGYPVQRLVALYLAARLSWNQVDQVIRNA LASPGSGGDLGEAIREQPEQARLALTLAAAESERFVRQGTGND EAGAASADVVSLTCPVAKDQNRTKGECAGPADSGDALLERN YPTGAEFLGDGGDVSFSTRGTQNWTVERLLQAHRQLEERGYV FVGYHGTFLEAAQSIVFGGVRARSQDLDAIWRGFYIAGDPALA YGYAQDQEPDARGRIRNGALLRVYVPRWSLPGFYRTGLTLAA PEAAGEVERLIGHPLPLRLDAITGPEEEGGRVTILGWPLAERTV VIPSAIPTDPRNVGGDLDPSSIPDKEQAISALPDYASQPGKPPRE DLKLGSGGGDQNAT | 13 |
| N-glycosylation consensus sequence | Asn-X-Ser(Thr), wherein X can be any amino acid except Pro | 14 |
| N-glycosylation consensus sequence | Asp(Glu)-X-Asn-Z-Ser(Thr), wherein X and Z are independently selected from any natural amino acid except Pro | 15 |

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

7. EMBODIMENTS

Embodiments 1

1. A prokaryotic host cell comprising:
   a. rfb(upec138) gene cluster (SEQ ID NO:12), rfb(upec163) gene cluster, or rfb(upec177) gene cluster;
   b. a nucleotide sequence encoding an oligosaccharyl transferase; and
   c. a nucleotide sequence encoding a carrier protein comprising a consensus sequence Asn-X-Ser(Thr), wherein X can be any amino acid except Pro (SEQ ID NO:14).
2. A prokaryotic host cell comprising:
   a. rmlB, rmlD, rmlA, rmlC, wzx, wekA, wekB, wzy, wbbJ, wbbK, and wbbL;
   b. a nucleotide sequence encoding an oligosaccharyl transferase;
   c. a nucleotide sequence encoding a carrier protein comprising a consensus sequence Asn-X-Ser(Thr), wherein X can be any amino acid except Pro (SEQ ID NO:14).
3. A prokaryotic host cell comprising:
   a. a nucleotide sequence encoding:
      i. dTDP-Glucose 4,6-dehydratase;
      ii. dTDP-6-Deoxy-D-glucose 3,5-epimerase;
      iii. Glucose-1-phosphate thymidylyltransferase;
      iv. dTDP-4-dehydrorhamnose 3,5-epimerase;
      v. O antigen flippase;
      vi. dTDP-Rha:Glc-Rha(Ac)-GlcNAc-UPP α-1,3-rhamnosyltransferase;
      vii. UDP-Glc:Glc-Rha(Ac)-GlcNAc-UPP β-1,6-glucosyltransferase;
      viii. O antigen polymerase;
      ix. O-acetyl transferase;
      x. UDP-Glc:Rha-GlcNAc-UPP α-1,3-glucosyltransferase and
      xi. dTDP-Rha: GlcNAc-UPP α-1,3-rhamnosyltransferase;
   b. a nucleotide sequence encoding an oligosaccharyl transferase;
   c. a nucleotide sequence encoding a carrier protein comprising a consensus sequence Asn-X-Ser(Thr), wherein X can be any amino acid except Pro (SEQ ID NO:14).

4. The host cell of claim 3 wherein:
a. the dTDP-Glucose 4,6-dehydratase comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a dTDP-Glucose 4,6-dehydratase encoded by SEQ ID NO:1;
b. the dTDP-6-Deoxy-D-glucose 3,5-epimerase comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a dTDP-6-Deoxy-D-glucose 3,5-epimerase encoded by SEQ ID NO:2;
c. the Glucose-1-phosphate thymidylyltransferase comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a Glucose-1-phosphate thymidylyltransferase encoded by SEQ ID NO:3;
d. the dTDP-4-dehydrorhamnose 3,5-epimerase comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a dTDP-4-dehydrorhamnose 3,5-epimerase encoded by SEQ ID NO:4;
e. the O antigen flippase comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an O antigen flippase encoded by SEQ ID NO:5;
f. the rhamnosyl transferase of (xi) comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a rhamnosyl transferase encoded by SEQ ID NO: 6;
g. the glucosyltransferase of (xii) comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a glucosyltransferase encoded by SEQ ID NO:7;
h. the O antigen polymerase comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an O antigen polymerase encoded by SEQ ID NO:8;
i. the O-acetyl transferase comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an O-acetyl transferase encoded by SEQ ID NO: 9;
j. the glucosyltransferase of (x) comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a glucosyltransferase encoded by SEQ ID NO:10: and
k. the rhamnosyltransferase of (xi) comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a rhamnosyltransferase encoded by SEQ ID NO:11.

5. The host cell of any one of claims 1 to 4, wherein the host cell is *Escherichia coli*.

6. The host cell of claim 5 wherein at least one of waaL gene, gtrA gene, gtrB gene, gtrS gene, and rfb cluster is deleted or functionally inactivated from the host cell's genome.

7. The host cell of any one of claims 1 to 6, wherein the carrier protein is selected from the group consisting of detoxified Exotoxin A of *P. aeruginosa* (EPA), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, and *C. jejuni* natural glycoproteins.

8. The host cell of any one of claims 1 to 7, wherein the carrier protein comprises an optimized N-glycosylation consensus sequence, Asp(Glu)-X-Asn-Z-Ser(Thr), wherein X and Z are independently selected from any natural amino acid except Pro (SEQ ID NO:15).

9. The host cell of any one of claims 1 to 8, wherein the carrier protein comprises one or more recombinantly introduced consensus sequences.

10. The host cell of any one of claims 1 to 9, wherein the carrier protein comprises a signal sequence for targeting the carrier protein into the periplasmic space of the host cell.

11. The host cell of claim 10 wherein the signal sequence is selected from the group consisting of the signal sequence from *E. coli* DsbA, *E. coli* outer membrane porin A (OmpA), *E. coli* maltose binding protein (MalE), *Erwinia carotovorans* pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI).

12. A method of making an N-glycosylated carrier protein, said method comprising:
a. culturing the host cell of any one of claims 1 to 11; and
b. purifying the N-glycosylated carrier protein.

13. An N-glycosylated carrier protein produced by the method of claim 12.

14. The N-glycosylated carrier protein of claim 13 comprising a compound of Formula O25B:

D—Glc
↓
─[→ D—Glc ⟶ L—Rha2Ac ⟶ D—GlcNAc ─]$_n$→
↑
L—Rha wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

15. The N-glycosylated carrier protein of claim 13 comprising a compound of Formula O25B':

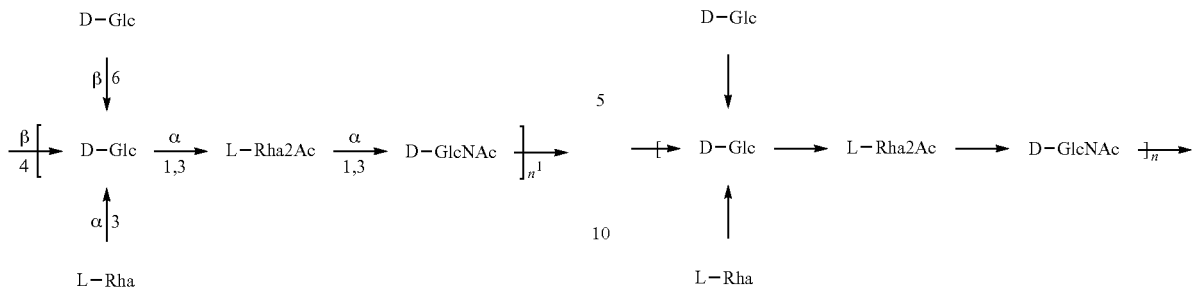

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

16. An isolated O antigen from an O25B strain such as upec138, upec163, or upec177.

17. A carrier protein N-linked to the O antigen of claim 15.

18. A population of isolated macromolecule comprising a structure of Formula O25B:

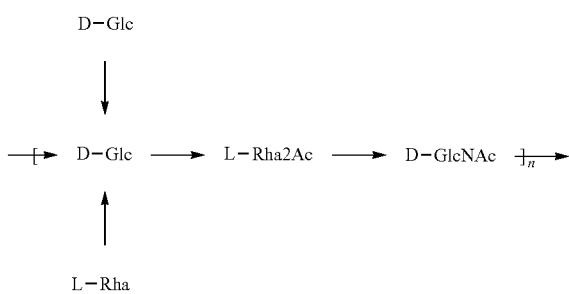

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

19. A population of isolated macromolecule comprising a structure of Formula O25B':

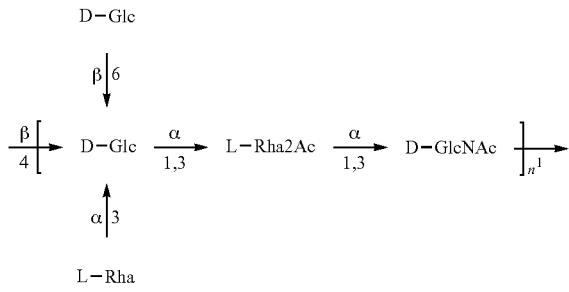

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

20. A pharmaceutical composition comprising a macromolecule comprising a structure of Formula O25B:

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

21. A pharmaceutical composition comprising a macromolecule comprising a structure of Formula O25B':

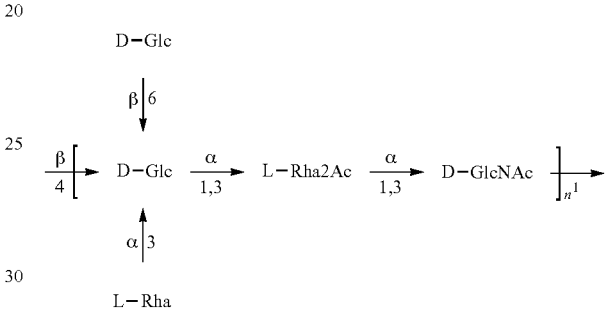

wherein n is an integer between 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20.

22. The pharmaceutical composition of claim 20 wherein the structure of Formula O25B is covalently bound to an Asn residue in a carrier protein.

23. The pharmaceutical composition of claim 21 wherein the structure of Formula O25B' is covalently bound to an Asn residue in a carrier protein.

24. The pharmaceutical composition of claim 20 or 21 wherein the Asn residue is positioned in a consensus sequence Asn-X-Ser(Thr), wherein X can be any amino acid except Pro (SEQ ID NO:14).

25. The prokaryotic host cell of any one of claims 1-11, wherein said oligosaccharyl transferase is heterologous to the host cell.

26. The prokaryotic host cell of 1-11, wherein said oligosaccharyl transferase is the C. Jejuni oligosaccharyl transferase, pglB.

27. The prokaryotic host cell of any one of claims 1-11, wherein said carrier protein is heterologous to the host cell.

28. The prokaryotic host cell of any one of claim 1-11, 25, 26, or 27, wherein said carrier protein is not an E. coli protein.

29. A method for generating an oligosaccharide comprising an L-Rha(2Ac), comprising incubating a saccharide or oligosaccharide with a rhamnosyl transferase comprising SEQ ID NO:11, wherein the saccharide or oligosaccharide comprises a terminal D-GlcNAc.

30. The method of claim 29, wherein the L-Rha(2Ac) and D-GlcNAc are linked via an alpha 1, 3 linkage.

31. The method of claim 29, wherein said incubation occurs in vitro.

32. The method of claim 29, wherein said oligosaccharide is generated in a host cell that recombinantly expresses a rhamnosyl transferase comprising SEQ ID NO:11.

Embodiments 2

1. A composition comprising (i) an O25B bioconjugate, comprising an *E. coli* O25B antigen covalently bound to an Asn residue of a carrier protein, (ii) an O1A bioconjugate, comprising an *E. coli* O1A antigen covalently bound to an Asn residue of a carrier protein, (iii) an O2 bioconjugate, comprising an *E. coli* O2 antigen covalently bound to an Asn residue of a carrier protein, and (iv) an O6 bioconjugate, comprising an *E. coli* O6 antigen covalently bound to an Asn residue of a carrier protein.

2. The composition of claim 1, wherein the O25B antigen, O1A antigen, O6 antigen, and O2 antigen comprise the following formulas, respectively:

a.

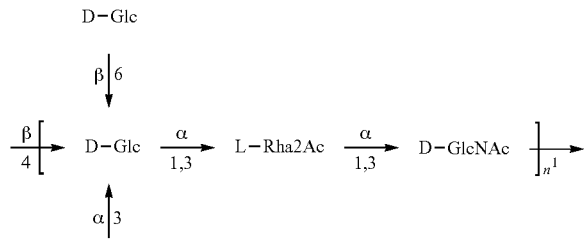

Formula O25B′ b.

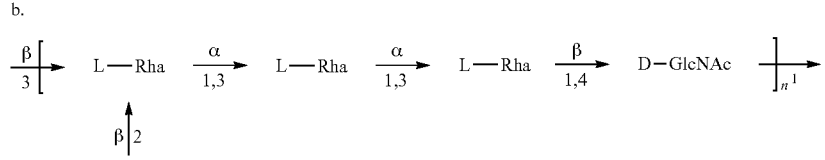

Formula O1A′ c.

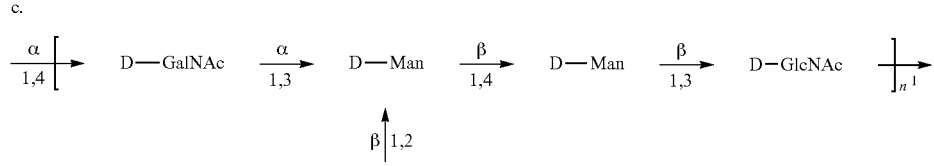

Formula O6Glc′ d.

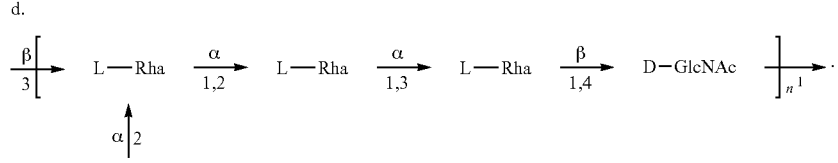

Formula O2′

3. The composition of claim 1 or 2, wherein the carrier protein is selected from the group consisting of detoxified Exotoxin A of *P. aeruginosa* (EPA), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, and *C. jejuni* natural glycoproteins.

4. The composition of claim 3, wherein the carrier protein is detoxified EPA, CRM197, or MBP.

5. The composition of any one of claims 1-4, wherein the Asn residue of the carrier protein is positioned in the consensus sequence Asp(Glu)-X-Asn-Z-Ser(Thr), wherein X and Z are independently selected from any natural amino acid except Pro (SEQ ID NO:15).

6. A method for treating an infection of a subject with extra-intestinal pathogenic *Escherichia coli*, wherein the method comprises administering to the subject an effective amount of the composition of any one of claims 1-5.

7. A method for preventing an infection of a subject with extra-intestinal pathogenic *Escherichia coli*, wherein the method comprises administering to the subject an effective amount of the composition of any one of claims 1-5.

8. A method for inducing an immune response in a subject against extra-intestinal pathogenic *Escherichia coli*, wherein the method comprises administering to the subject an effective amount of the composition of any one of claims 1-5.

9. A method for inducing the production of opsonophagocytic antibodies in a subject that are specific to extra-intestinal pathogenic *Escherichia coli*, wherein the method comprises administering to the subject an effective amount of the composition of any one of claims 1-5.

10. The method of claim 6, 8, or 9, wherein the subject has been diagnosed with a urinary tract infection.

11. The method of claim 7, 8, or 9, wherein the subject is at risk of developing a urinary tract infection.

12. The method of claim 6, 8, or 9, wherein the subject has been diagnosed with bacteremia.

13. The method of claim 7, 8, or 9, wherein the subject is at risk of developing bacteremia.

14. The method of claim 6, 8, or 9, wherein the subject has been diagnosed with sepsis.

15. The method of claim 7, 8, or 9, wherein the subject is at risk of developing sepsis.

16. The method of any one of claims 6-16, wherein the subject is a human.

What is claimed is:

1. A composition comprising a bioconjugate of an *E. coli* O25B antigen covalently coupled to a carrier protein, wherein the *E. coli* O25B antigen comprises the structure of Formula O25B':

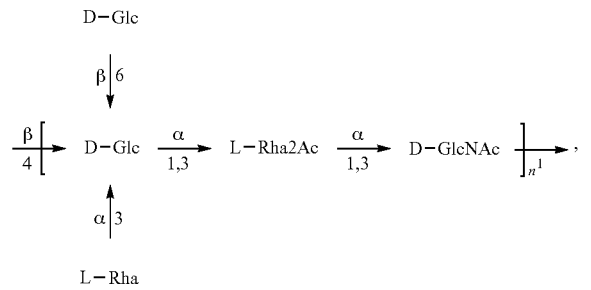

wherein n is an integer of 1 to 30.

2. The composition of claim 1, wherein the *E. coli* O25B antigen is covalently bound to an Asn residue in the carrier protein.

3. The composition of claim 1, wherein the carrier protein is selected from the group consisting of detoxified Exotoxin A of *P. aeruginosa* (EPA), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, and *C. jejuni* natural glycoproteins.

4. The composition of claim 3, wherein the carrier protein is detoxified EPA.

5. The composition of claim 4, wherein the O25B antigen is covalently bound to an Asn residue in the detoxified EPA, and the Asn residue of the detoxified EPA is positioned in the consensus sequence Asp(Glu)-X-Asn-Z-Ser(Thr), wherein X and Z are independently selected from any natural amino acid except Pro (SEQ ID NO: 15).

6. A method for (i) vaccinating a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition of claim 1.

7. The method of claim 6, wherein the subject is at risk of developing a urinary tract infection, bacteremia, or sepsis.

8. A method for (i) vaccinating a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition of claim 5.

9. The method of claim 8, wherein the subject is at risk of developing a urinary tract infection, bacteremia, or sepsis.

10. A recombinant prokaryotic host cell for producing a bioconjugate of an *E. coli* O25B antigen covalently coupled to a carrier protein, comprising:

(a) a nucleotide sequence comprising an rfb gene cluster encoding the *E. coli* O25B antigen, wherein the rfb gene cluster encodes:
  i. dTDP-Glucose 4,6-dehydratase;
  ii. dTDP-6-Deoxy-D-glucose 3,5-epimerase;
  iii. Glucose-1-phosphate thymidylyltransferase;
  iv. dTDP-4-dehydrorhamnose 3,5-epimerase;
  v. O antigen flippase;
  vi. dTDP-Rha:Glc-Rha(Ac)-GlcNAc-UPP α-1,3-rhamnosyltransferase;
  vii. UDP-Glc:Glc-Rha(Ac)-GlcNAc-UPP β-1,6-glucosyltransferase;
  viii. O antigen polymerase;
  ix. O-acetyl transferase;
  x. UDP-Glc:Rha-GlcNAc-UPP α-1,3-glucosyltransferase; and
  xi. dTDP-Rha: GlcNAc-UPP α-1,3-rhamnosyltransferase;

(b) a nucleotide sequence encoding an oligosaccharyl transferase; and (c) a nucleotide sequence encoding the carrier protein, wherein the carrier protein comprises a consensus sequence Asn-X-Ser(Thr), and X is any natural amino acid except Pro (SEQ ID NO: 14).

11. The recombinant prokaryotic host cell of claim 10, wherein the nucleotide sequence of (c) encodes the carrier protein comprising a consensus sequence Asp(Glu)-X-Asn-Z-Ser(Thr), wherein X and Z are independently selected from any natural amino acid except Pro (SEQ ID NO: 15).

12. The recombinant prokaryotic host cell of claim 10, wherein the nucleotide sequence of (a) comprises genes of rmlB, rmlD, rmlA, rmlC, wxz, wekA, wekB, wzy, wbbJ, wbbK, and wbbL.

13. The recombinant prokaryotic host cell of claim 10, wherein the nucleotide sequence of (a) comprises the rfb gene cluster having the nucleotide sequence of SEQ ID NO: 12.

14. The recombinant prokaryotic host cell of claim 10, wherein at least one of the waaL gene, gtrA gene, gtrB gene, gtrS gene, or rib cluster is deleted from or functionally inactivated in the genome of the prokaryotic host cell.

15. The recombinant prokaryotic host cell of claim 10, wherein the carrier protein is selected from the group consisting of detoxified Exotoxin A of *P. aeruginosa* (EPA), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, and *C. jejuni* natural glycoproteins.

16. The recombinant prokaryotic host cell of claim 10, wherein said host cell is an *E. coli* host cell.

17. A method of making the bioconjugate of the *E. coli* O25B antigen covalently coupled to the carrier protein, the method comprising:
(a) culturing the recombinant prokaryotic host cell of claim 10 under conditions for production of the bioconjugate; and
(b) purifying the bioconjugate.

18. A bioconjugate of an *E. coli* O25B antigen covalently coupled to a carrier protein,
wherein the bioconjugate is produced by a method comprising:
(a) culturing a recombinant prokaryotic host cell under conditions for production of the bioconjugate, the recombinant prokaryotic host cell comprising:
i. a nucleotide sequence comprising an rib gene cluster encoding the *E. coli* O25B antigen, wherein the rib gene cluster encodes:
a. dTDP-Glucose 4,6-dehydratase;
b. dTDP-6-Deoxy-D-glucose 3,5-epimerase;
c. Glucose-1-phosphate thymidylyltransferase;
d. dTDP-4-dehydrorhamnose 3,5-epimerase;
e. O antigen flippase;
f. dTDP-Rha:Glc-Rha(Ac)-GlcNAc-UPP α-1,3-rhamnosyltransferase;
g. UDP-Glc:Glc-Rha(Ac)-GlcNAc-UPP β-1,6-glucosyltransferase;
h. O antigen polymerase;
i. O-acetyl transferase;
j. UDP-Glc:Rha-GlcNAc-UPP α-1,3-glucosyltransferase; and
k. dTDP-Rha: GlcNAc-UPP α-1,3-rhamnosyltransferase;
ii. a nucleotide sequence encoding an oligosaccharyl transferase; and
iii. a nucleotide sequence encoding the carrier protein, wherein the carrier protein comprises a consensus sequence Asn-X-Ser(Thr), and X is any natural amino acid except Pro (SEQ ID NO: 14); and
(b) purifying the bioconjugate.

19. A composition comprising the bioconjugate of claim 18.

20. A method for (i) vaccinating a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition of claim 19.

* * * * *

SEQUENCE LISTING

<160> NUMBER OF SEQ ID NOS: 15

<210> SEQ ID NO 1
<211> LENGTH: 1086
<212> TYPE: DNA
<213> ORGANISM: E. Coli
<220> FEATURE:
<223> OTHER INFORMATION: rmlB (upec138)

<400> SEQUENCE: 1

```
gtgaagatac ttgttactgg tggcgcagga tttattggtt ctgctgttgt tcgtcacata      60
ataaataata cgcaagatag tgttgttaat gtcgataaat taacatacgc cggaaacctg     120
gaatcacttg cagatgtttc tgattctgaa cgctatttct ttgaacatgc ggatatttgt     180
gatgcagctg caatggcacg gattttgct cagcatcagc cggatgcagt gatgcacctg     240
gcagctgaaa gccatgttga ccgttcaatt acaggccctg cggcatttat tgaaaccaat     300
attgtgggta cttatgtcct tttagaagcg gctcggaatt attggtctgg tctggatgat     360
gaaaagaaaa aaaacttccg tttttcatcat atttctactg atgaggtgta tggtgactta     420
ccccatccgg atgaagtaaa tagcaatgaa acgttgccgc tatttacgga aacgacagca     480
tacgcgccaa gtagtccata ttctgcttct aaagcttcca gcgatcattt ggttcgcgca     540
tggaaacgta cttatggttt accgaccatt gtgactaatt gctcgaacaa ctatggtcct     600
tatcatttcc cggaaaagct tattccactg gttattctta attcactgga aggtaaggca     660
ttacctattt atggcaaagg agatcagatc cgcgactggt tgtatgtaga ggatcatgct     720
cgagcgttat ataccgtcgt aaccgaaggt aaagcgggcg aaacttataa cattggtgga     780
cacaacgaaa agaaaaacat cgacgtagtg ttcactattt gtgatttgtt ggatgagata     840
gtcccgaaag agaaatctta ccgcgagcaa attacttatg ttaccgatcg tccgggacac     900
gatcgccgtt atgcgattga tgctgagaag attggtcgcg aattgggatg gaaaccacag     960
gaaacgtttg agagtgggat tcgtaaaacg gtggaatggt acctgtccaa tacaaaatgg    1020
gttgataatg tgaaaagtgg tgcctatcaa tcgtggattg aacagaacta tgagggccgc    1080
cagtaa                                                                1086
```

<210> SEQ ID NO 2
<211> LENGTH: 900
<212> TYPE: DNA
<213> ORGANISM: E. Coli
<220> FEATURE:
<223> OTHER INFORMATION: rmlD (upec138)

<400> SEQUENCE: 2

```
atgaatatcc tccttttttgg caaaacaggg caggtaggtt gggaactaca gcgtgctctg       60
gcacctctgg gtaatttgat tgctcttgat gttcactcca ctgattactg tggtgatttt     120
```

```
agtaatcctg aaggtgtagc tgaaaccgta agaagcattc ggcctgatat tattgtcaac    180
gcagccgctc acaccgcagt agacaaagca gaatcagaac cgaagtttgc acaattactg    240
aacgcgacga gtgtcgaagc gatcgcgaaa gcagccaatg aagtcggcgc ctgggttatt    300
cactactcta ctgactacgt atttccgggg accggtgaaa taccatggca ggaggaggat    360
gcaaccgcac cgctaaatgt ttacggtgaa accaagttag cgggagaaaa agcattacaa    420
gagcattgtg cgaagcacct tattttccgg accagctggg tctatgcagg taaaggaaat    480
aacttcgcca aaacaatgtt gcgtctggca aaagagcgtg aagaattagc cgttattaat    540
gatcagtttg gtgcgccaac tggcgcagag ttactggctg attgtacggc acatgctatt    600
cgtgtggcac tgaataaacc ggaagtcgca ggcttgtacc atctggtagc tagtggtacc    660
acaacgtggc acgattatgc tgcgctggtt tttgaagagg cgcgcaaagc aggcattccc    720
cttgcactca acaagctcaa cgcagtacca acaacagcct atcctacacc agctcgtcgt    780
ccacataact ctcgccttaa tacagaaaaa tttcagcaga actttgcgct tgtcttgcct    840
gactggcagg ttggcgtgaa acgaatgctt aacgaattat ttacgactac agcaatttaa    900
```

<210> SEQ ID NO 3
<211> LENGTH: 879
<212> TYPE: DNA
<213> ORGANISM: E. Coli
<220> FEATURE:
<223> OTHER INFORMATION: rmlA (upec138)

<400> SEQUENCE: 3

```
atgaaaacgc gtaaaggtat tattttggcg ggtggttctg gtactcgtct ttatcctgtg     60
acgatggccg tcagtaaaca gctgttaccg atttatgata aaccgatgat ctattacccg    120
ctctctacac tgatgttagc gggtattcgc gatattctga ttatcagtac accacaggat    180
actcctcgtt ttcaacaact gctgggtgac gggagccagt ggggcctgaa tcttcagtac    240
aaagtgcaac cgagtccgga tggtcttgcg caggcgttta ttatcggtga agagtttatt    300
ggtggtgatg attgtgcttt ggtacttggt gataatatct tctacggcca cgacctgccg    360
aagttaatgg acgtagctgt taacaaagaa agtggtgcaa cggtatttgc ctatcacgtt    420
aatgatcctg aacgttatgg tgtcgtggag tttgataata acggtactgc aattagcctg    480
gaagaaaaac cgctggaacc aaaaagtaac tatgcggtta ctgggcttta tttctatgac    540
aatgacgttg tggaaatggc gaaaaacctt aagccttctg cccgaggtga actggaaatt    600
accgatatta accgtatttta tatggaacaa ggacgtttgt ctgtcgctat gatgggcgt    660 ggctatgcat ggctggatac agggacgcat caaagtctta ttgaagcaag caacttcatt    720
gccaccattg aagagcgcca gggactaaag gtttcctgtc cggaagaaat tgcttatcgt    780
aaagggttta ttgatgctga gcaggtaaaa gtattagccg aaccgttgaa gaaaaatgct    840
tatggtcagt atctgctcaa aatgattaaa ggttattaa                           879
```

<210> SEQ ID NO 4
<211> LENGTH: 543
<212> TYPE: DNA
<213> ORGANISM: E. Coli
<220> FEATURE:
<223> OTHER INFORMATION: rmlC (upec138)

<400> SEQUENCE: 4

```
atgaacgtaa ttaaaactga aattcctgat gtgctgattt ttgaaccaaa agtttttggg     60
```

```
gatgaacgtg gcttctttt tgagagtttt aatcagagga ttttgaaga agcagtaggt      120 cgtaaggttg agtttgttca ggataaccat tctaagtcca gtaaaggtgt tttacgtggt      180
cttcattatc agttagaacc ttatgctcaa ggaaaactgg tgcgctgtgt tgttggcgag      240 gttttgatg ttgcggttga tattcgtaaa tcgtcaccta catttgggaa atgggttggg      300
gtgaatttgt ctgctgagaa taagcgtcag ttgtggattc ctgagggatt tgcacatggt      360 ttttggtgc tgagtgattt agcagaagtt ttatataaaa cgaatcaata ttatgctcca      420
tcacatgaaa aaatattat atggaatgac ctcttgctta atattaaatg gccgagcaca      480
gcactgatca ctctgtctga taaggatgca aatggggaaa gatttgaact aagtgagttt      540
tga                                                                   543
```

```
<210> SEQ ID NO 5
<211> LENGTH: 1260
<212> TYPE: DNA
<213> ORGANISM: E. Coli
<220> FEATURE:
<223> OTHER INFORMATION: wzx (upec138)

<400> SEQUENCE: 5
atgtctctct taaaacatag tatatggaat gttgcgggct actttatacc aacattaatt       60
gcaattcccg cctttggatt aattgcgagg aaaattggtg tagaactatt tggtttgtat      120
acgttagcaa tgattttat agggtatgca agtatatttg atgctgggtt aacaagagct      180
gttgtgcgtg aaatagcatt actaaaaaac agagtggacg attgtaatac gataatagta      240
acttctatta tcgctgtgat attttaggg tttatcggag gcggggagt gtttctgctt      300 aaaggcgata ttattgaact gttaaatatc tcaccaatat attacgccga ttcgataaag      360
tctctagtat tattatcatc tctgataacct gtattcttag tcacgcaaat actattagca      420
gagcttgagg gtcgggaata ttttgggatt ctaaatatac aaaaaagtgt agggaattct      480
ttaattgcag ggttacctgc attattttgtt ttaattaatc aaacgctttt ttctgcaatt      540
attggtgtag cgattgcaag agttatatgc ttgtggttaa gctacattat gagcagggaa      600
agaataacta tcgatatctc atttttttca ataactgttt taaagcggtt atttagatat      660
ggcgggtggg taactataag taacataata tctcctatat tagcgagtat ggatagattt      720
attctatccc atatccaggg agcatcaaaa atatcattct atacagtccc taatgagctg      780
gtaactaggc ttggaatagt tccaggctct cttgggaaag ctgttttttcc aaaattaagt      840 catgcaagga attttacagc gtcatatgca gagcaaaaaa aagcttatat attaatgact      900
gtcattgtaa tgcctttggt tttatttgta tattattacg caaagtttat tttaacattg      960
tggatggggg ctgagtatgc agggatttcg gtcgaaatat tacggattat gcttataggg     1020
tatattttta actgttattc acaaatctct tttgccaaca tacaggcctt tggaaaagca     1080
aaatacactg catacatcca tatgatgaa tttattcctt atttgataat gttatatata     1140
atttcaaagg aatatggggt tattggtgtt gcgtggttat ggacaattcg agtaataatt     1200 gatttttga tgcttttata tatgagttat cgttgtaata atcttatgaa aaaagggtag     1260
```

```
<210> SEQ ID NO 6
<211> LENGTH: 966
<212> TYPE: DNA
<213> ORGANISM: E. Coli
<220> FEATURE:
<223> OTHER INFORMATION: wekA (upec138)

<400> SEQUENCE: 6
```

```
atgatatata ttgtggtatt aaattggaat ggggctatag ataccattaa ttgtgttaaa    60
agtttaatgg atttaaatgt tagcgattat aaaattatca ttgttgataa ctgttctatg   120
gataactcat atgatactat aaaagaaaat cttaattcat tatatattgc tgataaaagt   180
atcattgagg tgaagtatga ggatagaaat aaatataaaa ccttagaaaa cgataaaatc   240
atattaatac aatctccgca aaataatggg tacgcaagtg gtaataatat tggcatagag   300
ttcgctctta atcaggagaa tatgaaatac gtctgggttc tgaataatga tactgaagtg   360
gataaagagg ctttaactca tttaattagt aaatgtgatt cagataaaag tatagggatt   420
tgcggttctc gtttagtcta ttttgccgac agagagatgc agcaaggact aggtggggtg   480
cataacaaat ggttatgcac tacaaaaaat tatgaaatgg gaagattagt ttccaaaaaa   540
tatgatgatg aagtcattag taatgatata gattatataa ttggcgcatc gatgtttttc   600
tctagagaat gtttggaaac agttggattg atgaatgaag aatattttt tatactatgaa   660 gagttagata tttgcctcag agcaaaagca aagaacttta aattaggtat ttgctcagaa   720
agtttggttt atcataaaat aggtgcaagt actgatgggg gaaagagcat gatggctgat   780
ctttgctcaa taaaaaatag gctggtcatt acagaaaggt tttatcccca atattattgg   840
acggtatggt tgtcactttt tgttgtagca tttaaccgtg ctagaagagg tgagtttaat   900
aagatgaaaa gatgtttgaa tgttatgttt aacttcaaac gaaacaaagg tagcaaatgc   960
cattag                                                              966

<210> SEQ ID NO 7
<211> LENGTH: 1149
<212> TYPE: DNA
<213> ORGANISM: E. Coli
<220> FEATURE:
<223> OTHER INFORMATION: wekB (upec138)

<400> SEQUENCE: 7
atgaaagtgg cttttttatc tgcttatgat ccactatcta catccagttg gtctggcaca    60 cctattata tgctaaaggc attatcgaag agaaatattt ccattgaaat attaggaccg   120
gtaaatagct atatgatata catgttaaaa gtatataaat taatattaag gtgtttcgga   180
aaagaatatg attatagtca ttcgaagttg ctttccaggt attacggtag aatattcggt   240
aggaaattaa aaaaaattga tggtttggat tttattatcg cacctgcagg ttcctcacaa   300
attgcttttt taaaaacaac cataccaata atatatctat cggatacaac atatgatcaa   360
ttaaaaagct attatccgaa tttaaataaa aaaacaatta taatgatga ggatgcaagt   420 ttaatcgaac gcaaggctat tgaaaaagca acagtagtat ctttcccatc taaatgggca   480
atggattttt gcaggaatta ttacagatta gattttgata aattagttga ataccatgg   540 ggggctaatt tatttgatga tattcacttt gctaataaaa atataattca aaagaatagt   600
tatacttgtc ttttcttggg agttgattgg gaaagaaaag gtgggaaaac agccttgaaa   660
gcaattgaat atgtaaggca gttatatggg atcgatgtta gactaaaaat ttgtggatgt   720
actccgaatc aaaagatttt acctacttgg gttgaattaa ttgataaagt agataaaaat   780
aacgttgacg aatatcagaa attcatcgat gtgttatcta cgctgatat acttctttta   840 ccaaccattg ctgaatgtta tggaatggta ttttgtgaag ctgctgcttt tggattgcct   900
gttgtcgcta cagatacagg tggagtcagt tctatagtta tcaacgaaag gacggggata   960
ttaattaaag acccgttaga ctataagcac tttggaaatg caattcataa aataattagt  1020
```
tccgtagaga cttatcaaaa ctactcccaa aacgcaagaa ttagatataa taatatattg    1080
cattgggaca attgggctaa aaagataatt gagattatgt atgagcataa gaatagaaga    1140
atcaaatag                                                            1149

<210> SEQ ID NO 8
<211> LENGTH: 1218
<212> TYPE: DNA
<213> ORGANISM: E. Coli
<220> FEATURE:
<223> OTHER INFORMATION: wzy (upec138)

<400> SEQUENCE: 8
atgagcataa gaatagaaga atcaaatagc acaaaaagaa ttatatgttt atttatactt      60
tttcttgttt tccctgattt tttgttttat acattagggg ttgataattt tagcatttca     120
acgataatct caattacatt gcttttgtt tttttaagg ctaaaaatat ttgcaaagat       180
aattttctaa taatagtagc gttattcata ttgttgtgtt ttaactgttt gttaagtatg     240
ctatttaata ttgaacaggc tttaacattt aaagttgtac tttcaatata tagcatctta    300
ataatggcat acgtctcctc ttgttatgca cagacgttgt ggttatgttc tgaagaaata    360
cttaagagat ccgtcttta tttgttcgca tttctttgcc ttattggcat tataagtatt     420
cttttacaga agactgagat tatacatgat aaaagtatga ttctttttcc tgaaccatca    480
gcatttgcat tggtttttat acctatcttt tcattttgtt tatactatac aagagggggg    540
gggctactat tgctctatat attatctttg ggtattgcgt taggtatcca gaatttaaca    600
atgttggtag gcattgtgat tagtgttttt gtgatgaaaa aataactat aaggcaaact     660 attgttatac ttttgggggc atggattttt tccatgatat taagtgattt agacatttct    720
tactatacat cgcggcttga tttaaaaat actacgaacc tatcagtgct tgtatatctt     780
tcaggaattg aaagagcttt cttgaatttt attacaagtt atggtcttgg tattggtttt    840
caacaaatgg gagtgaatgg ggagatagga atatatcaac aaattttagc tgaacttgat    900 gccctatgt aaatatata cgatggctca tttatttctt ctaagttaat atctgagttt      960
ggggttattg tgcattaat gtgtatttt tatttttt attttccccg attttatctg        1020
cgtttcaaaa aaagtaagag atattcaccg cagtatattt tagcatatag cttctacatg    1080
tgtttcttca tccctcttt tatacgtggt gctggttata taaaccccta tgtgtttatg     1140 ttatttcat caatattttt gtgcaaatat cacgctaaaa atatcttgat gaaatctaat    1200
gtccagatag ctatataa                                                  1218

<210> SEQ ID NO 9
<211> LENGTH: 606
<212> TYPE: DNA
<213> ORGANISM: E. Coli
<220> FEATURE:
<223> OTHER INFORMATION: wbbJ (upec138)

<400> SEQUENCE: 9
atgtgcatta aaaaaaaact taagttaatt aaacgatatg gcctttatgg tggtcttagg      60
cttcttaaag atatattctt aacaaaattt ttattttgtt caaatgttag gattattaga    120
tttccatgtt atattagaaa agatggaagt gttagtttg gaaaaggttt tacatcaggt      180
gtaggattac gagttgatgc atttatggat gccgtagttt ccattggaga aaatgttcaa    240
attaatgact atgttcacat cgcggctatt aataatgtca ttattggtag agatacatta    300
atagcaagta aagtatttat tagtgatcat aatcatggta ttttttctaa atccgatatc    360

```
catagttcac caactattat tccttcgtct aggccccttg aatctgcacc tgtgtatatt    420
ggagagcgtg tgtggattgg cgaaaatgtg acaatattac caggtgcgtg tataggtaat    480
ggtgtagtta ttggcgcaaa cagtgttgtt cgtggtgaga ttcctaataa tgtgatcatt    540
gctggtgttc cagctaaaat tgttaaaaaa tataactatg agcgtatgca atgggaaaga    600
atatag                                                                606
```

<210> SEQ ID NO 10
<211> LENGTH: 1101
<212> TYPE: DNA
<213> ORGANISM: E. Coli
<220> FEATURE:
<223> OTHER INFORMATION: wbbK (upec138)

<400> SEQUENCE: 10

```
atgggaaaga atatagttgt aatatcggct gttaatttta caaccggagg cccctttacc     60
gtactaaaaa atgtgcttac agcaactaaa gatagagccg aatgtaaatt tattgcactg    120
gttcatagct ctgctgaact aatggaatta tttccgtggg ttgaatttat agagtatcca    180
gaagtcaagt cttcgtgggt taaaagatta tatttcgaat atataacttg caatagatta    240
tctaaggtga ttaaggcaac tcattgggta tgcttacatg atattacagc aaatgttagt    300
gtaccctata gatttgttta ttgccacaat cctgcaccgt tctataaata tttaagctat    360
cgagatatta taggagaacc taaatttat ctttttatc ttttttatgg cttttatac     420
aatatcaata taaaaagaa cacagcagtt tttgttcagc agcagtggct aaaaaaagaa    480
ttcgaaaaaa aatataagtt aaagaatgtt gttgttagtc gccctgaaga tatttgccct    540
tttgaaagtg atggtttggt aagaaataat aataaaaagg atgtgaggat atttacccca   600
gcagtgcccc gtatattaa aaactttgaa gttatcatac gtgctgcaca atattacaa     660
gataaaaata ttcatttta tcttacttt gatggtactg aaaataagta tgcaaaaaga    720
atatataaat tagcttccga actgaaaaat gtacatttcc tcggttaacct taatgcaacc    780
gagatggtta acttttatca agattccagat attattgtt tcccatcgaa actagaaacg    840
tggggattac cattatcaga agctaaaaca tacaaaaaat ggatatttgc ggcagactta    900
ccttatgctc atgaagtttt atataactat tcaaaaacta gatattttcc atttgacgat    960
gagaaaatac ttgttcgcta catattgag tacacaagta aaaatgca tgaagatata   1020
aaaaatagta gggtgaattt taataatgat gcattgactg ttttgaaca gtttattgaa    1080
tatatcctca agggaactg a                                             1101
```

<210> SEQ ID NO 11
<211> LENGTH: 564
<212> TYPE: DNA
<213> ORGANISM: E. Coli
<220> FEATURE:
<223> OTHER INFORMATION: wbbL (upec138)

<400> SEQUENCE: 11

```
atgattatga ataatgatta ttttctcttt cttaaccccg atgtattcat aaccagtgaa    60
agtttgatta ttatgttga ttatataatt agtaatgatt ataagtttag cacattatgt    120
ctttatcgag attttactaa aagcaaacat gattattcaa tacggagttt tccaacttta    180
tatgattttc tttgttcttt tttattgggg gtgaataaaa gtaaaattaa gaaggaaaat    240
atactttctg atactgtagt tgattggtgt gctggctcat ttatgcttat tcatgcttta    300
```

```
agtttcttaa atgtgaatgg ttttgatcaa aaatatttta tgtattgtga agatatttgac    360 ctttgtatgc gtttaaaatt aagtggagta gatctttact atactcccca ttttgatgct    420
attcattatg cgcagcatga aaatagaaga atatttacta aagcatttcg atggcatata    480
aggagtatta cgcgctacat attacggaaa ccaattcttt cttataaaaa ctatagaaaa    540
attacatccg aactggtaaa gtga                                           564
```

<210> SEQ ID NO 12
<211> LENGTH: 10653
<212> TYPE: DNA
<213> ORGANISM: E. Coli
<220> FEATURE:
<223> OTHER INFORMATION: E. coli rfb(upec138) gene cluster

<400> SEQUENCE: 12

```
gtgaagatac ttgttactgg tggcgcagga tttattggtt ctgctgttgt tcgtcacata     60
ataaataata cgcaagatag tgttgttaat gtcgataaat taacatacgc cggaaacctg    120
gaatcacttg cagatgtttc tgattctgaa cgctatttct ttgaacatgc ggatatttgt    180
gatgcagctg caatggcacg gatttttgct cagcatcagc cggatgcagt gatgcacctg    240
gcagctgaaa gccatgttga ccgttcaatt acaggccctg cggcatttat tgaaaccaat    300
attgtgggta cttatgtcct tttagaagcg gctcggaatt attggtctgg tctggatgat    360
gaaaagaaaa aaaacttccg ttttcatcat atttctactg atgaggtgta tggtgactta    420
ccccatccgg atgaagtaaa tagcaatgaa acgttgccgc tatttacgga aacgacagca    480
tacgcgccaa gtagtccata ttctgcttct aaagcttcca gcgatcattt ggttcgcgca    540
tggaaacgta cttatggttt accgaccatt gtgactaatt gctcgaacaa ctatggtcct    600
tatcatttcc cggaaaagct tattccactg gttattctta attcactgga aggtaaggca    660 ttacctatt atggcaaagg agatcagatc cgcgactggt tgtatgtaga ggatcatgct    720
cgagcgttat ataccgtcgt aaccgaaggt aaagcgggcg aaacttataa cattggtgga    780
cacaacgaaa agaaaaacat cgacgtagtg ttcactattt gtgatttgtt ggatgagata    840
gtcccgaaag agaaatctta ccgcgagcaa attacttatg ttaccgatcg tccgggacac    900
gatcgccgtt atgcgattga tgctgagaag attggtcgcg aattgggatg gaaaccacag    960
gaaacgtttg agagtgggat tcgtaaaacg gtggaatggt acctgtccaa tacaaaatgg   1020
gttgataatg tgaaaagtgg tgcctatcaa tcgtggattg aacagaacta tgagggccgc   1080
cagtaatgaa tatcctcctt tttggcaaaa cagggcaggt aggttgggaa ctacagcgtg   1140
ctctggcacc tctgggtaat ttgattgctc ttgatgttca ctccactgat tactgtggtg   1200
attttagtaa tcctgaaggt gtagctgaaa ccgtaagaag cattcggcct gatattattg   1260
tcaacgcagc cgctcacacc gcagtagaca aagcagaatc agaaccgaag tttgcacaat   1320
tactgaacgc gacgagtgtc gaagcgatcg cgaaagcagc caatgaagtc ggcgcctggg   1380
ttattcacta ctctactgac tacgtatttc cggggaccgg tgaaatacca tggcaggagg   1440
aggatgcaac cgcaccgcta aatgtttacg gtgaaaccaa gttagcggga gaaaaagcat   1500
tacaagagca ttgtgcgaag caccttattt tccggaccag ctgggtctat gcaggtaaag   1560
gaaataactt cgccaaaaca atgttgcgtc tggcaaaaga gcgtgaagaa ttagccgtta   1620
ttaatgatca gttttggtgcg ccaactggcg cagagttact ggctgattgt acggcacatg   1680
ctattcgtgt ggcactgaat aaaccggaag tcgcaggctt gtaccatctg gtagctagtg   1740
gtaccacaac gtggcacgat tatgctgcgc tggttttga agaggcgcgc aaagcaggca   1800
```

```
ttcccettgc actcaacaag ctcaacgcag taccaacaac agcctatcct acaccagctc   1860
gtcgtccaca taactctcgc cttaatacag aaaaatttca gcagaacttt gcgcttgtct   1920
tgcctgactg gcaggttggc gtgaaacgaa tgcttaacga attatttacg actacagcaa   1980
tttaatagtt tttgcatctt gttcgtaatg gtggagcaag atgtattaaa aggaatgatg   2040
aaatgaaaac gcgtaaaggt attattttgg cgggtggttc tggtactcgt ctttatcctg   2100
tgacgatggc cgtcagtaaa cagctgttac cgatttatga taaaccgatg atctattacc   2160
cgctctctac actgatgtta gcgggtattc gcgatattct gattatcagt acaccacagg   2220
atactcctcg ttttcaacaa ctgctgggtg acgggagcca gtggggcctg aatcttcagt   2280
acaaagtgca accgagtccg gatggtcttg cgcaggcgtt tattatcggt gaagagttta   2340
ttggtggtga tgattgtgct ttggtacttg gtgataatat cttctacggc cacgacctgc   2400
cgaagttaat ggacgtagct gttaacaaag aaagtggtgc aacggtattt gcctatcacg   2460
ttaatgatcc tgaacgttat ggtgtcgtgg agtttgataa taacggtact gcaattagcc   2520
tggaagaaaa accgctggaa ccaaaaagta actatgcggt tactgggctt tatttctatg   2580
acaatgacgt tgtggaaatg gcgaaaaacc ttaagccttc tgcccgaggt gaactggaaa   2640
ttaccgatat taaccgtatt tatatggaac aaggacgttt gtctgtcgct atgatggggc   2700
gtggctatgc atggctggat acagggacgc atcaaagtct tattgaagca agcaacttca   2760
ttgccaccat tgaagagcgc cagggactaa aggtttcctg tccggaagaa attgcttatc   2820
gtaaagggtt tattgatgct gagcaggtaa aagtattagc cgaaccgttg aagaaaaatg   2880
cttatggtca gtatctgctc aaaatgatta aggttatta ataagatgaa cgtaattaaa   2940
actgaaattc ctgatgtgct gattttgaa ccaaagttt tggggatga acgtggcttc   3000 ttttttgaga gttttaatca gaggatttt gaagaagcag taggtcgtaa ggttgagttt   3060
gttcaggata accattctaa gtccagtaaa ggtgttttac gtggtcttca ttatcagtta   3120
gaaccttatg ctcaaggaaa actggtgcgc tgtgttgttg gcgaggtttt tgatgttgcg   3180
gttgatattc gtaaatcgtc acctacattt gggaatggg ttggggtgaa tttgtctgct   3240
gagaataagc gtcagttgtg gattcctgag ggatttgcac atggtttttt ggtgctgagt   3300
gatttagcag aagttttata taaaacgaat caatattatg ctccatcaca tgaaaaaaat   3360
attatatgga atgacctctt gcttaatatt aaatggccga gcacagcact gatcactctg   3420
tctgataagg atgcaaatgg ggaaagattt gaactaagtg agttttgaaa tgtctctctt   3480
aaaacatagt atatgaatg ttgcgggcta ctttataca acattaattg caattcccgc   3540
ctttggatta attgcgagga aaattggtgt agaactattt ggtttgtata cgttagcaat   3600
gatttttata gggtatgcaa gtatatttga tgctgggtta acaagagctg ttgtgcgtga   3660
aatagcatta ctaaaaaaca gagtggacga ttgtaatacg ataatagtaa cttctattat   3720
cgctgtgata ttttagggt ttatcggagg cggggagtg tttctgctta aggcgatat   3780 tattgaactg ttaaatatct caccaatata ttacgccgat tcgataaagt ctctagtatt   3840
attatcatct ctgataccg tattcttagt cacgcaaata ctattagcag gcttgaggg   3900 tcgggaatat tttgggattc taaatataca aaaaagtgta gggaattctt taattgcagg   3960
gttacctgca ttatttgttt taattaatca aacgcttttt tctgcaatta ttggtgtagc   4020
gattgcaaga gttatatgct tgtggttaag ctacattatg agcagggaaa gaataactat   4080
cgatatctca ttttttcaa taactgtttt aaagcggtta tttagatatg gcgggtgggt   4140
```

```
aactataagt aacataatat ctcctatatt agcgagtatg gatagattta ttctatccca    4200
tatccaggga gcatcaaaaa tatcattcta tacagtccct aatgagctgg taactaggct    4260
tggaatagtt ccaggctctc ttgggaaagc tgttttttcca aaattaagtc atgcaaggaa   4320
ttttacagcg tcatatgcag agcaaaaaaa agcttatata ttaatgactg tcattgtaat    4380
gcctttggtt ttatttgtat attattacgc aaagtttatt ttaacattgt ggatgggggc    4440
tgagtatgca gggatttcgg tcgaaatatt acggattatg cttataggg tatattttaa     4500 ctgttattca caaatctctt ttgccaacat acaggccttt ggaaaagcaa aatacactgc    4560
atacatccat atgatggaat ttattcctta tttgataatg ttatatataa tttcaaagga    4620
atatggggtt attggtgttg cgtggttatg gacaattcga gtaataattg atttttttgat  4680 gcttttatat atgagttatc gttgtaataa tcttatgaaa aaagggtagc ctgatgatat    4740
atattgtggt attaaattgg aatggggcta tagataccat taattgtgtt aaaagtttaa    4800
tggatttaaa tgttagcgat tataaaatta tcattgttga taactgttct atggataact    4860
catatgatac tataaaagaa aatcttaatt cattatatat tgctgataaa agtatcattg    4920
aggtgaagta tgaggataga aataaatata aaaccttaga aaacgataaa atcatattaa    4980
tacaatctcc gcaaaataat gggtacgcaa gtggtaataa tattggcata gagttcgctc    5040
ttaatcagga gaatatgaaa tacgtctggg ttctgaataa tgatactgaa gtggataaag    5100
aggctttaac tcatttaatt agtaaatgtg attcagataa aagtataggg atttgcggtt    5160
ctcgtttagt ctattttgcc gacagagaga tgcagcaagg actaggtggg gtgcataaca    5220
aatggttatg cactacaaaa aattatgaaa tgggaagatt agtttccaaa aaatatgatg    5280
atgaagtcat tagtaatgat atagattata taattggcgc atcgatgttt ttctctagag    5340
aatgtttgga aacagttgga ttgatgaatg aagaatattt tttatactat gaagagttag    5400
atatttgcct cagagcaaaa gcaaagaact ttaaattagg tatttgctca gaaagtttgg    5460
tttatcataa aataggtgca agtactgatg ggggaaagag catgatggct gatctttgct    5520
caataaaaaa taggctggtc attacagaaa ggttttatcc ccaatattat tggacggtat    5580
ggttgtcact ttttgttgta gcatttaacc gtgctagaag aggtgagttt aataagatga    5640
aaagatgttt gaatgttatg tttaacttca aacgaaacaa aggtagcaaa tgccattaga    5700
atatgcactt aatcatggtg ttaataaatc tatagtttga tatgttatta aagggtattt    5760
aatgaaagtg gctttttta tctgcttatga tccactatct acatccagtt ggtctggcac    5820
accttattat atgctaaagg cattatcgaa gagaaatatt tccattgaaa tattaggacc    5880
ggtaaatagc tatatgatat acatgttaaa agtatataaa ttaatattaa ggtgtttcgg    5940
aaaagaatat gattatagtc attcgaagtt gctttccagg tattacggta gaatattcgg    6000
taggaaatta aaaaaaattg atggtttgga ttttattatc gcacctgcag gttcctcaca    6060
aattgctttt ttaaaaacaa ccataccaat aatatatcta tcggatacaa catatgatca    6120
attaaaaagc tattatccga atttaaataa aaaaacaatt ataaatgatg aggatgcaag    6180
tttaatcgaa cgcaaggcta ttgaaaaagc aacagtagta tctttcccat ctaaatgggc    6240
aatggatttt tgcaggaatt attacagatt agatttgat aaattagttg aaataccatg      6300
gggggctaat ttatttgatg atattcactt tgctaataaa aatataattc aaaagaatag    6360
ttatacttgt ctttcttgg gagttgattg ggaaagaaaa ggtgggaaaa cagccttgaa     6420
agcaattgaa tatgtaaggc agttatatgg gatcgatgtt agactaaaaa tttgtggatg    6480
tactccgaat caaaagattt tacctacttg ggttgaatta attgataaag tagataaaaa    6540
```

```
taacgttgac gaatatcaga aattcatcga tgtgttatct aacgctgata tacttctttt    6600
accaaccatt gctgaatgtt atggaatggt attttgtgaa gctgctgctt ttggattgcc    6660
tgttgtcgct acagatacag gtggagtcag ttctatagtt atcaacgaaa ggacggggat    6720
attaattaaa gacccgttag actataagca ctttggaaat gcaattcata aaataattag    6780
ttccgtagag acttatcaaa actactccca aaacgcaaga attagatata ataatatatt    6840
gcattgggac aattgggcta aaaagataat tgagattatg tatgagcata agaatagaag    6900
aatcaaatag cacaaaaaga attatatgtt tatttatact ttttcttgtt ttccctgatt    6960
ttttgtttta tacattaggg gttgataatt ttagcatttc aacgataatc tcaattacat    7020
tgcttttgt tttttaaga gctaaaaata tttgcaaaga taattttcta ataatagtag    7080
cgttattcat attgttgtgt tttaactgtt tgttaagtat gctatttaat attgaacagg    7140
ctttaacatt taaagttgta ctttcaatat atagcatctt aataatggca tacgtctcct    7200
cttgttatgc acagacgttg tggttatgtt ctgaagaaat acttaagaga tccgtctttt    7260
atttgttcgc atttctttgc cttattggca ttataagtat tcttttacag aagactgaga    7320
ttatacatga taaaagtatg attcttttc ctgaaccatc agcatttgca ttggtttta    7380
tacctatctt ttcattttgt ttatactata caagaggggg ggggctacta ttgctctata    7440
tattatcttt gggtattgcg ttaggtatcc agaatttaac aatgttggta ggcattgtga    7500
ttagtgtttt tgtgatgaaa aaaataacta taaggcaaac tattgttata cttttggggg    7560
catgdattttt tccatgata ttaagtgatt tagacatttc ttactataca tcgcggcttg    7620
atttaaaaa tactacgaac ctatcagtgc ttgtatatct ttcaggaatt gaaagagctt    7680
tcttgaattt tattacaagt tatggtcttg gtattggttt tcaacaaatg ggagtgaatg    7740
gggagatagg aatatatcaa caaatttag ctgaacttga tgccctatg ttaaatatat    7800
acgatggctc atttatttct tctaagttaa tatctgagtt tggggttatt ggtgcattaa    7860
tgtgtatttt ctatttttt tatttttccc gattttatct gcgtttcaaa aaaagtaaga    7920
gatattcacc gcagtatatt ttagcatata gcttctacat gtgtttcttc atccctcttt    7980
ttatacgtgg tgctggttat ataaacccct atgtgtttat gttatttca tcaatatttt    8040
tgtgcaaata tcacgctaaa aatatcttga tgaaatctaa tgtccagata gctatataat    8100
agtagattat attatcatta tcacgtaaat tacatattaa tagcatatat gataactagg    8160
acataaataa tgtgcattaa aaaaaaactt aagttaatta aacgatatgg cctttatggt    8220
ggtcttaggc ttcttaaaga tatattctta acaaaatttt tattttgttc aaatgttagg    8280
attattagat ttccatgtta tattagaaaa gatggaagtg ttagttttgg aaaaggtttt    8340
acatcaggtg taggattacg agttgatgca tttatggatg ccgtagtttc cattggagaa    8400
aatgttcaaa ttaatgacta tgttcacatc gcggctatta ataatgtcat tattggtaga    8460
gatacattaa tagcaagtaa agtatttatt agtgatcata atcatggtat tttttctaaa    8520
tccgatatcc atagttcacc aactattatt ccttcgtcta ggccccttga atctgcacct    8580
gtgtatattg gagagcgtgt gtggattggc gaaaatgtga caatattacc aggtgcgtgt    8640
ataggtaatg gtgtagttat tggcgcaaac agtgttgttc gtggtgagat tcctaataat    8700
gtgatcattg ctggtgttcc agctaaaatt gttaaaaaat ataactatga gcgtatgcaa    8760
tgggaaagaa tatagttgta atatcggctg ttaattttac aaccggaggc ccctttaccg    8820
tactaaaaaa tgtgcttaca gcaactaaag atagagccga atgtaaattt attgcactgg    8880
```

```
ttcatagctc tgctgaacta atggaattat ttccgtgggt tgaatttata gagtatccag    8940
aagtcaagtc ttcgtgggtt aaaagattat atttcgaata tataacttgc aatagattat    9000
ctaaggtgat taaggcaact cattgggtat gcttacatga tattacagca aatgttagtg    9060
taccctatag atttgtttat tgccacaatc ctgcaccgtt ctataaatat ttaagctatc    9120
gagatattat aggagaacct aaattttatc ttttttatct tttttatggg cttttataca    9180
atatcaatat aaaaaagaac acagcagttt tgttcagca gcagtggcta aaaaaagaat    9240
tcgaaaaaaa atataagtta aagaatgttg ttgttagtcg ccctgaagat atttgccctt    9300
ttgaaagtga tggtttggta agaaataata ataaaaagga tgtgaggata ttttacccag    9360
cagtgccccg tatatttaaa aactttgaag ttatcatacg tgctgcacaa atattacaag    9420
ataaaaatat tcatttttat cttacttttg atggtactga aaataagtat gcaaaaagaa    9480
tatataaatt agcttccgaa ctgaaaaatg tacatttcct cggttacctt aatgcaaccg    9540
agatggttaa cttttatcaa gattcagata ttatttgttt cccatcgaaa ctagaaacgt    9600
ggggattacc attatcagaa gctaaaacat acaaaaaatg gatatttgcg gcagacttac    9660
cttatgctca tgaagtttta tataactatt caaaaactag atattttcca tttgacgatg    9720
agaaaatact tgttcgctac atattagagt acacaagtaa aaatatgcat gaagatataa    9780
aaaatagtag ggtgaatttt aataatgatg cattgactgg ttttgaacag tttattgaat    9840
atatcctcaa ggggaactga cgtggtttat attataatcg tttcacatgg ccatgatgac    9900
tatatagaaa atcttttatt aaatttaaag ttgccctctg aagatttaa aataatagtt    9960
cgtgataaca aaagttcaat ggttttaaaa aaaacatgcg aaaaaaattg cgtaacctat    10020
ttgcatggag ggcaatatgg atttggacat aataataaca tagcagtgtc atatataatt    10080
aataacttca tgattatgaa taatgattat tttctctttc ttaaccccga tgtattcata    10140
accagtgaaa gtttgattaa ttatgttgat tatataatta gtaatgatta taagtttagc    10200
acattatgtc tttatcgaga ttttactaaa agcaaacatg attattcaat acggagtttt    10260
ccaactttat atgattttct ttgttctttt ttattggggg tgaataaaag taaaattaag    10320
aaggaaaata tactttctga tactgtagtt gattggtgtg ctggctcatt tatgcttatt    10380
catgctttaa gtttcttaaa tgtgaatggt tttgatcaaa aatattttat gtattgtgaa    10440
gatattgacc tttgtatgcg tttaaaatta agtggagtag atctttacta tactccccat    10500
tttgatgcta ttcattatgc gcagcatgaa aatagaagaa tatttactaa agcatttcga    10560
tggcatataa ggagtattac gcgctacata ttacggaaac caattctttc ttataaaaac    10620
tatagaaaaa ttacatccga actggtaaag tga                                 10653
```

<210> SEQ ID NO 13
<211> LENGTH: 652
<212> TYPE: PRT
<213> ORGANISM: Artificial Sequence
<220> FEATURE:
<223> OTHER INFORMATION: Detoxified EPA protein comprising 4 optimized
      N-glycosylation sequences

<400> SEQUENCE: 13

Gly Ser Gly Gly Gly Asp Gln Asn Ala Thr Gly Ser Gly Gly Gly Lys
1               5                   10                  15

Leu Ala Glu Glu Ala Phe Asp Leu Trp Asn Glu Cys Ala Lys Ala Cys
            20                  25                  30

Val Leu Asp Leu Lys Asp Gly Val Arg Ser Ser Arg Met Ser Val Asp
        35                  40                  45

```
Pro Ala Ile Ala Asp Thr Asn Gly Gln Gly Val Leu His Tyr Ser Met
     50                  55                  60
Val Leu Glu Gly Gly Asn Asp Ala Leu Lys Leu Ala Ile Asp Asn Ala
 65                  70                  75                  80
Leu Ser Ile Thr Ser Asp Gly Leu Thr Ile Arg Leu Glu Gly Gly Val
                 85                  90                  95
Glu Pro Asn Lys Pro Val Arg Tyr Ser Tyr Thr Arg Gln Ala Arg Gly
                100                 105                 110
Ser Trp Ser Leu Asn Trp Leu Val Pro Ile Gly His Glu Lys Pro Ser
                115                 120                 125
Asn Ile Lys Val Phe Ile His Glu Leu Asn Ala Gly Asn Gln Leu Ser
            130                 135                 140
His Met Ser Pro Ile Tyr Thr Ile Glu Met Gly Asp Glu Leu Leu Ala
145                 150                 155                 160
Lys Leu Ala Arg Asp Ala Thr Phe Phe Val Arg Ala His Glu Ser Asn
                165                 170                 175
Glu Met Gln Pro Thr Leu Ala Ile Ser His Ala Gly Val Ser Val Val
                180                 185                 190
Met Ala Gln Ala Gln Pro Arg Arg Glu Lys Arg Trp Ser Glu Trp Ala
            195                 200                 205
Ser Gly Lys Val Leu Cys Leu Leu Asp Pro Leu Asp Gly Val Tyr Asn
210                 215                 220
Tyr Leu Ala Gln Gln Arg Cys Asn Leu Asp Asp Thr Trp Glu Gly Lys
225                 230                 235                 240
Ile Tyr Arg Val Leu Ala Gly Asn Pro Ala Lys His Asp Leu Asp Ile
                245                 250                 255
Lys Asp Asn Asn Ser Thr Pro Thr Val Ile Ser His Arg Leu His
                260                 265                 270
Phe Pro Glu Gly Gly Ser Leu Ala Ala Leu Thr Ala His Gln Ala Cys
            275                 280                 285
His Leu Pro Leu Glu Ala Phe Thr Arg His Arg Gln Pro Arg Gly Trp
            290                 295                 300
Glu Gln Leu Glu Gln Cys Gly Tyr Pro Val Gln Arg Leu Val Ala Leu
305                 310                 315                 320
Tyr Leu Ala Ala Arg Leu Ser Trp Asn Gln Val Asp Gln Val Ile Arg
                325                 330                 335
Asn Ala Leu Ala Ser Pro Gly Ser Gly Gly Asp Leu Gly Glu Ala Ile
            340                 345                 350
Arg Glu Gln Pro Glu Gln Ala Arg Leu Ala Leu Thr Leu Ala Ala Ala
            355                 360                 365
Glu Ser Glu Arg Phe Val Arg Gln Gly Thr Gly Asn Asp Glu Ala Gly
        370                 375                 380
Ala Ala Ser Ala Asp Val Val Ser Leu Thr Cys Pro Val Ala Lys Asp
385                 390                 395                 400
Gln Asn Arg Thr Lys Gly Glu Cys Ala Gly Pro Ala Asp Ser Gly Asp
                405                 410                 415
Ala Leu Leu Glu Arg Asn Tyr Pro Thr Gly Ala Glu Phe Leu Gly Asp
            420                 425                 430
Gly Gly Asp Val Ser Phe Ser Thr Arg Gly Thr Gln Asn Trp Thr Val
            435                 440                 445
Glu Arg Leu Leu Gln Ala His Arg Gln Leu Glu Glu Arg Gly Tyr Val
    450                 455                 460
```

```
Phe Val Gly Tyr His Gly Thr Phe Leu Glu Ala Ala Gln Ser Ile Val
465                 470                 475                 480

Phe Gly Gly Val Arg Ala Arg Ser Gln Asp Leu Asp Ala Ile Trp Arg
            485                 490                 495

Gly Phe Tyr Ile Ala Gly Asp Pro Ala Leu Ala Tyr Gly Tyr Ala Gln
            500                 505                 510

Asp Gln Glu Pro Asp Ala Arg Gly Arg Ile Arg Asn Gly Ala Leu Leu
            515                 520                 525

Arg Val Tyr Val Pro Arg Trp Ser Leu Pro Gly Phe Tyr Arg Thr Gly
            530                 535                 540

Leu Thr Leu Ala Ala Pro Glu Ala Ala Gly Glu Val Glu Arg Leu Ile
545                 550                 555                 560

Gly His Pro Leu Pro Leu Arg Leu Asp Ala Ile Thr Gly Pro Glu Glu
                565                 570                 575

Glu Gly Gly Arg Val Thr Ile Leu Gly Trp Pro Leu Ala Glu Arg Thr
                580                 585                 590

Val Val Ile Pro Ser Ala Ile Pro Thr Asp Pro Arg Asn Val Gly Gly
                595                 600                 605

Asp Leu Asp Pro Ser Ser Ile Pro Asp Lys Glu Gln Ala Ile Ser Ala
            610                 615                 620

Leu Pro Asp Tyr Ala Ser Gln Pro Gly Lys Pro Pro Arg Glu Asp Leu
625                 630                 635                 640

Lys Leu Gly Ser Gly Gly Gly Asp Gln Asn Ala Thr
                645                 650

<210> SEQ ID NO 14
<211> LENGTH: 3
<212> TYPE: PRT
<213> ORGANISM: Artificial Sequence
<220> FEATURE:
<223> OTHER INFORMATION: N-glycosylation consensus sequence
<220> FEATURE:
<221> NAME/KEY: VARIANT
<222> LOCATION: (2)..(2)
<223> OTHER INFORMATION: Xaa = any amino acid
<220> FEATURE:
<221> NAME/KEY: VARIANT
<222> LOCATION: (3)..(3)
<223> OTHER INFORMATION: Xaa = Ser or Thr

<400> SEQUENCE: 14

Asn Xaa Xaa
1

<210> SEQ ID NO 15
<211> LENGTH: 5
<212> TYPE: PRT
<213> ORGANISM: Artificial Sequence
<220> FEATURE:
<223> OTHER INFORMATION: N-glycosylation consensus sequence
<220> FEATURE:
<221> NAME/KEY: VARIANT
<222> LOCATION: (1)..(1)
<223> OTHER INFORMATION: Xaa = Asp or Glu
<220> FEATURE:
<221> NAME/KEY: VARIANT
<222> LOCATION: (2)..(2)
<223> OTHER INFORMATION: Xaa = independently selected from any natural
      amino acid except Pro
<220> FEATURE:
<221> NAME/KEY: VARIANT
<222> LOCATION: (4)..(4)
<223> OTHER INFORMATION: Xaa = independently selected from any natural
      amino acid except Pro
<220> FEATURE:
```

```
<221> NAME/KEY: VARIANT
<222> LOCATION: (5)..(5)
<223> OTHER INFORMATION: Xaa = Ser or Thr

<400> SEQUENCE: 15

Xaa Xaa Asn Xaa Xaa
1               5
```